US012209246B2

(12) United States Patent
Shultz et al.

(10) Patent No.: US 12,209,246 B2
(45) Date of Patent: Jan. 28, 2025

(54) METHODS OF GENETICALLY ALTERING A WHOLE PLANT SEED

(71) Applicant: FLAGSHIP PIONEERING INNOVATIONS V, INC., Cambridge, MA (US)

(72) Inventors: Randall William Shultz, Acton, MA (US); John P. Casey, Jr., Boston, MA (US); Barry Andrew Martin, Newport, RI (US); Yajie Niu, Lexington, MA (US); Kristine Yu, Cambridge, MA (US); Brian Prescott Fiske, Cambridge, MA (US)

(73) Assignee: FLAGSHIP PIONEERING INNOVATIONS V, INC., Cambridge, MA (US)

( * ) Notice: Subject to any disclaimer, the term of this patent is extended or adjusted under 35 U.S.C. 154(b) by 259 days.

(21) Appl. No.: 17/650,212

(22) Filed: Feb. 7, 2022

(65) Prior Publication Data

US 2022/0251585 A1 Aug. 11, 2022

Related U.S. Application Data

(63) Continuation of application No. 16/345,919, filed as application No. PCT/US2017/059996 on Nov. 3, 2017, now abandoned.

(60) Provisional application No. 62/442,601, filed on Jan. 5, 2017, provisional application No. 62/418,078, filed on Nov. 4, 2016.

(51) Int. Cl.
*C12N 15/82* (2006.01)
*A01H 1/06* (2006.01)

(52) U.S. Cl.
CPC ........... *C12N 15/8213* (2013.01); *A01H 1/06* (2013.01); *C12N 15/8201* (2013.01); *C12N 15/8206* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | | | |
|---|---|---|---|---|
| 8,975,470 | B2 * | 3/2015 | Sela | C12N 15/8261 800/278 |
| 2011/0247100 | A1 | 10/2011 | Samboju et al. | |
| 2013/0198893 | A1 | 8/2013 | Zhao et al. | |
| 2014/0356414 | A1 | 12/2014 | Wang et al. | |
| 2015/0059010 | A1 | 2/2015 | Cigan et al. | |
| 2015/0082478 | A1 | 3/2015 | Cigan et al. | |
| 2016/0208272 | A1 * | 7/2016 | Cigan | C12N 15/8274 |
| 2018/0163232 | A1 | 6/2018 | Gao et al. | |

FOREIGN PATENT DOCUMENTS

| | | | |
|---|---|---|---|
| WO | 2014167514 | A1 | 10/2014 |
| WO | 2015038796 | A2 | 3/2015 |
| WO | 2015131101 | A1 | 9/2015 |
| WO | 2015171894 | A1 | 11/2015 |
| WO | 2015167956 | A1 | 1/2016 |
| WO | 2016105185 | A1 | 6/2016 |

OTHER PUBLICATIONS

Extended European Search Report in EP23178955.3, mailed Aug. 11, 2023, 8 pages.
Office Action in AU2017355507, mailed Jan. 27, 2023, 5 pages.
Office Action in EP17868054.2, mailed Feb. 3, 2023, 6 pages.
Intellectual Property Office of Singapore in connection with application No. 11201903982Y filed Nov. 3, 2017, "Written Opinion", 7 pages, Jan. 22, 2021.
Broothaerts et al., "Gene Transfer to Plants by Diverse Species of Bacteria", Letters to Nature, pp. 629-633, vol. 433 2005.
Fauser at al., "Both CRISPR/Cas-Based Nucleases and Nickases Can be Used Efficiently for Genome Engineering in *Arabidopsis thaliana*", The Plant Journal, pp. 348-359, vol. 79 2014.
International Search Report for PCT/US2017/059996, Feb. 1, 2018.
Martin-Ortigosa et al., "Mesoporous Silica Nanoparticle-Mediated Intracellular Cre Protein Delivery for Maize Genome Editing via IoxP Site Excision", Plant Physiology, pp. 537-547, vol. 164 2014.
Randolph-Anderson et al., "Sub-micron gold particles are superior to larger particles for efficient Biolistic® transformation of organelles and some cell types", Bio-Rad, US/EG Bulletin, pp. 1-4, 2015.
Sun et al., "Antisense Oligodeoxynucleotide Inhibition as a Potent Strategy in Plant Biology: Identification of SUSIBA2 as a Transcriptional Activator in Plant Sugar Signalling", The Plant Journal, pp. 128-138, vol. 44 2005.
Supplementry European Search Report for EP17868054.2 dated Apr. 17, 2020.
Woo et al., "DNA-Free Genome Editing in Plants with Preassembled CRISPR-Cas9 Ribonucleoproteins", Nature Biotechnology, 3 pages 2015.
Xing et al., "A CRISPR/Cas9 Toolkit for Multiplex Genome Editing in Plants", BMC Plant Biology, 12 pages, vol. 14, No. 327 2014.
Yoo et al., "DNA Uptake by Imbibition and Expression of a Foreign Gene in Rice", Physiologia Plantarum, pp. 453-459, vol. 94 1995.
Zhang et al., "Cationic lipids and polymers mediated vectors for delivery of siRNA", Journal of Controlled Release, 123, pp. 1-10, 2007.
Bortesi et al., "The CRISPR/Cas9 system for Plant Genome Editing and Beyond", Biotechnology Advances, Jan.-Feb. 2015, pp. 41-52, vol. 33, Issue 1.
Singapore Search Report and Written Opinion for Application No. 11201903982Y dated Jul. 23, 2020.
Official action for EP17868054.2, dated Nov. 26, 2020.

(Continued)

*Primary Examiner* — Cynthia E Collins
(74) *Attorney, Agent, or Firm* — McKee, Voorhees & Sease, PLC

(57) ABSTRACT

Disclosed herein are compositions and methods for effecting alterations at a defined location in the genome of a non-epidermal plant cell. Further disclosed are methods for providing plants having a modified phenotype or a modified genome.

10 Claims, No Drawings

Specification includes a Sequence Listing.

(56) References Cited

OTHER PUBLICATIONS

Pellegrineschi et al., "The effect of pretreatment with mild heat and drought stresses on the explant and biolistic transformation frequency of three durum wheat cultivars", Plant Cell Rep., pp. 950-960, vol. 20, Springer-Verlag 2002.

Brukhin et al., "Plant Growth and Development—Basic Knowledge and Current Views", Math. Model. Nat. Phenom., vol. 6, No. 2, pp. 1-53, 2011.

* cited by examiner

SEQUENCE LISTING

```
<160> NUMBER OF SEQ ID NOS: 60

<210> SEQ ID NO 1
<211> LENGTH: 3079
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: synthetic construct

<400> SEQUENCE: 1
```

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtggaat tctaaagatc taaaataaat    420
ggtaaaatgt caaatcaaaa ctaggctgca gtatgcagag cagagtcatg atgatactac    480
ttactacacc gattcttgtg tgcagaaaaa tatgttaaaa taattgaatc tttctctagc    540
caaatttgac aacaatgtac accgttcata ttgagagacg atgcttcttg tttgctttcg    600
gtggaagctg catatactca acattactcc ttcagcgagt tttccaactg agtcccacat    660
tgcccagacc taacacggta ttcttgttta taatgaaatg tgccaccaca tggattgaag    720
caagagacgt tctagggttt tagagctaga aatagcaagt taaaataagg ctagtccgtt    780
atcaacttga aaaagtggca ccgagtcggt gctttttttg gatccggcgc gccgcatgca    840
agcttggcgt aatcatggtc atagctgttt cctgtgtgaa attgttatcc gctcacaatt    900
ccacacaaca tacgagccgg aagcataaag tgtaaagcct ggggtgccta atgagtgagc    960
taactcacat taattgcgtt gcgctcactg cccgctttcc agtcgggaaa cctgtcgtgc   1020
cagctgcatt aatgaatcgg ccaacgcgcg gggagaggcg gtttgcgtat tgggcgctct   1080
tccgcttcct cgctcactga ctcgctgcgc tcggtcgttc ggctgcggcg agcggtatca   1140
gctcactcaa aggcggtaat acggttatcc acagaatcag gggataacgc aggaaagaac   1200
atgtgagcaa aaggccagca aaaggccagg aaccgtaaaa aggccgcgtt gctggcgttt   1260
ttccataggc tccgcccccc tgacgagcat cacaaaaatc gacgctcaag tcagaggtgg   1320
cgaaacccga caggactata aagataccag gcgtttcccc ctggaagctc cctcgtgcgc   1380
tctcctgttc cgaccctgcc gcttaccgga tacctgtccg cctttctccc ttcgggaagc   1440
gtggcgcttt ctcatagctc acgctgtagg tatctcagtt cggtgtaggt cgttcgctcc   1500
aagctgggct gtgtgcacga accccccgtt cagcccgacc gctgcgcctt atccggtaac   1560
tatcgtcttg agtccaaccc ggtaagacac gacttatcgc cactggcagc agccactggt   1620
aacaggatta gcagagcgag gtatgtaggc ggtgctacag agttcttgaa gtggtggcct   1680
aactacggct acactagaag aacagtattt ggtatctgcg ctctgctgaa gccagttacc   1740
ttcggaaaaa gagttggtag ctcttgatcc ggcaaacaaa ccaccgctgg tagcggtggt   1800
tttttgttt gcaagcagca gattacgcgc agaaaaaaag gatctcaaga agatcctttg   1860
atcttttcta cggggtctga cgctcagtgg aacgaaaact cacgttaagg gattttggtc   1920
atgagattat caaaaaggat cttcacctag atccttttaa attaaaaatg aagttttaaa   1980
tcaatctaaa gtatatatga gtaaacttgg tctgacagtt accaatgctt aatcagtgag   2040
gcacctatct cagcgatctg tctatttcgt tcatccatag ttgcctgact ccccgtcgtg   2100
tagataacta cgatacggga gggcttacca tctggcccca gtgctgcaat gataccgcga   2160
gacccacgct caccggctcc agatttatca gcaataaacc agccagccgg aagggccgag   2220
cgcagaagtg gtcctgcaac tttatccgcc tccatccagt ctattaattg ttgccgggaa   2280
gctagagtaa gtagttcgcc agttaatagt ttgcgcaacg ttgttgccat tgctacaggc   2340
```

atcgtggtgt cacgctcgtc gtttggtatg gcttcattca gctccggttc ccaacgatca 2400
aggcgagtta catgatcccc catgttgtgc aaaaaagcgg ttagctcctt cggtcctccg 2460
atcgttgtca gaagtaagtt ggccgcagtg ttatcactca tggttatggc agcactgcat 2520
aattctctta ctgtcatgcc atccgtaaga tgcttttctg tgactggtga gtactcaacc 2580
aagtcattct gagaatagtg tatgcggcga ccgagttgct cttgcccggc gtcaatacgg 2640
gataataccg cgccacatag cagaacttta aaagtgctca tcattggaaa acgttcttcg 2700
gggcgaaaac tctcaaggat cttaccgctg ttgagatcca gttcgatgta acccactcgt 2760
gcacccaact gatcttcagc atcttttact ttcaccagcg tttctgggtg agcaaaaaca 2820
ggaaggcaaa atgccgcaaa aaagggaata agggcgacac ggaaatgttg aatactcata 2880
ctcttccttt ttcaatatta ttgaagcatt tatcagggtt attgtctcat gagcggatac 2940
atatttgaat gtatttagaa aaataaacaa ataggggttc cgcgcacatt tccccgaaaa 3000
gtgccacctg acgtctaaga aaccattatt atcatgacat taacctataa aaataggcgt 3060
atcacgaggc cctttcgtc 3079

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: synthetic construct

<400> SEQUENCE: 2
gaagcaagag acgttctagg 20

<210> SEQ ID NO 3
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: synthetic construct

<400> SEQUENCE: 3
gttttagagc tagaaatagc aagttaaaat aaggctagtc cgttatcaac ttgaaaaagt 60
ggcaccgagt cggtgc 76

<210> SEQ ID NO 4
<211> LENGTH: 96
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: synthetic construct

<400> SEQUENCE: 4
gaagcaagag acgttctagg gttttagagc tagaaatagc aagttaaaat aaggctagtc 60
cgttatcaac ttgaaaaagt ggcaccgagt cggtgc 96

<210> SEQ ID NO 5
<211> LENGTH: 8569
<212> TYPE: DNA

```
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: synthetic construct

<400> SEQUENCE: 5

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt ctaaagatct ggcgcgccgg    420

cccgggctgg ttattgtttt tgtcaatgag ctatctttta gtcttatgtt attggtgaat    480

ctgtccttaa gttgcatcat ttaacacatc tcctcattag agaaaaaaat tcttccctaa    540

acgattggta gtaaaaacat ctaataagaa ataagaaaga aaaattagga aaaaggaaag    600

ttcattaaaa aaaatatttt gaattatttt ttaaaaaata tctaaatatt ttttaaatga    660

ataattttat ataaactgta actaaatgta tacaagtaat gtatgttaaa aaaatacttg    720

aaaaatctac tgaaaatata tcttacaagg tgaaattaaa taagaaagaa tttagtggaa    780

taattatgat tttatttaaa aaataattat taaagatttt tttgctccat aataagaaaa    840

cttttcaatt attcttttct ggtccataat aaaaaaaatc tagcatgaca gcttttccat    900

agatttttaa taatgtaaaa gcagccgact tcaggcaatg gatagtgggg cccgtatcaa    960

cttcggacgc tccacttgca acggggtggg cccaatataa caacgacgtc gtaacagata   1020

aagcgaagat tgaaggtgca tgtgactccg tcaagattac gaaaccgcca actaccacgc   1080

aaattgcaat tctcaatttc ctagaaggac tctccgaaaa tgcatccaat accaaatatt   1140

acccgtgtca taggcaccaa gtgacaccat acatgaacac gcgtcacaat atgactggag   1200

aagggttcca caccttatgc tataaaacgc cccacacccc tcctccttcc ttcgcagttc   1260

aattccaata tattccattc tctctgtgta tttccctacc tctcccttca aggttagtcg   1320

atttcttctg tttttcttct tcgttctttc catgaattgt gtatgttctt tgatcaatac   1380

gatgttgatt tgattgtgtt ttgtttggtt tcatcgatct tcaattttca taatcagatt   1440

cagcttttat tatctttaca acaacgtcct taatttgatg attctttaat cgtagatttg   1500

ctctaattag agctttttca tgtcagatcc ctttacaaca agccttaatt gttgattcat   1560

taatcgtaga ttagggcttt tttcattgat tacttcagat ccgttaaacg taaccataga   1620

tcagggcttt ttcatgaatt acttcagatc cgttaaacaa cagccttatt ttttatactt   1680

ctgtggtttt tcaagaaatt gttcagatcc gttgacaaaa agccttattc gttgattcta   1740

tatcgttttt cgagagatat tgctcagatg tgttagcaac tgccttgttt gttgattcta   1800

ttgccgtgga ttagggtttt ttttcacgag attgcttcag atccgtactt aagattacgt   1860

aatggatttt gattctgatt tatctgtgat tgttgactcg acaggatcgg taccccatgg   1920

ataagaagta ctctatcgga ctcgatatcg gaactaactc tgtgggatgg gctgtgatca   1980

ccgatgagta caaggtgcca tctaagaagt tcaaggttct cggaaacacc gataggcact   2040

ctatcaagaa aaaccttatc ggtgctctcc tcttcgattc tggtgaaact gctgaggcta   2100
```

```
ccagactcaa gagaaccgct agaagaaggt acaccagaag aaagaacagg atctgctacc   2160
tccaagagat cttctctaac gagatggcta aagtggatga ttcattcttc cacaggctcg   2220
aagagtcatt cctcgtggaa gaagataaga agcacgagag gcaccctatc ttcggaaaca   2280
tcgttgatga ggtggcatac cacgagaagt accctactat ctaccacctc agaaagaagc   2340
tcgttgattc tactgataag gctgatctca ggctcatcta cctcgctctc gctcacatga   2400
tcaagttcag aggacacttc ctcatcgagg gtgatctcaa ccctgataac tctgatgtgg   2460
ataagttgtt catccagctc gtgcagacct acaaccagct tttcgaagag aaccctatca   2520
acgcttcagg tgtggatgct aaggctatcc tctctgctag gctctctaag tcaagaaggc   2580
ttgagaacct cattgctcag ctccctggtg agaagaagaa cggacttttc ggaaacttga   2640
tcgctctctc tctcggactc acccctaact tcaagtctaa cttcgatctc gctgaggatg   2700
caaagctcca gctctcaaag gatacctacg atgatgatct cgataacctc ctcgctcaga   2760
tcggagatca gtacgctgat ttgttcctcg ctgctaagaa cctctctgat gctatcctcc   2820
tcagtgatat cctcagagtg aacaccgaga tcaccaaggc tccactctca gcttctatga   2880
tcaagagata cgatgagcac caccaggatc tcacacttct caaggctctt gttagacagc   2940
agctcccaga gaagtacaaa gagattttct tcgatcagtc taagaacgga tacgctggtt   3000
acatcgatgg tggtgcatct caagaagagt tctacaagtt catcaagcct atcctcgaga   3060
agatggatgg aaccgaggaa ctcctcgtga agctcaatag agaggatctt ctcagaaagc   3120
agaggacctt cgataacgga tctatccctc atcagatcca cctcggagag ttgcacgcta   3180
tccttagaag gcaagaggat ttctacccat tcctcaagga taacagggaa aagattgaga   3240
agattctcac cttcagaatc ccttactacg tgggacctct cgctagagga aactcaagat   3300
tcgcttggat gaccagaaag tctgaggaaa ccatcacccc ttggaacttc gaagaggtgg   3360
tggataaggg tgctagtgct cagtctttca tcgagaggat gaccaacttc gataagaacc   3420
ttccaaacga gaaggtgctc cctaagcact ctttgctcta cgagtacttc accgtgtaca   3480
acgagttgac caaggttaag tacgtgaccg agggaatgag gaagcctgct tttttgtcag   3540
gtgagcaaaa gaaggctatc gttgatctct tgttcaagac caacagaaag gtgaccgtga   3600
agcagctcaa agaggattac ttcaagaaaa tcgagtgctt cgattcagtt gagatttctg   3660
gtgttgagga taggttcaac gcatctctcg gaacctacca cgatctcctc aagatcatta   3720
aggataagga tttcttggat aacgaggaaa acgaggatat cttggaggat atcgttctta   3780
ccctcaccct ctttgaagat agagagatga ttgaagaaag gctcaagacc tacgctcatc   3840
tcttcgatga taaggtgatg aagcagttga agagaagaag atacactggt tggggaaggc   3900
tctcaagaaa gctcattaac ggaatcaggg ataagcagtc tggaaagaca atccttgatt   3960
tcctcaagtc tgatggattc gctaacagaa acttcatgca gctcatccac gatgattctc   4020
tcacctttaa agaggatatc cagaaggctc aggtttcagg acagggtgat agtctccatg   4080
agcatatcgc taacctcgct ggatctcctg caatcaagaa gggaatcctc cagactgtga   4140
aggttgtgga tgagttggtg aaggtgatgg gaaggcataa gcctgagaac atcgtgatcg   4200
aaatggctag agagaaccag accactcaga agggacagaa gaactctagg gaaaggatga   4260
agaggatcga ggaaggtatc aaagagcttg gatctcagat cctcaaagag caccctgttg   4320
agaacactca gctccagaat gagaagctct acctctacta cctccagaac ggaagggata   4380
tgtatgtgga tcaagagttg gatatcaaca ggctctctga ttacgatgtt gatcatatcg   4440
tgccacagtc attcttgaag gatgattcta tcgataacaa ggtgctcacc aggtctgata   4500
```

```
agaacagggg taagagtgat aacgtgccaa gtgaagaggt tgtgaagaaa atgaagaact   4560
attggaggca gctcctcaac gctaagctca tcactcagag aaagttcgat aacttgacta   4620
aggctgagag gggaggactc tctgaattgg ataaggcagg attcatcaag aggcagcttg   4680
tggaaaccag gcagatcact aagcacgttg cacagatcct cgattctagg atgaacacca   4740
agtacgatga gaacgataag ttgatcaggg aagtgaaggt tatcaccctc aagtcaaagc   4800
tcgtgtctga tttcagaaag gatttccaat tctacaaggt gagggaaatc aacaactacc   4860
accacgctca cgatgcttac cttaacgctg ttgttggaac cgctctcatc aagaagtatc   4920
ctaagctcga gtcagagttc gtgtacggtg attacaaggt gtacgatgtg aggaagatga   4980
tcgctaagtc tgagcaagag atcggaaagg ctaccgctaa gtatttcttc tactctaaca   5040
tcatgaattt cttcaagacc gagattaccc tcgctaacgg tgagatcaga aagaggccac   5100
tcatcgagac aaacggtgaa acaggtgaga tcgtgtggga taagggaagg gatttcgcta   5160
ccgttagaaa ggtgctctct atgccacagg tgaacatcgt taagaaaacc gaggtgcaga   5220
ccggtggatt ctctaaagag tctatcctcc ctaagaggaa ctctgataag ctcattgcta   5280
ggaagaagga ttgggaccct aagaaatacg gtggtttcga ttctcctacc gtggcttact   5340
ctgttctcgt tgtggctaag gttgagaagg gaaagagtaa gaagctcaag tctgttaagg   5400
aacttctcgg aatcactatc atggaaaggt catctttcga gaagaaccca atcgatttcc   5460
tcgaggctaa gggatacaaa gaggttaaga aggatctcat catcaagctc ccaaagtact   5520
cactcttcga actcgagaac ggtagaaaga ggatgctcgc ttctgctggt gagcttcaaa   5580
agggaaacga gcttgctctc ccatctaagt acgttaactt tctttacctc gcttctcact   5640
acgagaagtt gaagggatct ccagaagata acgagcagaa gcaacttttc gttgagcagc   5700
acaagcacta cttggatgag atcatcgagc agatctctga gttctctaaa agggtgatcc   5760
tcgctgatgc aaacctcgat aaggtgttgt ctgcttacaa caagcacaga gataagccta   5820
tcagggaaca ggcagagaac atcatccatc tcttcaccct taccaacctc ggtgctcctg   5880
ctgctttcaa gtacttcgat acaaccatcg ataggaagag atacacctct accaaagaag   5940
tgctcgatgc taccctcatc catcagtcta tcactggact ctacgagact aggatcgatc   6000
tctcacagct cggtggtgat tcaagggctg atcctaagaa gaagaggaag gtttgagcgg   6060
ccgcgatcgt tcaaacattt ggcaataaag tttcttaaga ttgaatcctg ttgccggtct   6120
tgcgatgatt atcatataat ttctgttgaa ttacgttaag catgtaataa ttaacatgta   6180
atgcatgacg ttatttatga gatgggtttt tatgattaga gtcccgcaat tatacattta   6240
atacgcgata gaaaacaaaa tatagcgcgc aaactaggat aaattatcgc gcgcggtgtc   6300
atctatgtta ctagatcgga tccgcatgca agcttggcgt aatcatggtc atagctgttt   6360
cctgtgtgaa attgttatcc gctcacaatt ccacacaaca tacgagccgg aagcataaag   6420
tgtaaagcct ggggtgccta atgagtgagc taactcacat taattgcgtt gcgctcactg   6480
cccgctttcc agtcgggaaa cctgtcgtgc cagctgcatt aatgaatcgg ccaacgcgcg   6540
gggagaggcg gtttgcgtat tgggcgctct tccgcttcct cgctcactga ctcgctgcgc   6600
tcggtcgttc ggctgcggcg agcggtatca gctcactcaa aggcggtaat acggttatcc   6660
acagaatcag gggataacgc aggaaagaac atgtgagcaa aaggccagca aaaggccagg   6720
aaccgtaaaa aggccgcgtt gctggcgttt ttccataggc tccgcccccc tgacgagcat   6780
cacaaaaatc gacgctcaag tcagaggtgg cgaaacccga caggactata aagataccag   6840
```

```
gcgtttcccc ctggaagctc cctcgtgcgc tctcctgttc cgaccctgcc gcttaccgga   6900

tacctgtccg cctttctccc ttcgggaagc gtggcgcttt ctcatagctc acgctgtagg   6960

tatctcagtt cggtgtaggt cgttcgctcc aagctgggct gtgtgcacga accccccgtt   7020

cagcccgacc gctgcgcctt atccggtaac tatcgtcttg agtccaaccc ggtaagacac   7080

gacttatcgc cactggcagc agccactggt aacaggatta gcagagcgag gtatgtaggc   7140

ggtgctacag agttcttgaa gtggtggcct aactacggct acactagaag aacagtattt   7200

ggtatctgcg ctctgctgaa gccagttacc ttcggaaaaa gagttggtag ctcttgatcc   7260

ggcaaacaaa ccaccgctgg tagcggtggt ttttttgttt gcaagcagca gattacgcgc   7320

agaaaaaaag gatctcaaga agatcctttg atcttttcta cggggtctga cgctcagtgg   7380

aacgaaaact cacgttaagg gattttggtc atgagattat caaaaaggat cttcacctag   7440

atccttttaa attaaaaatg aagttttaaa tcaatctaaa gtatatatga gtaaacttgg   7500

tctgacagtt accaatgctt aatcagtgag gcacctatct cagcgatctg tctatttcgt   7560

tcatccatag ttgcctgact ccccgtcgtg tagataacta cgatacggga gggcttacca   7620

tctggcccca gtgctgcaat gataccgcga gacccacgct caccggctcc agatttatca   7680

gcaataaacc agccagccgg aagggccgag cgcagaagtg gtcctgcaac tttatccgcc   7740

tccatccagt ctattaattg ttgccgggaa gctagagtaa gtagttcgcc agttaatagt   7800

ttgcgcaacg ttgttgccat tgctacaggc atcgtggtgt cacgctcgtc gtttggtatg   7860

gcttcattca gctccggttc ccaacgatca aggcgagtta catgatcccc catgttgtgc   7920

aaaaaagcgg ttagctcctt cggtcctccg atcgttgtca gaagtaagtt ggccgcagtg   7980

ttatcactca tggttatggc agcactgcat aattctctta ctgtcatgcc atccgtaaga   8040

tgcttttctg tgactggtga gtactcaacc aagtcattct gagaatagtg tatgcggcga   8100

ccgagttgct cttgcccggc gtcaatacgg gataataccg cgccacatag cagaacttta   8160

aaagtgctca tcattggaaa acgttcttcg gggcgaaaac tctcaaggat cttaccgctg   8220

ttgagatcca gttcgatgta acccactcgt gcacccaact gatcttcagc atcttttact   8280

ttcaccagcg tttctgggtg agcaaaaaca ggaaggcaaa atgccgcaaa aaagggaata   8340

agggcgacac ggaaatgttg aatactcata ctcttccttt ttcaatatta ttgaagcatt   8400

tatcagggtt attgtctcat gagcggatac atatttgaat gtatttagaa aaataaacaa   8460

ataggggttc cgcgcacatt tccccgaaaa gtgccacctg acgtctaaga aaccattatt   8520

atcatgacat taacctataa aaataggcgt atcacgaggc cctttcgtc              8569
```

```
<210> SEQ ID NO 6
<211> LENGTH: 4104
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: synthetic construct

<400> SEQUENCE: 6

atggataaga agtactctat cggactcgat atcggaacta actctgtggg atggctgtg     60

atcaccgatg agtacaaggt gccatctaag aagttcaagg ttctcggaaa caccgatagg    120

cactctatca agaaaaacct tatcggtgct ctcctcttcg attctggtga aactgctgag    180

gctaccagac tcaagagaac cgctagaaga aggtacacca gaagaaagaa caggatctgc    240
```

-continued

```
tacctccaag agatcttctc taacgagatg gctaaagtgg atgattcatt cttccacagg    300
ctcgaagagt cattcctcgt ggaagaagat aagaagcacg agaggcaccc tatcttcgga    360
aacatcgttg atgaggtggc ataccacgag aagtacccta ctatctacca cctcagaaag    420
aagctcgttg attctactga taaggctgat ctcaggctca tctacctcgc tctcgctcac    480
atgatcaagt tcagaggaca cttcctcatc gagggtgatc tcaaccctga taactctgat    540
gtggataagt tgttcatcca gctcgtgcag acctacaacc agcttttcga agagaaccct    600
atcaacgctt caggtgtgga tgctaaggct atcctctctg ctaggctctc taagtcaaga    660
aggcttgaga acctcattgc tcagctccct ggtgagaaga agaacggact tttcggaaac    720
ttgatcgctc tctctctcgg actcacccct aacttcaagt ctaacttcga tctcgctgag    780
gatgcaaagc tccagctctc aaaggatacc tacgatgatg atctcgataa cctcctcgct    840
cagatcggag atcagtacgc tgatttgttc ctcgctgcta agaacctctc tgatgctatc    900
ctcctcagtg atatcctcag agtgaacacc gagatcacca aggctccact ctcagcttct    960
atgatcaaga gatacgatga gcaccaccag gatctcacac ttctcaaggc tcttgttaga   1020
cagcagctcc cagagaagta caaagagatt ttcttcgatc agtctaagaa cggatacgct   1080
ggttacatcg atggtggtgc atctcaagaa gagttctaca agttcatcaa gcctatcctc   1140
gagaagatgg atggaaccga ggaactcctc gtgaagctca atagagagga tcttctcaga   1200
aagcagagga ccttcgataa cggatctatc cctcatcaga tccacctcgg agagttgcac   1260
gctatcctta gaaggcaaga ggatttctac ccattcctca aggataacag ggaaaagatt   1320
gagaagattc tcaccttcag aatcccttac tacgtgggac ctctcgctag aggaaactca   1380
agattcgctt ggatgaccag aaagtctgag gaaaccatca ccccttggaa cttcgaagag   1440
gtggtggata agggtgctag tgctcagtct ttcatcgaga ggatgaccaa cttcgataag   1500
aaccttccaa acgagaaggt gctccctaag cactctttgc tctacgagta cttcaccgtg   1560
tacaacgagt tgaccaaggt taagtacgtg accgagggaa tgaggaagcc tgctttttg    1620
tcaggtgagc aaaagaaggc tatcgttgat ctcttgttca agaccaacag aaaggtgacc   1680
gtgaagcagc tcaaagagga ttacttcaag aaaatcgagt gcttcgattc agttgagatt   1740
tctggtgttg aggataggtt caacgcatct ctcggaacct accacgatct cctcaagatc   1800
attaaggata aggatttctt ggataacgag gaaaacgagg atatcttgga ggatatcgtt   1860
cttaccctca ccctctttga agatagagag atgattgaag aaaggctcaa gacctacgct   1920
catctcttcg atgataaggt gatgaagcag ttgaagagaa gaagatacac tggttgggga   1980
aggctctcaa gaaagctcat taacggaatc agggataagc agtctggaaa gacaatcctt   2040
gatttcctca agtctgatgg attcgctaac agaaacttca tgcagctcat ccacgatgat   2100
tctctcacct ttaaagagga tatccagaag gctcaggttt caggacaggg tgatagtctc   2160
catgagcata tcgctaacct cgctggatct cctgcaatca agaagggaat cctccagact   2220
gtgaaggttg tggatgagtt ggtgaaggtg atgggaaggc ataagcctga gaacatcgtg   2280
atcgaaatgg ctagagagaa ccagaccact cagaagggac agaagaactc tagggaaagg   2340
atgaagagga tcgaggaagg tatcaaagag cttggatctc agatcctcaa agagcaccct   2400
gttgagaaca ctcagctcca gaatgagaag ctctacctct actacctcca gaacggaagg   2460
gatatgtatg tggatcaaga gttggatatc aacaggctct ctgattacga tgttgatcat   2520
atcgtgccac agtcattctt gaaggatgat tctatcgata acaaggtgct caccaggtct   2580
gataagaaca ggggtaagag tgataacgtg ccaagtgaag aggttgtgaa gaaaatgaag   2640
```

```
aactattgga ggcagctcct caacgctaag ctcatcactc agagaaagtt cgataacttg   2700

actaaggctg agaggggagg actctctgaa ttggataagg caggattcat caagaggcag   2760

cttgtggaaa ccaggcagat cactaagcac gttgcacaga tcctcgattc taggatgaac   2820

accaagtacg atgagaacga taagttgatc agggaagtga aggttatcac cctcaagtca   2880

aagctcgtgt ctgatttcag aaaggatttc caattctaca aggtgaggga aatcaacaac   2940

taccaccacg ctcacgatgc ttaccttaac gctgttgttg gaaccgctct catcaagaag   3000

tatcctaagc tcgagtcaga gttcgtgtac ggtgattaca aggtgtacga tgtgaggaag   3060

atgatcgcta agtctgagca agagatcgga aaggctaccg ctaagtattt cttctactct   3120

aacatcatga atttcttcaa gaccgagatt accctcgcta acggtgagat cagaaagagg   3180

ccactcatcg agacaaacgg tgaaacaggt gagatcgtgt gggataaggg aagggatttc   3240

gctaccgtta gaaaggtgct ctctatgcca caggtgaaca tcgttaagaa aaccgaggtg   3300

cagaccggtg gattctctaa agagtctatc ctccctaaga ggaactctga taagctcatt   3360

gctaggaaga aggattggga ccctaagaaa tacggtggtt tcgattctcc taccgtggct   3420

tactctgttc tcgttgtggc taaggttgag aagggaaaga gtaagaagct caagtctgtt   3480

aaggaacttc tcggaatcac tatcatggaa aggtcatctt tcgagaagaa cccaatcgat   3540

ttcctcgagg ctaagggata caaagaggtt aagaaggatc tcatcatcaa gctcccaaag   3600

tactcactct tcgaactcga gaacggtaga aagaggatgc tcgcttctgc tggtgagctt   3660

caaaagggaa acgagcttgc tctcccatct aagtacgtta actttcttta cctcgcttct   3720

cactacgaga agttgaaggg atctccagaa gataacgagc agaagcaact tttcgttgag   3780

cagcacaagc actacttgga tgagatcatc gagcagatct ctgagttctc taaaagggtg   3840

atcctcgctg atgcaaacct cgataaggtg ttgtctgctt acaacaagca cagagataag   3900

cctatcaggg aacaggcaga gaacatcatc catctcttca cccttaccaa cctcggtgct   3960

cctgctgctt tcaagtactt cgatacaacc atcgatagga agagatacac ctctaccaaa   4020

gaagtgctcg atgctaccct catccatcag tctatcactg gactctacga gactaggatc   4080

gatctctcac agctcggtgg tgat                                         4104
```

<210> SEQ ID NO 7
<211> LENGTH: 1368
<212> TYPE: PRT
<213> ORGANISM: Streptococcus pyogenes

<400> SEQUENCE: 7

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110
```

```
His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525
```

```
Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
```

```
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                 1005

Val Tyr  Gly Asp Tyr Lys Val  Tyr Asp Val Arg Lys  Met Ile Ala
    1010                 1015                 1020

Lys Ser  Glu Gln Glu Ile Gly  Lys Ala Thr Ala Lys  Tyr Phe Phe
    1025                 1030                 1035

Tyr Ser  Asn Ile Met Asn Phe  Phe Lys Thr Glu Ile  Thr Leu Ala
    1040                 1045                 1050

Asn Gly  Glu Ile Arg Lys Arg  Pro Leu Ile Glu Thr  Asn Gly Glu
    1055                 1060                 1065

Thr Gly  Glu Ile Val Trp Asp  Lys Gly Arg Asp Phe  Ala Thr Val
    1070                 1075                 1080

Arg Lys  Val Leu Ser Met Pro  Gln Val Asn Ile Val  Lys Lys Thr
    1085                 1090                 1095

Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350
```

```
Gly Leu  Tyr Glu Thr Arg Ile  Asp Leu Ser Gln Leu  Gly Gly Asp
    1355                 1360                 1365


<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: synthetic construct

<400> SEQUENCE: 8

cctaagaaga agaggaaggt t                                              21


<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: synthetic construct

<400> SEQUENCE: 9

Pro Lys Lys Lys Arg Lys Val
1               5


<210> SEQ ID NO 10
<211> LENGTH: 4137
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: synthetic construct

<400> SEQUENCE: 10

atggataaga agtactctat cggactcgat atcggaacta actctgtggg atgggctgtg     60

atcaccgatg agtacaaggt gccatctaag aagttcaagg ttctcggaaa caccgatagg    120

cactctatca agaaaaacct tatcggtgct ctcctcttcg attctggtga aactgctgag    180

gctaccagac tcaagagaac cgctagaaga aggtacacca gaagaaagaa caggatctgc    240

tacctccaag agatcttctc taacgagatg gctaaagtgg atgattcatt cttccacagg    300

ctcgaagagt cattcctcgt ggaagaagat aagaagcacg agaggcaccc tatcttcgga    360

aacatcgttg atgaggtggc ataccacgag aagtacccta ctatctacca cctcagaaag    420

aagctcgttg attctactga taaggctgat ctcaggctca tctacctcgc tctcgctcac    480

atgatcaagt tcagaggaca cttcctcatc gagggtgatc tcaaccctga taactctgat    540

gtggataagt tgttcatcca gctcgtgcag acctacaacc agcttttcga agagaaccct    600

atcaacgctt caggtgtgga tgctaaggct atcctctctg ctaggctctc taagtcaaga    660

aggcttgaga acctcattgc tcagctccct ggtgagaaga agaacggact tttcggaaac    720

ttgatcgctc tctctctcgg actcacccct aacttcaagt ctaacttcga tctcgctgag    780

gatgcaaagc tccagctctc aaaggatacc tacgatgatg atctcgataa cctcctcgct    840

cagatcggag atcagtacgc tgatttgttc ctcgctgcta agaacctctc tgatgctatc    900

ctcctcagtg atatcctcag agtgaacacc gagatcacca aggctccact ctcagcttct    960
```

```
atgatcaaga gatacgatga gcaccaccag gatctcacac ttctcaaggc tcttgttaga   1020
cagcagctcc cagagaagta caaagagatt ttcttcgatc agtctaagaa cggatacgct   1080
ggttacatcg atggtggtgc atctcaagaa gagttctaca agttcatcaa gcctatcctc   1140
gagaagatgg atggaaccga ggaactcctc gtgaagctca atagagagga tcttctcaga   1200
aagcagagga ccttcgataa cggatctatc cctcatcaga tccacctcgg agagttgcac   1260
gctatcctta gaaggcaaga ggatttctac ccattcctca aggataacag ggaaaagatt   1320
gagaagattc tcaccttcag aatcccttac tacgtgggac ctctcgctag aggaaactca   1380
agattcgctt ggatgaccag aaagtctgag gaaaccatca ccccttggaa cttcgaagag   1440
gtggtggata agggtgctag tgctcagtct ttcatcgaga ggatgaccaa cttcgataag   1500
aaccttccaa acgagaaggt gctccctaag cactctttgc tctacgagta cttcaccgtg   1560
tacaacgagt tgaccaaggt taagtacgtg accgagggaa tgaggaagcc tgctttttg    1620
tcaggtgagc aaaagaaggc tatcgttgat ctcttgttca agaccaacag aaaggtgacc   1680
gtgaagcagc tcaaagagga ttacttcaag aaaatcgagt gcttcgattc agttgagatt   1740
tctggtgttg aggataggtt caacgcatct ctcggaacct accacgatct cctcaagatc   1800
attaaggata aggatttctt ggataacgag gaaaacgagg atatcttgga ggatatcgtt   1860
cttaccctca ccctctttga agatagagag atgattgaag aaaggctcaa gacctacgct   1920
catctcttcg atgataaggt gatgaagcag ttgaagagaa gaagatacac tggttgggga   1980
aggctctcaa gaaagctcat taacggaatc agggataagc agtctggaaa gacaatcctt   2040
gatttcctca agtctgatgg attcgctaac agaaacttca tgcagctcat ccacgatgat   2100
tctctcacct ttaaagagga tatccagaag gctcaggttt caggacaggg tgatagtctc   2160
catgagcata tcgctaacct cgctggatct cctgcaatca agaagggaat cctccagact   2220
gtgaaggttg tggatgagtt ggtgaaggtg atgggaaggc ataagcctga gaacatcgtg   2280
atcgaaatgg ctagagagaa ccagaccact cagaagggac agaagaactc tagggaaagg   2340
atgaagagga tcgaggaagg tatcaaagag cttggatctc agatcctcaa agagcaccct   2400
gttgagaaca ctcagctcca gaatgagaag ctctacctct actacctcca gaacggaagg   2460
gatatgtatg tggatcaaga gttggatatc aacaggctct ctgattacga tgttgatcat   2520
atcgtgccac agtcattctt gaaggatgat tctatcgata acaaggtgct caccaggtct   2580
gataagaaca ggggtaagag tgataacgtg ccaagtgaag aggttgtgaa gaaaatgaag   2640
aactattgga ggcagctcct caacgctaag ctcatcactc agagaaagtt cgataacttg   2700
actaaggctg agaggggagg actctctgaa ttggataagg caggattcat caagaggcag   2760
cttgtggaaa ccaggcagat cactaagcac gttgcacaga tcctcgattc taggatgaac   2820
accaagtacg atgagaacga taagttgatc agggaagtga aggttatcac cctcaagtca   2880
aagctcgtgt ctgatttcag aaaggatttc caattctaca aggtgaggga aatcaacaac   2940
taccaccacg ctcacgatgc ttaccttaac gctgttgttg gaaccgctct catcaagaag   3000
tatcctaagc tcgagtcaga gttcgtgtac ggtgattaca aggtgtacga tgtgaggaag   3060
atgatcgcta agtctgagca agagatcgga aaggctaccg ctaagtattt cttctactct   3120
aacatcatga atttcttcaa gaccgagatt accctcgcta acggtgagat cagaaagagg   3180
ccactcatcg agacaaacgg tgaaacaggt gagatcgtgt gggataaggg aagggatttc   3240
gctaccgtta gaaaggtgct ctctatgcca caggtgaaca tcgttaagaa aaccgaggtg   3300
```

```
cagaccggtg gattctctaa agagtctatc ctccctaaga ggaactctga taagctcatt   3360

gctaggaaga aggattggga ccctaagaaa tacggtggtt tcgattctcc taccgtggct   3420

tactctgttc tcgttgtggc taaggttgag aagggaaaga gtaagaagct caagtctgtt   3480

aaggaacttc tcggaatcac tatcatggaa aggtcatctt tcgagaagaa cccaatcgat   3540

ttcctcgagg ctaagggata caaagaggtt aagaaggatc tcatcatcaa gctcccaaag   3600

tactcactct tcgaactcga gaacggtaga aagaggatgc tcgcttctgc tggtgagctt   3660

caaaagggaa acgagcttgc tctcccatct aagtacgtta actttcttta cctcgcttct   3720

cactacgaga agttgaaggg atctccagaa gataacgagc agaagcaact tttcgttgag   3780

cagcacaagc actacttgga tgagatcatc gagcagatct ctgagttctc taaaagggtg   3840

atcctcgctg atgcaaacct cgataaggtg ttgtctgctt acaacaagca cagagataag   3900

cctatcaggg aacaggcaga gaacatcatc catctcttca cccttaccaa cctcggtgct   3960

cctgctgctt tcaagtactt cgatacaacc atcgatagga agagatacac ctctaccaaa   4020

gaagtgctcg atgctaccct catccatcag tctatcactg gactctacga gactaggatc   4080

gatctctcac agctcggtgg tgattcaagg gctgatccta agaagaagag gaaggtt      4137
```

<210> SEQ ID NO 11
<211> LENGTH: 1379
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: synthetic construct

<400> SEQUENCE: 11

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205
```

```
Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620
```

```
Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
```

```
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215

Glu Leu  Gln Lys Gly Asn Glu  Leu Ala Leu Pro Ser  Lys Tyr Val
    1220                1225                1230

Asn Phe  Leu Tyr Leu Ala Ser  His Tyr Glu Lys Leu  Lys Gly Ser
    1235                1240                1245

Pro Glu  Asp Asn Glu Gln Lys  Gln Leu Phe Val Glu  Gln His Lys
    1250                1255                1260

His Tyr  Leu Asp Glu Ile Ile  Glu Gln Ile Ser Glu  Phe Ser Lys
    1265                1270                1275

Arg Val  Ile Leu Ala Asp Ala  Asn Leu Asp Lys Val  Leu Ser Ala
    1280                1285                1290

Tyr Asn  Lys His Arg Asp Lys  Pro Ile Arg Glu Gln  Ala Glu Asn
    1295                1300                1305

Ile Ile  His Leu Phe Thr Leu  Thr Asn Leu Gly Ala  Pro Ala Ala
    1310                1315                1320

Phe Lys  Tyr Phe Asp Thr Thr  Ile Asp Arg Lys Arg  Tyr Thr Ser
    1325                1330                1335

Thr Lys  Glu Val Leu Asp Ala  Thr Leu Ile His Gln  Ser Ile Thr
    1340                1345                1350

Gly Leu  Tyr Glu Thr Arg Ile  Asp Leu Ser Gln Leu  Gly Gly Asp
    1355                1360                1365

Ser Arg  Ala Asp Pro Lys Lys  Lys Arg Lys Val
    1370                1375


<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: synthetic construct
```

<400> SEQUENCE: 12

Gly Arg Lys Lys Arg Arg Gln Arg Arg Arg Pro Pro Gln
1 5 10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: synthetic construct

<400> SEQUENCE: 13

Gly Arg Lys Lys Arg Arg Gln Arg Arg Arg Pro Gln
1 5 10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: synthetic construct

<400> SEQUENCE: 14

Tyr Gly Arg Lys Lys Arg Arg Gln Arg Arg Arg
1 5 10

<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: synthetic construct

<400> SEQUENCE: 15

Lys Leu Ala Leu Lys Leu Ala Leu Lys Ala Leu Lys Ala Ala Leu Lys
1 5 10 15

Leu Ala

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: synthetic construct

<400> SEQUENCE: 16

Arg Gln Ile Arg Ile Trp Phe Gln Asn Arg Arg Met Arg Trp Arg Arg
1 5 10 15

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic peptide

```
<220> FEATURE:
<223> OTHER INFORMATION: synthetic construct

<400> SEQUENCE: 17

Cys Ser Ile Pro Pro Glu Val Lys Phe Asn Lys Pro Phe Val Tyr Leu
1               5                   10                  15

Ile


<210> SEQ ID NO 18
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: synthetic construct

<400> SEQUENCE: 18

Arg Arg Arg Gln Arg Arg Lys Lys Arg Gly Gly Asp Ile Met Gly Glu
1               5                   10                  15

Trp Gly Asn Glu Ile Phe Gly Ala Ile Ala Gly Phe Leu Gly
            20                  25                  30


<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: synthetic construct

<400> SEQUENCE: 19

Phe Val Gln Trp Phe Ser Lys Phe Leu Gly Arg Ile Leu
1               5                   10


<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: synthetic construct

<400> SEQUENCE: 20

Leu Leu Ile Ile Leu Arg Arg Arg Ile Arg Lys Gln Ala His Ala His
1               5                   10                  15

Ser Lys


<210> SEQ ID NO 21
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: synthetic construct

<400> SEQUENCE: 21

Leu Gly Thr Tyr Thr Gln Asp Phe Asn Lys Phe His Thr Phe Pro Gln
1               5                   10                  15
```

```
Thr Ala Ile Gly Val Gly Ala Pro
            20


<210> SEQ ID NO 22
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: synthetic construct

<400> SEQUENCE: 22

Gly Ala Ala Glu Ala Ala Ala Arg Val Tyr Asp Leu Gly Leu Arg Arg
1               5                   10                  15

Leu Arg Gln Arg Arg Arg Leu Arg Arg Glu Arg Val Arg Ala
            20                  25                  30


<210> SEQ ID NO 23
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: synthetic construct

<400> SEQUENCE: 23

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25


<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: synthetic construct

<400> SEQUENCE: 24

Arg Gln Ile Lys Ile Trp Phe Gln Asn Arg Arg Met Lys Trp Lys Lys
1               5                   10                  15

Gly Gly


<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: synthetic construct

<400> SEQUENCE: 25

Arg Arg Arg Arg Arg Arg Arg Arg
1               5


<210> SEQ ID NO 26
<211> LENGTH: 9
<212> TYPE: PRT
```

<213> ORGANISM: Artificial Sequence
<220> FEATURE:
<223> OTHER INFORMATION: Description of Artificial Sequence: Synthetic peptide
<220> FEATURE:
<223> OTHER INFORMATION: synthetic construct

<400> SEQUENCE: 26

```
Arg Arg Arg Arg Arg Arg Arg Arg Arg
1               5
```

<210> SEQ ID NO 27
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: synthetic construct

<400> SEQUENCE: 27

```
Lys Lys Leu Phe Lys Lys Ile Leu Lys Tyr Leu Lys Lys Leu Phe Lys
1               5                   10                  15

Lys Ile Leu Lys Tyr Leu Lys Lys Lys Lys Lys Lys Lys Lys
            20                  25                  30
```

<210> SEQ ID NO 28
<211> LENGTH: 14548
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: synthetic construct
<220> FEATURE:
<221> NAME/KEY: modified_base
<222> LOCATION: (13426)..(13426)
<223> OTHER INFORMATION: a, c, or g

<400> SEQUENCE: 28

```
agtactttga tccaacccct ccgctgctat agtgcagtcg gcttctgacg ttcagtgcag     60

ccgtcttctg aaaacgacat gtcgcacaag tcctaagtta cgcgacaggc tgccgccctg    120

cccttttcct ggcgttttct tgtcgcgtgt tttagtcgca taaagtagaa tacttgcgac    180

tagaaccgga gacattacgc catgaacaag agcgccgccg ctggcctgct gggctatgcc    240

cgcgtcagca ccgacgacca ggacttgacc aaccaacggg ccgaactgca cgcggccggc    300

tgcaccaagc tgttttccga gaagatcacc ggcaccaggc gcgaccgccc ggagctggcc    360

aggatgcttg accacctacg ccctggcgac gttgtgacag tgaccaggct agaccgcctg    420

gcccgcagca cccgcgacct actggacatt gccgagcgca tccaggaggc cggcgcgggc    480

ctgcgtagcc tggcagagcc gtgggccgac accaccacgc cggccggccg catggtgttg    540

accgtgttcg ccggcattgc cgagttcgag cgttccctaa tcatcgaccg cacccggagc    600

gggcgcgagg ccgccaaggc ccgaggcgtg aagtttggcc cccgccctac cctcaccccg    660

gcacagatcg cgcacgcccg cgagctgatc gaccaggaag gccgcaccgt gaaagaggcg    720

gctgcactgc ttggcgtgca tcgctcgacc ctgtaccgcg cacttgagcg cagcgaggaa    780

gtgacgccca ccgaggccag gcggcgcggt gccttccgtg aggacgcatt gaccgaggcc    840

gacgccctgg cggccgccga gaatgaacgc caagaggaac aagcatgaaa ccgcaccagg    900

acggccagga cgaaccgttt ttcattaccg aagagatcga ggcggagatg atcgcggccg    960
```

```
ggtacgtgtt cgagccgccc gcgcacgtct caaccgtgcg gctgcatgaa atcctggccg   1020
gtttgtctga tgccaagctg gcggcctggc cggccagctt ggccgctgaa gaaaccgagc   1080
gccgccgtct aaaaaggtga tgtgtatttg agtaaaacag cttgcgtcat gcggtcgctg   1140
cgtatatgat gcgatgagta aataaacaaa tacgcaaggg gaacgcatga aggttatcgc   1200
tgtacttaac cagaaaggcg ggtcaggcaa gacgaccatc gcaacccatc tagcccgcgc   1260
cctgcaactc gccggggccg atgttctgtt agtcgattcc gatccccagg gcagtgcccg   1320
cgattgggcg gccgtgcggg aagatcaacc gctaaccgtt gtcggcatcg accgcccgac   1380
gattgaccgc gacgtgaagg ccatcggccg gcgcgacttc gtagtgatcg acggagcgcc   1440
ccaggcggcg gacttggctg tgtccgcgat caaggcagcc gacttcgtgc tgattccggt   1500
gcagccaagc ccttacgaca tatgggccac cgccgacctg gtggagctgg ttaagcagcg   1560
cattgaggtc acggatggaa ggctacaagc ggcctttgtc gtgtcgcggg cgatcaaagg   1620
cacgcgcatc ggcggtgagg ttgccgaggc gctggccggg tacgagctgc ccattcttga   1680
gtcccgtatc acgcagcgcg tgagctaccc aggcactgcc gccgccggca caaccgttct   1740
tgaatcagaa cccgagggcg acgctgcccg cgaggtccag gcgctggccg ctgaaattaa   1800
atcaaaactc atttgagtta atgaggtaaa gagaaaatga gcaaaagcac aaacacgcta   1860
agtgccggcc gtccgagcgc acgcagcagc aaggctgcaa cgttggccag cctggcagac   1920
acgccagcca tgaagcgggt caactttcag ttgccggcgg aggatcacac caagctgaag   1980
atgtacgcgg tacgccaagg caagaccatt accgagctgc tatctgaata catcgcgcag   2040
ctaccagagt aaatgagcaa atgaataaat gagtagatga attttagcgg ctaaaggagg   2100
cggcatggaa aatcaagaac aaccaggcac cgacgccgtg gaatgcccca tgtgtggagg   2160
aacgggcggt tggccaggcg taagcggctg ggttgtctgc cggccctgca atggcactgg   2220
aacccccaag cccgaggaat cggcgtgacg gtcgcaaacc atccggcccg gtacaaatcg   2280
gcgcggcgct gggtgatgac ctggtggaga agttgaaggc cgcgcaggcc gcccagcggc   2340
aacgcatcga ggcagaagca cgccccggtg aatcgtggca agcggccgct gatcgaatcc   2400
gcaaagaatc ccggcaaccg ccggcagccg gtgcgccgtc gattaggaag ccgcccaagg   2460
gcgacgagca accagatttt ttcgttccga tgctctatga cgtgggcacc cgcgatagtc   2520
gcagcatcat ggacgtggcc gttttccgtc tgtcgaagcg tgaccgacga gctggcgagg   2580
tgatccgcta cgagcttcca gacgggcacg tagaggtttc cgcagggccg gccggcatgg   2640
ccagtgtgtg ggattacgac ctggtactga tggcggtttc ccatctaacc gaatccatga   2700
accgataccg ggaagggaag ggagacaagc ccggccgcgt gttccgtcca cacgttgcgg   2760
acgtactcaa gttctgccgg cgagccgatg gcggaaagca gaaagacgac ctggtagaaa   2820
cctgcattcg gttaaacacc acgcacgttg ccatgcagcg tacgaagaag gccaagaacg   2880
gccgcctggt gacggtatcc gagggtgaag ccttgattag ccgctacaag atcgtaaaga   2940
gcgaaaccgg gcggccggag tacatcgaga tcgagctagc tgattggatg taccgcgaga   3000
tcacagaagg caagaacccg gacgtgctga cggttcaccc cgattacttt ttgatcgatc   3060
ccggcatcgg ccgttttctc taccgcctgg cacgccgcgc cgcaggcaag gcagaagcca   3120
gatggttgtt caagacgatc tacgaacgca gtggcagcgc cggagagttc aagaagttct   3180
gtttcaccgt gcgcaagctg atcgggtcaa atgacctgcc ggagtacgat ttgaaggagg   3240
aggcggggca ggctggcccg atcctagtca tgcgctaccg caacctgatc gagggcgaag   3300
```

```
catccgccgg ttcctaatgt acggagcaga tgctagggca aattgcccta gcaggggaaa   3360
aaggtcgaaa aggtctcttt cctgtggata gcacgtacat tgggaaccca aagccgtaca   3420
ttgggaaccg gaacccgtac attgggaacc caaagccgta cattgggaac cggtcacaca   3480
tgtaagtgac tgatataaaa gagaaaaaag gcgatttttc cgcctaaaac tctttaaaac   3540
ttattaaaac tcttaaaacc cgcctggcct gtgcataact gtctggccag cgcacagccg   3600
aagagctgca aaaagcgcct acccttcggt cgctgcgctc cctacgcccc gccgcttcgc   3660
gtcggcctat cgcggccgct ggccgctcaa aaatggctgg cctacggcca ggcaatctac   3720
cagggcgcgg acaagccgcg ccgtcgccac tcgaccgccg gcgcccacat caaggcaccc   3780
tgcctcgcgc gtttcggtga tgacggtgaa aacctctgac acatgcagct cccggagacg   3840
gtcacagctt gtctgtaagc ggatgccggg agcagacaag cccgtcaggg cgcgtcagcg   3900
ggtgttggcg ggtgtcgggg cgcagccatg acccagtcac gtagcgatag cggagtgtat   3960
actggcttaa ctatgcggca tcagagcaga ttgtactgag agtgcaccat atgcggtgtg   4020
aaataccgca cagatgcgta aggagaaaat accgcatcag gcgctcttcc gcttcctcgc   4080
tcactgactc gctgcgctcg gtcgttcggc tgcggcgagc ggtatcagct cactcaaagg   4140
cggtaatacg gttatccaca gaatcagggg ataacgcagg aaagaacatg tgagcaaaag   4200
gccagcaaaa ggccaggaac cgtaaaaagg ccgcgttgct ggcgtttttc cataggctcc   4260
gcccccctga cgagcatcac aaaaatcgac gctcaagtca gaggtggcga aacccgacag   4320
gactataaag ataccaggcg tttccccctg gaagctccct cgtgcgctct cctgttccga   4380
ccctgccgct taccggatac ctgtccgcct ttctcccttc gggaagcgtg gcgctttctc   4440
atagctcacg ctgtaggtat ctcagttcgg tgtaggtcgt tcgctccaag ctgggctgtg   4500
tgcacgaacc ccccgttcag cccgaccgct gcgccttatc cggtaactat cgtcttgagt   4560
ccaacccggt aagacacgac ttatcgccac tggcagcagc cactggtaac aggattagca   4620
gagcgaggta tgtaggcggt gctacagagt tcttgaagtg gtggcctaac tacggctaca   4680
ctagaaggac agtatttggt atctgcgctc tgctgaagcc agttaccttc ggaaaaagag   4740
ttggtagctc ttgatccggc aaacaaacca ccgctggtag cggtggtttt tttgtttgca   4800
agcagcagat tacgcgcaga aaaaaaggat ctcaagaaga tcctttgatc ttttctacgg   4860
ggtctgacgc tcagtggaac gaaaactcac gttaagggat tttggtcatg catgatatat   4920
ctcccaattt gtgtagggct tattatgcac gcttaaaaat aataaaagca gacttgacct   4980
gatagtttgg ctgtgagcaa ttatgtgctt agtgcatcta atcgcttgag ttaacgccgg   5040
cgaagcggcg tcggcttgaa cgaatttcta gctagacatt atttgccgac taccttggtg   5100
atctcgcctt tcacgtagtg gacaaattct tccaactgat ctgcgcgcga ggccaagcga   5160
tcttcttctt gtccaagata agcctgtcta gcttcaagta tgacgggctg atactgggcc   5220
ggcaggcgct ccattgccca gtcggcagcg acatccttcg gcgcgatttt gccggttact   5280
gcgctgtacc aaatgcggga caacgtaagc actacatttc gctcatcgcc agcccagtcg   5340
ggcggcgagt tccatagcgt taaggtttca tttagcgcct caaatagatc ctgttcagga   5400
accggatcaa agagttcctc cgccgctgga cctaccaagg caacgctatg ttctcttgct   5460
tttgtcagca agatagccag atcaatgtcg atcgtggctg gctcgaagat acctgcaaga   5520
atgtcattgc gctgccattc tccaaattgc agttcgcgct tagctggata acgccacgga   5580
atgatgtcgt cgtgcacaac aatggtgact tctacagcgc ggagaatctc gctctctcca   5640
ggggaagccg aagtttccaa aaggtcgttg atcaaagctc gccgcgttgt ttcatcaagc   5700
```

```
cttacggtca ccgtaaccag caaatcaata tcactgtgtg gcttcaggcc gccatccact   5760
gcggagccgt acaaatgtac ggccagcaac gtcggttcga gatggcgctc gatgacgcca   5820
actacctctg atagttgagt cgatacttcg gcgatcaccg cttcccccat gatgtttaac   5880
tttgttttag ggcgactgcc ctgctgcgta acatcgttgc tgctccataa catcaaacat   5940
cgacccacgg cgtaacgcgc ttgctgcttg gatgcccgag gcatagactg taccccaaaa   6000
aaacatgtca taacaagaag ccatgaaaac cgccactgcg ccgttaccac cgctgcgttc   6060
ggtcaaggtt ctggaccagt tgcgtgacgg cagttacgct acttgcatta cagcttacga   6120
accgaacgag gcttatgtcc actgggttcg tgcccgaatt gatcacaggc agcaacgctc   6180
tgtcatcgtt acaatcaaca tgctaccctc cgcgagatca tccgtgtttc aaacccggca   6240
gcttagttgc cgttcttccg aatagcatcg gtaacatgag caaagtctgc cgccttacaa   6300
cggctctccc gctgacgccg tcccggactg atgggctgcc tgtatcgagt ggtgattttg   6360
tgccgagctg ccggtcgggg agctgttggc tggctggtgg caggatatat tgtggtgtaa   6420
acaaattgac gcttagacaa cttaataaca cattgcggac gtttttaatg tactgaatta   6480
acgccgaatt gctctagcca atacgcaaac cgcctctccc cgcgcgttgg ccgattcatt   6540
aatgcagctg gcacgacagg tttcccgact ggaaagcggg cagtgagcgc aacgcaatta   6600
atgtgagtta gctcactcat taggcacccc aggctttaca ctttatgctt ccggctcgta   6660
tgttgtgtgg aattgtgagc ggataacaat ttcacacagg aaacagctat gacatgatta   6720
cgaattcaaa aattacggat atgaatatag gcatatccgt atccgaatta tccgtttgac   6780
agctagcaac gattgtacaa ttgcttcttt aaaaaaggaa gaaagaaaga aagaaaagaa   6840
tcaacatcag cgttaacaaa cggccccgtt acggcccaaa cggtcatata gagtaacggc   6900
gttaagcgtt gaaagactcc tatcgaaata cgtaaccgca aacgtgtcat agtcagatcc   6960
cctcttcctt caccgcctca aacacaaaaa taatcttcta cagcctatat atacaacccc   7020
cccttctatc tctcctttct cacaattcat catctttctt tctctacccc caattttaag   7080
aaatcctctc ttctcctctt cattttcaag gtaaatctct ctctctctct ctctctctgt   7140
tattccttgt tttaattagg tatgtattat tgctagtttg ttaatctgct tatcttatgt   7200
atgccttatg tgaatatctt tatcttgttc atctcatccg tttagaagct ataaatttgt   7260
tgatttgact gtgtatctac acgtggttat gtttatatct aatcagatat gaatttcttc   7320
atattgttgc gtttgtgtgt accaatccga aatcgttgat ttttttcatt taatcgtgta   7380
gctaattgta cgtatacata tggatctacg tatcaattgt tcatctgttt gtgtttgtat   7440
gtatacagat ctgaaaacat cacttctctc atctgattgt gttgttacat acatagatat   7500
agatctgtta tatcattttt tttattaatt gtgtatatat atatgtgcat agatctggat   7560
tacatgattg tgattattta catgattttg ttatttacgt atgtatatat gtagatctgg   7620
actttttgga gttgttgact tgattgtatt tgtgtgtgta tatgtgtgtt ctgatcttga   7680
tatgttatgt atgtgcagcg aattcggcgc gccatggata agaagtactc tatcggactc   7740
gatatcggaa ctaactctgt gggatgggct gtgatcaccg atgagtacaa ggtgccatct   7800
aagaagttca aggttctcgg aaacaccgat aggcactcta tcaagaaaaa ccttatcggt   7860
gctctcctct tcgattctgg tgaaactgct gaggctacca gactcaagag aaccgctaga   7920
agaaggtaca ccagaagaaa gaacaggatc tgctacctcc aagagatctt ctctaacgag   7980
atggctaaag tggatgattc attcttccac aggctcgaag agtcattcct cgtggaagaa   8040
```

```
gataagaagc acgagaggca ccctatcttc ggaaacatcg ttgatgaggt ggcataccac   8100
gagaagtacc ctactatcta ccacctcaga aagaagctcg ttgattctac tgataaggct   8160
gatctcaggc tcatctacct cgctctcgct cacatgatca agttcagagg acacttcctc   8220
atcgagggtg atctcaaccc tgataactct gatgtggata agttgttcat ccagctcgtg   8280
cagacctaca accagctttt cgaagagaac cctatcaacg cttcaggtgt ggatgctaag   8340
gctatcctct ctgctaggct ctctaagtca agaaggcttg agaacctcat tgctcagctc   8400
cctggtgaga agaagaacgg acttttcgga aacttgatcg ctctctctct cggactcacc   8460
cctaacttca agtctaactt cgatctcgct gaggatgcaa agctccagct ctcaaaggat   8520
acctacgatg atgatctcga taacctcctc gctcagatcg gagatcagta cgctgatttg   8580
ttcctcgctg ctaagaacct ctctgatgct atcctcctca gtgatatcct cagagtgaac   8640
accgagatca ccaaggctcc actctcagct tctatgatca agagatacga tgagcaccac   8700
caggatctca cacttctcaa ggctcttgtt agacagcagc tcccagagaa gtacaaagag   8760
atttcttcg atcagtctaa gaacggatac gctggttaca tcgatggtgg tgcatctcaa   8820
gaagagttct acaagttcat caagcctatc ctcgagaaga tggatggaac cgaggaactc   8880
ctcgtgaagc tcaatagaga ggatcttctc agaaagcaga ggaccttcga taacggatct   8940
atccctcatc agatccacct cggagagttg cacgctatcc ttagaaggca agaggatttc   9000
tacccattcc tcaaggataa cagggaaaag attgagaaga ttctcacctt cagaatccct   9060
tactacgtgg gacctctcgc tagaggaaac tcaagattcg cttggatgac cagaaagtct   9120
gaggaaacca tcaccccttg gaacttcgaa gaggtggtgg ataagggtgc tagtgctcag   9180
tctttcatcg agaggatgac caacttcgat aagaaccttc caaacgagaa ggtgctccct   9240
aagcactctt tgctctacga gtacttcacc gtgtacaacg agttgaccaa ggttaagtac   9300
gtgaccgagg gaatgaggaa gcctgctttt ttgtcaggtg agcaaaagaa ggctatcgtt   9360
gatctcttgt tcaagaccaa cagaaaggtg accgtgaagc agctcaaaga ggattacttc   9420
aagaaaatcg agtgcttcga ttcagttgag atttctggtg ttgaggatag gttcaacgca   9480
tctctcggaa cctaccacga tctcctcaag atcattaagg ataaggattt cttggataac   9540
gaggaaaacg aggatatctt ggaggatatc gttcttaccc tcaccctctt tgaagataga   9600
gagatgattg aagaaaggct caagacctac gctcatctct tcgatgataa ggtgatgaag   9660
cagttgaaga gaagaagata cactggttgg ggaaggctct caagaaagct cattaacgga   9720
atcagggata agcagtctgg aaagacaatc cttgatttcc tcaagtctga tggattcgct   9780
aacagaaact tcatgcagct catccacgat gattctctca cctttaaaga ggatatccag   9840
aaggctcagg tttcaggaca gggtgatagt ctccatgagc atatcgctaa cctcgctgga   9900
tctcctgcaa tcaagaaggg aatcctccag actgtgaagg ttgtggatga gttggtgaag   9960
gtgatgggaa ggcataagcc tgagaacatc gtgatcgaaa tggctagaga gaaccagacc  10020
actcagaagg gacagaagaa ctctagggaa aggatgaaga ggatcgagga aggtatcaaa  10080
gagcttggat ctcagatcct caaagagcac cctgttgaga acactcagct ccagaatgag  10140
aagctctacc tctactacct ccagaacgga agggatatgt atgtggatca agagttggat  10200
atcaacaggc tctctgatta cgatgttgat catatcgtgc cacagtcatt cttgaaggat  10260
gattctatcg ataacaaggt gctcaccagg tctgataaga acaggggtaa gagtgataac  10320
gtgccaagtg aagaggttgt gaagaaaatg aagaactatt ggaggcagct cctcaacgct  10380
aagctcatca ctcagagaaa gttcgataac ttgactaagg ctgagagggg aggactctct  10440
```

```
gaattggata aggcaggatt catcaagagg cagcttgtgg aaaccaggca gatcactaag  10500
cacgttgcac agatcctcga ttctaggatg aacaccaagt acgatgagaa cgataagttg  10560
atcagggaag tgaaggttat caccctcaag tcaaagctcg tgtctgattt cagaaaggat  10620
ttccaattct acaaggtgag ggaaatcaac aactaccacc acgctcacga tgcttacctt  10680
aacgctgttg ttggaaccgc tctcatcaag aagtatccta agctcgagtc agagttcgtg  10740
tacggtgatt acaaggtgta cgatgtgagg aagatgatcg ctaagtctga gcaagagatc  10800
ggaaaggcta ccgctaagta tttcttctac tctaacatca tgaatttctt caagaccgag  10860
attaccctcg ctaacggtga gatcagaaag aggccactca tcgagacaaa cggtgaaaca  10920
ggtgagatcg tgtgggataa gggaagggat ttcgctaccg ttagaaaggt gctctctatg  10980
ccacaggtga acatcgttaa gaaaaccgag gtgcagaccg gtggattctc taaagagtct  11040
atcctcccta agaggaactc tgataagctc attgctagga agaaggattg ggaccctaag  11100
aaatacggtg gtttcgattc tcctaccgtg gcttactctg ttctcgttgt ggctaaggtt  11160
gagaagggaa agagtaagaa gctcaagtct gttaaggaac ttctcggaat cactatcatg  11220
gaaaggtcat ctttcgagaa gaacccaatc gatttcctcg aggctaaggg atacaaagag  11280
gttaagaagg atctcatcat caagctccca aagtactcac tcttcgaact cgagaacggt  11340
agaaagagga tgctcgcttc tgctggtgag cttcaaaagg gaaacgagct tgctctccca  11400
tctaagtacg ttaactttct ttacctcgct tctcactacg agaagttgaa gggatctcca  11460
gaagataacg agcagaagca acttttcgtt gagcagcaca agcactactt ggatgagatc  11520
atcgagcaga tctctgagtt ctctaaaagg gtgatcctcg ctgatgcaaa cctcgataag  11580
gtgttgtctg cttacaacaa gcacagagat aagcctatca gggaacaggc agagaacatc  11640
atccatctct tcacccttac caacctcggt gctcctgctg ctttcaagta cttcgataca  11700
accatcgata ggaagagata cacctctacc aaagaagtgc tcgatgctac cctcatccat  11760
cagtctatca ctggactcta cgagactagg atcgatctct cacagctcgg tggtgattca  11820
agggctgatc ctaagaagaa gaggaaggtt tgaggcgcgc cgagctccag gcctcccagc  11880
tttcgtccgt atcatcggtt tcgacaacgt tcgtcaagtt caatgcatca gtttcattgc  11940
ccacacacca gaatcctact aagtttgagt attatggcat tggaaaagct gttttcttct  12000
atcatttgtt ctgcttgtaa tttactgtgt tctttcagtt tttgttttcg gacatcaaaa  12060
tgcaaatgga tggataagag ttaataaatg atatggtcct tttgttcatt ctcaaattat  12120
tattatctgt tgtttttact ttaatgggtt gaatttaagt aagaaaggaa ctaacagtgt  12180
gatattaagg tgcaatgtta gacatataaa acagtctttc acctctcttt ggttatgtct  12240
tgaattggtt tgtttcttca cttatctgtg taatcaagtt tactatgagt ctatgatcaa  12300
gtaattatgc aatcaagtta agtacagtat aggcttgagc tccctaggct tttttcttc  12360
ttcttcgttc atacagtttt tttttgttta tcagcttaca ttttcttgaa ccgtagcttt  12420
cgttttcttc tttttaactt tccattcgga gtttttgtat cttgtttcat agtttgtccc  12480
aggattagaa tgattaggca tcgaaccttc aagaatttga ttgaataaaa catcttcatt  12540
cttaagatat gaagataatc ttcaaaaggc ccctgggaat ctgaaagaag agaagcaggc  12600
ccatttatat gggaaagaac aatagtattt cttatatagg cccatttaag ttgaaaacaa  12660
tcttcaaaag tcccacatcg cttagataag aaaacgaagc tgagtttata tacagctaga  12720
gtcgaagtag tgattggaag caagagacgt tctagggttt tagagctaga aatagcaagt  12780
```

```
taaaataagg ctagtccgtt atcaacttga aaaagtggca ccgagtcggt gctttttttc  12840

tagacccagc tttcttgtac aaagttggca ttacctaggc ccgggcctga ggacgcgtcc  12900

atggttaatt aagacgtccg gaccgactag tggatcctct agagtcgacc tgcaggcatg  12960

caagcttctt cgtcaacatg gtggagcacg acacgcttgt ctactccaaa aatatcaaag  13020

atacagtctc agaagaccaa agggcaattg agacttttca acaaagggta atatccggaa  13080

acctcctcgg attccattgc ccagctatct gtcactttat tgtgaagata gtggaaaagg  13140

aaggtggctc ctacaaatgc catcattgcg ataaaggaaa ggccatcgtt gaagatgcct  13200

ctgccgacag tggtcccaaa gatggacccc cacccacgag gagcatcgtg gaaaaagaag  13260

acgttccaac cacgtcttca aagcaagtgg attgatgtga tatctccact gacgtaaggg  13320

atgacgcaca atcaatccca ctatccttcg caagaccctt ttaaggggga agttcatttc  13380

atttggagag gacacgctga aatcaccagt ctctctgtac aaatcnatct ctctctataa  13440

tattgtgtaa gtagttccca gataagggaa ttagggttct tatagggttt cgctcagctg  13500

ttgagcatat aagaaaccct tagtcgatag atctgttggg gatctaccat gagcccagaa  13560

cgacgcccgg ccgacatccg ccgtgccacc gaggcggaca tgccggcggt ctgcaccatc  13620

gtcaaccact acatcgagac aagcacggtc aacttccgta ccgagccgca ggaaccgcag  13680

gagtggacgg acgacctcgt ccgtctgcgg gagcgctatc cctggctcgt cgccgaggtg  13740

gacggcgagg tcgccggcat cgcctacgcg ggcccctgga aggcacgcaa cgcctacgac  13800

tggacggccg agtcgaccgt gtacgtctcc ccccgccacc agcggacggg actgggctcc  13860

acgctctaca cccacctgct gaagtccctg gaggcacagg gcttcaagag cgtggtcgct  13920

gtcatcgggc tgcccaacga cccgagcgtg cgcatgcacg aggcgctcgg atatgccccc  13980

cgcggcatgc tgcgggcggc cggcttcaag cacgggaact ggcatgacgt gggtttctgg  14040

cagctggact tcagcctgcc ggtaccgccc cgtccggtcc tgcccgtcac cgagatctga  14100

tgacccaact tagtatgtat ttgtatttgt aaaatacttc tatcaataaa atttctaatt  14160

cctaaaacca aaatccaggg gtaccgaaca agcttggcac tggccgtcgt tttacaacgt  14220

cgtgactggg aaaaccctgg cgttacccaa cttaatcgcc ttgcagcaca tccccctttc  14280

gccagctggc gtaatagcga agaggcccgc accgatcgcc cttcccaaca gttgcgcagc  14340

ctgaatggcg aatgagcttg agcttggatc agattgtcgt ttcccgcctt cagtttaaac  14400

tatcagtgtt tgacaggata tattggcggg taaacctaag agaaaagagc gtttattaga  14460

ataacggata tttaaaaggg cgtgaaaagg tttatccgtt cgtccatttg tatgtgcatg  14520

ccaaccacag ggttcccctc gggatcaa                                     14548
```

<210> SEQ ID NO 29
<211> LENGTH: 14548
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: synthetic construct
<220> FEATURE:
<221> NAME/KEY: modified_base
<222> LOCATION: (13426)..(13426)
<223> OTHER INFORMATION: a, c, or g

<400> SEQUENCE: 29

```
agtactttga tccaacccct ccgctgctat agtgcagtcg gcttctgacg ttcagtgcag     60
```

```
ccgtcttctg aaaacgacat gtcgcacaag tcctaagtta cgcgacaggc tgccgccctg    120
cccttttcct ggcgttttct tgtcgcgtgt tttagtcgca taaagtagaa tacttgcgac    180
tagaaccgga gacattacgc catgaacaag agcgccgccg ctggcctgct gggctatgcc    240
cgcgtcagca ccgacgacca ggacttgacc aaccaacggg ccgaactgca cgcggccggc    300
tgcaccaagc tgttttccga gaagatcacc ggcaccaggc gcgaccgccc ggagctggcc    360
aggatgcttg accacctacg ccctggcgac gttgtgacag tgaccaggct agaccgcctg    420
gcccgcagca cccgcgacct actggacatt gccgagcgca tccaggaggc cggcgcgggc    480
ctgcgtagcc tggcagagcc gtgggccgac accaccacgc cggccggccg catggtgttg    540
accgtgttcg ccggcattgc cgagttcgag cgttccctaa tcatcgaccg cacccggagc    600
gggcgcgagg ccgccaaggc ccgaggcgtg aagtttggcc cccgccctac cctcaccccg    660
gcacagatcg cgcacgcccg cgagctgatc gaccaggaag gccgcaccgt gaaagaggcg    720
gctgcactgc ttggcgtgca tcgctcgacc ctgtaccgcg cacttgagcg cagcgaggaa    780
gtgacgccca ccgaggccag gcggcgcggt gccttccgtg aggacgcatt gaccgaggcc    840
gacgccctgg cggccgccga gaatgaacgc caagaggaac aagcatgaaa ccgcaccagg    900
acggccagga cgaaccgttt ttcattaccg aagagatcga ggcggagatg atcgcggccg    960
ggtacgtgtt cgagccgccc gcgcacgtct caaccgtgcg gctgcatgaa atcctggccg   1020
gtttgtctga tgccaagctg gcggcctggc cggccagctt ggccgctgaa gaaaccgagc   1080
gccgccgtct aaaaaggtga tgtgtatttg agtaaaacag cttgcgtcat gcggtcgctg   1140
cgtatatgat gcgatgagta aataaacaaa tacgcaaggg gaacgcatga aggttatcgc   1200
tgtacttaac cagaaaggcg ggtcaggcaa gacgaccatc gcaacccatc tagcccgcgc   1260
cctgcaactc gccggggccg atgttctgtt agtcgattcc gatccccagg gcagtgcccg   1320
cgattgggcg gccgtgcggg aagatcaacc gctaaccgtt gtcggcatcg accgcccgac   1380
gattgaccgc gacgtgaagg ccatcggccg gcgcgacttc gtagtgatcg acggagcgcc   1440
ccaggcggcg gacttggctg tgtccgcgat caaggcagcc gacttcgtgc tgattccggt   1500
gcagccaagc ccttacgaca tatgggccac cgccgacctg gtggagctgg ttaagcagcg   1560
cattgaggtc acggatggaa ggctacaagc ggcctttgtc gtgtcgcggg cgatcaaagg   1620
cacgcgcatc ggcggtgagg ttgccgaggc gctggccggg tacgagctgc ccattcttga   1680
gtcccgtatc acgcagcgcg tgagctaccc aggcactgcc gccgccggca caaccgttct   1740
tgaatcagaa cccgagggcg acgctgcccg cgaggtccag gcgctggccg ctgaaattaa   1800
atcaaaactc atttgagtta atgaggtaaa gagaaaatga gcaaaagcac aaacacgcta   1860
agtgccggcc gtccgagcgc acgcagcagc aaggctgcaa cgttggccag cctggcagac   1920
acgccagcca tgaagcgggt caactttcag ttgccggcgg aggatcacac caagctgaag   1980
atgtacgcgg tacgccaagg caagaccatt accgagctgc tatctgaata catcgcgcag   2040
ctaccagagt aaatgagcaa atgaataaat gagtagatga attttagcgg ctaaaggagg   2100
cggcatggaa aatcaagaac aaccaggcac cgacgccgtg gaatgcccca tgtgtggagg   2160
aacgggcggt tggccaggcg taagcggctg ggttgtctgc cggccctgca atggcactgg   2220
aacccccaag cccgaggaat cggcgtgacg gtcgcaaacc atccggcccg gtacaaatcg   2280
gcgcggcgct gggtgatgac ctggtggaga agttgaaggc cgcgcaggcc gcccagcggc   2340
aacgcatcga ggcagaagca cgccccggtg aatcgtggca agcggccgct gatcgaatcc   2400
gcaaagaatc ccggcaaccg ccggcagccg gtgcgccgtc gattaggaag ccgcccaagg   2460
```

```
gcgacgagca accagatttt ttcgttccga tgctctatga cgtgggcacc cgcgatagtc   2520
gcagcatcat ggacgtggcc gttttccgtc tgtcgaagcg tgaccgacga gctggcgagg   2580
tgatccgcta cgagcttcca gacgggcacg tagaggtttc cgcagggccg gccggcatgg   2640
ccagtgtgtg ggattacgac ctggtactga tggcggtttc ccatctaacc gaatccatga   2700
accgataccg ggaagggaag ggagacaagc ccggccgcgt gttccgtcca cacgttgcgg   2760
acgtactcaa gttctgccgg cgagccgatg gcggaaagca gaaagacgac ctggtagaaa   2820
cctgcattcg gttaaacacc acgcacgttg ccatgcagcg tacgaagaag gccaagaacg   2880
gccgcctggt gacggtatcc gagggtgaag ccttgattag ccgctacaag atcgtaaaga   2940
gcgaaaccgg gcggccggag tacatcgaga tcgagctagc tgattggatg taccgcgaga   3000
tcacagaagg caagaacccg gacgtgctga cggttcaccc cgattacttt ttgatcgatc   3060
ccggcatcgg ccgttttctc taccgcctgg cacgccgcgc cgcaggcaag gcagaagcca   3120
gatggttgtt caagacgatc tacgaacgca gtggcagcgc cggagagttc aagaagttct   3180
gtttcaccgt gcgcaagctg atcgggtcaa atgacctgcc ggagtacgat ttgaaggagg   3240
aggcggggca ggctggcccg atcctagtca tgcgctaccg caacctgatc gagggcgaag   3300
catccgccgg ttcctaatgt acggagcaga tgctagggca aattgcccta gcaggggaaa   3360
aaggtcgaaa aggtctcttt cctgtggata gcacgtacat tgggaaccca aagccgtaca   3420
ttgggaaccg gaacccgtac attgggaacc caaagccgta cattgggaac cggtcacaca   3480
tgtaagtgac tgatataaaa gagaaaaaag gcgatttttc cgcctaaaac tctttaaaac   3540
ttattaaaac tcttaaaacc cgcctggcct gtgcataact gtctggccag cgcacagccg   3600
aagagctgca aaaagcgcct acccttcggt cgctgcgctc cctacgcccc gccgcttcgc   3660
gtcggcctat cgcggccgct ggccgctcaa aaatggctgg cctacggcca ggcaatctac   3720
cagggcgcgg acaagccgcg ccgtcgccac tcgaccgccg gcgcccacat caaggcaccc   3780
tgcctcgcgc gtttcggtga tgacggtgaa aacctctgac acatgcagct cccggagacg   3840
gtcacagctt gtctgtaagc ggatgccggg agcagacaag cccgtcaggg cgcgtcagcg   3900
ggtgttggcg ggtgtcgggg cgcagccatg acccagtcac gtagcgatag cggagtgtat   3960
actggcttaa ctatgcggca tcagagcaga ttgtactgag agtgcaccat atgcggtgtg   4020
aaataccgca cagatgcgta aggagaaaat accgcatcag gcgctcttcc gcttcctcgc   4080
tcactgactc gctgcgctcg gtcgttcggc tgcggcgagc ggtatcagct cactcaaagg   4140
cggtaatacg gttatccaca gaatcagggg ataacgcagg aaagaacatg tgagcaaaag   4200
gccagcaaaa ggccaggaac cgtaaaaagg ccgcgttgct ggcgtttttc cataggctcc   4260
gcccccctga cgagcatcac aaaaatcgac gctcaagtca gaggtggcga aacccgacag   4320
gactataaag ataccaggcg tttccccctg gaagctccct cgtgcgctct cctgttccga   4380
ccctgccgct taccggatac ctgtccgcct ttctcccttc gggaagcgtg gcgctttctc   4440
atagctcacg ctgtaggtat ctcagttcgg tgtaggtcgt tcgctccaag ctgggctgtg   4500
tgcacgaacc ccccgttcag cccgaccgct gcgccttatc cggtaactat cgtcttgagt   4560
ccaacccggt aagacacgac ttatcgccac tggcagcagc cactggtaac aggattagca   4620
gagcgaggta tgtaggcggt gctacagagt tcttgaagtg gtggcctaac tacggctaca   4680
ctagaaggac agtatttggt atctgcgctc tgctgaagcc agttaccttc ggaaaaagag   4740
ttggtagctc ttgatccggc aaacaaacca ccgctggtag cggtggtttt tttgtttgca   4800
```

```
agcagcagat tacgcgcaga aaaaaaggat ctcaagaaga tcctttgatc ttttctacgg   4860
ggtctgacgc tcagtggaac gaaaactcac gttaagggat tttggtcatg catgatatat   4920
ctcccaattt gtgtagggct tattatgcac gcttaaaaat aataaaagca gacttgacct   4980
gatagtttgg ctgtgagcaa ttatgtgctt agtgcatcta atcgcttgag ttaacgccgg   5040
cgaagcggcg tcggcttgaa cgaatttcta gctagacatt atttgccgac taccttggtg   5100
atctcgcctt tcacgtagtg gacaaattct tccaactgat ctgcgcgcga ggccaagcga   5160
tcttcttctt gtccaagata agcctgtcta gcttcaagta tgacgggctg atactgggcc   5220
ggcaggcgct ccattgccca gtcggcagcg acatccttcg gcgcgatttt gccggttact   5280
gcgctgtacc aaatgcggga caacgtaagc actacatttc gctcatcgcc agcccagtcg   5340
ggcggcgagt tccatagcgt taaggtttca tttagcgcct caaatagatc ctgttcagga   5400
accggatcaa agagttcctc cgccgctgga cctaccaagg caacgctatg ttctcttgct   5460
tttgtcagca agatagccag atcaatgtcg atcgtggctg gctcgaagat acctgcaaga   5520
atgtcattgc gctgccattc tccaaattgc agttcgcgct tagctggata acgccacgga   5580
atgatgtcgt cgtgcacaac aatggtgact tctacagcgc ggagaatctc gctctctcca   5640
ggggaagccg aagtttccaa aaggtcgttg atcaaagctc gccgcgttgt ttcatcaagc   5700
cttacggtca ccgtaaccag caaatcaata tcactgtgtg gcttcaggcc gccatccact   5760
gcggagccgt acaaatgtac ggccagcaac gtcggttcga gatggcgctc gatgacgcca   5820
actacctctg atagttgagt cgatacttcg gcgatcaccg cttcccccat gatgtttaac   5880
tttgttttag ggcgactgcc ctgctgcgta acatcgttgc tgctccataa catcaaacat   5940
cgacccacgg cgtaacgcgc ttgctgcttg gatgcccgag gcatagactg taccccaaaa   6000
aaacatgtca taacaagaag ccatgaaaac cgccactgcg ccgttaccac cgctgcgttc   6060
ggtcaaggtt ctggaccagt tgcgtgacgg cagttacgct acttgcatta cagcttacga   6120
accgaacgag gcttatgtcc actgggttcg tgcccgaatt gatcacaggc agcaacgctc   6180
tgtcatcgtt acaatcaaca tgctaccctc cgcgagatca tccgtgtttc aaacccggca   6240
gcttagttgc cgttcttccg aatagcatcg gtaacatgag caaagtctgc cgccttacaa   6300
cggctctccc gctgacgccg tcccggactg atgggctgcc tgtatcgagt ggtgattttg   6360
tgccgagctg ccggtcgggg agctgttggc tggctggtgg caggatatat tgtggtgtaa   6420
acaaattgac gcttagacaa cttaataaca cattgcggac gtttttaatg tactgaatta   6480
acgccgaatt gctctagcca atacgcaaac cgcctctccc cgcgcgttgg ccgattcatt   6540
aatgcagctg gcacgacagg tttcccgact ggaaagcggg cagtgagcgc aacgcaatta   6600
atgtgagtta gctcactcat taggcacccc aggctttaca ctttatgctt ccggctcgta   6660
tgttgtgtgg aattgtgagc ggataacaat ttcacacagg aaacagctat gacatgatta   6720
cgaattcaaa aattacggat atgaatatag gcatatccgt atccgaatta tccgtttgac   6780
agctagcaac gattgtacaa ttgcttcttt aaaaaaggaa gaaagaaaga aagaaaagaa   6840
tcaacatcag cgttaacaaa cggccccgtt acggcccaaa cggtcatata gagtaacggc   6900
gttaagcgtt gaaagactcc tatcgaaata cgtaaccgca aacgtgtcat agtcagatcc   6960
cctcttcctt caccgcctca aacacaaaaa taatcttcta cagcctatat atacaacccc   7020
cccttctatc tctcctttct cacaattcat catctttctt tctctacccc caattttaag   7080
aaatcctctc ttctcctctt cattttcaag gtaaatctct ctctctctct ctctctctgt   7140
tattccttgt tttaattagg tatgtattat tgctagtttg ttaatctgct tatcttatgt   7200
```

```
atgccttatg tgaatatctt tatcttgttc atctcatccg tttagaagct ataaatttgt   7260
tgatttgact gtgtatctac acgtggttat gtttatatct aatcagatat gaatttcttc   7320
atattgttgc gtttgtgtgt accaatccga aatcgttgat ttttttcatt taatcgtgta   7380
gctaattgta cgtatacata tggatctacg tatcaattgt tcatctgttt gtgtttgtat   7440
gtatacagat ctgaaaacat cacttctctc atctgattgt gttgttacat acatagatat   7500
agatctgtta tatcattttt tttattaatt gtgtatatat atatgtgcat agatctggat   7560
tacatgattg tgattattta catgattttg ttatttacgt atgtatatat gtagatctgg   7620
actttttgga gttgttgact tgattgtatt tgtgtgtgta tatgtgtgtt ctgatcttga   7680
tatgttatgt atgtgcagcg aattcggcgc gccatggata agaagtactc tatcggactc   7740
gatatcggaa ctaactctgt gggatgggct gtgatcaccg atgagtacaa ggtgccatct   7800
aagaagttca aggttctcgg aaacaccgat aggcactcta tcaagaaaaa ccttatcggt   7860
gctctcctct tcgattctgg tgaaactgct gaggctacca gactcaagag aaccgctaga   7920
agaaggtaca ccagaagaaa gaacaggatc tgctacctcc aagagatctt ctctaacgag   7980
atggctaaag tggatgattc attcttccac aggctcgaag agtcattcct cgtggaagaa   8040
gataagaagc acgagaggca ccctatcttc ggaaacatcg ttgatgaggt ggcataccac   8100
gagaagtacc ctactatcta ccacctcaga aagaagctcg ttgattctac tgataaggct   8160
gatctcaggc tcatctacct cgctctcgct cacatgatca agttcagagg acacttcctc   8220
atcgagggtg atctcaaccc tgataactct gatgtggata agttgttcat ccagctcgtg   8280
cagacctaca accagctttt cgaagagaac cctatcaacg cttcaggtgt ggatgctaag   8340
gctatcctct ctgctaggct ctctaagtca agaaggcttg agaacctcat tgctcagctc   8400
cctggtgaga agaagaacgg acttttcgga aacttgatcg ctctctctct cggactcacc   8460
cctaacttca agtctaactt cgatctcgct gaggatgcaa agctccagct ctcaaaggat   8520
acctacgatg atgatctcga taacctcctc gctcagatcg gagatcagta cgctgatttg   8580
ttcctcgctg ctaagaacct ctctgatgct atcctcctca gtgatatcct cagagtgaac   8640
accgagatca ccaaggctcc actctcagct tctatgatca agagatacga tgagcaccac   8700
caggatctca cacttctcaa ggctcttgtt agacagcagc tcccagagaa gtacaaagag   8760
attttcttcg atcagtctaa gaacggatac gctggttaca tcgatggtgg tgcatctcaa   8820
gaagagttct acaagttcat caagcctatc ctcgagaaga tggatggaac cgaggaactc   8880
ctcgtgaagc tcaatagaga ggatcttctc agaaagcaga ggaccttcga taacggatct   8940
atccctcatc agatccacct cggagagttg cacgctatcc ttagaaggca agaggatttc   9000
tacccattcc tcaaggataa cagggaaaag attgagaaga ttctcacctt cagaatccct   9060
tactacgtgg gacctctcgc tagaggaaac tcaagattcg cttggatgac cagaaagtct   9120
gaggaaacca tcaccccttg gaacttcgaa gaggtggtgg ataagggtgc tagtgctcag   9180
tctttcatcg agaggatgac caacttcgat aagaaccttc caaacgagaa ggtgctccct   9240
aagcactctt tgctctacga gtacttcacc gtgtacaacg agttgaccaa ggttaagtac   9300
gtgaccgagg gaatgaggaa gcctgctttt ttgtcaggtg agcaaaagaa ggctatcgtt   9360
gatctcttgt tcaagaccaa cagaaaggtg accgtgaagc agctcaaaga ggattacttc   9420
aagaaaatcg agtgcttcga ttcagttgag atttctggtg ttgaggatag gttcaacgca   9480
tctctcggaa cctaccacga tctcctcaag atcattaagg ataaggattt cttggataac   9540
```

```
gaggaaaacg aggatatctt ggaggatatc gttcttaccc tcaccctctt tgaagataga   9600
gagatgattg aagaaaggct caagacctac gctcatctct tcgatgataa ggtgatgaag   9660
cagttgaaga gaagaagata cactggttgg ggaaggctct caagaaagct cattaacgga   9720
atcagggata agcagtctgg aaagacaatc cttgatttcc tcaagtctga tggattcgct   9780
aacagaaact tcatgcagct catccacgat gattctctca cctttaaaga ggatatccag   9840
aaggctcagg tttcaggaca gggtgatagt ctccatgagc atatcgctaa cctcgctgga   9900
tctcctgcaa tcaagaaggg aatcctccag actgtgaagg ttgtggatga gttggtgaag   9960
gtgatgggaa ggcataagcc tgagaacatc gtgatcgaaa tggctagaga gaaccagacc  10020
actcagaagg gacagaagaa ctctagggaa aggatgaaga ggatcgagga aggtatcaaa  10080
gagcttggat ctcagatcct caaagagcac cctgttgaga acactcagct ccagaatgag  10140
aagctctacc tctactacct ccagaacgga agggatatgt atgtggatca agagttggat  10200
atcaacaggc tctctgatta cgatgttgat catatcgtgc cacagtcatt cttgaaggat  10260
gattctatcg ataacaaggt gctcaccagg tctgataaga acaggggtaa gagtgataac  10320
gtgccaagtg aagaggttgt gaagaaaatg aagaactatt ggaggcagct cctcaacgct  10380
aagctcatca ctcagagaaa gttcgataac ttgactaagg ctgagagggg aggactctct  10440
gaattggata aggcaggatt catcaagagg cagcttgtgg aaaccaggca gatcactaag  10500
cacgttgcac agatcctcga ttctaggatg aacaccaagt acgatgagaa cgataagttg  10560
atcagggaag tgaaggttat caccctcaag tcaaagctcg tgtctgattt cagaaaggat  10620
ttccaattct acaaggtgag ggaaatcaac aactaccacc acgctcacga tgcttacctt  10680
aacgctgttg ttggaaccgc tctcatcaag aagtatccta agctcgagtc agagttcgtg  10740
tacggtgatt acaaggtgta cgatgtgagg aagatgatcg ctaagtctga gcaagagatc  10800
ggaaaggcta ccgctaagta tttcttctac tctaacatca tgaatttctt caagaccgag  10860
attaccctcg ctaacggtga gatcagaaag aggccactca tcgagacaaa cggtgaaaca  10920
ggtgagatcg tgtgggataa gggaagggat ttcgctaccg ttagaaaggt gctctctatg  10980
ccacaggtga acatcgttaa gaaaaccgag gtgcagaccg gtggattctc taaagagtct  11040
atcctcccta agaggaactc tgataagctc attgctagga agaaggattg ggaccctaag  11100
aaatacggtg gtttcgattc tcctaccgtg gcttactctg ttctcgttgt ggctaaggtt  11160
gagaagggaa agagtaagaa gctcaagtct gttaaggaac ttctcggaat cactatcatg  11220
gaaaggtcat ctttcgagaa gaacccaatc gatttcctcg aggctaaggg atacaaagag  11280
gttaagaagg atctcatcat caagctccca aagtactcac tcttcgaact cgagaacggt  11340
agaaagagga tgctcgcttc tgctggtgag cttcaaaagg gaaacgagct tgctctccca  11400
tctaagtacg ttaactttct ttacctcgct tctcactacg agaagttgaa gggatctcca  11460
gaagataacg agcagaagca acttttcgtt gagcagcaca agcactactt ggatgagatc  11520
atcgagcaga tctctgagtt ctctaaaagg gtgatcctcg ctgatgcaaa cctcgataag  11580
gtgttgtctg cttacaacaa gcacagagat aagcctatca gggaacaggc agagaacatc  11640
atccatctct tcacccttac caacctcggt gctcctgctg ctttcaagta cttcgataca  11700
accatcgata ggaagagata cacctctacc aaagaagtgc tcgatgctac cctcatccat  11760
cagtctatca ctggactcta cgagactagg atcgatctct cacagctcgg tggtgattca  11820
agggctgatc ctaagaagaa gaggaaggtt tgaggcgcgc cgagctccag gcctcccagc  11880
tttcgtccgt atcatcggtt tcgacaacgt tcgtcaagtt caatgcatca gtttcattgc  11940
```

```
ccacacacca gaatcctact aagtttgagt attatggcat tggaaaagct gttttcttct  12000
atcatttgtt ctgcttgtaa tttactgtgt tctttcagtt tttgttttcg gacatcaaaa  12060
tgcaaatgga tggataagag ttaataaatg atatggtcct tttgttcatt ctcaaattat  12120
tattatctgt tgtttttact ttaatgggtt gaatttaagt aagaaaggaa ctaacagtgt  12180
gatattaagg tgcaatgtta gacatataaa acagtctttc acctctcttt ggttatgtct  12240
tgaattggtt tgtttcttca cttatctgtg taatcaagtt tactatgagt ctatgatcaa  12300
gtaattatgc aatcaagtta agtacagtat aggcttgagc tccctaggct tttttcttc  12360
ttcttcgttc atacagtttt tttttgttta tcagcttaca ttttcttgaa ccgtagcttt  12420
cgttttcttc tttttaactt tccattcgga gtttttgtat cttgtttcat agtttgtccc  12480
aggattagaa tgattaggca tcgaaccttc aagaatttga ttgaataaaa catcttcatt  12540
cttaagatat gaagataatc ttcaaaaggc ccctgggaat ctgaaagaag agaagcaggc  12600
ccatttatat gggaaagaac aatagtattt cttatatagg cccatttaag ttgaaaacaa  12660
tcttcaaaag tcccacatcg cttagataag aaaacgaagc tgagtttata tacagctaga  12720
gtcgaagtag tgattggccg ttaatttgag agtccagttt tagagctaga aatagcaagt  12780
taaaataagg ctagtccgtt atcaacttga aaaagtggca ccgagtcggt gcttttttc  12840
tagacccagc tttcttgtac aaagttggca ttacctaggc ccgggcctga ggacgcgtcc  12900
atggttaatt aagacgtccg gaccgactag tggatcctct agagtcgacc tgcaggcatg  12960
caagcttctt cgtcaacatg gtggagcacg acacgcttgt ctactccaaa aatatcaaag  13020
atacagtctc agaagaccaa agggcaattg agacttttca acaaagggta atatccggaa  13080
acctcctcgg attccattgc ccagctatct gtcactttat tgtgaagata gtggaaaagg  13140
aaggtggctc ctacaaatgc catcattgcg ataaaggaaa ggccatcgtt gaagatgcct  13200
ctgccgacag tggtcccaaa gatggacccc cacccacgag gagcatcgtg gaaaaagaag  13260
acgttccaac cacgtcttca aagcaagtgg attgatgtga tatctccact gacgtaaggg  13320
atgacgcaca atcaatccca ctatccttcg caagaccctt ttaaggggga agttcatttc  13380
atttggagag gacacgctga aatcaccagt ctctctgtac aaatcnatct ctctctataa  13440
tattgtgtaa gtagttccca gataagggaa ttagggttct tatagggttt cgctcagctg  13500
ttgagcatat aagaaaccct tagtcgatag atctgttggg gatctaccat gagcccagaa  13560
cgacgcccgg ccgacatccg ccgtgccacc gaggcggaca tgccggcggt ctgcaccatc  13620
gtcaaccact acatcgagac aagcacggtc aacttccgta ccgagccgca ggaaccgcag  13680
gagtggacgg acgacctcgt ccgtctgcgg gagcgctatc cctggctcgt cgccgaggtg  13740
gacggcgagg tcgccggcat cgcctacgcg ggcccctgga aggcacgcaa cgcctacgac  13800
tggacggccg agtcgaccgt gtacgtctcc ccccgccacc agcggacggg actgggctcc  13860
acgctctaca cccacctgct gaagtccctg gaggcacagg gcttcaagag cgtggtcgct  13920
gtcatcgggc tgcccaacga cccgagcgtg cgcatgcacg aggcgctcgg atatgccccc  13980
cgcggcatgc tgcgggcggc cggcttcaag cacgggaact ggcatgacgt gggtttctgg  14040
cagctggact tcagcctgcc ggtaccgccc cgtccggtcc tgcccgtcac cgagatctga  14100
tgacccaact tagtatgtat ttgtatttgt aaaatacttc tatcaataaa atttctaatt  14160
cctaaaacca aaatccaggg gtaccgaaca agcttggcac tggccgtcgt tttacaacgt  14220
cgtgactggg aaaaccctgg cgttacccaa cttaatcgcc ttgcagcaca tccccctttc  14280
```

gccagctggc gtaatagcga agaggcccgc accgatcgcc cttcccaaca gttgcgcagc 14340
ctgaatggcg aatgagcttg agcttggatc agattgtcgt ttcccgcctt cagtttaaac 14400
tatcagtgtt tgacaggata tattggcggg taaacctaag agaaaagagc gtttattaga 14460
ataacggata tttaaaaggg cgtgaaaagg tttatccgtt cgtccatttg tatgtgcatg 14520
ccaaccacag ggttcccctc gggatcaa 14548

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: synthetic construct

<400> SEQUENCE: 30
gccgttaatt tgagagtcca 20

<210> SEQ ID NO 31
<211> LENGTH: 96
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: synthetic construct

<400> SEQUENCE: 31
gccgttaatt tgagagtcca gttttagagc tagaaatagc aagttaaaat aaggctagtc 60
cgttatcaac ttgaaaaagt ggcaccgagt cggtgc 96

<210> SEQ ID NO 32
<211> LENGTH: 3632
<212> TYPE: DNA
<213> ORGANISM: Zea mays

<400> SEQUENCE: 32
ccacggctat gttccactcc aggtggaggc tgcagccccg gtttcgcaag ccgcgccgtg 60
gtttgcttgc ccacaggcgg ccaaaccgca ccctccttcc cgtcgtttcc catctcttcc 120
tcctttagag ctaccactat ataaatcagg gctcattttc tcgctcctca caggctcatc 180
tcgctttgga tcgattggtt tcgtaactgg tgagggactg agggtctcgg agtggattga 240
tttgggattc tgttcgaaga tttgcggagg ggggcaatgg cgaccgcggg gaaggtgatc 300
aagtgcaaag gtccgccttg tttctcctct gtctcttgat ctgactaatc ttggtttatg 360
attcgttgag taattttggg gaaagcttcg tccacagttt tttttcgatg aacagtgccg 420
cagtggcgct gatcttgtat gctatcctgc aatcgtggtg aacttatttc ttttatatcc 480
tttactccca tgaaaaggct agtaatcttt ctcgatgtaa catcgtccag cactgctatt 540
accgtgtggt ccatccgaca gtctggctga acacatcata cgatctatgg agcaaaaatc 600
tatcttccct gttctttaat gaaggacgtc attttcatta gtatgatcta ggaatgttgc 660
aacttgcaag gaggcgtttc tttctttgaa tttaactaac tcgttgagtg gccctgtttc 720
tcggacgtaa ggcctttgct gctccacaca tgtccattcg aattttaccg tgtttagcaa 780
gggcgaaaag tttgcatctt gatgatttag cttgactatg cgattgcttt cctggacccg 840
tgcagctgcg gtggcatggg aggccggcaa gccactgtcg atcgaggagg tggaggtagc 900

-continued

```
gcctccgcag gccatggagg tgcgcgtcaa gatcctcttc acctcgctct gccacaccga    960
cgtctacttc tgggaggcca aggtatctaa tcagccatcc catttgtgat ctttgtcagt   1020
agatatgata caacaactcg cggttgactt gcgccttctt ggcggcttat ctgtcttagg   1080
ggcagactcc cgtgttccct cggatctttg gccacgaggc tggagggtat gttctattcc   1140
ccgatttact tcactatgtt gctgactata tatgtgctgt gtttatattt tgcatattta   1200
ttatgttttt gcgtctgagt ttatgggtat ggttggtggt ctttgtttac tgttttacta   1260
gatgcatgtg gaagagtcag aagaaatagt ttttgtttga aatggtatac caacggttgg   1320
atattatctg tgtggacatc agatgttctg ggttactggc agtggacttt gacagattta   1380
tctatgattc tttcattagc agtttcttca gctaatttac tcttactatt ttttcagtat   1440
acaaaggcac gtacagctag ggttgtgtag aatcatttta gatctgttat ctgaggcaaa   1500
tttgcttatt ctagccgcct gaaatttctt gattttgcca gtatcataga gagtgttgga   1560
gagggtgtga ctgacgtagc tccgggcgac catgtccttc ctgtgttcac tggggagtgc   1620
aaggagtgtg cccactgcaa gtcggcagag agcaacatgt gtgatctgct caggatcaac   1680
accgaccgcg gtgtgatgat tgccgatggc aagtcgcggt tttcaatcaa tgggaagcct   1740
atctaccact ttgttgggac ttccaccttc agcgagtaca ccgtcatgca tgtgggttgt   1800
gttgcaaaga tcaaccctca ggctcccctt gataaagttt gcgtccttag ctgtggtatt   1860
tctaccggta agttcattta ctacattttg gtgtggatgc tggggtacat ttatcttgag   1920
atgctgagtt acacaaattc tttctctgtt taggtcttgg tgcatcaatt aatgttgcaa   1980
aacctccgaa gggttcgaca gtggctgttt tcggtttagg agccgttggt cttgccgtaa   2040
gtgttgaaac gatttgcttg ttctatgaat ttcaattgca atgagaatgt gtgttgggtt   2100
tgcatctgat taccctgcgc atggttaggc tgcagaaggt gcaaggattg ctggagcgtc   2160
aaggatcatt ggtgtcgacc tgaaccccag cagattcgaa gaaggtacag tacacacaca   2220
tatgtatata tgtatgatgt atcccttcga tcgaaggcat gccttggtcg aataactgag   2280
tagtcatttt attacgttat tttgacaagt cagtagttca tccatttgtc ccattttttc   2340
agctaggaag tttggttaca ctggccttgg tctaataact gagtagtcat tttattacgt   2400
tgtttcgaca agtcagtagc tcatccatct gtcccatttt tttcagctag gaagtttggt   2460
tacactggac ttggtctaat aactgagtag tcattttatt acgttgtttc gacaagtcat   2520
tagctcatcc atctgtccca tttttcagct aggaagttcg gttgcactga atttgtgaac   2580
ccaaaagacc acaacaagcc agtgcaggag gtctgtctct ttacccaaga caacaaaagg   2640
ttatcacagc ttatgctgaa cttggccata acattcaata attcctttat ggtctaggta   2700
cttgctgaga tgaccaacgg aggggtcgac cgcagtgtgg aatgcactgg caacattaat   2760
gctatgatcc aagctttcga atgtgttcat gatgtaagta tatgtataca ctctcagcta   2820
ctttccttct ccaggttccc ttcatccaga catgcatgtt ctaactgccg cgctcgtgat   2880
ccagggctgg ggtgttgctg tgctggtggg tgtgccacat aaggacgctg agttcaagac   2940
ccacccgatg aacttcctga acgaaaggac cctgaagggg accttctttg gcaactataa   3000
gccacgcact gatctgccaa atgtggtgga gctgtacatg aaaaaggtaa attgcaaagt   3060
gccgttcctt cagtttcctt acctgccgag cttttgctga aaaactgtta agaatcgttc   3120
ctgcaattct gcttggctct gcacaggagc tggaggtgga gaagttcatc acgcacagcg   3180
tcccgttcgc cgagatcaac aaggcgttcg acctgatggc caagggggag ggcatccgct   3240
```

```
gcatcatccg catggagaac tagatttcgc tgtctagttt gtgatctggc ctgggcttgg   3300

ggttaataaa agaggcaatg ctagcctgcc ctttcgatga ggaggtacat acacgctggc   3360

gatggaccgc gcttgtgtgt cgcgttcagt ttggcttttg ccaagcagta gggtagcttc   3420

ccgtgtcggt aattatatgg tatgaaccat cacctttttgg ctctacatgg tatgaacgta  3480

agatacaaat tccaactacc tctagctcgc ttgtgtggta tctgtatcag tattcatgtg   3540

tttgtttgct tatgtgtttg tttgcttgta tttgctggtg cttgtatcgc gggatgcaat   3600

gagttgttgt ttggttgttg tcaaccaggc tc                                 3632
```

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: synthetic construct

<400> SEQUENCE: 33

```
ggcaagccac tgtcgatcg                                                  19
```

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: synthetic construct

<400> SEQUENCE: 34

```
ggcctcccag aagtagacgt                                                 20
```

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: synthetic construct

<400> SEQUENCE: 35

```
acgcgcacct ccatggcctg                                                 20
```

<210> SEQ ID NO 36
<211> LENGTH: 720
<212> TYPE: DNA
<213> ORGANISM: Zea mays

<400> SEQUENCE: 36

```
gaacagtgcc gcagtggcgc tgatcttgta tgctatcctg caatcgtggt gaacttattt     60

cttttatatc ctttactccc atgaaaaggc tagtaatctt tctcgatgta acatcgtcca    120

gcactgctat taccgtgtgg tccatccgac agtctggctg aacacatcat acgatctatg    180

gagcaaaaat ctatcttccc tgttctttaa tgaaggacgt cattttcatt agtatgatct    240

aggaatgttg caacttgcaa ggaggcgttt ctttctttga atttaactaa ctcgttgagt    300

ggccctgttt ctcggacgta aggcctttgc tgctccacac atgtccattc gaattttacc    360
```

gtgtttagca agggcgaaaa gtttgcatct tgatgattta gcttgactat gcgattgctt 420
tcctggaccc gtgcagctgc ggtggcatgg gaggccggca agccactgtc gatcgaggag 480
gtggaggtag cgcctccgca ggccatggag gtgcgcgtca agatcctctt cacctcgctc 540
tgccacaccg acgtctactt ctgggaggcc aaggtatcta atcagccatc ccatttgtga 600
tctttgtcag tagatatgat acaacaactc gcggttgact tgcgccttct tggcggctta 660
tctgtcttag gggcagactc ccgtgttccc tcggatcttt ggccacgagg ctggagggta 720

<210> SEQ ID NO 37
<211> LENGTH: 163
<212> TYPE: DNA
<213> ORGANISM: Zea mays

<400> SEQUENCE: 37
atgcgattgc tttcctggac ccgtgcagct gcggtggcat gggaggccgg caagccactg 60
tcgatcgagg aggtggaggt agcgcctccg caggccatgg aggtgcgcgt caagatcctc 120
ttcacctcgc tctgccacac cgacgtctac ttctgggagg cca 163

<210> SEQ ID NO 38
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: synthetic construct

<400> SEQUENCE: 38
ggccucccag aaguagacgu guuuuagagc uaugcu 36

<210> SEQ ID NO 39
<211> LENGTH: 9128
<212> TYPE: DNA
<213> ORGANISM: Glycine max

<400> SEQUENCE: 39
gaaatcttta tattcgacta agaatttcag tgaagggttg ttacaaaatt tgatgtagtg 60
tcagtaacaa aatttaggtg gtcataaaat gcatttgaaa atactctaaa aaatatatgt 120
atcgtgtgag aggagtgatt ctttatatca gaatctgata aataaatttg aagtatatat 180
tatataggcg gacatggatt attagaatta ttcttttgaa aaaaaaatca tgtgattttt 240
taaaaagaat tcatgtgtgt tttggtctta attatttata aaagaattta atggtcggga 300
tctgagtgtt ttgatcttta tcatttatga taaaaattta atggttgcaa tttttttaaa 360
agaattcata tgatgtgtgt tttagtctta attatttata aaagaattta atggttggga 420
tcatgtatga atgttttaat ctttgattat ttataataaa atttaatggt tgacattttt 480
tttaaagaat tcatatgatg agtgtgattt agttttaatt atttatgaaa gaatttaata 540
gtgagatcag gcatgaatgt tttaattttg atcatttatc ataaaattta atggcggaaa 600
tttctttaag cattttaatc tcgattatta ttaataaagt ttaatagttg aagtttcctt 660
agatgtctat ggagttacac taatataaaa tatatttact cttacacatt taacaatttt 720
ttataaatgt aatttaatga ttgaaattaa tatcgtgtta actaataaag attgatttaa 780
ttgataaaaa ataaaatcat attttttatg aaatataaat ttaatgtttg ttatcgatat 840
gaaattcttg ttaatatata ataaaaagta actaatatct cttattcaaa ttgtatcact 900

-continued

```
aagttcatcc aacacaaatt cagtctaaat caggttattg taggagttaa aactttgaaa    960
tgagtaatga tacacaaaat tttcttaatt tatacaccat ctcaacacct cttatttatg   1020
tatatgtctt tgttcatacc acctcataaa tcttattaaa gttacatatt ttcttatttt   1080
ctctctccgg atgtcttgta gcccaatggt atcaaacatt ttattgtgat ttagtttgac   1140
gggggttgac actttgtcct aatcttcctc acaatccact caggaatatt cattcattct   1200
taaaacacac ctcagtcaca caacacaact ctcgtctctt ttatgtactg ccgtggtgct   1260
ttctccactg cctaaaccga ctctctctct ctgcctctgc aagcttgtta cttggtactc   1320
ttttcacttc ttcaactctt gttttttttt atttcccaca tcaactttca aagtgcctga   1380
attccgcaac agtaatacca ttaacacgtc tctcttttga ttcaggcttt gtttgattga   1440
ttgccccaat ggccgcgtgt ggctatatat ctgctgccaa cttcaatcat cttgttggcg   1500
ccagaaactt atccaaattc agttcttcgg atgccacaat ttcgttatca tttggcggga   1560
gcgattcaat gggtcttagt ttgcgacccg ctccaattcg tgctcctaag aggaaccatt   1620
tctctccctt gcgtgtcgtt tgcgtcgatt atcctcgacc ggagctcgaa aacactgtta   1680
atttcgtcga agctgcttac ttgtcttcca ccttccgtgc ttctccgcgt ccactaaaac   1740
ccttgaacat cgttattgct ggcgcaggta ttaacctagc catgcctatg cttgtaccca   1800
tttcgtttta tgcatcaaaa ttgtattttt tttatcgaca aatgctggtt gttcgtattg   1860
ttatttcgtt ttatgcatca aaagtgtatc tttgctgcca aatttgtgtt tttcttgctc   1920
ttgttgttct gggtgttttc aaattaggac ctgttatacc acccttttca tttcatgtat   1980
ggtcttctat tctaatgtta gtgtgtgtta gaaaacaact tagaagcctg cttgggctac   2040
gcattaggaa ttcctttctt tgtgattaaa tagatgtaca catctcaatg cttgattaca   2100
ttgtattgtg acagtcctcc tgtgtcggta aggaaaaaag ttatggaatt ttaggatctt   2160
caatttttgc tgaaatttca aataaaaggt atcctgatat catgttggat atttaaagac   2220
aaaaaaattt gtaaactaat ctttgcacat tagttttggc ctctctgcct attggattga   2280
tgcatgtttc attattgcag gattggctgg tttatcaact gcaaaatatt tggctgatgc   2340
tgggcataaa cctatattgc tggaagcaag agacgttcta ggtggaaagg ttttcctgct   2400
aatttaatct cttacgtcaa ttagttgtca ctttgtgtgc attctgctca ttattttagc   2460
atgctgttta atgaaataag aaatttgttt gtgttgttcc gtcataatct atttgatgtg   2520
ttggctttat aacttcatca tcaggcttgt tgaagattac cgcagtaatg taaaacatat   2580
ttataataaa tcaattttga tgcattgtgt ttttacacta ttgtttcatt ttctaaggtt   2640
gctgcatgga aagacaagga tggagactgg tatgagacag gtctacacat cttctgtaag   2700
ttcattaaaa tctcgggttt aacttttttt ttttcctgct atgcatccaa atagttagga   2760
ttttgatcct tgctacccca ctcttctgat taagaattaa atttcagtta aaaggtttgg   2820
gttaaattgt gctctgtcca agctcaaaag gcttttcctt gagtgggcaa tttggcctcc   2880
tagcagtgct ttcggatgag ttagtccatg gcacacttat tgaaatattt tgatatatct   2940
ttttagtttt tctttctaaa tgaatcattt attggacatc atattattta atcaatacag   3000
atcttttaat tattagaatc cttattttgt agttatcttt gctttacaac tttttccccc   3060
tccccacagt tggggcttac cctaatgtac agaacttatt tggagaactt ggcattaatg   3120
atcggttaca atggaaggag cattctatga tttttgctat gccaaataag cctggagagt   3180
ttagtcgatt tgattttccc gatgtccttc ccgccccatt aaatggtaag atgtaagacc   3240
tactgtatgt gtgtatattt atatacctaa ctgcagttgg atgtctctat aaaaagcaca   3300
```

```
ttgaatgcct ttatctttgg aaatcctaca atgctgaatt tgcagttgtc tgacataaaa   3360
tgtgtaatac catctagcaa ttatcctgcc tatgttacga gtaatgctcg aaaaccagaa   3420
ttcagatgaa gaaaatttta gtttccttga aaattttaac acaatttgct agtcaaattt   3480
ttgatttcga atatatctca atgcatttga taatcattga aacaagatgt gttaaattgt   3540
ttccatttta tgtaaattaa aaattgcaaa cccaaacaga gaagaagcat tttggtgttt   3600
agcttggttt ctatattctt ttctatttct ttcttcacta atctggtttg caggttggga   3660
acaaattttt ctcttctaaa aagaaccaag tgatgcttaa attctccaat tttattttaa   3720
catctgcatc attccccttt taagattctg tttcattatg ctttactttc taaatgttaa   3780
ccagtattta cgagttgcat gccatgaatg tcaatacagg aatatgggca atattgagga   3840
acaatgagat gctgacctgg ccagagaaag tcaaatttgc aattgggctt ctaccagcta   3900
tgcttggtgg acagccatat gttgaggctc aagatggtct ttcagttcaa gaatggatga   3960
aaaagcaggt atagcacttt tcttgattgt gtaaccttag cagtccatta atagatttaa   4020
gtaacttggc tatatcacca gtcatgggct actgcaactt aaaaattgca gagaaaagtc   4080
ttgtttgttg acaatggact gttgaccatc tgatgactat tctgaaatgg ggtgattcag   4140
gaatagactt tcatgtgact tgatgatgat gacaatgggt ccttttatca ttagagaaag   4200
gatatctgta gttgtaattg taagattgta ttacttgata tttacttaat gctttaaaat   4260
gtatttcatc tacctcgggt tgatttcact gggacagaat ggaaccttgt catggtctgt   4320
gttgcaaata atttgaaaat aacaaaatgt tttctccttg ttatagggcg tacctgagcg   4380
agtaaccgat gaggtgttca tagcaatgtc gaaggcacta aacttcatca atcctgatga   4440
actttcaatg caatgtatat tgattgcttt aaaccgattt cttcaggtgc gaacatttcc   4500
ttttcttaaa acactattct actagaatta ttgtatgatt gacaaggtca ttttattccc   4560
attataatag ttgaatggaa tcagattagt aataaacttt aagatggcct tttatttcac   4620
aaacatgttt ctggaactta ggatcaagtt tttttctttt ccttttcttt ttcttcaact   4680
aattgttata ttattaaatt attctatagg agaaacatgg ttctaagatg gccttttttgg  4740
atggcaatcc ccctgaaaga ctttgtatgc cgatagttga tcatattcag tccttgggtg   4800
gtgaagttca tctaaattcg cgcattcaaa aaattgagct aaatgatgat ggaacggtga   4860
agagcttctt actaaataat gggaaagtga tggaaggaga tgcttatgtg tttgcaacac   4920
ctggtatttt tcttcttatt ttcccaatgt attaattaat tgttttcatg acattcttaa   4980
tcttcatacc ttaacatttt tgaggttctt tttcttgaaa acagtggata ttctgaagct   5040
tcttctacca gacaactgga aagggattcc gtatttccag agactggata aattagttgg   5100
agtcccagtc ataaatgttc acatatggta agtaatggct tttgacgttt aaaaccatat   5160
gcatgcatat gttagactcc aattttaaat taaattatta cagtcatcag tatttcattt   5220
ttctgtctaa tatataaaaa ttcaaatatt cactgaaaag tttggaatag aaatctatgc   5280
gatttttctt aaattgtatt aatgacaatt gacaatttat aattaatgtt cttctaattg   5340
aatggttgta atagttttgg taaatggaaa ctttaaatag agttgtggta aaataatgtc   5400
actatcacta attgatgtaa taatattctt tgttaacttt ttcataaaga aattcctctt   5460
actttattaa tgttttgtca aaattttggg taacaccaac aaaaaataatt tgtaatgttt  5520
gtggataatg attatattat aatctccact gttgtggtga catactatat atgcatgtgt   5580
ttgcaggttt gacagaaaac tgaagaacac atatgatcac cttctcttta gcaggtcttc   5640
```

```
cacaaacttt gaaacacctg taatgtctgg aagggataga aatgctgttc atttaatgtc   5700
tgttttgttt ttctgatgcg tagatgcata ttgactactg agtcaacttt tgtgcttcat   5760
aagttgtgaa actcgacaag tataaaacag aaaggtttac taagggataa gaacattttt   5820
cattataata ttgtgaaata acaatcagaa gccaaactga atattgtaat atggaaatag   5880
tgtagaagat atcctctccc taaatgttgg ccctctaatg atgtgccaaa ctgaatattg   5940
taatatggaa atagtgacct atctattact aacatgtgat tacaggagag agacaccact   6000
ttattgaggt ttgtgacata ccctaatctt ggaatggagt attggtctca ttcttctata   6060
atttactaaa gaaagaaagt gataaaagga attaaaaatt tgtggccaag gagatccttt   6120
ctcccattgt ttgcttaact tggctgagtt tgttcaagaa tttattcagg gtgttgatgg   6180
tgtctagcat gaggtggttt attgtgactt tgtgattctg tgtatatggt agtgtttctt   6240
tcatctacaa tttccaattg ccaatgatta catctcgtca atagccaatg ataaaaggat   6300
tttttttct attgcaattg caattgatac aatctagtta tttgctggcg ggtttttaat   6360
tttattgtgt atgttccaag tgtctgagga ttttagggat gaaagatcac ttattttttg   6420
ctgtgtgaaa tgaacttttt ttcttctttg ctttcttgat ggtatttgtg gattataaat   6480
aaagtatttt catcacctca catcttgtat attttatatg tttcttcttg cagaagtccc   6540
cttctaagtg tatatgctga tatgtcagta acttgcaagg taaaaaccac ttcttacatg   6600
ccactgattt gcactgattt atttcctcaa cccatgcaaa agttgtggcc tgcatgtata   6660
ggttagcata ttcgttctta tatgtataat taactagggt cacctaaatg aattggagat   6720
ggtgctttct ggataagcag ttaaccctct ctacaaatta tttcagtttc cagacattta   6780
tgtaatattc ttttgttgtt tgaggctgaa tttcttctgc ttatgttttg tctgcttatc   6840
atcaaatgtt ggaatgttgt ttgagttctg tttgacgatc aaatgcagga gtattatagc   6900
ccaaaccagt ctatgttaga gttggttttt gcaccagccg aagaatggat ttcacgtagt   6960
gatgaagata ttattcaagc cacgatggct gagcttgcca aactcttccc taatgaaata   7020
tctgcagacc aaagcaaagc aaagattctc aagtaccatg ttgttaaaac accaaggttt   7080
gattgaataa ccagtctggc aatgtctttg ttgttactga actgatggtg acatttatag   7140
cccttacatt cagctgtgtt ctgaatccta atggaactac tggctacatt gtttcaggtc   7200
agtttacaaa actgttccaa attgtgaacc ttgtcgtccc ttacaaagat ctcctttaga   7260
aggtttctat ttagctggag attacacaaa acaaaaatat ttagcttcaa tggaaggcgc   7320
tgttctttct gggaagcttt gtgcacaggc tattgtacag gtaaaatctg tcacaaaaat   7380
atctatgtaa ctcagcgatt cattagcaag aaatgtgatt atctatatat aaatgctttc   7440
ttagttattt tgtgagagaa acttggttat taattcagca ggatgaataa cactacattg   7500
tttcagcagg ataaaaatct ttccactttt attttttggt tgaaacattt ttactgattt   7560
ccaattatcc tcaaaactta tgctgtctct gaatgatttt tatatgtatc tccattaccc   7620
ccctgcgaaa ggcctttggt tatgaaacat tatttgaaat tagtatgaaa gagttagcat   7680
aatgaggatt gatcttctgc atagtttgat ttgaatgttt ttcttatcag tgctgtcatt   7740
gaggcttgct aaaaattatt gcaggattct gagctactag ctactcgggg ccagaaaaga   7800
atggctaaag caagtgttgt gtaacaaaaa caggaattga aaatgagtca tggtagaata   7860
caggagcatc aattcaagat tggtattctt tatgtggtca ggactcagga gaataaaaaa   7920
gaaaggctca ccgtcaacta tgtgcaataa gctataggga acaaatgaca tgtgtcgata   7980
cttgaaaatt cagcgcattg ttttgtatcc tccaagttac tggatcaatg tttgtattgg   8040
```

```
aacgaaatat gccatcattt aaacttgtat atccagtaat tttatatatc aagatttgtc   8100

acaacctttc gctgagtagc taattattcc caaaagggca tatattatat ataagattta   8160

tatatgcaat gcatataata tttatacaaa ataacaataa atataattga cagaatttga   8220

atctagcaga aaaaattagt ttttataaca tgacaagcta agatttgatt tttttgttgg   8280

caaaatttat atataagatt taatttttta tatattatct ataaaaaatt gtatttaaca   8340

tatcttatat aaatttataa tttttttata tataaagtaa aaatacatta taaattaaaa   8400

cttaaaaatt aaataaatga gtattattat aatattgttt tagaatttgt aagaataata   8460

ttaaagataa taaaatttgt aaatattata tggtaataaa gatatgttat aatttttttta   8520

acactcatta ggtattcata tctttctttc tatcttccgt tttagaattt gttataatat   8580

cttcaatatt aattatgccc gaatggaaaa agaggcctac gggaaaacca ttacctttgg   8640

gcacaagtca aagctttcta ttcaggagca gaggcaaaat ttgccaattt acaagttaaa   8700

gaaggaactg attcaggctg ttcatgataa tcgggtgttg gtagtgattg gagaaaccgg   8760

ttcaggatct tgctgaagcg gggtacacca caaagggaat agtttggttg tcgatttgaa   8820

gaggaagttg gttattccat tcagtttgac ccaaattcgt ggcgtttgag taaacgccga   8880

gcatgaaatg taattcatct acttcctcta gattctatgt tttggatact gttgtatatt   8940

gcctttagtt ttttatgtaa cttttctctt tatccataaa caaggttgtt gcccttaact   9000

acatttgttt tctgtttact ggaatatata tatgtatatg tgaaactgga atctaatgaa   9060

ccaggagagt gatgatttcc catatgtttt gatgtatttt tggtatgaaa atgaaatact   9120

catgctaa                                                            9128
```

```
<210> SEQ ID NO 40
<211> LENGTH: 10582
<212> TYPE: DNA
<213> ORGANISM: Glycine max

<400> SEQUENCE: 40

aatgaatcaa acccaaaggt atttctttac aaatatttcc tttcagtatt agatcctgct     60

tttctatgag atccatggat tgtctgtgga catgattcac aatagaacac tatggcgtcg    120

tttgatcctt cccaactcgt gggaaaatgc ttagttgttg ttgttgcatt agctcctcga    180

tctatgtctt ttcatataat catttatgca ctattttgag ttattggggc aagatattgc    240

tttttgtctt tgttttccta actgaaactg aatttaattt tgtgatgctt tatatgctca    300

tagttagtaa gaagaccaga caataatagc aaatttttgt aagtgatcta tctgtttata    360

tacatttcct aaagattggt gatgattttt tttaatgttt tctgaatatt atcaggaatt    420

catgtagagg aaatgttctg gaacttgttt tgtacttttt catgcatttt tgggttctcc    480

tcatttttaa tactgcagga aacttttttg agtaatgctc agttgttcac caagtctgta    540

gctgtaactt gtatatgttt ctaaaaaaat gaatatatac tacatatacc ttgagttatc    600

ctttggttga tttttggttc ttcagttaca ttaaatttgt tcttggcgta attatcttgt    660

tcactcgatt tatgaacaaa tatcaaattt tgaaggtttt tttaaaaaat aaacacggta    720

tgtgataatg agaaataaaa tgtaggtagg gatgggtctg aatgagagaa agttggttgt    780

attggacatc ggaagaagtt agacgtagtc acgtaataat actctctctc ctgactgaaa    840

tatatatata tatatatata tatatatata tatatatata tatatatata tataaactct    900

ttgttattca aagataatgc ttccaaaata ctcttcatat ttaattagag ttttattttc    960
```

-continued

```
aatcatcttt tctttttat cttatataat taatatagtg ggtactagtc actgtactgg   1020
ccagagaggt aaacgttagt aatactaaga caggtaggta ttattgtcgt ttcattggac   1080
ggggcttgac actttgtcgt aatcttcctc acaatccact caggaatatt cattcatttc   1140
ttaaacgtta aaacacacca cacgacacta ctctcttctc ttctcttctc ttctacgtac   1200
tgccgtggtg ctttcaccac tgcttaccac taaccttcct ctctctctct gccgctgcaa   1260
gcttggtact ctcaactcaa ttctccacct tattcttttc acttcttcag ctcttgtttt   1320
ttcccaaatc tactttcaaa gtgcctgaat tctgcaacag taatattaac actcctctct   1380
tttgttcagg ctttatttcc ccaatggccg cttgtggcta tatatctgct gccaacttca   1440
attatctcgt tggcgccaga aacatatcca aattcgcttc ttcagacgcc acaatttcgt   1500
tttcatttgg cgggagcgac tcaatgggtc ttactttgcg acccgctccg attcgtgctc   1560
ctaagaggaa ccatttctct cccttgcgtg tcgtttgcgt cgattatcca cgcccggagc   1620
tcgaaaacac cgttaatttc gttgaagctg cttacttgtc ttccaccttt cgtgcttctc   1680
cgcgtcctct aaaacccttg aacatcgtta ttgccggtgc aggtaataac caacctatgc   1740
ctatgctcat acccatttcg tattatgcat aaaaaattgt atctttgctt ccaattttgt   1800
gtttttcttt gctttagttg ttctgggtgt tttcagatta ggactcgtta taccctttc   1860
atttcgtgca tggtcttcta atgttggtgt gtgttagaaa aaacttcgaa gccagcttgg   1920
gctacgcatt aggaatttcc ttctttgtga ttaaatagat gtacgcatct caatgcttga   1980
ttacattgtg ttgtgacagt cctgtgtcgg taaggaaaaa agttatggaa ttttaggtac   2040
cctgatatca tgttggatat ttaaagacaa actaatcttt gcacattagt tttggcctct   2100
ctgtctattg gattgatgca tgtttcaaat tatcgcagga ttggctggtt tatcaactgc   2160
aaaatatttg gctgatgctg ggcataaacc tatattgctg gaagcaagag acgttctaag   2220
tggaaaggtt ttcctgctaa tttaatccct ttcggcaata agttgtcact tagtgcgcct   2280
tcttttcatt attttaacaa gctgtttaat gaaataagaa atttgtttgt gttgttccat   2340
cataatctat ttgatgcgtt ggctttataa cttcatcatc aggtttgttg aaggttacca   2400
cagtatatac aacatattta taataaatca attttaatgt attgtgtttt tatactattg   2460
tttcattttc taaggttgct gcatggaaag acaaggatgg agactggtac gagacaggcc   2520
tacacatctt ttgtaagttc attaaaatct tgggtttaac tcttttttt ttctgctatg   2580
catccatttc cttaacttgt tttttttct taaaaaaatt ccgctttcat tttaataata   2640
tcatgccttt gttgagcctt ttttttcctt tgataaaagc ggattgaaaa aagagtaaaa   2700
tgctggagga tcaggaatat ttctagagct actaaagaaa ccactagaga ataaaattaa   2760
agagataaca aaagggggg tgagaggtcg caggtctaaa ttttccacta acatttctaa   2820
caaaactaac aaactaatat ttttcgataa aaaaaaaaga taaaacaaag gtcataattg   2880
gtagagttga tccttgacac tatcaaagcc tttgccttca tgaccaaata gttaggattt   2940
tgatccttgc taccccactc ttctgattaa gaattaaatt tcagttaaaa ggtttgggtt   3000
atattgtgtt ttgtccaagt tcaaaaggct atagcttgag tgggcaattt ggcctgtcaa   3060
tgggattgat tagcagaata ttattagtta cgaattgaca taaattgcaa aatatttgtt   3120
attattggca catatttgtt gcattcaact ttccacatga aagaccttgg tcaactcact   3180
catctcttga ggttagaagt acactttcaa caaaaaggaa tttttgtcaa tcaacacaaa   3240
tatattcaag atctaattca attagttggt ctcactaatt atgctcctgt tgaaacttca   3300
atggaaatta atctgaaatt gcgacgagat gaaggtgacc ttctactaga cctaactttc   3360
```

```
tatcgtaagc tggctgtaag tattatttac ctaaccatca ctagaccagg catctcattt   3420
gctgtccaca cagttagcaa attcatgcaa tttcctcggc atttgcatct ttcagcagta   3480
cactgtatta ttaagtatct acttggtact tccagctgtg gtttttcttt ccttactggt   3540
gcatcaatac aacttcaagc atacagtgat tttgattggg atggatgtcc aaacacacag   3600
aaatccacta ctggttggtg tatgttctta ggggaagctc caatctcttg gaaatgcaag   3660
aaacaagact caatctccaa atcgtccact gaagcagaat accgtgccat gtctactgca   3720
tgctttgaga ttatttggct tcgcggtctc ctttcagagc ttgatttttc acaagcaaaa   3780
cctgctccac tgcatgctga caatacaagt gtcattcaaa ttccacaaat cctgtttacc   3840
atgaaagaac gaagcacata gaggttgatt gtcactcaat tcgggaggcg tatgaccatt   3900
gagttatcat cttgcctcat gtttctacat atgttcaact cgctaacatt ctcacaaaat   3960
ccttgatacg tcagtgtcat aatttcctag tcagcaaatt gatgctttta gacttactag   4020
tatcaatttg aggggggggtg tcaatgggat tgattagcag aatattagtt attaattgat   4080
acaaattgca gaatatttgt tattggcaca aatatgttgg caattcaaaa cagcagatct   4140
tacatgatta tacagctgta attatctcgt taattagtta tcccagctat aggatagcat   4200
ttattgtaga ttgactattt aatgcataga tgtagaaatc aaattgtatg aacactattt   4260
aatgcagaat tctcggagaa cacagttttt catctgcaac tttcttagtc taatatggcc   4320
tcctaacaga gcttttggat gagttagtcc atgccacact tattaaacta ctttgatatg   4380
ttttttttagt ttttctttct aaatgaatca tttattggaa atcatattat ttaatcaata   4440
cagatctttc aattatcgga atccttatgt tgcagttatc tttgctttac aacttttttcc   4500
ccctccccac agttggggct taccctaatg tgcagaacct ttttggagaa cttggcatta   4560
atgatcggtt acaatggaaa gagcattcta tgatttttgc tatgccaaat aagcctggag   4620
agtttagtcg atttgatttt cctgaagttc ttccctcccc attgaatggt aagatgtaag   4680
acctattgta tgtgtgtata tttatatacc taactgaagt tggatgtctc tataaaaagt   4740
acattgaatg cctttatctt tggaaatcct acaatgcaga atttgtagtt gtctgccata   4800
aaatgtgtaa tactatctag ttattatcct gcctatttta tgagtagtgc tcgaaaacca   4860
gaattcagat gaagaaaatt ttagtttcct tgaaaatttt aacacgattt gctagtcaaa   4920
ttttgatttt gaatatatct caatgcattt gataatcatt gaatcaaggt gtgttaaatt   4980
gtttccattt tatataaatt aaaaattaca aacccaaaca tagaagaagc attttggagt   5040
ttagcttggt ttctatattc ttttctattt ctttcttcac taatctggtt tgcaggtcag   5100
gaacatattc tcttctgaaa agaaccaact gatgcttaaa ttctccaatt ttattttttac   5160
atctgcatca ttccccctttt aagattctgt tttattatgc tttacgtttt aaatgttaac   5220
cagtatttac aagttgcatg ccatgaatgt gaatacagga atatgggcaa tattgaggaa   5280
caatgagatg cttacatggc cagagaaagt aaaatttgca attgggcttc tcccagctat   5340
gcttggcgga cagccatatg ttgaggctca agatggtctt tctgttcaag aatggatgaa   5400
aaagcaggta tagcacttgt cttgattgtg taaccttagc agtccattaa tagatttaag   5460
taacttggct atatcaccag tcatggccta ctgcgactta aaaattgcag agaaaagtct   5520
tgtttgtttg ttatcattag agaaaggata tctatagttg ttattgtaag atttcattac   5580
ttgatattta cttgatgctt taaaatatat ttcatctacc tcaggttgat ttcactggga   5640
cagaatggaa ccttctcatg gtctgttgca aataattgaa aataacaaaa tgtttctcc   5700
```

```
ttattatagg gcgtacctga acgggtaact gatgaggtgt tcatagcaat gtctaaggca   5760
ctaaacttca tcaatcctga tgaactttca atgcaatgta tattgattgc tttaaaccga   5820
tttcttcagg tgtgatcatt tccttttctt aaacactatt tcactagcat tattgtgtga   5880
ttgacagggt cattttattt ccattagaat agttgaatgg aatcagatta gtaataaact   5940
ttaagatggc cttttatttc gcaaacatgt tttgtggaac ttacgatcaa gtttttttccc   6000
tctttttctt taactaattg ttatattatc aaattattct ataggagaaa catggttcta   6060
agatggcctt tttggatggc aatccacccg aaagactttg tatgccgata gttgatcata   6120
ttcagtcctt gggtggtgaa gttcatctaa attcgcgcat tcaaaaaatt gagctaaatg   6180
atgatggaac ggtgaagagc ttcttactaa ataatgggaa agtgatggaa ggggatgctt   6240
atgtgtttgc aactccaggt gttttttctt cttcttattt tacgaatgta ataattaatt   6300
gttttcatga cattcttaat cttcactcct taacattttt taggttcttt ttcttgaaaa   6360
cagtggatat tctgaagctt cttctaccag ataactggaa agggattcca tatttccaga   6420
gattggataa attagttggc gtcccagtca taaatgttca catatggtaa gtgatggctt   6480
ttgatgttga aaaccatatg catgcatatg ttaaactcct attttaaatt aaattattac   6540
agtcatcatt atttcatttt gctgtctaat gtataaaaac tcaaatattc actgaagagt   6600
ttggaataga aatctatgca attcgtctta aattgtatta atgacaattg gcaatttata   6660
attaatttc ttcttctaat tgaatggttg taatagtttt ggtaaatgga aactttattt   6720
gttaactttt tttgtggtaa aataatgtca ctatcactaa ttgatgtagt aatattcttt   6780
gttatttttt ttttaaaaga aattcctctc actttattga tctttttttca aaattttgga   6840
taacgccaac aaagttaatt tgtaatgttt gtggataatg attatattat tatctccact   6900
ggtgtgatga catactatat atgcatcgca tttgcaggtt tgacagaaaa ctgaagaaca   6960
catatgatca ccttctcttt agcaggtctt cctcaaactt tgaaacacct gtaatgtctg   7020
gaagggatag aaattctgtt catttaatgc ctgttttgtt tttctgatac atagatgtat   7080
attgagtcaa cttttgtgct tcataagttg ataaaatttg acaagtataa cacataaatg   7140
tttactaagg gataagaaca tttttcatta taatattgca aaataacaat cagaagccaa   7200
actgaatatt gttatacgca aatagtgtag aagatatcct ctccctagac actctaatat   7260
tgtgtcattt atttggttgg gaaattgata ctgacctatc tattactaac atgtgataac   7320
aggagagagg atatctattg aggcttgtga catgccctaa tcttggaatg aagtattggt   7380
ctcattctgc tattacttaa taaagaaaga aagtgataaa gggaattaaa aatttgtggc   7440
caaggagatc ctttctccca ttgtttgctt aacttggttg agagtttgtt caagaattta   7500
ttcagggtgt tgatggggtt tagcatgagg tggtttattg tgattgtgta tttggtagtg   7560
tttcatctac aatttccaat tgctaaggat aaaaggaata tttttactcc gattgcaatt   7620
gatacaatct ggttatttgc tagaggattt ttaattgtgt tgtgtatctc caagtgtctg   7680
gggattttag ggatgaacat cacttaagtt ttgctgtgtg aaatgaactt tttttcttct   7740
ttgctttctt gatggtattt gtggattata aataaagtat tttcattacc tcacatcttg   7800
tatattttat atttttcttc atgcagaagt ccccttctga gtgtatatgc tgacatgtca   7860
gtaacttgca aggtagaaac cacttcatac atgttttgca ctgatttatt tcctcaaccc   7920
atgcaaaagt tgtggactgc atgtctaggt tagcatattc ctttatatat ttatatataa   7980
ctagggtcac ctaaatgagt tggagatagc gctttctgga taaacagtaa accctctcta   8040
caaattaatt cagttttcag acatttatat aatactcttg ttgtttgagg ctgaatttct   8100
```

-continued

```
tctgcatatg gtgatatcat caaatgttgg aatgttgttt gagtaactgt ttcactgtaa   8160
tgcaggaata ttatagccca aaccagtcaa tgttagagtt ggtttttgca ccagccgaag   8220
aatggatttc acgtagtgac gatgatatta ttcaagccac gatgactgag cttgccaaac   8280
tctttcctga tgaaatttct gcagaccaaa gcaaagctaa gattctcaag taccatgttg   8340
ttaaaacacc aaggtttgat tgaataccca cagagggtgg attatttctt ttagcttctt   8400
ttataaagat ggatttggaa tgtctttgtt gttacttaac taatagtgac atttgtgttc   8460
tgaatcctaa tggaactgac tacattgttt caggtcggtt tacaaaactg ttccaaattg   8520
tgaaccttgt cgacccattc aaagatctcc tatagaaggt ttctatttag ctggagatta   8580
cacaaaacaa aaatatttag cttcaatgga aggcgctgtt ctttctggga agctttgtgc   8640
acaggctatt gtacaggtaa aatctgacac aaaaatatct atgtaactcg cagcaataca   8700
ttagcaagaa atgtgataat ctatatatac atgctttctt ggtaattttg tgagagaaac   8760
ttgattgtga attcagcagg atgaataacg ctacattgtg ttgtggaaat catacactga   8820
agttctcagc ttttattcgt tgatttaatg aatctttcca ctttaatttt ttgattgaaa   8880
catttttatt aagttccaat catcctcaaa acttatgctg tctctgaatg attcttgtat   8940
gtatctccaa tgccccccctc atgcaaaaga ccttcggtta tgaacattat ttgaaattaa   9000
tatgaaagaa ttagcttaat gaggattgat cttctgcata ggttgatttg aatgtttttc   9060
taatcattgg tgtcattgag gctttttaaa aattatgcag gattctgagc tactagctac   9120
tcggggccag aaaagaatgg ctaaagcaag tgttgtgtaa caaaaacaag aattgaaaga   9180
gtcatggtag agtacaggag catcatttca actttggcat tctttgtctg tggtcaggac   9240
tcaggagacc ttcaacttta ttagttcata cgaataaaga aaggctcagc ttctgaaatt   9300
tagctcaccg tcgtcaactg tgtgcaataa gctatacgga acaaacgaca tgtgtcaact   9360
taaagtcagc ccattgtttt gttatcctcc aattttctgg atcaatgttt gtattggaaa   9420
gaaatatgtc attattcaaa cttgtttata tccacttttt ttatttatca acatttgtca   9480
caacctttcg ttgagtagca aattattccc agaaaggcac attacatata tatatatgca   9540
ttgtatatta cacacaatca tatatatatt tatacaaaat aacatataat aaatatcacc   9600
gacaaaatgg ttagttttat taacatgaca agctaaaatt tgaaatttag ttggtaaaga   9660
tacttctcac gtatagtgtt caattgtgtc ttgaattgtt tctcaagaag gatactttcg   9720
gaaacaaaat aaatgcaatg tatataataa tatatattaa cttatatagt tgcataatgt   9780
tataactgta tatattatcg ataagaaaaa ttgtatttaa cgtattatct tatatataaa   9840
tttataattt ttttgacata taaaattaaa ataattataa attaaaatta aaaaattaaa   9900
taaatagata ccaatttttt aagatatttg taagaataat actaaagata ataaaataaa   9960
aaaatttaaa cagaataaca aattatctaa atttgaagta aataaaataa cctaaatttt  10020
aaatagtacg agagtttatc atatttaaaa cttaagtaac ttttatatct tatcctatcc  10080
ttgactcacc aaaggatgga gtttcatgtg gtttcacatt tttggagtaa tgtatatttt  10140
gagattaatt atggtgagga atgaaggttg aaatatctat ggtgggccca tgtcacaaat  10200
cctgggaatt gggagacgaa ggaaacgcgt aacacgctct ctaagtctgt gcatggtcat  10260
tggtcagttt gtttcttgtg cctcaagtaa accctaagca ttaatacttg ctacttgcta  10320
tgcgcgtttc aatctgaaga agatgatggc tttggaggat ctccaatact tgtcgctcct  10380
ttctaaggtt tgcaccgagt tggagtccca caccggcacc gccgacaagg tcctcgccga  10440
```

```
attcatcacc gatttggcca gctcatcgga gaaccttcag gaattcaacg ccaagctcaa  10500

cgacaacggt gccgacatgc ctgattacct tgtccgaact ctcttcacca ttattcgctc  10560

cgttcttttc cccaacccta ca                                           10582


<210> SEQ ID NO 41
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: synthetic construct

<400> SEQUENCE: 41

gaagcaagag acguucuagg                                                 20


<210> SEQ ID NO 42
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: synthetic construct

<400> SEQUENCE: 42

gguugcugca uggaaagaca                                                 20


<210> SEQ ID NO 43
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: synthetic construct

<400> SEQUENCE: 43

ccauauguug aggcucaaga                                                 20


<210> SEQ ID NO 44
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: synthetic construct

<400> SEQUENCE: 44

gaucauauuc aguccuuggg                                                 20


<210> SEQ ID NO 45
<211> LENGTH: 6649
<212> TYPE: DNA
<213> ORGANISM: Triticum aestivum

<400> SEQUENCE: 45

gagcaaagtt cacagtggta tcaaggcata tgctcttccc aatctggacc atctcaccaa     60

cgatatcaac aacggtacct aatgcaagca ttctcaaagc agtcgtgcat ttctacaaag    120

gagtccgcaa caatccctct tgagcctgaa gtagggatca tgtgcctcca ctctgtccac    180
```

```
atcgtacaaa aacaagggtt tgcgcgtaag gaagcatcga cgaaaaaatg tattagggaa    240
tgttggtccg ggccgaaagt ggtccttata gagcaaccgt gcaccaacga ccctatcccg    300
gtttagaact ctcctccctt tgaccaaacg ttttgaaatt cagaatatgc tccacttccc    360
tctccatttc ctcctggatg ctggtcttca tcagcaactc aacatcttcg ttgtccgaat    420
ccaacgaatc aatgaactct tttgcaaatg aatgcaccaa gtccttgtct tgatactcct    480
catccgacga acccattgtt ttggctaaaa aaacccattg ttcgtgcagt ccggcaggca    540
ggactggaac cagaaagaag acgggccatg aaaacgtgtg aggtggccgc ggtatattcc    600
agggaaaacg tagagcgcac cagccgccaa aaggcatcct ccgccaccac atcttccccg    660
atttgtccct ttcgcaccac ccccaaaccc cccagccggc gacgagcctt atcccgcgcc    720
gtacataaag ctcccctcgc gcctggagtc tggactccct cccgtcccca cccgcctcgc    780
ctcgccgctg cgtccctctc ctcccccggc ggcggtaagt cgcctctccc atctgttatt    840
cccttcgccg gcgcgtttcc agtcccgcgg ttccgcgcga gcagagctcg ggcggcgggg    900
cgggcgttga ggattttcca agggtttaat tattgttcta cttcagatta gaggcgttga    960
atttcccgat cgaccgcgaa aatcatcacc gtatgctgcg tgcccgattt gcttaccgtg   1020
cagccagacc aggccttatt cgcccatttc atgtccttgt tctaactaat ctaaacgggc   1080
acaaccactc ctacatggaa acacacgggg tcttaggaat ttaaaacgaa ctctatgtca   1140
actgcagagt aaatggattg cctggacctg tcatatcttc atgcttttat ttatgctcat   1200
tttctctaaa tgaaggcaag accacaccac tttgagtgga ccaaattccg tgtcatttgg   1260
cttctaggca gattgtggct tttgtttacc caagttactg caatctggat cgattgaatc   1320
gcgacacaac ttggttgact tgataacaga gggcctcatg agctgcgagt ttaattgctc   1380
ttcttggtta tgcagttttc ttccgcgccc attggtcaaa taaggttgac aagaatctca   1440
cactgcttgc ttcagtatgg ataccagctg cctatcatct atcaacatag ctggagcgaa   1500
gcaagtaaga tcttttgccg gacaacttca tacacagagg tgcttcacaa gcagcagtgt   1560
ccaggcacta aaaaccagtc accgtacgac ctcccttggc ttaaggaata aagtaaaagg   1620
atcacgccgt ggacttcgtg ctctgcaggt taatattttg cctgtgtttc tattttgcgg   1680
aaaagcttat tgtttgtttt atctccccat agcatttctt gtcaaataat tgcttgcctt   1740
ctttgcaggt tgtttgccaa gattttccaa ggcctccact agagaacacg attaactatt   1800
tggaagctgg ccagctttct tcgtcgttta gaagcagtga acgccccagt aaaccattac   1860
aggtcgtgat tgctggtgca ggtctgaagt ctgatgtaac tccaaaattt aaacatgtat   1920
actttttcgc acaccagata cccttgagtg aatcaccatt gcctcttagc gttactagtt   1980
tctggtgtga actttgcagg attggctggt ctatcaactg caaagtacct ggcagatgct   2040
ggccataaac ccatagtgct tgaggcaaga gatgtgttgg gcggaaaggt ctgatcatta   2100
cttacatact tgcttatctc aattctaaaa ttgtgctcct tatgtgatct taattttcat   2160
ttattgtctt cagccttgtt tcttattatt tctatcgttg tatgccttga acagttagct   2220
gcatggaagg atgaagatgg tgattggtac gagactggcc ttcatatttt ttgtaagctc   2280
tggttctggc tctggttctt cgaggttatg tttgtgcttc tgtgtgttat ctaggttatt   2340
tccattacca gtgtataggt agatgtttca gacaaatatg ataaaacacc ttgagtgaag   2400
tacgaactga tctctgagga gtcatgttca ggtactgaaa ttgcaaaaaa gaaggaaagt   2460
gttttgttct gtcaactttt attgttgttt gaatttctac cagatgggcc ttactttttt   2520
```

-continued

```
tttaataata tttttagtgg actttatgca tggccattat taagaaatga attcttccgg   2580
aagtaaagat cggtcccaaa ctcttttaag cctggaagtt tgtacactaa tatcacatac   2640
aatagcttag attttaatgt tccatacggc ctggttggcc tggttgaata gtttcttttt   2700
atctataatt ttttcttcta ccagccttct cttcccttcc aatagcatgt gtacgatagt   2760
acgatacttt tcattctgtg catatatgta accatatgtt tttttctttt cagttggagc   2820
ttatcccaat gtacagaatt tgtttgctga gcttggtatt agtgatcgct tgcaatggaa   2880
ggaacactcc atgatatttg ccatgccaaa caaaccagga gaatacagcc gttttgattt   2940
tccagagact ttgccggcgc ccttaaatgg taaggttata catagccctg gtgttgctca   3000
atagaagaaa gaatgccaag aaaactcaga aatgcatcct agtgttagtt ctttaagtgc   3060
taatatatga atcaactagt gggtttatta gtaaatataa acaagtttga tcatggctgt   3120
tgagctactc tgccaatcaa tgtcaggtta tcgttgacaa tgcatgcatt taacaggagt   3180
gtgggccata ctgaaaaaca atgaaatgct tacttggccg gagaaggtga agtttgctat   3240
tgggcttcta cctgcaatgc ttggtggcca agcttacgtt gaagctcaag atggcttaac   3300
tgtttcagaa tggatggaaa agcaggtatg agctcactgt gtcatttaga ttcgtcactg   3360
tagtaaacat attgcaatct ctatgaggct acattgtaac gagaaaatat gtgtttgcta   3420
atacattggt gccttttatt gtcatattct ttggtccata aatgctcaag cttccatctt   3480
tcatcttcaa ccaagccctt ttgtatgcaa atttaggctt aaacaatgct tgtagtttta   3540
tgaatctttc aagttaaatc ccaagtgtgc agacgaagag aatgcaggtt cttctttgtt   3600
aattaataca cagcaggttc acctttctta tttgtactaa aatgttgata accagcgtca   3660
attaatatgg attggtggga gtattttctt tcttttgttg tcccagtaaa tgagtcaata   3720
cagtttctga tacagttatt taatcagcac agggtgttcc tgatcgggtc aacgacgagg   3780
tttttattgc aatgtccaag gcactcaatt tcataaaccc tgacgagtta tccatgcagt   3840
gcattctgat tgctctaaac cgatttctcc aggtacaact tcatttcctc tattcctact   3900
gtagacatag ttgacatatt ctgtccttta ttacctttag aagatacaaa cattcgttca   3960
cacaatcaca ccataatgac aacttggggg tattacttaa tgaaaaaact gtgtaaatgt   4020
gtaggagaag catggctcga aaatggcatt cttggatggt aatcctcctg aaaggctatg   4080
catgcctatt gttaaccaca ttcagtcttt gggtggtgag gtccggctga attctcgtat   4140
tcagaaaatt gaactgaacc cggacggaac agtgaagcac tttgcactta ctgatgggac   4200
tcaaataact ggagatgcat atgtttttgc agcaccaggt gcgatttatt ttcaagaatc   4260
atgcttcctt tgcacctatt cagtttaact gactagcttg tgattcagtt gatatcttca   4320
agcttcttgt accacaagag tggagagaga tctcttattt caaaaggctg gataagttgg   4380
tgggagttcc tgtcatcaat gttcatatat ggttagttga tttaaagggt tgtaagttac   4440
gacgtcattt atgtgctgtg gttctacttg tgcccgtgtg ctccatgaat ttttgaaata   4500
cctcttagtg tttctgttga tttgaatatt tcaggtttga cagaaaactg aaaaacacgt   4560
atgaccacct tcttttcagc aggtatgtct tttggtcata ctgatcttat tgttgacgcc   4620
taatgaattt gttgtccagt attcagattg ggtgcattct ttcctactcc atgtttgaat   4680
tcttggttga tactgtactg aataacatat gtcccttaca atatattgat ctttctgttt   4740
caggagttca cttttaagcg tttatgcaga catgtcttta gcgtgcaagg tactaacttg   4800
acgatttagg cttagtttgc agttcacttc taagtattgc atgcgggtta accttaattt   4860
atatttcact atgaacaaat gccccaaagt ctatacgcct atgtaaaaaa tatgcatgtg   4920
```

```
ccgcagaagg aattcattat taaactaata attactgctg gcattgcaaa ttttagttat   4980

ctcaaagaat gaagtatggc atccttttgt cattgctgac atgtcagttg actgctgatt   5040

tattaatcgt aattgctttt tttcctataa taatatcgta atagcttagg acaaagaacc   5100

aaggacatga acgcatactc atcgtttcat tttcatattc ttttctaact gtttacagga   5160

gtactatgat ccaaaccgtt caatgctgga gctggtcttt gctccagcag aggaatggat   5220

cgggcggagt gacaccgaaa tcatcgaagc aactatgcta gagctagcca agttgtttcc   5280

tgatgaaatc gctgctgacc agagtaaagc aaagattctt aaataccatg ttgtgaagac   5340

accgaggtca ggacatttcc ctaacaccct tcctgataaa gtgatggcta ataaaagagg   5400

cggctttgat gtgcccttct tctcttacat ggtttattac acttcctggc tcgctgttac   5460

aggtccgttt acaagactgt cccgaactgc gaaccttgcc gacccctgca acgatcaccg   5520

atcgaagggt tctatctggc cggcgattac acaaagcaga aatacctggc ttccatggag   5580

ggtgcggttt tgtcagggaa gttttgtgct cagtccatag tgcaggtaaa tgctctctcc   5640

attgtattgg gtgttgatag atgcataaaa cttgtacgct gttgtcttgg tgcatcacgg   5700

cgcgtcatta tcgtagtcta atatgttatc gcgtttctgc tcgcaggatt ctaagatgct   5760

gtcccgcagg agccaggaga gcctgcaatc cgaagccccg gtcgcctcca agttgtagct   5820

agttagcgcg attcaaaatt tttttggcgt ttcctatatg tcattgtcac attgttgtag   5880

agtccaccag tgaattgagc tgacatccat attggaacta aaagggaaat ttgtaaaaca   5940

aagaagacct tttgcagaag ggcaaaagtg ataaaaggaa tcttagatat cattatcttg   6000

tttgctgttg gaaactgaac cggtaaccgt aaccgattgc ttttcatgtt ccctggagta   6060

atcttctata tctaaatagc tagtccccat taacatattt atctcaacat gcaagcatgc   6120

cacctcatta ttcaacatgc ataaggaaag acccacctca acatgcaact attcatatta   6180

aaaatccact acaacatgca tgcatgtaaa atttcatttt attatgctat ttacatttaa   6240

ttcttatata ctttcaaaaa ctattgtttt aagaattcat gtttcatata attaaaatct   6300

cattgaaata ttgcaaacat tcccgaaaca acgtgcgggg catcatctag taaaacccaa   6360

ggcttgtgcc agcaacggag aagaaaagca tggacaatat cctaatgata acttcttttt   6420

tgggtgcgga gagaaatcct gatgatatct actccttccg ttccataatg taagacgttt   6480

tttgatacta cactagtata aaaaaatatc ttatattatg gaacggaggg agtaaggtca   6540

gctgcaattt tcaaaagagg gcatacagac tattagtctc tcaagatatt ccttgtgggc   6600

ccctcaataa ttgtacttgt gagatatttc ctgtggcata tcaacagga               6649
```

<210> SEQ ID NO 46
<211> LENGTH: 7152
<212> TYPE: DNA
<213> ORGANISM: Triticum aestivum

<400> SEQUENCE: 46

```
tgttgaatga aaaactttta tagtgtctgt tctgaccata aaattgatct gaaaccgtaa     60

actcgccgga acttacaggt ttggcgtttt taaggggtct gctagagatg ctttaagagt    120

tcgccttgga gatggcctaa aggctctcgt cgctacgaga gaattctccg cgacagcgac    180

caaacaacca tgttcgtgca acgcgaacca acctgtggtt ggatggttag agggactgtg    240

gtatccccag ctcattagga ttcaaatcct ggtgctcgca tttatttctg aatttatttc    300

agaatttccg acgatgcaca tccagtggga ggagacgttc ccgtcgacga cgaggtgcct    360
```

```
acggtgactt tgtaaatttc aagatgatat gccgacttat ttcttcggag gtgcttatag    420
gggtagggta tgcgtgtgta cgatcatatg agtgagtata tgcgcgtgta tatgagcgct    480
tgcgtctgta ctgtgtaaaa aaaaaaatgt tcgtgcaact ccgcacaggc caggcacgat    540
gcgtccggtc gaaccagaag acaggccatg aaaacgtgtg aggtggccgc ggtatattcc    600
acggaaaacg tagagcgcac caggcgccaa aaggcatcct ccgccaccac atcttcctcg    660
cctcagtgac tccccccgcc tttgtccctt tccccccgcc ccagccggcg acgagcctta    720
tcccgcgccg gacataaagc ccctcccctc gcgactccct cctccctctt cccatccgcc    780
tcgccgctcg gtccatctcc tccgccctcc tccggtaagt ctcccctccc cgcacgaggc    840
agccaggcgg ctttactccg tcattccctt gcgccggcgc ggctccagtt cccccgttta    900
gcggaatcct cgcgccgctg cctagaatcc gcgcggcaag cgttgggtag cagccccgga    960
gttggggatt ttctcggggt ttattatact tcagattaga ttagaggcgt cggaactccc   1020
gatcgactgc gaaaatcagc cgtagacttc accgggcgga tgctgcgtgc ttgatttgct   1080
caccctgcag ccacacccca ttcgcccatt tcatgctttg gttcaacaag ttactacaat   1140
caactcatgt ttctgctgca aaataagtga tggatcatgt ggagctctca tatctatagt   1200
tgacacagct gccctgatcc ttttctctac acttttattc tcatctcctc aactgaaaga   1260
ccgctccact ctcaatggac aaaattctct gtcatttggc tctcggcaaa ttgtgacttg   1320
ttatggcagt ctgaatcgat tgacctgtta caacacttgg cttaatagca gagggcctcg   1380
tgagctacga gtctaattgc tcttcttgat tatgcagatt tctcctgcgc ctgttggttg   1440
aataaggttg acaagaatct gccggactac ttgcttcagt atggatacca gctgcctatc   1500
atctatgaac atagctggag cgaagcaagt aagatctttt gctggacaac ttcatacgca   1560
gaggtgtttc acaagtagca gcgtccaggc actaaaaact agtcatcgta cgacctccct   1620
tggcttaagg aataaagtaa aaggatcacg tcatggactt cgtgctctgc aggttaatct   1680
tttgcctctg tttctatttt tggaaaagcc tattcgttat tttatctccc catagcattt   1740
cttgtcaaat aattgcttgc cttctttgca ggttgtttgc caagattttc caaggcctcc   1800
actagagaac acgattaact atttggaagc tggccagctt tcttcgtcgt ttagaagcag   1860
tgaacgcccc agtaaaccat tacaggtcgt gattgctggt gcaggtctga agtctgatgt   1920
aactcgaaaa ttagaacatg tataattttt cacacaccag ataaccttga gagaatcacc   1980
attgcctctt agcattacta gtttctggtg tgaattttgc aggactggct ggtctatcaa   2040
ctgcaaaata cctggcagac gctggccaca aacccatagt gcttgaggca agagatgtgt   2100
tgggcggaaa ggtctgatcg ttgcttacat acttgcttat ctcatctcta aagttgtgct   2160
cgttatgtga tcttaatttt catttattgt cttcagccta agtagctcat attcactgtt   2220
atcgttgttg tttcttattg tttctatcgt tgtatgcctt gaacagttag ctgcatggaa   2280
ggatgaagat ggtgattggt acgagactgg ccttcatatt ttttgtaagc tctggttctg   2340
gttcttcaag gttctctttg tgcttctgtg tgttatctag gttacttcca ttaccagtgt   2400
ataggtagat gtttcagaca aatatgataa aacaccttga gtgaagtacg aactgatctc   2460
tgaggagtca tgttcaggtt ctgaaatcgc aaaaagaagg aaagtgtttc gttctgtcaa   2520
ctattatttt tgtttgaatt tctactagat gggccttatt taaaagaaat gtttttagtg   2580
gactttatgc atggccatta ttaagaaagg aattcttgcc gaagtaaaat cggtcccaaa   2640
ctcttttaag cctggaagtt tgtacactaa catcacatac aatagtttag attttaatgt   2700
tccatacggc atggttggct tggttgaata gtttcttttt atctataaat ttttcttcta   2760
```

```
ccagccttct ctttccttct aatagcatgt gtacgatact tttcattctg tgcatatatg   2820
taaccatatg ttttttcttt tcagttggag cttatcccaa tgtacagaat ttgtttgctg   2880
agcttggtat tagtgatcgc ttgcaatgga aggaacactc catgatattt gccatgccaa   2940
acaaaccagg agaatacagc cgttttgatt tcccagagac tttgccggcg cccttaaatg   3000
gtaaggttat acatagtcct ggtgttgctc aatagaagaa agaatgccaa gagaactcag   3060
aaatgcatcc tagtgttagt tcttttaagt gctaatatgt gaatcaacta gtgggtcaat   3120
tagtaaatac aaacaactat gatcatggct gttgagctac tctgccaatc aatatcaggt   3180
tatcattgac tatgcatgca tttaacagga gtgtgggcca tactgaaaaa caatgaaatg   3240
cttacttggc cggagaaggt gaagtttgct attgggcttc taccagcaat gcttggtggc   3300
caagcttacg ttgaagctca agatggctta actgtttccg aatggatgga aaagcaggta   3360
tgagctcact gtgtcattta gcctcgtcac tgtagtaaac atattgcaat ctctatgagg   3420
ctaggttgta acgaggtttt gtttgctaat acatttctgc cttttattgt catattcttt   3480
ggtcctatgc tcaagcttcc atctttcatc ttcaaccaag ccctttgta tgcaaattag    3540
gcttaagcaa tgcttatagt tttatgaatc tttcaagtta aatcccaagt gagcaaacga   3600
agagaatgca ggttcttatt tgctaattaa tgcacagcag gttcaccttt cttatttgaa   3660
ctaaaatgtt gataagtgct attttctttc ttttgttgtt ctcagtaatt gagtcaatac   3720
agtttctgat acagttattt aatcagcaca gggtgttcct gatcgagtca acgacgaggt   3780
ttttattgca atgtccaagg cactgaattt cataaaccct gacgagttat ccatgcagtg   3840
cattctgatt gctctaaaca gatttctcca ggtacaactt cagttcctct attcctcctg   3900
aagacataga tgacatattc tgtcctttat tacctttaga agatgcaagc attcattcac   3960
acaatcacac cataataaca acttgggggc attacttaat gaaaaaactg taaatgtgta   4020
ggagaagcat ggctcgaaaa tggcattctt ggatggtaat cctcctgaaa ggctatgcat   4080
gcctattgtt aaccacattc agtctttggg tggtgaggtc cggctgaatt ctcgtattca   4140
gaaaattgaa ctgaaccctg acggaacagt gaagcacttt gcacttactg atgggactca   4200
aataactgga gatgcatatg tttttgcagc accaggtgcg atttattttc aagaatcatg   4260
cttcctttgc acctattcag tttaactgac tagcttgtga ttcagttgat atcttcaagc   4320
ttcttgtacc acaagagtgg agagagatct cttatttcaa aaggctggat aagttggtgg   4380
gagttcctgt catcaatgtt catatatggt tagttgattt aaatgtttgg ttgtaagtta   4440
agacgtcatt tatgtgttgt ggttctactt gtgcccgtgt gccccatgaa tttttgaaat   4500
acctcttagt gtttctgttg atttgaatat ttcaggtttg acagaaaact gaagaacacg   4560
tatgaccacc ttcttttcag caggtatgtc ttttggtcat actgatctta ttgttgacgc   4620
ctaatgaata tgttgtccag tattcaaatt gggtgcattc tttcctactc catgtttgaa   4680
ttcttggttg atactgtact aaataacata tgtcccttac aatatatcaa tctttctgtt   4740
tcaggagttc acttttaagc gtttatgcag acatgtcttt agcgtgcaag gtactaactt   4800
gatgatttag gcttagtttg cagttcactt ctaagtattg cacgtgggtt aacctgaatt   4860
tatatttcac tatgaccaaa tgccccaaag tctatacgcc tatgtaaaaa atatgcatgt   4920
gccgcagaag gaattcatta ttaaactaat aattactgtt ggcattgcaa attttagtta   4980
tcttaaagaa tgaagtatgg catccttttg tcattgctga catgtcagtt gactgctgat   5040
ttattaatcg taattgtttt ttttcctctg atgataataa ccgtaatagc ttaggaaaaa   5100
```

```
gaatgaagga catgaactag tactcatcct ttctctttct ttttcttttc taactgttta   5160
caggagtact atgatccaaa ccgttcgatg ctggagttgg tttttgctcc agcagaggaa   5220
tggatcggac ggagtgacac cgaaatcatc gaagcaacta tgctagagct agccaagttg   5280
tttcctgatg aaatcgctgc tgaccagagt aaagcaaaga ttcttaaata ccatgttgtg   5340
aagacaccga ggtcaggaca tttccctgac acccttcctg ataaagtgat aactaatcaa   5400
gaggcggctt tgatgcgctc ttcttctctt acatggttta cacttcctgg ctcgctgtta   5460
caggtccgtt tacaagaccg tcccgaattg cgaaccttgc cgacctctgc aacgatcacc   5520
gatcgaaggg ttttatctgg ccggcgatta cacaaagcag aaatacttgg cttccatgga   5580
gggtgcggtt ttgtcaggaa agttttgtgc tcagtccata gtgcaggtaa atgctctctc   5640
cgttgtattg ggcgttcata gatgcatcaa acttgtacgc tgttgtcttc gtgcatcacg   5700
gtgccccgtt atcatagtct aatatgctat cgcgtttctg ctcgcaggat tctaagatgc   5760
tgtcccgcag gagccaggag agcctgcaat ccgaagcccc cgtcgcctcc aagttgtagc   5820
tagttagcgc gattcaattt tttttagcgt ttcctatatg tcattgtcac attgttgtag   5880
agtccaccag tgaattgagc tgacagccac atattgggac aaaaagggag atttgtaaaa   5940
caaagaagac cttttgcaga agggcaaaag tgataaaggg atcttagata ttattatctt   6000
gtttgcagtt ggaaaccgaa gcagtaaccg tggccgattg ctttttcatg tcccctggag   6060
taaaacccaa gtcaaggttt gtgtgtgcga aggagaagaa agcatggaca atatcctaac   6120
gatatctaag atcttttgtc tgcttggata tattgatggg cttggtcagc tgcaattttc   6180
agaagggtgt gtgtacaggc tggattagtc tctcaagata ttccttgtgg gcccctcaat   6240
aattgtactt gtgagatatt tcctgtggta ggtatgtcaa caggagatcg actcaaaaaa   6300
aaatcatcag gagatagtac tccctccgtt cctaaatata agtcttttta gacatttcaa   6360
atgaactaca gcatatggat gtatgtagac atattttaaa gtatagattc attcattttg   6420
ctccgtatgt agtcatttgt tgaaatcttt aaaaagactt atatttggga acggagatgg   6480
tagtactggc aggctagtag gccatacata tatctgaggt gctagtaggg catatcattt   6540
tatttttcct tttcaaaaag ggcggatcat atctcgtggc atgggtcttc gctagctgta   6600
tgagattgtc tggaatggat gttccattcc atgtgggctg tagctcaagc cttcttgttg   6660
tggataatga ctgaacaaaa gcatccaaaa ttcaaaagga aggagaaaaa tcccactccg   6720
tgattagata ttatgaggag aattatctga ggcccgaatg cttgcattag gcttcggtac   6780
gtgattcatg gtaggagggc atgttagagt acgggcgccc gtcaagacta ggcctatcac   6840
ggtgcacatt cgtacacgta cgtagctcca tattatgaca acgatattta ccggcaaaaa   6900
caagatgtca tacaatgtac tccctccatt cctaattata agtcctttta gagattttaa   6960
tatgaactac atacggcgca aaatgaatga atctacattc taaactacgt ctatatgcat   7020
ctgtatgtac tccctccgtt cggaattact cgtccaaaaa atgaatgtat ctagacgtgt   7080
tttagttgta gatacattca tttttgtgat aagtaattcc gaacggaggg agtagttgaa   7140
atatctgaaa ag                                                       7152
```

<210> SEQ ID NO 47
<211> LENGTH: 6716
<212> TYPE: DNA
<213> ORGANISM: Triticum aestivum

<400> SEQUENCE: 47

```
gcaaagtgta ggacgggagg agcgggactt accacggcgg cgtccggggc ggcgaaaatg     60
```

```
acagtgagga gttccgtgac ggtggtggaa ccactgtgga gccggaacga cgtcggggca    120
agggtgacga cgaagctagt ggagggccgg ctgggacgat ggagaagaga ggagacgaaa    180
atggcaggtt tggctaggtc gggggcgatt taatgaaatt tgcagtggat cctgtatgtc    240
tgatccgatg tgtcgaaagc gtccgggcgc gtttagggct ccccatattt gccctgagtt    300
ttgatatgag ggtgtcagt  tcggacgtat agggccagtt tgagagggcc gtccatgtca    360
cgattttccg gctaatgctc caaggtcatt cgaccgcaaa aaaacactcg gacgcgctag    420
tccaaacgtt caggggcgat tttgtgacgt gcaatggagt tgccctgaac gccctcgttg    480
gtgctacgag agaattctcg tggacagcca ccaaacaacc atgttggtgc aactcctgca    540
ggccaaagaa gacaggccct gaaaacgtgt gaggtggccg cggtatattc cacgggaaac    600
gtagagcgca ccacgcgcca aaaggcatcc tccgccacca catcttcctc gcctcagcga    660
ctcccccagc tttgtccctt cccccccgcc ccaggccagg ccaaaccccc aaccggcgac    720
gagccttatc ccgcgccgtg cataaagctc ccccgtgccc ctcccctcgc gcctggactc    780
tggactccct ccgcctcgcc gctccgcccc tctcctccgc ccccctggtg gtaagtctcc    840
cctccccgca cgaggcagcc aggcggcttt accctgccat tccctttgcg ccggcgcggc    900
tccagttccc ccgtttagcg cactgctacc aataatccgc gcggcaagcg ttggggcggg    960
gtgggtagca gcccagccct ggagttgggg attttctggg ggtttattat actttaggtt   1020
cgattagagg cggtgaaatt cccgatcgac cgcgaaaatc ggccctagac ttcaccggat   1080
ggatgctgcg tgcttgattt gctcaccctg cagccacacc ccattcgccc atttcatgta   1140
ttaggaaata aatggatcgt ttggagctct catatctgca gttgatgata cggctgccct   1200
catccttttc tctacacttc tattctcatc tcctcaattg aaaaaccgct ccactctaaa   1260
tggatggaat cctgtcattt ggctctcggc aaattgtgac ttgttatggc agtccgaatc   1320
gattggcttg ttacacagct tgtcttaata gcggagggcc tcatgagcta ccagtctaat   1380
tgctcttctt gattatgcag atttctcctg cgcctgttgg ttgaatataa ggttgacaag   1440
aatctgccag tgtacttgct tcagtatgga caccggctgt ctatcgtcta tgaacatagc   1500
tggagcaaag caagtaagat cttttgctgg gcaacttcat acacagaggt gcttcacaag   1560
cagcagtgtc caagcactaa aaactagcca tcgtacgacc tttagttcga cttcccctgg   1620
cttaaggaat aaaggaaaag gatcacgacg tggacttcgt gctctgcagg ttaagatttt   1680
gcctctgttt ctattttcgg aaaagcctat tcgttatttc atctccccat agcatatttc   1740
tcatgaaata attgtttgcc ccttttgcag gttgtttgcc aagattttcc aaggcctcca   1800
ctagagaaca caattaacta tttggaagct ggccagcttt cttcgtcgtt tagaagcagt   1860
gaacgcccca gtaaaccatt acaggtcgtg attgctggtg caggtctgaa gtctgatgta   1920
actccaaaat ttaaacatgt ataatttttc gcacaccaga taccccttgag agaatcacca   1980
ttgcctctta gcgttactag tttctggtgt gaattttgca ggattggctg gtctatcaac   2040
tgcaaagtac ctggcagatg ctggccataa acccatagtg cttgaggcaa gagatgtgtt   2100
gggcggaaag gtctgatcat tacttacata cttgcttatc tcatctctaa aattgtgctc   2160
gttatgtgat cttaattttc atttattgtc ttcagccttg tttcttattg tttctatcgt   2220
tgtatgcctt gaacagttag ctgcatggaa ggatgaagat ggtgattggt acgagactgg   2280
ccttcatatt ttttgtaagc tctggttctg gttctttgag gttctctttc tgcttctgtg   2340
tgttatctag gttacttcca ttaccagtgt ataggtagat gtttcagaca aatatgataa   2400
```

-continued

```
aacaccttga gtgaagtaca aactgatctc tgaggagtca tgttcaggtt ctgaaactgc   2460
aaaaaagaag gaaagtgttt cattctgtca actattattt ttgtttgaat ttctactagg   2520
tgggccttat tttaaaaaaa gtgtttttag tggactttat gcatggccat tattaagaaa   2580
ggaattcttg cggaagtaaa gatcggtccc aaactctttt aagcctggaa gtttgtacac   2640
gaacatcaca tacattagtt tagattttaa tgttccatac ggcatggttg gcttggttga   2700
atagtttctt tttgtctata aatttttctt ctaccagcct tctctttcct tctaatagca   2760
tgtgtatgat acttttcatt ctgtgcatat atgtaagtat gtaaccatat gtttttcttt   2820
tcagttggag cttatcccaa tgtgcagaat ttgtttgctg agcttggtat tagtgatcgc   2880
ttgcaatgga aggaacactc catgatattt gccatgccaa acaaaccagg agaatacagc   2940
cgttttgatt tcccagagac tttgccggcg cccttaaatg gtaaggttat acatagccct   3000
ggttttgctc aatagaagaa agaatgccaa gagaactcag aaatgcatcc tagtgttagt   3060
tctttaagtg ctaatatatg aatcaactag tgggtcaatt agtaaataca aacaagtttg   3120
atcatggctg tagagctact ctgccaatca atgtcaggtt atcgttgact atgcatgcat   3180
ttaacaggag tgtgggccat actgaaaaac aatgaaatgc ttacttggcc ggagaaggtg   3240
aagtttgcta ttgggcttct acctgcaatg cttggtggcc aagcttacgt tgaagctcaa   3300
gatggcttaa ctgtttcaga atggatggaa aagcaggtat gagctcactg tgtcatttag   3360
attcgtcact gcagtaaaca tattgcaatc tctatgaggc tacgttgtaa caagaaaata   3420
tttgtttgct aatccattgc tgccttctat tgtcatattc tttggtccat aaatgctcaa   3480
gcttccatct ttcatcttca accaagccct tttgtatgca aatttaggct taaacaatgc   3540
ttgtagtttt atgaatcttt caagttaaat cccaagtgag caaacgaaga gaatgtaggt   3600
tcttctttgt taattattac acagcaggtt cacctttctt atttgtacta aaatgttgat   3660
gaccagcgtc aattaatatg gatcggaggg agtattttct ttcttttgtt ctcagtaaat   3720
gagtcaatac agtttctgat acagttattt aatcagcaca gggtgttcct gatcgagtca   3780
acgacgaggt ttttattgca atgtccaagg cactcaattt cataaaccct gacgagttat   3840
ccatgcagtg catcctgatt gctctaaacc gatttctcca ggtacaactt catttcctct   3900
attcctcctg gagacatagt tgacatattc tgtcctttat tacctttaga agatacaaac   3960
attcgttgac acaatcacac cataacgaca acttaggggt attacttaat gaaaaaactg   4020
tgtaaatgtg taggagaagc atggctcgaa aatggcattc ttggatggta atcctcctga   4080
aaggctatgc atgcctattg ttaaccacat tcagtctttg ggtggtgagg tccggctgaa   4140
ttctcgtatt cagaaaattg aactgaaccc tgacggaact gtgaagcact ttgcacttac   4200
tgatgggact caaataactg gagatgcata tgtttgtgca gcaccaggtg cgatttattt   4260
tcaagaatca tgcttccttt gcacctattc agtttaactg actagcttgt gattcagtcg   4320
atatcttcaa gcttcttgta ccacaagagt ggagagagat ctcttatttc aaaaggctgg   4380
ataagttggt gggagttcct gtcatcaatg ttcatatatg gttagttgat ttaaatgttt   4440
ggttctaagt taacacgcca tttatgtgtt gtggttctac ttgtggccgt gtgccccatg   4500
aatttttgaa atacctctta gtgtttctgt tgatttttgg atatttcagg tttgacagaa   4560
aactgaaaaa cacgtatgac caccttcttt tcagcaggta tgtcttttgg tcatactgat   4620
cttattgttg acgcctaatg aatttgttgt ccagtattca aattgggtgc attctttcct   4680
actccatgtt tgaattcttg gttgatactg tactatataa catatgtccc ttacaatata   4740
ttgatctttc tgtttcagga gttcactttt aagcgtttat gcagacatgt ctttagcgtg   4800
```

```
caaggtacta acttgacgat ttatgcttag tttgcagttc acttctaagt attgcatgcg   4860
ggttaacctg aatttatatt tcactatgac caaatgcccc aaagtctata cgcctatgta   4920
aaaaatatgc atgtgccgca gaaggacttc attattaaac taataattac tgttggcatt   4980
gcaaatttta gttatctcaa agaatgaagt atggcatcct tttgtcattg ctgacatgtc   5040
agttgactgc tgatttatta atcgtaattg ctttttttcct ataataatac cgtaatagct   5100
taggacaaag aaccaaggac atgaacacat actcatcgtt tctctttcct tttcttttct   5160
aactgtttac aggagtacta tgatccaaac cgttcaatgc tggagttggt ctttgctcca   5220
gcagaggaat ggatcgggcg gagtgacacc gaaatcatcg aagcaactat gctcgagcta   5280
gccaagttgt ttcctgatga aatcgctgct gaccagagta aagcaaagat tcttaaatac   5340
catgttgtga agacaccgag gtcaggacat ttccctgaca cccttcctga taaagtgata   5400
actaatcaaa aggaggcttg ttgtgctctt cttctcttac aaaccttaca cttttctggc   5460
tcgctgttac aggtccgttt acaagaccgt gccgaattgc gaaccttgcc gaccactgca   5520
acgatcaccg atcgaagggt tctatctggc cggcgattac acaaagcaga aatacttggc   5580
ttccatggag ggtgcggttt tgtcaggaaa gttttgtgct cagtccatag tgcaggtaaa   5640
tgctctctcc tgttctggtt ctttgtgcat cgcgggtgcg gccattatcg tagtctaata   5700
tgctatcgtg tttctgctcg caggattcta agatgctgtc ccgcaggagc caggagagcc   5760
tgcaatccga agcccccgtg gcttcccagt tgtagctagc tagcgcgatt caattgttta   5820
gcattttcta tgtgtcattg tcacattgtt gtagagtcca ccagtgaatt gagctgacaa   5880
ccatactgga acaaaaagga gatttgtaaa acaaagaaga actttgcaga agggcaaaag   5940
tgataaaggg atcttagata tcattatctt gtttgcagtt ggaaaccgaa gcagtaaccg   6000
attgctttcc atgttccctg gagtaaaacc caaggtttgt gccagtaacg gagaagaaag   6060
catggacaat atcctaatga taacttttta tttggagaga gaaatctttt tttttggaa    6120
aaggaggaat ggccccggcc tctgcatcag aaagatgtgt tcggagagaa aaatcttgat   6180
gatatttttt tgaggaaaat cctgatgata tctaagctgc gtggatatat tgatgggctt   6240
ggtcagctgc aattttcaaa agagggtgtg tagaaactgg attagtctct caagatattc   6300
cttgtggacc cctcaataat tgtcttttga gatatttcct gtggtaggta catcaacagg   6360
agatatatgg tagtactgct aggccatgca tatctgagct gccagtaggc catatcattt   6420
tatttttcct tttcgaaaga ggcggatcat atcctctcct gccatggctt tgctagctgt   6480
atgagatcgt ctggagagga tgttccattc cgtctgggct gtagctcaag ccttcctgtt   6540
gtggataatg actgaacaaa ggcatccaaa aattcaaaaa agaagaagat aaaaatccta   6600
ctccatgatt agatattatg aagagaatta tctgaaacct gaatgcttgc attaggtttg   6660
gctacgcgat tcatagcaac ggcgtggtaa gaggacatgt tagagtacgg gcggcc       6716
```

```
<210> SEQ ID NO 48
<211> LENGTH: 9453
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: synthetic construct

<400> SEQUENCE: 48

tcgcgcgttt cggtgatgac ggtgaaaacc tctgacacat gcagctcccg gagacggtca     60
```

```
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt ggagatcggt acttcgcgaa    420
tgcgtcgaga tgggtcccgt atcatatgtc ttattcttct tgagcacagt tattacagca    480
gattttgtag aatagttatc gcatcaaaat tttcctatgt cacctttgat catgtgttat    540
gtgtgcctct tgagtcttag ggttaatgtg gttgtaatgt gtttaaaaaa ctatatgaaa    600
gctcgtgtgt tgctacggga gagagatacc tcgaatgaat gtgagagatc tccatttgag    660
ttgtgtacct tgagagagtg aaagatcaca ctatttatag acggttaata atggttactg    720
aggtcgattc accacatcgt cttaaacatt taatgagcat cctccacgtg aaaagtagag    780
atgatagcgt gtaagagtgg ttcggccgat atccctcagc cgcctttcac tatctttttt    840
gcccgagtca ttgtcatgtg aaccttggca tgtataatcg gtgaattgcg tcgattttcc    900
tcttataggt gggccaatga atccgtgtga tcgcgtctga ttggctagag atatgtttct    960
tccttgttgg atgtattttc atacataatc atatgcatac aaatatttca ttacacttta   1020
tagaaatggt cagtaataaa ccctatcact atgtctggtg tttcatttta tttgctttta   1080
aacgaaaatt gacttcctga ttcaatattt aaggatcgtc aacggtgtgc agttactaaa   1140
ttctggtttg taggaactat agtaaactat tcaagtcttc acttattgtg cactcacctc   1200
tcgccacatc accacagatg ttattcacgt cttaaatttg aactacacat catattgaca   1260
caatattttt tttaaataag cgattaaaac ctagcctcta tgtcaacaat ggtgtacata   1320
accagcgaag tttagggagt aaaaaacatc gccttacaca aagttcgctt taaaaaataa   1380
agagtaaatt ttactttgga ccacccttca accaatgttt cactttagaa cgagtaattt   1440
tattattgtc actttggacc accctcaaat ctttttttcca tctacatcca atttatcatg   1500
tcaaagaaat ggtctacata cagctaagga gatttatcga cgaatagtag ctagcataag   1560
taggctgacg ccgaggatat ccagcccctc gtctgcgata taggaactgg ttaggtcaag   1620
gtaagctgtt tggatctcag ggtggtttcc gtttaccgaa atgctgcatt tcttggtagc   1680
aaaactgagg tggtttgtgt caggctggaa aaccatggat ggattacaag gatgatgatg   1740
ataaggatta caaggatgat gatgataaga tggctccaaa gaagaagaga aaggttggaa   1800
tccacggagt tccagctgct gataagaagt actctatcgg acttgacatc ggaaccaact   1860
ctgttggatg ggctgttatc accgatgagt acaaggttcc atctaagaag ttcaaggttc   1920
ttggaaacac cgatagacac tctatcaaga agaaccttat cggtgctctt cttttcgatt   1980
ctggagagac cgctgaggct accagattga agagaaccgc tagaagaaga tacaccagaa   2040
gaaagaacag aatctgctac cttcaggaaa tcttctctaa cgagatggct aaggttgatg   2100
attctttctt ccacagactt gaggagtctt tccttgttga ggaggataag aagcacgaga   2160
gacacccaat cttcggaaac atcgttgatg aggttgctta ccacgagaag tacccaacca   2220
tctaccacct tagaaagaag ttggttgatt ctaccgataa ggctgatctt agacttatct   2280
accttgctct tgctcacatg atcaagttca gaggacactt ccttatcgag ggagacctta   2340
acccagataa ctctgatgtt gataagttgt tcatccagct tgttcagacc tacaaccagc   2400
```

```
ttttcgagga gaacccaatc aacgcttctg gagttgatgc taaggctatc ctttctgcta   2460

gactttctaa gtctcgtaga cttgagaacc ttatcgctca gcttccagga gagaagaaga   2520

acggactttt cggaaacctt atcgctcttt ctcttggact taccccaaac ttcaagtcta   2580

acttcgatct tgctgaggat gctaagttgc agctttctaa ggatacctac gatgatgatc   2640

ttgataacct tcttgctcag atcggagatc agtacgctga tcttttcctt gctgctaaga   2700

acctttctga tgctatcctt ctttctgaca tccttagagt taacaccgag atcaccaagg   2760

ctccactttc tgcttctatg atcaagagat acgatgagca ccaccaggat cttacccttt   2820

tgaaggctct tgttagacag cagcttccag agaagtacaa ggaaatcttc ttcgatcagt   2880

ctaagaacgg atacgctgga tacatcgatg gaggagcttc tcaggaggag ttctacaagt   2940

tcatcaagcc aatccttgag aagatggatg gaaccgagga gcttcttgtt aagttgaaca   3000

gagaggatct tcttagaaag cagagaacct tcgataacgg atctatccca caccagatcc   3060

accttggaga gcttcacgct atccttcgta gacaggagga tttctaccca ttcttgaagg   3120

ataacagaga gaagatcgag aagatcctta ccttcagaat cccatactac gttggaccac   3180

ttgctagagg aaactctcgt ttcgcttgga tgaccagaaa gtctgaggag accatcaccc   3240

cttggaactt cgaggaggta agtttctgct tctacctttg atatatatat aataattatc   3300

attaattagt agtaatataa tatttcaaat atttttttca aaataaaaga atgtagtata   3360

tagcaattgc ttttctgtag tttataagtg tgtatatttt aatttataac ttttctaata   3420

tatgaccaaa atttgttgat gtgcaggttg ttgataaggg agcttctgct cagtctttca   3480

tcgagagaat gaccaacttc gataagaacc ttccaaacga gaaggttctt ccaaagcact   3540

ctcttcttta cgagtacttc accgtttaca acgagcttac caaggttaag tacgttaccg   3600

agggaatgag aaagccagct ttcctttctg gagagcagaa gaaggctatc gttgatcttc   3660

ttttcaagac caacagaaag gttaccgtta agcagttgaa ggaggattac ttcaagaaga   3720

tcgagtgctt cgattctgtt gaaatctctg gagttgagga tagattcaac gcttctcttg   3780

gaacctacca cgatcttttg aagatcatca aggataagga tttccttgat aacgaggaga   3840

acgaggacat ccttgaggac atcgttctta cccttaccct tttcgaggat agagagatga   3900

tcgaggagag actcaagacc tacgctcacc ttttcgatga taaggttatg aagcagttga   3960

agagaagaag atacaccgga tggggtagac tttctcgtaa gttgatcaac ggaatcagag   4020

ataagcagtc tggaaagacc atccttgatt tcttgaagtc tgatggattc gctaacagaa   4080

acttcatgca gcttatccac gatgattctc ttaccttcaa ggaggacatc cagaaggctc   4140

aggtttctgg acagggagat tctcttcacg agcacatcgc taaccttgct ggatctccag   4200

ctatcaagaa gggaatcctt cagaccgtta aggttgttga tgagcttgtt aaggttatgg   4260

gtagacacaa gccagagaac atcgttatcg agatggctag agagaaccag accacccaga   4320

agggacagaa gaactctcgt gagagaatga agagaatcga ggagggaatc aaggagcttg   4380

gatctcaaat cttgaaggag cacccagttg agaacaccca gcttcagaac gagaagttgt   4440

acctttacta ccttcagaac ggaagagata tgtacgttga tcaggagctt gacatcaaca   4500

gactttctga ttacgatgtt gatcacatcg ttccacagtc tttcttgaag gatgattcta   4560

tcgataacaa ggttcttacc cgttctgata agaacagagg aaagtctgat aacgttccat   4620

ctgaggaggt tgttaagaag atgaagaact actggagaca gcttcttaac gctaagttga   4680

tcacccagag aaagttcgat aaccttacca aggctgagag aggaggactt tctgagcttg   4740

ataaggctgg attcatcaag agacagcttg ttgagaccag acagatcacc aagcacgttg   4800
```

```
ctcagatcct tgattctcgt atgaacacca agtacgatga gaacgataag ttgatcagag   4860
aggttaaggt tatcaccttg aagtctaagt tggtttctga tttcagaaag gatttccagt   4920
tctacaaggt tagagagatc aacaactacc accacgctca cgatgcttac cttaacgctg   4980
ttgttggaac cgctcttatc aagaagtacc caaagttgga gtctgagttc gtttacggag   5040
attacaaggt ttacgatgtt agaaagatga tcgctaagtc tgagcaggag atcggaaagg   5100
ctaccgctaa gtacttcttc tactctaaca tcatgaactt cttcaagacc gagatcaccc   5160
ttgctaacgg agagatcaga aagagaccac ttatcgagac caacggagag accggagaga   5220
tcgtttggga taagggaaga gatttcgcta ccgttagaaa ggttctttct atgccacagg   5280
ttaacatcgt taagaaaacc gaggttcaga ccggaggatt ctctaaggag tctatccttc   5340
caaagagaaa ctctgataag ttgatcgcta gaaagaagga ttgggaccca aagaagtacg   5400
gaggattcga ttctccaacc gttgcttact ctgttcttgt tgttgctaag gttgagaagg   5460
gaaagtctaa gaagttgaag tctgttaagg agcttcttgg aatcaccatc atggagcgtt   5520
cttctttcga gaagaaccca atcgatttcc ttgaggctaa gggatacaag gaggttaaga   5580
aggatcttat catcaagttg ccaaagtact ctcttttcga gcttgagaac ggaagaaaga   5640
gaatgcttgc ttctgctgga gagcttcaga agggaaacga gcttgctctt ccatctaagt   5700
acgttaactt cctttacctt gcttctcact acgagaagtt gaagggatct ccagaggata   5760
acgagcagaa gcagcttttc gttgagcagc acaagcacta ccttgatgag atcatcgagc   5820
aaatctctga gttctctaag agagttatcc ttgctgatgc taaccttgat aaggttcttt   5880
ctgcttacaa caagcacaga gataagccaa tcagagagca ggctgagaac atcatccacc   5940
ttttcaccct taccaacctt ggtgctccag ctgctttcaa gtacttcgat accaccatcg   6000
atagaaaaag atacacctct accaaggagg ttcttgatgc tacccttatc caccagtcta   6060
tcaccggact ttacgagacc agaatcgatc tttctcagct tggaggagat aagagaccag   6120
ctgctaccaa gaaggctgga caggctaaga agaagaagtg agagctcttc ttcggaccca   6180
agaatgctaa gccaagagga gctgttatcg ccgtcctcct gcttgtttct ctctttttgt   6240
tgctgtttct tcattagcgt ggacaaagtt ttcaaccggc ctatctgtta tcattttctt   6300
ctattcaaag actgtaatac ctattgctac ctgtggttct cacttgtgat tttggacaca   6360
tatgttcggt ttattcaaat ttaatcagat gcctgatgag ggtaccagaa aaaatacgtg   6420
ttctggttgt ttttgagttg cgattattct atgaaatgaa taacatcgaa gttatcatcc   6480
cagtattttc gcatgaatgt tcttttcttc tgtcttgtgc atcagtgatc tagtgcatgg   6540
gagtttgtat tgtgatgttc gacatcacgt aacttccact ttgcctttgc tgttcgatat   6600
tttaatgaca tgtcacacac acttctgata cttttctttc ttggctattg tgccagcatg   6660
atgcaagatg catcacagca tcagatatat tctcatcgtc aggctttagc agcacacgag   6720
cacgctttgc cgcttaaaag ttgtacggcg cagcttagac atcccctgta gaagtgataa   6780
tcttttcact tttccttaaa caaattgaga ggggaaatgg aaccatgtgg atcagagaag   6840
cttttgtttc tttacacaag aatatttggt acagtggggg tcctatgttc gtgggttcgt   6900
ggcttggctg cctgtcttca accaagtgtt ttcagttcaa catgttagcg tgtagaaaga   6960
gcacaattct gtttatctcc aaggtaaaat gtggcattct gttaaagaac atgatcctgc   7020
caatttttta agtttcaatg gaagaggaat gtaaagcttt ctatggtttg tgtacacaac   7080
acagtggaag aggagtgcaa gctttctatg gtttgtgtgc gcgttgtgtg tcagcacttc   7140
```

-continued

```
aattttgtta gaaaatgaaa gaaaaaacgg tccgatcgga tgccgggacc gacgagtgca   7200
gaggcgtgca agcgagcttg gcgtaatcat ggtcatagct gtttcctgtg tgaaattgtt   7260
atccgctcac aattccacac aacatacgag ccggaagcat aaagtgtaaa gcctggggtg   7320
cctaatgagt gagctaactc acattaattg cgttgcgctc actgcccgct ttccagtcgg   7380
gaaacctgtc gtgccagctg cattaatgaa tcggccaacg cgcggggaga ggcggtttgc   7440
gtattgggcg ctcttccgct tcctcgctca ctgactcgct gcgctcggtc gttcggctgc   7500
ggcgagcggt atcagctcac tcaaaggcgg taatacggtt atccacagaa tcaggggata   7560
acgcaggaaa gaacatgtga gcaaaaggcc agcaaaaggc caggaaccgt aaaaaggccg   7620
cgttgctggc gtttttccat aggctccgcc cccctgacga gcatcacaaa aatcgacgct   7680
caagtcagag gtggcgaaac ccgacaggac tataaagata ccaggcgttt ccccctggaa   7740
gctccctcgt gcgctctcct gttccgaccc tgccgcttac cggatacctg tccgcctttc   7800
tcccttcggg aagcgtggcg ctttctcata gctcacgctg taggtatctc agttcggtgt   7860
aggtcgttcg ctccaagctg ggctgtgtgc acgaaccccc cgttcagccc gaccgctgcg   7920
ccttatccgg taactatcgt cttgagtcca acccggtaag acacgactta tcgccactgg   7980
cagcagccac tggtaacagg attagcagag cgaggtatgt aggcggtgct acagagttct   8040
tgaagtggtg gcctaactac ggctacacta gaagaacagt atttggtatc tgcgctctgc   8100
tgaagccagt taccttcgga aaaagagttg gtagctcttg atccggcaaa caaaccaccg   8160
ctggtagcgg tggttttttt gtttgcaagc agcagattac gcgcagaaaa aaaggatctc   8220
aagaagatcc tttgatcttt tctacggggt ctgacgctca gtggaacgaa aactcacgtt   8280
aagggatttt ggtcatgaga ttatcaaaaa ggatcttcac ctagatcctt ttaaattaaa   8340
aatgaagttt taaatcaatc taaagtatat atgagtaaac ttggtctgac agttaccaat   8400
gcttaatcag tgaggcacct atctcagcga tctgtctatt tcgttcatcc atagttgcct   8460
gactccccgt cgtgtagata actacgatac gggagggctt accatctggc cccagtgctg   8520
caatgatacc gcgagaccca cgctcaccgg ctccagattt atcagcaata aaccagccag   8580
ccggaagggc cgagcgcaga agtggtcctg caactttatc cgcctccatc cagtctatta   8640
attgttgccg ggaagctaga gtaagtagtt cgccagttaa tagtttgcgc aacgttgttg   8700
ccattgctac aggcatcgtg gtgtcacgct cgtcgtttgg tatggcttca ttcagctccg   8760
gttcccaacg atcaaggcga gttacatgat cccccatgtt gtgcaaaaaa gcggttagct   8820
ccttcggtcc tccgatcgtt gtcagaagta agttggccgc agtgttatca ctcatggtta   8880
tggcagcact gcataattct cttactgtca tgccatccgt aagatgcttt tctgtgactg   8940
gtgagtactc aaccaagtca ttctgagaat agtgtatgcg gcgaccgagt tgctcttgcc   9000
cggcgtcaat acgggataat accgcgccac atagcagaac tttaaaagtg ctcatcattg   9060
gaaaacgttc ttcggggcga aaactctcaa ggatcttacc gctgttgaga tccagttcga   9120
tgtaacccac tcgtgcaccc aactgatctt cagcatcttt tactttcacc agcgtttctg   9180
ggtgagcaaa aacaggaagg caaaatgccg caaaaaaggg aataagggcg acacggaaat   9240
gttgaatact catactcttc ctttttcaat attattgaag catttatcag ggttattgtc   9300
tcatgagcgg atacatattt gaatgtattt agaaaaataa acaaataggg gttccgcgca   9360
catttccccg aaaagtgcca cctgacgtct aagaaaccat tattatcatg acattaacct   9420
ataaaaatag gcgtatcacg aggccctttc gtc                                 9453
```

<210> SEQ ID NO 49
<211> LENGTH: 3493
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: synthetic construct

<400> SEQUENCE: 49
ctgcattaat gaatcggcca acgcgcgggg agaggcggtt tgcgtattgg gcgctcttcc 60
gcttcctcgc tcactgactc gctgcgctcg gtcgttcggc tgcggcgagc ggtatcagct 120
cactcaaagg cggtaatacg gttatccaca gaatcagggg ataacgcagg aaagaacatg 180
aattaattct catgtttgac agcttatcat cgattagctt taatgcggta gtttatcaca 240
gttaaattgc taacgcagtc aggcaccgtg tatgaaatct aacaatgcgc tcatcgtcat 300
cctcggcacc gtcaccctgg atgctgtagg cataggcttg gttatgccgg tactgccggg 360
cctcttgcgg gatatcgtcc attccgacag catcgccagt cactatggcg tgctgctagc 420
gctatatgcg ttgatgcaat ttctatgcgc acccgttctc ggagcactgt ccgaccgctt 480
tggccgccgc ccagtcctgc tcgcttcgct acttggagcc actatcgact acgcgatcat 540
ggcgaccaca cccgtcctgt ggattctcta cgccggacgc atcgtggccg gcatcaccgg 600
cgccacaggt gcggttgctg gcgcctatat cgccgacatc accgatgggg aagatcgggc 660
tcgccacttc gggctcatga gcgcttgttt cggcgtgggt atggtggcag gccccgtggc 720
cgggggactg ttgggcgcca tctccttaca tgcaccattc cttgcggcgg cggtgctcaa 780
cggcctcaac ctactactgg gctgcttcct aatgcaggag tcgcataagg gagagcgccg 840
acccatgccc ttgagagcct tcaacccagt cagctccttc cggtgggcgc ggggcatgac 900
tatcgtcgcc gcacttatga ctgtcttctt tatcatgcaa ctcgtaggac aggtgccggc 960
agcgctctgg gtcattttcg gcgaggaccg ctttcgctgg agcgcgacga tgatcggcct 1020
gtcgcttgcg gtattcggaa tcttgcacgc cctcgctcaa gccttcgtca ctggtcccgc 1080
caccaaacgt ttcggcgaga agcaggccat tatcgccggc atggcggccg acgcgctggg 1140
ctacgtcttg ctggcgttcg cgacgcgagg ctggatggcc ttccccatta tgattcttct 1200
cgcttccggc ggcatcggga tgcccgcgtt gcaggccatg ctgtccaggc aggtagatga 1260
cgaccatcag ggacagcttc aaggatcgct cgcggctctt accagcctaa cttcgatcat 1320
tggaccgctg atcgtcacgg cgatttatgc cgcctcggcg agcacatgga acgggttggc 1380
atggattgta ggcgccgccc tataccttgt ctgcctcccc gcgttgcgtc gcggtgcatg 1440
gagccgggcc acctcgacct gaatggaagc cggcggcacc tcgctaacgg attcaccact 1500
ccaagaattg gagccaatca attcttgcgg agaactgtga atgcgcaaac caacccttga 1560
tcggggaaga acagtatgtc gagctatttt ttgacttact ggggatcaag cctgattggg 1620
agaaaataaa atatccccta tagtgagtcg tattacatgg tcatagctgt ttcctggcag 1680
ctctggcccg tgtctcaaaa tctctgatgt tacattgcac aagataaaaa tatatcatca 1740
tgcctcctct agaggtctcg ctatggtacc gagctcggat ccactagtaa cggccgccag 1800
tgtgctggaa ttgcccttgg atcatgaacc aacggcctgg ctgtatttgg tggttgtgta 1860
gggagatggg gagaagaaaa gcccgattct cttcgctgtg atgggctgga tgcatgcggg 1920
ggagcgggag gcccaagtac gtgcacggtg agcggcccac agggcgagtg tgagcgcgag 1980
aggcgggagg aacagtttag taccacattg cccagctaac tcgaacgcga ccaacttata 2040
aacccgcgcg ctgtcgcttg tgttcctgat cgagtcaacg acggttttag agctagaaat 2100
agcaagttaa aataaggcta gtccgttatc aacttgaaaa agtggcaccg agtcggtgct 2160
ttttttgtcc cttcgaaggg caattctgca gatatccatc acactggcgg ccgctcgagg 2220
tcgagggtat cgataagctt catgggagac cctcgagcca cccatgacca aaatccctta 2280
acgtgagtta cgcgtcgttc cactgagcgt cagaccccgt agaaaagatc aaaggatctt 2340
cttgagatcc tttttttctg cgcgtaatct gctgcttgca aacaaaaaaa ccaccgctac 2400
cagcggtggt ttgtttgccg gatcaagagc taccaactct ttttccgaag gtaactggct 2460
tcagcagagc gcagatacca aatactgttc ttctagtgta gccgtagtta ggccaccact 2520
tcaagaactc tgtagcaccg cctacatacc tcgctctgct aatcctgtta ccagtggctg 2580
ctgccagtgg cgataagtcg tgtcttaccg ggttggactc aagacgatag ttaccggata 2640
aggcgcagcg gtcgggctga acggggggtt cgtgcacaca gcccagcttg gagcgaacga 2700
cctacaccga actgagatac ctacagcgtg agctatgaga aagcgccacg cttcccgaag 2760
ggagaaaggc ggacaggtat ccggtaagcg gcagggtcgg aacaggagag cgcacgaggg 2820
agcttccagg gggaaacgcc tggtatcttt atagtcctgt cgggtttcgc cacctctgac 2880
ttgagcgtcg atttttgtga tgctcgtcag gggggcggag cctatggaaa aacgccagca 2940
acgcggcctt tttacggttc ctggcctttt gctggccttt tgctcacatg ttctttcctg 3000
cgttatcccc tgattctgtg gataaccgta ttaccgcctt tgagtgagct gataccgctc 3060
gccgcagccg aacgaccgag cgcagcgagt cagtgagcga ggaagcggaa gagcgcccaa 3120
tacgcaaacc gcctctcccc gcgcgttggc cgattcatta atgcagctgg cacgacaggt 3180
ttcccgactg gaaagcgggc agtgagcgca acgcaattaa tacgcgtacc gctagccagg 3240
aagagtttgt agaaacgcaa aaaggccatc cgtcaggatg gccttctgct tagtttgatg 3300
cctggcagtt tatggcgggc gtcctgcccg ccaccctccg ggccgttgct tcacaacgtt 3360
caaatccgct cccggcggat ttgtcctact caggagagcg ttcaccgaca aacaacagat 3420
aaaacgaaag gcccagtctt ccgactgagc ctttcgtttt atttgatgcc tggcagttcc 3480
ctactctcgc gtt 3493

<210> SEQ ID NO 50
<211> LENGTH: 3493
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: synthetic construct

<400> SEQUENCE: 50
ctgcattaat gaatcggcca acgcgcgggg agaggcggtt tgcgtattgg gcgctcttcc 60
gcttcctcgc tcactgactc gctgcgctcg gtcgttcggc tgcggcgagc ggtatcagct 120
cactcaaagg cggtaatacg gttatccaca gaatcagggg ataacgcagg aaagaacatg 180
aattaattct catgtttgac agcttatcat cgattagctt taatgcggta gtttatcaca 240
gttaaattgc taacgcagtc aggcaccgtg tatgaaatct aacaatgcgc tcatcgtcat 300
cctcggcacc gtcaccctgg atgctgtagg cataggcttg gttatgccgg tactgccggg 360
cctcttgcgg gatatcgtcc attccgacag catcgccagt cactatggcg tgctgctagc 420
gctatatgcg ttgatgcaat ttctatgcgc acccgttctc ggagcactgt ccgaccgctt 480

```
tggccgccgc ccagtcctgc tcgcttcgct acttggagcc actatcgact acgcgatcat    540
ggcgaccaca cccgtcctgt ggattctcta cgccggacgc atcgtggccg gcatcaccgg    600
cgccacaggt gcggttgctg gcgcctatat cgccgacatc accgatgggg aagatcgggc    660
tcgccacttc gggctcatga gcgcttgttt cggcgtgggt atggtggcag gccccgtggc    720
cgggggactg ttgggcgcca tctccttaca tgcaccattc cttgcggcgg cggtgctcaa    780
cggcctcaac ctactactgg gctgcttcct aatgcaggag tcgcataagg gagagcgccg    840
acccatgccc ttgagagcct tcaacccagt cagctccttc cggtgggcgc ggggcatgac    900
tatcgtcgcc gcacttatga ctgtcttctt tatcatgcaa ctcgtaggac aggtgccggc    960
agcgctctgg gtcattttcg gcgaggaccg ctttcgctgg agcgcgacga tgatcggcct   1020
gtcgcttgcg gtattcggaa tcttgcacgc cctcgctcaa gccttcgtca ctggtcccgc   1080
caccaaacgt ttcggcgaga agcaggccat tatcgccggc atggcggccg acgcgctggg   1140
ctacgtcttg ctggcgttcg cgacgcgagg ctggatggcc ttccccatta tgattcttct   1200
cgcttccggc ggcatcggga tgcccgcgtt gcaggccatg ctgtccaggc aggtagatga   1260
cgaccatcag ggacagcttc aaggatcgct cgcggctctt accagcctaa cttcgatcat   1320
tggaccgctg atcgtcacgg cgatttatgc cgcctcggcg agcacatgga acgggttggc   1380
atggattgta ggcgccgccc tataccttgt ctgcctcccc gcgttgcgtc gcggtgcatg   1440
gagccgggcc acctcgacct gaatggaagc cggcggcacc tcgctaacgg attcaccact   1500
ccaagaattg gagccaatca attcttgcgg agaactgtga atgcgcaaac caacccttga   1560
tcggggaaga acagtatgtc gagctatttt ttgacttact ggggatcaag cctgattggg   1620
agaaaataaa atatccccta tagtgagtcg tattacatgg tcatagctgt ttcctggcag   1680
ctctggcccg tgtctcaaaa tctctgatgt tacattgcac aagataaaaa tatatcatca   1740
tgcctcctct agaggtctcg ctatggtacc gagctcggat ccactagtaa cggccgccag   1800
tgtgctggaa ttgcccttgg atcatgaacc aacggcctgg ctgtatttgg tggttgtgta   1860
gggagatggg gagaagaaaa gcccgattct cttcgctgtg atgggctgga tgcatgcggg   1920
ggagcgggag gcccaagtac gtgcacggtg agcggcccac agggcgagtg tgagcgcgag   1980
aggcgggagg aacagtttag taccacattg cccagctaac tcgaacgcga ccaacttata   2040
aacccgcgcg ctgtcgcttg tgttttgcca tgccaaacaa accgttttag agctagaaat   2100
agcaagttaa aataaggcta gtccgttatc aacttgaaaa agtggcaccg agtcggtgct   2160
tttttgtcc cttcgaaggg caattctgca gatatccatc acactggcgg ccgctcgagg   2220
tcgagggtat cgataagctt catgggagac cctcgagcca cccatgacca aaatccctta   2280
acgtgagtta cgcgtcgttc cactgagcgt cagaccccgt agaaaagatc aaaggatctt   2340
cttgagatcc tttttttctg cgcgtaatct gctgcttgca aacaaaaaaa ccaccgctac   2400
cagcggtggt ttgtttgccg gatcaagagc taccaactct ttttccgaag gtaactggct   2460
tcagcagagc gcagatacca aatactgttc ttctagtgta gccgtagtta ggccaccact   2520
tcaagaactc tgtagcaccg cctacatacc tcgctctgct aatcctgtta ccagtggctg   2580
ctgccagtgg cgataagtcg tgtcttaccg ggttggactc aagacgatag ttaccggata   2640
aggcgcagcg gtcgggctga acggggggtt cgtgcacaca gcccagcttg gagcgaacga   2700
cctacaccga actgagatac ctacagcgtg agctatgaga aagcgccacg cttcccgaag   2760
ggagaaaggc ggacaggtat ccggtaagcg gcagggtcgg aacaggagag cgcacgaggg   2820
```

```
agcttccagg gggaaacgcc tggtatcttt atagtcctgt cgggtttcgc cacctctgac   2880

ttgagcgtcg atttttgtga tgctcgtcag gggggcggag cctatggaaa aacgccagca   2940

acgcggcctt tttacggttc ctggcctttt gctggccttt tgctcacatg ttctttcctg   3000

cgttatcccc tgattctgtg gataaccgta ttaccgcctt tgagtgagct gataccgctc   3060

gccgcagccg aacgaccgag cgcagcgagt cagtgagcga ggaagcggaa gagcgcccaa   3120

tacgcaaacc gcctctcccc gcgcgttggc cgattcatta atgcagctgg cacgacaggt   3180

ttcccgactg gaaagcgggc agtgagcgca acgcaattaa tacgcgtacc gctagccagg   3240

aagagtttgt agaaacgcaa aaaggccatc cgtcaggatg gccttctgct tagtttgatg   3300

cctggcagtt tatggcgggc gtcctgcccg ccaccctccg ggccgttgct tcacaacgtt   3360

caaatccgct cccggcggat ttgtcctact caggagagcg ttcaccgaca aacaacagat   3420

aaaacgaaag gcccagtctt ccgactgagc ctttcgtttt atttgatgcc tggcagttcc   3480

ctactctcgc gtt                                                      3493
```

```
<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: synthetic construct

<400> SEQUENCE: 51

tttgccatgc caaacaaacc                                                 20


<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: synthetic construct

<400> SEQUENCE: 52

tcctgatcgg gtcaacgacg                                                 20


<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: synthetic construct

<400> SEQUENCE: 53

tcctgatcga gtcaacgacg                                                 20


<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: synthetic construct
```

<400> SEQUENCE: 54
cttttcagtt ggagcttatc cca 23

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: synthetic construct

<400> SEQUENCE: 55
cctgctgaaa agaaggtggt catac 25

<210> SEQ ID NO 56
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: synthetic construct

<400> SEQUENCE: 56
gtacgatagt acgatacttt tcattctg 28

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: synthetic construct

<400> SEQUENCE: 57
gagctcatac ctgcttttcc 20

<210> SEQ ID NO 58
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: synthetic construct

<400> SEQUENCE: 58
gtagctcata ttcactgtta tcgttgttg 29

<210> SEQ ID NO 59
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: synthetic construct

<400> SEQUENCE: 59 gatactttc attctgtgca tatatgtaag tatg 34

```
<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: synthetic construct
<220> FEATURE:
<221> NAME/KEY: modified_base
<222> LOCATION: (1)..(6)
<223> OTHER INFORMATION: a, c, or g

<400> SEQUENCE: 60

nnnnnncagt tggagcttat cccaatgtac                                   30
```

METHODS OF GENETICALLY ALTERING A WHOLE PLANT SEED

PRIORITY CLAIMS AND RELATED APPLICATIONS

This application is a Continuation Application of U.S. Ser. No. 16/345,919, filed Apr. 29, 2019, which is the U.S. national stage of PCT/US2017/059996, filed Nov. 3, 2017, which application claims the benefit of priority to U.S. Provisional Patent Applications 62/418,078, filed on Nov. 4, 2016, and 62/442,601, filed on Jan. 5, 2017, which are incorporated by reference in their entirety herein.

INCORPORATION OF SEQUENCE LISTING

The sequence listings contained in the files named "10001P1_ST25. txt" (which is 98 kilobytes measured in operating system Windows 7 x64, created on 4 Nov. 2016 and electronically filed via EFS-Web on 4 Nov. 2016) and "98062-02_ST25. txt" (which is ~100 kilobytes measured in operating system Windows 8.1 x64, created on 4 Jan. 2017 and electronically filed via EFS-Web on 5 Jan. 2017), are incorporated herein by reference in their entirety. The sequence listing contained in the file named P13438US03_SL, which is 176 kilobytes measured in operating system Windows 7 x64, created on 2 November 2017, is electronically filed herewith via EFS-Web and incorporated herein by reference in its entirety.

FIELD

Aspects of this invention relate to agricultural biotechnology. Disclosed herein are novel plant cells, plants and seeds derived from such plant cells and having enhanced traits, and methods of making and using such plant cells and derived plants and seeds.

BACKGROUND

Recent advances in genome editing technologies have provided opportunities for precise modification of the genome in many types of organisms, including plants and animals. For example, technologies based on genome editing proteins, such as zinc finger nucleases, TALENs, and CRISPR systems are advancing rapidly and it is now possible to target genetic changes to specific DNA sequences in the genome.

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1. Other CRISPR nucleases useful for editing genomes include C2c1 and C2c3 (see Shmakov et al. (2015) *Mol. Cell,* 60:385-397) and CasX and CasY (see Burstein et al. (2016) *Nature*, doi:10.1038/nature21059). Plant RNA promoters for expressing CRISPR guide RNA and plant codon-optimized CRISPR Cas9 endonuclease are disclosed in International Patent Application PCT/US2015/018104 (published as WO 2015/131101 and claiming priority to U.S. Provisional Patent Application 61/945,700). Methods of using CRISPR technology for genome editing in plants are disclosed in in US Patent Application Publications US 2015/0082478A1 and US 2015/0059010A1 and in International Patent Application PCT/US2015/038767 A1 (published as WO 2016/007347 and claiming priority to U.S. Provisional Patent Application 62/023,246).

SUMMARY

Disclosed herein are methods for providing novel plant cells, plants, and seeds having one or more altered genetic sequences.

In one aspect, the invention provides a method of delivering a guide RNA (gRNA) (or other sequence-editing guide nucleic acid capable of directing a nuclease to a specific target sequence) to a non-epidermal plant cell in a plant or part of a plant. The gRNA can be provided as a CRISPR RNA (crRNA) or as a single guide RNA (sgRNA) or as a polynucleotide that encodes or is processed to a crRNA or sgRNA, wherein the gRNA has a nucleotide sequence designed to alter a target nucleotide sequence in the non-epidermal plant cell. In embodiments, the non-epidermal cell is a cell capable of division and differentiation, such as a meristem cell or a cell in a plant embryo or seed or seedling. In embodiments, the non-epidermal plant cell is in a monocot plant or in a dicot plant, and can be haploid or diploid. In embodiments, the non-epidermal plant cell contains a nuclease, such as a Cas9 nuclease or other RNA-guided nuclease, that is capable of altering the target nucleotide sequence; in other embodiments the nuclease is provided to the non-epidermal plant cell, either together with the crRNA (or other genome-editing polynucleotide) or separately. The nuclease can be provided as a functional enzyme (e.g., as a ribonucleoprotein or micelle or other molecular or supramolecular complex), or as a polynucleotide that encodes the functional nuclease. The target nucleotide sequence is one or more nucleotide sequences, including protein-coding sequence or non-coding sequence or a combination thereof. Embodiments include a plant nuclear sequence, a plant plastid sequence, a plant mitochondrial sequence, a sequence of a symbiont, pest, or pathogen of a plant, and combinations thereof. The crRNA (or other sequence-editing polynucleotide) and the RNA-guided nuclease are provided separately (e.g., in discrete compositions or in discrete steps), or alternatively are provided simultaneously (e.g., combined in a single composition, or in a single step or treatment). Embodiments of the method include one or more delivery steps or treatments, including treatment with at least one chemical, enzymatic, or physical agent or use of techniques such as application of heat or cold, ultrasonication, centrifugation, and electroporation, whereby the gRNA is delivered to the non-epidermal plant cell. In embodiments, the method further includes growing or regeneration of a seedling, plantlet, or plant from the non-epidermal plant cell having the altered target nucleotide sequence. Related aspects include: the non-epidermal plant cell with the altered target nucleotide sequence provided by the method; pluralities, arrays, and heterogeneous populations of such non-epidermal plant cells; and callus, seedlings, plantlets, and plants and their seeds, grown or regenerated from the non-epidermal plant cell and having the altered target nucleotide sequence, and pluralities, arrays, and heterogeneous populations thereof.

In another aspect, the invention provides a method of providing a plant having a genetic alteration, including the step of delivering an effector molecule such as a sequence-specific nuclease or a guide nucleic acid to a plant cell capable of division and differentiation, resulting in a genetic alteration of the plant cell, and growing or regenerating a plant from the resulting genetically altered plant cell, wherein the plant includes differentiated cells or tissues having the genetic alteration. In embodiments, the plant cell is in a plant or part of a plant, is monocot or dicot, is haploid or diploid, and is capable of division and differentiation or capable of growth or regeneration into callus, a seedling, a plantlet, or a plant. Embodiments include those wherein the effector molecule is at least one selected from the group consisting of: a polynucleotide, a ribonucleoprotein, a polypeptide (for example, a protein, an enzyme, or a nuclease), and a polynucleotide encoding a polypeptide; or a combination thereof. Embodiments of the method include one or more delivery steps or treatments, including treatment with chemical or physical agents or use of techniques such as application of heat or cold, ultrasonication, centrifugation, and electroporation. Related aspects include plants having a genetic alteration provided by the method, heterogeneous populations or libraries of such plants, succeeding generations or seeds of such plants, parts of the plants, or products made from the plants or their seeds.

In another aspect, the invention provides a method of identifying a nucleotide sequence (or alteration of a nucleotide sequence) associated with a phenotype of interest, including altering the genome of a population of plant cells or protoplasts, optionally growing or regenerating a population of calli, seedlings, plantlets, or plants from the population of plant cells or protoplasts, and selecting the plant cells or protoplasts (or calli, seedlings, plantlets, or plants) exhibiting the phenotype of interest. Embodiments of the method include culturing or growing the plant cells or protoplasts (or calli, seedlings, plantlets, or plants) under conditions that permit expression of the phenotype of interest.

DETAILED DESCRIPTION OF THE INVENTION

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as well as necessarily defines the exact complements, as is known to one of ordinary skill in the art. Where a term is provided in the singular, the inventors also contemplate aspects of the invention described by the plural of that term.

By "polynucleotide" is meant a nucleic acid molecule containing multiple nucleotides and refers to "oligonucleotides" (defined here as a polynucleotide molecule of between 2-25 nucleotides in length) and polynucleotides of 26 or more nucleotides. Polynucleotides are generally described as single- or double-stranded. Where a polynucleotide contains double-stranded regions formed by intra- or intermolecular hybridization, the length of each double-stranded region is conveniently described in terms of the number of base pairs. Aspects of this invention include the use of polynucleotides or compositions containing polynucleotides; embodiments include one or more oligonucleotides or polynucleotides or a mixture of both, including single- or double-stranded RNA or single- or double-stranded DNA or double-stranded DNA/RNA hybrids or chemically modified analogues or a mixture thereof. In various embodiments, the polynucleotide includes a combination of ribonucleotides and deoxyribonucleotides (e.g., synthetic polynucleotides consisting mainly of ribonucleotides but with one or more terminal deoxyribonucleotides or synthetic polynucleotides consisting mainly of deoxyribonucleotides but with one or more terminal dideoxyribonucleotides), or includes non-canonical nucleotides such as inosine, thiouridine, or pseudouridine. In embodiments, the polynucleotide includes chemically modified nucleotides (see, e.g., Verma and Eckstein (1998) *Annu. Rev. Biochem.,* 67:99-134); for example, the naturally occurring phosphodiester backbone of an oligonucleotide or polynucleotide can be partially or completely modified with phosphorothioate, phosphorodithioate, or methylphosphonate internucleotide linkage modifications, modified nucleoside bases or modified sugars can be used in oligonucleotide or polynucleotide synthesis, and oligonucleotides or polynucleotides can be labelled with a fluorescent moiety (e.g., fluorescein or rhodamine) or other label (e.g., biotin). Modified nucleic acids, particularly modified RNAs, are disclosed in U.S. Pat. No. 9,464,124, incorporated by reference in its entirety herein.

CRISPR (Clustered Regularly Interspaced Short Palindromic Repeats)/Cas (CRISPR-associated) systems, or CRISPR systems, are adaptive defense systems originally discovered in bacteria and archaea. CRISPR systems use RNA-guided nucleases termed CRISPR-associated or "Cas" endonucleases (e.g., Cas9 or Cpf1) to cleave foreign DNA. In a typical CRISPR/Cas system, a Cas endonuclease is directed to a target nucleotide sequence (e.g., a site in the genome that is to be sequence-edited) by sequence-specific, non-coding "guide RNAs" that target single- or double-stranded DNA sequences. In microbial hosts, CRISPR loci encode both Cas endonucleases and "CRISPR arrays" of the non-coding RNA elements that determine the specificity of the CRISPR-mediated nucleic acid cleavage.

Three classes (I-III) of CRISPR systems have been identified across a wide range of bacterial hosts. The well characterized class II CRISPR systems use a single Cas endonuclease (rather than multiple Cas proteins). One class II CRISPR system includes a type II Cas endonuclease such as Cas9, a CRISPR RNA ("crRNA"), and a trans-activating crRNA ("tracrRNA"). The crRNA contains a "guide RNA", typically a 20-nucleotide RNA sequence that corresponds to (i.e., is identical or nearly identical to, or alternatively is complementary or nearly complementary to) a 20-nucleotide target DNA sequence. The crRNA also contains a region that binds to the tracrRNA to form a partially double-stranded structure which is cleaved by RNase III, resulting in a crRNA/tracrRNA hybrid. The crRNA/tracrRNA hybrid then directs the Cas9 endonuclease to recognize and cleave the target DNA sequence.

The target DNA sequence must generally be adjacent to a "protospacer adjacent motif" ("PAM") that is specific for a given Cas endonuclease; however, PAM sequences are short and relatively non-specific, appearing throughout a given genome. CRISPR endonucleases identified from various prokaryotic species have unique PAM sequence requirements; examples of PAM sequences include 5'-NGG (*Streptococcus pyogenes*), 5'-NNAGAA (*Streptococcus thermophilus* CRISPR1), 5'-NGGNG (*Streptococcus thermophilus* CRISPR3), and 5'-NNNGATT (*Neisseria meningitidis*). Some endonucleases, e.g., Cas9 endonucleases, are associated with G-rich PAM sites, e.g., 5'-NGG, and perform blunt-end cleaving of the target DNA at a location 3 nucleotides upstream from (5' from) the PAM site.

Another class II CRISPR system includes the type V endonuclease Cpf1, which is a smaller endonuclease than is Cas9; examples include AsCpf1 (from *Acidaminococcus* sp.) and LbCpf1 (from *Lachnospiraceae* sp.). Cpf1-associated CRISPR arrays are processed into mature crRNAs without the requirement of a tracrRNA; in other words, a Cpf1 system requires only the Cpf1 nuclease and a crRNA to cleave the target DNA sequence. Cpf1 endonucleases, are associated with T-rich PAM sites, e.g., 5'-TTN. Cpf1 can also recognize a 5'-CTA PAM motif. Cpf1 cleaves the target DNA by introducing an offset or staggered double-strand break with a 4- or 5-nucleotide 5' overhang, for example, cleaving a target DNA with a 5-nucleotide offset or staggered cut located 18 nucleotides downstream from (3' from) from the PAM site on the coding strand and 23 nucleotides downstream from the PAM site on the complimentary strand; the 5-nucleotide overhang that results from such offset cleavage allows more precise genome editing by DNA insertion by homologous recombination than by insertion at blunt-end cleaved DNA. See, e.g., Zetsche et al. (2015) *Cell,* 163:759-771. Other CRISPR nucleases useful in methods and compositions of the invention include C2c1 and C2c3 (see Shmakov et al. (2015) *Mol. Cell,* 60:385-397) and CasX and CasY (see Burstein et al. (2016) *Nature*, doi:10.1038/nature21059). Like other CRISPR nucleases, C2c1 from *Alicyclobacillus acidoterrestris* (AacC2c1) requires a guide RNA and PAM recognition site; C2c1 cleavage results in a staggered seven-nucleotide DSB in the target DNA (see Yang et al. (2016) Cell, 167:1814-1828. e12) and is reported to have high mismatch sensitivity, thus reducing off-target effects (see Liu et al. (2016) *Mol. Cell*, available on line at dx[dot]doi[dot]org/10[dot]1016/j[dot]molcel[dot]2016[dot]11.040). Yet other CRISPR nucleases include nucleases identified from the genomes of uncultivated microbes, such as CasX and CasY; see Burstein et al. (2016) *Nature*, doi:10.1038/nature21059.

For the purposes of gene editing, CRISPR arrays can be designed to contain one or multiple guide RNA sequences corresponding to a desired target DNA sequence; see, for example, Cong et al. (2013) *Science,* 339:819-823; Ran et al. (2013) *Nature Protocols,* 8:2281-2308. At least 16 or 17 nucleotides of gRNA sequence are required by Cas9 for DNA cleavage to occur; for Cpf1 at least 16 nucleotides of gRNA sequence are needed to achieve detectable DNA cleavage and at least 18 nucleotides of gRNA sequence were reported necessary for efficient DNA cleavage in vitro; see Zetsche et al. (2015) Cell, 163:759-771. In practice, guide RNA sequences are generally designed to have a length of between 17-24 nucleotides (frequently 19, 20, or 21 nucleotides) and exact complementarity (i.e., perfect base-pairing) to the targeted gene or nucleic acid sequence; guide RNAs having less than 100% complementarity to the target sequence can be used (e. g., a gRNA with a length of 20 nucleotides and between 1-4 mismatches to the target sequence) but can increase the potential for off-target effects. The design of effective guide RNAs for use in plant genome editing is disclosed in US Patent Application Publication 2015/0082478 A1, the entire specification of which is incorporated herein by reference. More recently, efficient gene editing has been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing); see, for example, Cong et al. (2013) *Science,* 339:819-823; Xing et al. (2014) *BMC Plant Biol.,* 14:327-340. Chemically modified sgRNAs have been demonstrated to be effective in genome editing; see, for example, Hendel et al. (2015) *Nature Biotechnol.,* 985-991.

CRISPR-type genome editing has value in various aspects of agriculture research and development. CRISPR elements, i.e., CRISPR endonucleases and CRISPR single-guide RNAs, are useful in effecting genome editing without remnants of the CRISPR elements or selective genetic markers occurring in progeny. Alternatively, genome-inserted CRISPR elements are useful in plant lines adapted for multiplex genetic screening and breeding. For instance, a plant species can be created to express one or more of a CRISPR endonuclease such as a Cas9- or a Cpf1-type endonuclease or combinations with unique PAM recognition sites. Cpf1 endonuclease and corresponding guide RNAs and PAM sites are disclosed in US Patent Application Publication 2016/0208243 A1, which is incorporated herein by reference for its disclosure of DNA encoding Cpf1 endonucleases and guide RNAs and PAM sites. Introduction of one or more of a wide variety of CRISPR guide RNAs that interact with CRISPR endonucleases integrated into a plant genome or otherwise provided to a plant is useful for genetic editing for providing desired phenotypes or traits, for trait screening, or for trait introgression. Multiple endonucleases can be provided in expression cassettes with the appropriate promoters to allow multiple genome editing in a spatially or temporally separated fashion in either in chromosome DNA or episome DNA.

Whereas wild-type Cas9 generates double-strand breaks (DSBs) at specific DNA sequences targeted by a gRNA, a number of CRISPR endonucleases having modified functionalities are available, for example: (1) a "nickase" version of Cas9 generates only a single-strand break; (2) a catalytically inactive Cas9 ("dCas9") does not cut the target DNA but interferes with transcription; dCas9 can further be fused with a repressor peptide; (3) a catalytically inactive Cas9 ("dCas9") fused to an activator peptide can activate or increase gene expression; (4) a catalytically inactive Cas9 (dCas9) fused to FokI nuclease ("dCas9-FokI") can be used to generate DSBs at target sequences homologous to two gRNAs. See, e.g., the numerous CRISPR/Cas9 plasmids disclosed in and publicly available from the Addgene repository (Addgene, 75 Sidney St., Suite 550A, Cambridge, MA 02139; addgene[dot]org/crispr/). A "double nickase" Cas9 that introduces two separate double-strand breaks, each directed by a separate guide RNA, is described as achieving more accurate genome editing by Ran et al. (2013) *Cell,* 154:1380-1389.

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1. Plant RNA promoters for expressing CRISPR guide RNA and plant codon-optimized CRISPR Cas9 endonuclease are disclosed in International Patent Application PCT/US2015/018104 (published as WO 2015/131101 and claiming priority to U.S. Provisional Patent Application No. 61/945,700). Methods of using CRISPR technology for genome editing in plants are disclosed in in US Patent Application Publications US 2015/0082478A1 and US 2015/0059010A1 and in International Patent Application PCT/US2015/038767 A1 (published as WO 2016/007347 and claiming priority to US Provisional Patent Application 62/023,246). All of the patent publications referenced in this paragraph are incorporated herein by reference in their entirety.

In some embodiments, one or more vectors driving expression of one or more polynucleotides encoding elements of a genome-editing system (e.g., encoding a guide RNA or a nuclease) are introduced into a plant cell, whereby these elements, when expressed, result in alteration of a target nucleotide sequence. In embodiments, a vector includes a regulatory element such as a promoter operably linked to one or more polynucleotides encoding elements of a genome-editing system. In such embodiments, expression of these polynucleotides can be controlled by selection of the appropriate promoter, particularly promoters functional in a plant cell; useful promoters include constitutive, conditional, inducible, and temporally or spatially specific promoters (e.g., a tissue specific promoter, a developmentally regulated promoter, or a cell cycle regulated promoter). In embodiments the promoter is operably linked to nucleotide sequences encoding multiple guide RNAs, wherein the sequences encoding guide RNAs are separated by a cleavage site such as a nucleotide sequence encoding a microRNA recognition/cleavage site or a self-cleaving ribozyme (see, e.g., Ferré-D'Amaré and Scott (2014) *Cold Spring Harbor Perspectives Biol.,* 2:a003574). In embodiments, the promoter is a pol II promoter operably linked to a nucleotide sequence encoding one or more guide RNAs. In embodiments, the promoter operably linked to one or more polynucleotides encoding elements of a genome-editing system is a constitutive promoter that drives DNA expression in plant cells including in the nucleus or in an organelle such as a chloroplast or mitochondrion. Examples of constitutive promoters include a CaMV 35S promoter as disclosed in U.S. Pat. Nos. 5,858,742 and 5,322,938, a rice actin promoter as disclosed in U.S. Pat. No. 5,641,876, a maize chloroplast aldolase promoter as disclosed in U.S. Pat. No. 7,151,204, and a opaline synthase (NOS) and octapine synthase (OCS) promoter from *Agrobacterium tumefaciens*. In embodiments, the promoter operably linked to one or more polynucleotides encoding elements of a genome-editing system is a promoter from figwort mosaic virus (FMV), a RUBISCO promoter, or a pyruvate phosphate dikinase (PDK) promoter, which is active in the chloroplasts of mesophyll cells. Other contemplated promoters include cell-specific or tissue-specific or developmentally regulated promoters, for example, a promoter that limits the expression of the nucleic acid targeting system to germline or reproductive cells (e.g., promoters of genes encoding DNA ligases, recombinases, replicases, or other genes specifically expressed in germline or reproductive cells); in such embodiments, the nuclease-mediated genetic modification (e.g., chromosomal or episomal double-stranded DNA cleavage) is limited only those cells from which DNA is inherited in subsequent generations, which is advantageous where it is desirable that expression of the genome-editing system be limited in order to avoid genotoxicity or other unwanted effects. All of the patent publications referenced in this paragraph are incorporated herein by reference in their entirety.

In some embodiments, elements of a genome-editing system (e.g., an RNA-guided nuclease and a guide RNA) are operably linked to separate regulatory elements on separate vectors. In other embodiments, two or more elements of a genome-editing system expressed from the same or different regulatory elements or promoters are combined in a single vector, optionally with one or more additional vectors providing any additional necessary elements of a genome-editing system not included in the first vector. For example, multiple guide RNAs can be expressed from one vector, with the appropriate RNA-guided nuclease expressed from a second vector. In another example, one or more vectors for the expression of one or more guide RNAs (e.g., crRNAs or sgRNAs) are delivered to a plant cell that expresses the appropriate RNA-guided nuclease, or to a plant cell that otherwise contains the nuclease, such as by way of prior administration thereto of a vector for in vivo expression of the nuclease.

Genome-editing system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In embodiments, the endonuclease and the nucleic acid-targeting guide RNA may be operably linked to and expressed from the same promoter. In embodiments, a single promoter drives expression of a transcript encoding an endonuclease and the guide RNA, embedded within one or more intron sequences (e.g., each in a different intron, two or more in at least one intron, or all in a single intron), which can be plant-derived; such use of introns is especially contemplated when the expression vector is being transformed or transfected into a monocot cell.

Expression vectors provided herein may contain a DNA segment near the 3' end of an expression cassette that acts as a signal to terminate transcription and directs polyadenylation of the resultant mRNA. These are commonly referred to as "3'-untranslated regions" or "3'-UTRs" or "polyadenylation signals". Useful 3' elements include: *Agrobacterium tumefaciens* nos 3', tml 3', tmr 3', tms 3', ocs 3', and tr7 3' elements disclosed in U.S. Pat. No. 6,090,627, incorporated herein by reference, and 3' elements from plant genes such as the heat shock protein 17, ubiquitin, and fructose-1,6-biphosphatase genes from wheat (*Triticum aestivum*), and the glutelin, lactate dehydrogenase, and beta-tubulin genes from rice (*Oryza sativa*), disclosed in US Patent Application Publication 2002/0192813 A1, incorporated herein by reference.

In certain embodiments, a vector or an expression cassette includes additional components, e.g., a polynucleotide encoding a drug resistance or herbicide gene or a polynucleotide encoding a detectable marker such as green fluorescent protein (GFP) or beta-glucuronidase (gus) to allow convenient screening or selection of cells expressing the vector. In embodiments, the vector or expression cassette includes additional elements for improving delivery to the plant cell or for directing or modifying expression of one or more genome-editing system elements, for example, fusing a sequence encoding a cell-penetrating peptide, localization signal, transit, or targeting peptide to the RNA-guided nuclease, or adding a nucleotide sequence to stabilize a guide RNA; such fusion proteins (and the polypeptides encoding such fusion proteins) or combination polypeptides, as well as expression cassettes and vectors for their expression in a cell, are specifically claimed. In embodiments, an RNA-guided nuclease (e.g., Cas9, Cpf1, CasY, CasX, C2c1, or C2c3) is fused to a localization signal, transit, or targeting peptide, e.g., a nuclear localization signal (NLS), a chloroplast transit peptide (CTP), or a mitochondrial targeting peptide (MTP); in a vector or an expression cassette, the nucleotide sequence encoding any of these can be located either 5' and/or 3' to the DNA encoding the nuclease. For example, a plant-codon-optimized Cas9 (pco-Cas9) from *Streptococcus pyogenes* and *S. thermophilus* containing nuclear localization signals and codon-optimized for expression in maize is disclosed in PCT/US2015/018104 (published as WO/2015/131101 and claiming priority to U.S. Provisional Patent Application No. 61/945,700), incorporated herein by reference. In another example, a chloroplast-targeting RNA is appended to the 5' end of an mRNA encoding an endonuclease to drive the accumulation of the mRNA in chloroplasts; see Gomez, et al. (2010) *Plant Signal Behav.,* 5: 1517-1519. In an embodiment, a Cas9 from *Streptococcus pyogenes* is fused to a nuclear localization signal (NLS), such as the NLS from SV40. In an embodiment, a Cas9 from *Streptococcus pyogenes* is fused to a cell-penetrating peptide (CPP), such as octa-arginine or nona-arginine or a homoarginine 12-mer oligopeptide, or a CPP disclosed in the database of cell-penetrating peptides CPPsite 2.0, publicly available at crdd[dot]osdd[dot]net/raghava/cppsite/. In an embodiment, a Cas9 from *Streptococcus pyogenes* is fused to a chloroplast transit peptide (CTP) sequence. In embodiments, a CTP sequence is obtained from any nuclear gene that encodes a protein that targets a chloroplast, and the isolated or synthesized CTP DNA is appended to the 5' end of the DNA that encodes a nuclease targeted for use in a chloroplast. Chloroplast transit peptides and their use are described in U.S. Pat. Nos. 5,188,642, 5,728,925, and 8,420,888, all of which are incorporated herein by reference in their entirety. Specifically, the CTP nucleotide sequences provided with the sequence identifier (SEQ ID) numbers 12-15 and 17-22 of U.S. Pat. No. 8,420,888 are incorporated herein by reference. In an embodiment, a Cas9 from *Streptococcus pyogenes* is fused to a mitochondrial targeting peptide (MTP), such as a plant MTP sequence; see, e.g., Jores et al. (2016) *Nature Communications,* 7:12036-12051.

Plasmids designed for use in plants and encoding CRISPR genome editing elements (CRISPR nucleases and guide RNAs) are publicly available from plasmid repositories such as Addgene (Cambridge, Massachusetts; also see "addgene [dot]com"). In embodiments, such plasmids are used to co-express both CRISPR nuclease mRNA and guide RNA (s); in other embodiments, CRISPR endonuclease mRNA and guide RNA are delivered from separate plasmids. In embodiments, the plasmids are *Agrobacterium* TI plasmids. Materials and methods for preparing expression cassettes and vectors for CRISPR endonuclease and guide RNA for stably integrated and/or transient plant transformation are disclosed in PCT/US2015/018104 (published as WO/2015/131101 and claiming priority to U.S. Provisional Patent Application 61/945,700), US Patent Application Publication 2015/0082478 A1, and PCT/US2015/038767 (published as WO/2016/007347 and claiming priority to U.S. Provisional Patent Application No. 62/023,246), all of which are incorporated herein by reference in their entirety. In embodiments, such expression cassettes are isolated linear fragments, or are part of a larger construct that includes bacterial replication elements and selectable markers; such embodiments are useful, e.g., for particle bombardment or nanoparticle delivery or protoplast transformation. In embodiments, the expression cassette is adjacent to or located between T-DNA borders or contained within a binary vector, e.g., for *Agrobacterium*-mediated transformation. In embodiments, a plasmid encoding a CRISPR nuclease is delivered to a plant cell for stable integration of the CRISPR nuclease into the plant cell's genome, or alternatively for transient expression of the CRISPR nuclease. In embodiments, plasmids encoding a CRISPR nuclease are delivered to a plant cell to achieve stable or transient expression of the CRISPR nuclease, and one or multiple guide RNAs (such as a library of individual guide RNAs or multiple pooled guide RNAs) or plasmids encoding the guide RNAs are delivered to the plant cell individually or in combinations, thus providing libraries or arrays of plant cells, plant parts or tissues, embryos, seeds, or intact plants, in which a variety of genome edits are provided by the different guide RNAs.

In certain embodiments where the genome-editing system is a CRISPR system, expression of the guide RNA is driven by a plant U6 spliceosomal RNA promoter, which can be native to the plant being edited or from a different plant, e.g., a U6 promoter from maize, tomato, or soybean such as those disclosed in PCT/US2015/018104 (published as WO 2015/131101 and claiming priority to U.S. Provisional Patent Application No. 61/945,700), incorporated herein by reference, or a homologue thereof; such a promoter is operably linked to DNA encoding the guide RNA for directing an endonuclease, followed by a suitable 3' element such as a U6 poly-T terminator. In another embodiment, an expression cassette for expressing guide RNAs in plants is used, wherein the promoter is a plant U3, 7SL (signal recognition particle RNA), U2, or U5 promoter, or chimerics thereof, e.g., as described in PCT/US2015/018104 (published as WO 2015/131101 and claiming priority to US Provisional Patent Application 61/945,700), incorporated herein by reference. When multiple or different guide RNA sequences are used, a single expression construct may be used to correspondingly direct the genome editing activity to the multiple or different target sequences in a cell. In various embodiments, a single vector includes 1, 2, 3, 4, 5, 6, 7, 8, 9, 10, about 15, about 20, or more guide RNA sequences; in other embodiments, 1, 2, 3, 4, 5, 6, 7, 8, 9, 10, about 15, about 20, or more guide RNA sequences are provided on multiple vectors, which can be delivered to one or multiple cells (e.g., delivered to an array of plant cells, plant parts or tissues, embryos, seeds, or plants).

In embodiments, one or more guide RNAs and the corresponding RNA-guided nuclease are delivered together or simultaneously. In other embodiments, one or more guide RNAs and the corresponding RNA-guided nuclease are delivered separately; these can be delivered in separate, discrete steps and using the same or different delivery techniques. In an example, an RNA-guided nuclease is delivered to a plant cell by particle bombardment, on carbon nanotubes, or by *Agrobacterium*-mediated transformation, and one or more guide RNAs is delivered to the plant cell in a separate step using the same or different delivery technique. In embodiments, an RNA-guided nuclease encoded by a DNA molecule or an mRNA is delivered to a plant cell with enough time prior to delivery of the guide RNA to permit expression of the nuclease in the plant cell; for example, an RNA-guided nuclease encoded by a DNA molecule or an mRNA is delivered to a plant cell between 1-12 hours (e.g., about 1, 2, 3, 4, 5, 6, 7, 8, 9, 10, 11, or 12 hours, or between about 1-6 hours or between about 2-6 hours) prior to the delivery of the guide RNA to the plant cell. In embodiments, whether the RNA-guided nuclease is delivered simultaneously with or separately from an initial dose of guide RNA, succeeding "booster" doses of guide RNA are delivered subsequent to the delivery of the initial dose; for example, a second "booster" dose of guide RNA is delivered to a plant cell between 1-12 hours (e.g., about 1, 2, 3, 4, 5, 6, 7, 8, 9, 10, 11, or 12 hours, or between about 1-6 hours or between about 2-6 hours) subsequent to the delivery of the initial dose of guide RNA to the plant cell. Similarly, in some embodiments, multiple deliveries of an RNA-guided nuclease or of a DNA molecule or an mRNA encoding an RNA-guided nuclease are used to increase efficiency of the genome modification.

In embodiments, the desired genome modification involves homologous recombination, wherein one or more double-stranded DNA break in the target nucleotide sequence is generated by the RNA-guided nuclease and guide RNA(s), followed by repair of the break(s) using a homologous recombination mechanism ("homology-directed repair"). In such embodiments, a donor template that encodes the desired nucleotide sequence to be inserted or knocked-in at the double-stranded break is provided to the cell; examples of suitable templates include single-stranded DNA templates and double-stranded DNA templates (e.g., in the form of a plasmid). In general, a donor template encoding a nucleotide change over a region of less than about 50 nucleotides is conveniently provided in the form of single-stranded DNA; larger donor templates (e.g., more than 100 nucleotides) are often conveniently provided as double-stranded DNA plasmids. In embodiments, the various compositions and methods described herein for delivering guide RNAs and nucleases are also generally useful for delivering the donor template polynucleotide to the plant cell; this delivery can be simultaneous with, or separate from (generally after) delivery of the nuclease and guide RNA to the cell. For example, a donor template can be transiently introduced into a plant cell, optionally with the nuclease and/or gRNA; in embodiments, the donor template is provided to the cell in a quantity that is sufficient to achieve the desired homology-directed repair but that does not persist in the cell after a given period of time (e.g., after one or more cell division cycles). In embodiments, a donor template has a core nucleotide sequence that differs from the target nucleotide sequence (e.g., a homologous endogenous genomic region) by at least 1, at least 5, at least 10, at least 20, at least 30, at least 40, at least 50, or more nucleotides. This core sequence is flanked by "homology arms" or regions of high sequence identity with the targeted nucleotide sequence; in embodiments, the regions of high identity include at least 10, at least 50, at least 100, at least 150, at least 200, at least 300, at least 400, at least 500, at least 600, at least 750, or at least 1000 nucleotides on each side of the core sequence. In embodiments where the donor template is in the form of a single-stranded DNA, the core sequence is flanked by homology arms including at least 10, at least 20, at least 30, at least 40, at least 50, at least 60, at least 70, at least 80, or at least 100 nucleotides on each side of the core sequence. In embodiments where the donor template is in the form of a double-stranded DNA plasmid, the core sequence is flanked by homology arms including at least 500, at least 600, at least 700, at least 800, at least 900, or at least 1000 nucleotides on each side of the core sequence. In an embodiment, two separate double-strand breaks are introduced into the cell's target nucleotide sequence with a "double nickase" Cas9 (see Ran et al. (2013) *Cell,* 154: 1380-1389), followed by delivery of the donor template.

Methods of Altering a Target Nucleotide Sequence in a Plant Cell

In one aspect the invention provides a method of delivering a guide RNA (gRNA) to a plant cell, particularly a non-epidermal plant cell, wherein the non-epidermal plant cell is in a plant or part of a plant, wherein the gRNA has a nucleotide sequence designed to alter a target nucleotide sequence in the non-epidermal plant cell, wherein the gRNA is provided as a polynucleotide composition including: (i) a CRISPR RNA (crRNA) that includes the gRNA, or a polynucleotide that encodes a crRNA, or a polynucleotide that is processed into a crRNA; or (ii) a single guide RNA (sgRNA) that includes the gRNA, or a polynucleotide that encodes an sgRNA, or a polynucleotide that is processed into an sgRNA; wherein the delivery of the polynucleotide composition includes at least one treatment selected from the group consisting of: direct application; soaking or imbibition; vacuum infiltration; application of negative or positive pressure; introduction into the vascular system; microinjection; application of ultrasound or vibration; application of hydrodynamic pressure, friction, cavitation or shear stress; vortexing; centrifugation; mechanical cell wall or cell membrane deformation or breakage; enzymatic cell wall or cell membrane breakage or permeabilization; abrasion; electroporation; and treatment with at least one chemical, enzymatic, or physical agent; whereby the gRNA is delivered to the non-epidermal plant cell. In embodiments, delivery of the gRNA results in alteration of the target nucleotide sequence in the non-epidermal plant cell.

The target nucleotide sequence is one or more nucleotide sequences, including protein-coding sequence or non-coding sequence or a combination thereof. Embodiments include a plant nuclear sequence, a plant plastid sequence, a plant mitochondrial sequence, a sequence of a symbiont, pest, or pathogen of a plant, and combinations thereof. Embodiments include exons, introns, regulatory sequences including promoters, other 5' elements and 3' elements, and genomic loci encoding non-coding RNAs including long non-coding RNAs (lncRNAs), microRNAs (miRNAs), and trans-acting siRNAs (ta-siRNAs). In embodiments, multiple target nucleotide sequences are altered, for example, by delivery of multiple gRNAs to the non-epidermal plant cell; the multiple target nucleotide sequences can be part of the same gene (e.g., different locations in a single coding region or in different exons of a protein-coding gene) or different genes.

In embodiments, the guide RNA (gRNA) has a sequence of between 16-24 nucleotides in length (e.g., 16, 17, 18, 19, 20, 21, 22, 23, or 24 nucleotides in length). Specific embodiments include gRNAs of 19, 20, or 21 nucleotides in length and having 100% complementarity to the target nucleotide sequence. In many embodiments the gRNA has exact complementarity (i.e., perfect base-pairing) to the target nucleotide sequence; in certain other embodiments the gRNA has less than 100% complementarity to the target nucleotide sequence. The design of effective gRNAs for use in plant genome editing is disclosed in US Patent Application Publication 2015/0082478 A1, the entire specification of which is incorporated herein by reference. Efficient Cas9-mediated gene editing has been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing).

Thus, in certain embodiments wherein the nuclease is a Cas9-type nuclease, the gRNA can be provided as a polynucleotide composition including: (a) a CRISPR RNA (crRNA) that includes the gRNA together with a separate tracrRNA, or (b) at least one polynucleotide that encodes a crRNA and a tracrRNA (on a single polynucleotide or on separate polynucleotides), or (c) at least one polynucleotide that is processed into one or more crRNAs and a tracrRNA. In other embodiments wherein the nuclease is a Cas9-type nuclease, the gRNA can be provided as a polynucleotide composition including a CRISPR RNA (crRNA) that includes the gRNA, and the required tracrRNA is provided in a separate composition or in a separate step, or is otherwise provided to the plant cell (for example, to a plant cell located in a plant part or tissue, embryo, seed, or plants stably or transiently expressing the tracrRNA from a polynucleotide encoding the tracrRNA). In other embodiments wherein the nuclease is a Cas9-type nuclease, the gRNA can be provided as a polynucleotide composition including: (a) a single guide RNA (sgRNA) that includes the gRNA, or (b) a polynucleotide that encodes an sgRNA, or (c) a polynucleotide that is processed into an sgRNA. Cpf1-mediated gene editing does not require a tracrRNA; thus, in embodiments wherein the nuclease is a Cpf1-type nuclease, the gRNA is provided as a polynucleotide composition including (a) a CRISPR RNA (crRNA) that includes the gRNA, or (b) a polynucleotide that encodes a crRNA, or (c) a polynucleotide that is processed into a crRNA.

In embodiments of the method, the polynucleotide composition optionally includes an RNA-guided nuclease, or a polynucleotide that encodes the RNA-guided nuclease. In other embodiments of the method, the method further includes the step of providing to the non-epidermal plant cell an RNA-guided nuclease or a polynucleotide that encodes the RNA-guided nuclease. In other embodiments of the method, the non-epidermal plant cell includes an RNA-guided nuclease or a polynucleotide that encodes the RNA-guided nuclease; in an example the non-epidermal plant cell is in or from a transgenic plant that expresses the RNA-guided nuclease. In embodiments, the RNA-guided nuclease is selected from the group consisting of an RNA-guided DNA endonuclease, a type II Cas nuclease, a Cas9, a type V Cas nuclease, a Cpf1, a CasY, a CasX, a C2c1, a C2c3, an engineered RNA-guided nuclease, and a codon-optimized RNA-guided nuclease. In embodiments, the polynucleotide that encodes the RNA-guided nuclease is, for example, DNA that encodes the RNA-guided nuclease and is stably integrated in the genome of the non-epidermal plant cell, DNA or RNA that encodes the RNA-guided nuclease and is transiently present in or introduced into the non-epidermal plant cell; such DNA or RNA can be introduced, e.g., by using a vector such as a plasmid or viral vector or as an mRNA.

In embodiments of the method that further include the step of providing to the non-epidermal plant cell an RNA-guided nuclease or a polynucleotide that encodes the RNA-guided nuclease, the RNA-guided nuclease is provided simultaneously with the polynucleotide composition that includes the gRNA, or in a separate step that precedes or follows the step of providing the polynucleotide composition. In embodiments, the polynucleotide composition that includes the gRNA further includes an RNA-guided nuclease or a polynucleotide that encodes the RNA-guided nuclease. In other embodiments, there is provided a separate composition that includes an RNA-guided nuclease or a polynucleotide that encodes the RNA-guided nuclease. In embodiments, the RNA-guided nuclease is provided as a ribonucleoprotein (RNP) complex, e.g., a preassembled RNP that includes the RNA-guided nuclease complexed with a polynucleotide including the gRNA or encoding a gRNA, or a preassembled RNP that includes a polynucleotide that encodes the RNA-guided nuclease (and optionally encodes the gRNA, or is provided with a separate polynucleotide including the gRNA or encoding a gRNA), complexed with a protein. In embodiments, the RNA-guided nuclease is a fusion protein, i.e., wherein the RNA-guided nuclease is covalently bound through a peptide bond to a cell-penetrating peptide, a nuclear localization signal peptide, a chloroplast transit peptide, or a mitochondrial targeting peptide; such fusion proteins are conveniently encoded in a single nucleotide sequence, optionally including codons for linking amino acids. In embodiments, the RNA-guided nuclease or a polynucleotide that encodes the RNA-guided nuclease is provided as a complex with a cell-penetrating peptide or other transfecting agent. In embodiments, the RNA-guided nuclease or a polynucleotide that encodes the RNA-guided nuclease is complexed with, or covalently or non-covalently bound to, a further element, e.g., a carrier molecule, an antibody, an antigen, a viral movement protein, a polymer, a detectable label (e.g., a moiety detectable by fluorescence, radioactivity, or enzymatic or immunochemical reaction), a quantum dot, or a particulate or nanoparticulate. In embodiments, the RNA-guided nuclease or a polynucleotide that encodes the RNA-guided nuclease is provided in a solution, or is provided in a liposome, micelle, emulsion, reverse emulsion, suspension, or other mixed-phase composition.

The RNA-guided nuclease is provided to the non-epidermal plant cell by any suitable technique. In embodiments, the RNA-guided nuclease is provided by directly contacting the non-epidermal plant cell with the RNA-guided nuclease or the polynucleotide that encodes the RNA-guided nuclease. In embodiments, the RNA-guided nuclease is provided by transporting the RNA-guided nuclease or a polynucleotide that encodes the RNA-guided nuclease into the non-epidermal plant cell using a chemical, enzymatic, or physical agent as provided in detail below in the paragraphs following the heading "Delivery Agents". In embodiments, the RNA-guided nuclease is provided by bacterially mediated (e.g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection of the non-epidermal plant cell with a polynucleotide encoding the RNA-guided nuclease; see, e.g., Broothaerts et al. (2005) *Nature,* 433:629-633. In an embodiment, the RNA-guided nuclease is provided by transcription in the non-epidermal plant cell of a DNA that encodes the RNA-guided nuclease and is stably integrated in the genome of the non-epidermal plant cell or that is provided to the non-epidermal plant cell in the form of a plasmid or expression vector (e.g., a viral vector) that encodes the RNA-guided nuclease (and optionally encodes one or more gRNAs, crRNAs, or sgRNAs, or is optionally provided with a separate plasmid or vector that encodes one or more gRNAs, crRNAs, or sgRNAs). In embodiments, the RNA-guided nuclease is provided to the non-epidermal plant cell as a polynucleotide that encodes the RNA-guided nuclease, e.g., in the form of an mRNA encoding the nuclease.

Where a polynucleotide is concerned (e.g., a crRNA that includes the gRNA together with a separate tracrRNA, or at least one polynucleotide that encodes a crRNA and a tracrRNA (on a single polynucleotide or on separate polynucleotides), or at least one polynucleotide that is processed into one or more crRNAs and a tracrRNA, or an sgRNA that includes the gRNA, or a polynucleotide that encodes an sgRNA, or a polynucleotide that is processed into an sgRNA, or a polynucleotide that encodes the RNA-guided nuclease), embodiments of the polynucleotide include: (a) double-stranded RNA; (b) single-stranded RNA; (c) chemically modified RNA; (d) double-stranded DNA; (e) single-stranded DNA; (f) chemically modified DNA; or (g) a combination of (a)-(f). Where expression of a polynucleotide is involved (e.g., expression of a crRNA from a DNA encoding the crRNA, or expression and translation of a RNA-guided nuclease from a DNA encoding the nuclease), in some embodiments it is sufficient that expression be transient, i.e., not necessarily permanent or stable in the plant cell. Certain embodiments of the polynucleotide further include additional nucleotide sequences that provide useful functionality; non-limiting examples of such additional nucleotide sequences include an aptamer or riboswitch sequence, nucleotide sequence that provides secondary structure such as stem-loops or that provides a sequence-specific site for an enzyme (e.g., a sequence-specific recombinase or endonuclease site), T-DNA (e.g., DNA sequence encoding a gRNA, crRNA, tracrRNA, or sgRNA is enclosed between left and right T-DNA borders from *Agrobacterium* spp. or from other bacteria that infect or induce tumours in plants), a DNA nuclear-targeting sequence, a regulatory sequence such as a promoter sequence, and a transcript-stabilizing sequence. Certain embodiments of the polynucleotide include those wherein the polynucleotide is complexed with, or covalently or non-covalently bound to, a non-nucleic acid element, e.g., a carrier molecule, an antibody, an antigen, a viral movement protein, a cell-penetrating or pore-forming peptide, a polymer, a detectable label, a quantum dot, or a particulate or nanoparticulate.

Generally, the non-epidermal plant cell is not an isolated plant cell (e.g., not a plant cell or protoplast isolated from plant tissue or in suspension or plate culture) and is a cell located in an intact or growing plant or in a plant part or tissue. In embodiments, the non-epidermal plant cell is capable of division and further differentiation. In embodiments, the non-epidermal plant cell is located in a plant or part of a plant selected from the group consisting of a plant tissue, a whole plant, an intact nodal bud, a shoot apex or shoot apical meristem, a root apex or root apical meristem, lateral meristem, intercalary meristem, a seedling (e.g., a germinating seed or small seedling or a larger seedling with one or more true leaves), a whole seed (e.g., an intact seed, or a seed with part or all of its seed coat removed or treated to make permeable), a halved seed or other seed fragment, an embryo (e.g., a mature dissected zygotic embryo, a developing embryo, a dry or rehydrated or freshly excised embryo), and callus.

In embodiments, the non-epidermal cell is diploid or polyploid. In embodiments, the non-epidermal plant cell is haploid or can be induced to become haploid; techniques for making and using haploid plants and plant cells are known in the art, see, e. g., methods for generating haploids in *Arabidopsis thaliana* by crossing of a wild-type strain to a haploid-inducing strain that expresses altered forms of the centromere-specific histone CENH3, as described by Maruthachalam and Chan in "How to make haploid *Arabidopsis thaliana*", a protocol publicly available at www[dot]openwetware[dot]org/images/d/d3/Haploid Arabidopsisprotocol[dot]pdf; Ravi et al. (2014) *Nature Communications,* 5:5334, doi: 10.1038/ncomms6334). Examples of haploid cells include but are not limited to plant cells in haploid plants and plant cells in reproductive tissues, e.g., flowers, developing flowers or flower buds, ovaries, ovules, megaspores, anthers, pollen, and microspores. In embodiments where the non-epidermal plant cell is haploid, the method can further include the step of chromosome doubling (e.g., by spontaneous chromosomal doubling by meiotic non-reduction, or by using a chromosome doubling agent such as colchicine, oryzalin, or trifluralin) in the non-epidermal plant cell including the altered target nucleotide sequence to produce a doubled haploid cell that is homozygous for the altered target nucleotide sequence; yet other embodiments include regeneration of a doubled haploid plant from the doubled haploid cell, wherein the regenerated doubled haploid plant is homozygous for the altered target nucleotide sequence. Thus, aspects of the invention are related to the haploid cell having the altered target nucleotide sequence as well as a doubled haploid cell or a doubled haploid plant that is homozygous for the altered target nucleotide sequence. Another aspect of the invention is related to a hybrid plant having at least one parent plant that is a doubled haploid plant provided by the method. Production of doubled haploid plants by these methods provides homozygosity in one generation, instead of requiring several generations of self-crossing to obtain homozygous plants; this may be particularly advantageous in slow-growing plants, such as fruit and other trees, or for producing hybrid plants that are offspring of at least one doubled-haploid plant.

In embodiments, the plant is a dicot or a monocot. In embodiments, the plant is a gymnosperm, such as a conifer. Plants of interest include row crop plants, fruit-producing plants and trees, vegetables, trees, and ornamental plants including ornamental flowers, shrubs, trees, groundcovers, and turf grasses. Examples of commercially important cultivated crops, trees, and plants include: alfalfa (*Medicago sativa*), almonds (*Prunus dulcis*), apples (*Malus x domestica*), apricots (*Prunus armeniaca, P. brigantine, P. mandshurica, P. mume, P. sibirica*), asparagus (*Asparagus officinalis*), bananas (*Musa* spp.), barley (*Hordeum vulgare*), beans (*Phaseolus* spp.), blueberries and cranberries (*Vaccinium* spp.), cacao (*Theobroma cacao*), canola and rapeseed or oilseed rape, (*Brassica napus*), carnation (*Dianthus caryophyllus*), carrots (*Daucus carota sativus*), cassava (*Manihot esculentum*), cherry (*Prunus avium*), chickpea (*Cider arietinum*), chicory (*Cichorium intybus*), chili peppers and other capsicum peppers (*Capsicum annuum, C. frutescens, C. chinense, C. pubescens, C. baccatum*), chrysanthemums (*Chrysanthemum* spp.), coconut (*Cocos nucifera*), coffee (*Coffea* spp. including *Coffea arabica* and *Coffea canephora*), cotton (*Gossypium hirsutum L.*), cowpea (*Vigna unguiculata*), cucumber (*Cucumis sativus*), currants and gooseberries (*Ribes* spp.), eggplant or aubergine (*Solanum melongena*), eucalyptus (*Eucalyptus* spp.), flax (*Linum usitatissumum* L.), geraniums (*Pelargonium* spp.), grapefruit (*Citrus x paradisi*), grapes (*Vitus* spp.) including wine grapes (*Vitus vinifera*), guava (*Psidium guajava*), irises (*Iris* spp.), lemon (*Citrus limon*), lettuce (*Lactuca sativa*), limes (*Citrus* spp.), maize (*Zea mays L.*), mango (*Mangifera indica*), mangosteen (*Garcinia mangostana*), melon (*Cucumis melo*), millets (*Setaria* spp, *Echinochloa* spp, *Eleusine* spp, *Panicum* spp., *Pennisetum* spp.), oats (*Avena sativa*), oil palm (*Ellis quineensis*), olive (*Olea europaea*), onion (*Allium cepa*), orange (*Citrus sinensis*), papaya (*Carica papaya*), peaches and nectarines (*Prunus persica*), pear (*Pyrus* spp.), pea (*Pisa sativum*), peanut (*Arachis hypogaea*), peonies (*Paeonia* spp.), petunias (*Petunia* spp.), pineapple (*Ananas comosus*), plantains (*Musa* spp.), plum (*Prunus domestica*), poinsettia (*Euphorbia pulcherrima*), Polish canola (*Brassica rapa*), poplar (*Populus* spp.), potato (*Solanum tuberosum*), pumpkin (*Cucurbita pepo*), rice (*Oryza sativa* L.), roses (*Rosa* spp.), rubber (*Hevea brasiliensis*), rye (*Secale cereale*), safflower (*Carthamus tinctorius* L), sesame seed (*Sesame indium*), sorghum (*Sorghum bicolor*), soybean (*Glycine max* L.), squash (*Cucurbita pepo*), strawberries (*Fragaria* spp., *Fragaria x ananassa*), sugar beet (*Beta vulgaris*), sugarcanes (*Saccharum* spp.), sunflower (*Helianthus annus*), sweet potato (*Ipomoea batatas*), tangerine (*Citrus tangerina*), tea (*Camellia sinensis*), tobacco (*Nicotiana tabacum* L.), tomato (*Lycopersicon esculentum*), tulips (*Tulipa* spp.), turnip (*Brassica rapa rapa*), walnuts (*Juglans* spp. L.), watermelon (*Citrulus lanatus*), wheat (*Tritium aestivum*), and yams (*Discorea* spp.).

Embodiments of the method involve various treatments employed to deliver the polynucleotide composition to the non-epidermal plant cell. In embodiments, one or more treatments is employed to deliver the polynucleotide composition into the non-epidermal plant cell, e.g., through barriers such as a seed coat, a cell wall, a plasma membrane or nuclear envelope or other lipid bilayer, or through multiple cell layers or tissues. In an embodiment, the polynucleotide composition is delivered directly, for example by direct contact of the polynucleotide composition with the non-epidermal plant cell. Polynucleotide compositions in the form of a liquid, a solution, a suspension, an emulsion, a reverse emulsion, a colloid, a dispersion, a gel, liposomes, micelles, an injectable material, an aerosol, a solid, a powder, a particulate, a nanoparticle, or a combination thereof can be applied directly to a plant or plant part, to the surface or to the interior (e.g., through an incision, abrasion, or puncture, by spraying or dipping or soaking or otherwise directly contacting, by injection or microinjection). For example, a seed or seed fragment or embryo is soaked in or imbibes a liquid polynucleotide composition, whereby the gRNA is delivered to non-epidermal cells in the seed or seed fragment or embryo. In embodiments, the polynucleotide composition is delivered using negative or positive pressure, for example, using vacuum infiltration or application of hydrodynamic or fluid pressure. In embodiments, the polynucleotide composition is introduced into the vascular system of a plant or plant part, e.g., by injection or microinjection into the phloem, or by vascular uptake through a stem or petiole; see, e.g., Sun et al. (2005) *Plant J.,* 44:128-138. In embodiments, the polynucleotide composition is introduced into non-vascular tissues by injection or microinjection or through the application of negative or positive pressure. Other techniques useful for delivering the polynucleotide composition to a non-epidermal plant cell include: ultrasound or sonication; vibration, friction, shear stress, vortexing, cavitation; centrifugation or application of mechanical force; mechanical cell wall or cell membrane deformation or breakage; enzymatic cell wall or cell membrane breakage or permeabilization; abrasion or mechanical scarification (e.g., abrasion with carborundum or other particulate abrasive or scarification with a file or sandpaper) or chemical scarification (e.g., treatment with an acid or caustic agent); and electroporation. In embodiments, the polynucleotide composition is provided by bacterially mediated (e.g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection of the non-epidermal plant cell with a polynucleotide encoding the gRNA; see, e.g., Broothaerts et al. (2005) *Nature,* 433:629-633.

In embodiments, a treatment employed in delivery of the polynucleotide composition to the non-epidermal plant cell is carried out under a specific thermal regime, which can involve one or more appropriate temperatures, e.g., chilling or cold stress (exposure to temperatures below that at which normal plant growth occurs), or heating or heat stress (exposure to temperatures above that at which normal plant growth occurs), or treating at a combination of different temperatures. In embodiments, a specific thermal regime is carried out on the non-epidermal plant cell, or on the plant or plant part in which the non-epidermal plant cell is located, in one or more steps separate from the polynucleotide composition delivery.

Delivery Agents: Embodiments of the method include treatment of the non-epidermal plant cell, or the plant or plant part in which the non-epidermal plant cell is located, with one or more delivery agents which can include at least one chemical, enzymatic, or physical agent, or a combination thereof. In embodiments, the polynucleotide composition further includes one or more one chemical, enzymatic, or physical agent for delivery. In embodiments of the method that further include the step of providing to the non-epidermal plant cell an RNA-guided nuclease or a polynucleotide that encodes the RNA-guided nuclease, a composition including the RNA-guided nuclease or polynucleotide that encodes the RNA-guided nuclease further includes one or more one chemical, enzymatic, or physical agent for delivery. Treatment with the chemical, enzymatic or physical agent can be carried out simultaneously with the polynucleotide composition delivery, with the RNA-guided nuclease delivery, or in one or more separate steps that precede or follow the polynucleotide composition delivery or the RNA-guided nuclease delivery. In embodiments, a chemical, enzymatic, or physical agent, or a combination of these, is associated or complexed with the polynucleotide composition, with the gRNA or polynucleotide that encodes or is processed to the gRNA, or with the RNA-guided nuclease or polynucleotide that encodes the RNA-guided nuclease; examples of such associations or complexes include those involving non-covalent interactions (e.g., ionic or electrostatic interactions, hydrophobic or hydrophilic interactions, formation of liposomes, micelles, or other heterogeneous composition) and covalent interactions (e.g., peptide bonds, bonds formed using cross-linking agents). In non-limiting examples, a gRNA or polynucleotide that encodes or is processed to the gRNA is provided as a liposomal complex with a cationic lipid; a gRNA or polynucleotide that encodes or is processed to the gRNA is provided as a complex with a carbon nanotube; and an RNA-guided nuclease is provided as a fusion protein between the nuclease and a cell-penetrating peptide. Examples of agents useful for delivering a gRNA or polynucleotide that encodes or is processed to the gRNA or a nuclease or polynucleotide that encodes the nuclease include the various cationic liposomes and polymer nanoparticles reviewed by Zhang et al. (2007) J. *Controlled Release,* 123:1-10, and the cross-linked multilamellar liposomes described in US Patent Application Publication 2014/0356414 A1, incorporated by reference in its entirety herein.

In embodiments, the chemical agent is at least one selected from the group consisting of:

(a) solvents (e.g., water, dimethylsulfoxide, dimethylformamide, acetonitrile, N-pyrrolidine, pyridine, hexamethylphosphoramide, alcohols, alkanes, alkenes, dioxanes, polyethylene glycol, and other solvents miscible or emulsifiable with water or that will dissolve phosphonucleotides in non-aqueous systems);

(b) fluorocarbons (e.g., perfluorodecalin, perfluoromethyldecalin);

(c) glycols or polyols (e.g., propylene glycol, polyethylene glycol);

(d) surfactants, including cationic surfactants, anionic surfactants, non-ionic surfactants, and amphiphilic surfactants, e.g., alkyl or aryl sulfates, phosphates, sulfonates, or carboxylates; primary, secondary, or tertiary amines; quaternary ammonium salts; sultaines, betaines; cationic lipids; phospholipids; tallowamine; bile acids such as cholic acid; saponins or glycosylated triterpenoids or glycosylated sterols (e.g., saponin commercially available as catalogue number 47036-50g-F, Sigma-Aldrich, St. Louis, MO); long chain alcohols; organosilicone surfactants including nonionic organosilicone surfactants such as trisiloxane ethoxylate surfactants or a silicone polyether copolymer such as a copolymer of polyalkylene oxide modified heptamethyl trisiloxane and allyloxypolypropylene glycol methylether (commercially available as SILWET L-77™ brand surfactant having CAS Number 27306-78-1 and EPA Number CAL. REG. NO. 5905-50073-AA, Momentive Performance Materials, Inc., Albany, N.Y.); specific examples of useful surfactants include sodium lauryl sulfate, the Tween series of surfactants, Triton-X100, Triton-X114, CHAPS and CHAPSO, Tergitol-type NP-40, Nonidet P-40;

(e) lipids, lipoproteins, lipopolysaccharides;

(f) acids, bases, caustic agents;

(g) peptides, proteins, or enzymes (e.g., cellulase, pectolyase, maceroenzyme, pectinase), including cell-penetrating or pore-forming peptides (e.g., (BO100)2K8, Genscript; poly-lysine, poly-arginine, or poly-homoarginine peptides; gamma zein, see US Patent Application publication No. 2011/0247100, incorporated herein by reference in its entirety; transcription activator of human immunodeficiency virus type 1 ("HIV-1 Tat") and other Tat proteins, see, e.g., www[dot]lifetein[dot]com/Cell PenetratingPeptides[dot] html and Jarver (2012) *Mol. Therapy—Nucleic Acids,* 1: e27,1-17); octa-arginine or nona-arginine; poly-homoarginine (see Unnamalai et al. (2004) *FEBS Letters,* 566:307-310); see also the database of cell-penetrating peptides CPPsite 2.0 publicly available at crdd[dot]osdd[dot]net/raghava/cppsite/(h)

(h) RNase inhibitors;

(i) cationic branched or linear polymers such as chitosan, poly-lysine, DEAE-dextran, polyvinylpyrrolidone ("PVP"), or polyethylenimine ("PEI", e.g., PEI, branched, MW 25,000, CAS #9002-98-6; PEI, linear, MW 5000, CAS #9002-98-6; PEI linear, MW 2500, CAS #9002-98-6);

(j) dendrimers (see, e.g., US Patent Application Publication 2011/0093982, incorporated herein by reference in its entirety);

(k) counter-ions, amines or polyamines (e.g., spermine, spermidine, putrescine), osmolytes, buffers, and salts (e.g., calcium phosphate, ammonium phosphate);

(l) polynucleotides (e.g., non-specific double-stranded DNA, salmon sperm DNA);

(m) transfection agents (e.g., Lipofectin®, Lipofectamine®, and Oligofectamine®, and Invivofectamine® (all from Thermo Fisher Scientific, Waltham, MA), PepFect (see Ezzat et al. (2011) *Nucleic Acids Res.,* 39:5284-5298), Transit® transfection reagents (Minis Bio, LLC, Madison, WI), and poly-lysine, poly-homoarginine, and poly-arginine molecules including octo-arginine and nono-arginine as described in Lu et al. (2010) J. *Agric. Food Chem.,* 58:2288-2294);

(n) antibiotics, including non-specific DNA double-strand-break-inducing agents (e.g., phleomycin, bleomycin, talisomycin);

(o) antioxidants (e.g., glutathione, dithiothreitol, ascorbate); and (p) chelating agents (e.g., EDTA, EGTA).

In embodiments, the chemical agent is provided simultaneously with the gRNA (or polynucleotide encoding the gRNA or that is processed to the gRNA), for example, the polynucleotide composition including the gRNA further includes one or more chemical agent. In embodiments, the gRNA or polynucleotide encoding the gRNA or that is processed to the gRNA is covalently or non-covalently linked or complexed with one or more chemical agent; for example, the gRNA or polynucleotide encoding the gRNA or that is processed to the gRNA can be covalently linked to a peptide or protein (e.g., a cell-penetrating peptide or a pore-forming peptide) or non-covalently complexed with cationic lipids, polycations (e.g., polyamines), or cationic polymers (e.g., PEI). In embodiments, the gRNA or polynucleotide encoding the gRNA or that is processed to the gRNA is complexed with one or more chemical agents to form, e.g., a solution, liposome, micelle, emulsion, reverse emulsion, suspension, colloid, or gel.

In embodiments, the physical agent is at least one selected from the group consisting of particles or nanoparticles (e.g., particles or nanoparticles made of materials such as carbon, silicon, silicon carbide, gold, tungsten, polymers, or ceramics) in various size ranges and shapes, magnetic particles or nanoparticles (e.g., silenceMag Magnetotransfection™ agent, OZ Biosciences, San Diego, CA), abrasive or scarifying agents, needles or microneedles, matrices, and grids. In embodiments, particulates and nanoparticulates are useful in delivery of the polynucleotide composition or the nuclease or both. Useful particulates and nanoparticles include those made of metals (e.g., gold, silver, tungsten, iron, cerium), ceramics (e.g., aluminum oxide, silicon carbide, silicon nitride, tungsten carbide), polymers (e.g., polystyrene, polydiacetylene, and poly(3,4-ethylenedioxythiophene) hydrate), semiconductors (e.g., quantum dots), silicon (e.g., silicon carbide), carbon (e.g., graphite, graphene, graphene oxide, or carbon nanosheets, nanocomplexes, or nanotubes), and composites (e.g., polyvinylcarbazole/graphene, polystyrene/graphene, platinum/graphene, palladium/graphene nanocomposites). In embodiments, such particulates and nanoparticulates are further covalently or non-covalently functionalized, or further include modifiers or cross-linked materials such as polymers (e.g., linear or branched polyethylenimine, poly-lysine), polynucleotides (e.g., DNA or RNA), polysaccharides, lipids, polyglycols (e.g., polyethylene glycol, thiolated polyethylene glycol), polypeptides or proteins, and detectable labels (e.g., a fluorophore, an antigen, an antibody, or a quantum dot). In various embodiments, such particulates and nanoparticles are neutral, or carry a positive charge, or carry a negative charge. Embodiments of compositions including particulates include those formulated, e.g., as liquids, colloids, dispersions, suspensions, aerosols, gels, and solids. Embodiments include nanoparticles affixed to a surface or support, e.g., an array of carbon nanotubes vertically aligned on a silicon or copper wafer substrate. Embodiments include polynucleotide compositions including particulates (e.g., gold or tungsten or magnetic microparticles or nanoparticles) delivered by a Biolistic-type technique or with magnetic force. The size of the particles used in Biolistics is generally in the "microparticle" range, for example, gold microcarriers in the 0.6, 1.0, and 1.6 micrometer size ranges (see, e.g., instruction manual for the Helios® Gene Gun System, Bio-Rad, Hercules, CA; Randolph-Anderson et al. (2015) "Sub-micron gold particles are superior to larger particles for efficient Biolistic® transformation of organelles and some cell types", Bio-Rad US/EG Bulletin 2015), but successful Biolistics delivery using larger (40 nanometer) nanoparticles has been reported in cultured animal cells; see O'Brian and Lummis (2011) *BMC Biotechnol.,* 11:66-71. Other embodiments of useful particulates are nanoparticles, which are generally in the nanometer (nm) size range or less than 1 micrometer, e.g., with a diameter of less than about 1 nm, less than about 3 nm, less than about 5 nm, less than about 10 nm, less than about 20 nm, less than about 40 nm, less than about 60 nm, less than about 80 nm, and less than about 100 nm. Specific, non-limiting embodiments of nanoparticles commercially available (all from Sigma-Aldrich Corp., St. Louis, MO) include gold nanoparticles with diameters of 5, 10, or 15 nm; silver nanoparticles with particle sizes of 10, 20, 40, 60, or 100 nm; palladium "nanopowder" of less than 25 nm particle size; single-, double-, and multi-walled carbon nanotubes, e.g., with diameters of 0.7-1.1, 1.3-2.3, 0.7-0.9, or 0.7-1.3 nm, or with nanotube bundle dimensions of 2-10 nm by 1-5 micrometers, 6-9 nm by 5 micrometers, 7-15 nm by 0.5-10 micrometers, 7-12 nm by 0.5-10 micrometers, 110-170 nm by 5-9 micrometers, 6-13 nm by 2.5-20 micrometers. Embodiments include polynucleotide compositions including materials such as gold, silicon, cerium, or carbon, e.g., gold or gold-coated nanoparticles, silicon carbide whiskers, carborundum, porous silica nanoparticles, gelatin/silica nanoparticles, nanoceria or cerium oxide nanoparticles (CNPs), carbon nanotubes (CNTs) such as single-, double-, or multi-walled carbon nanotubes and their chemically functionalized versions (e.g., carbon nanotubes functionalized with amide, amino, carboxylic acid, sulfonic acid, or polyethylene glycol moeities), and graphene or graphene oxide or graphene complexes; see, for example, Wong et al. (2016) *Nano Lett.,* 16:1161-1172; Giraldo et al. (2014) *Nature Materials,* 13:400-409; Shen et al. (2012) *Theranostics,* 2:283-294; Kim et al. (2011) *Bioconjugate Chem.,* 22:2558-2567; Wang et al. (2010) *J Am. Chem. Soc. Comm.,* 132: 9274-9276; Zhao et al. (2016) *Nanoscale Res. Lett.,* 11:195-203; Choi et al. (2016) *J Controlled Release,* 235:222-235; and Zhai et al. (2014) *Environ. Sci. Technol. Lett.,* 1:146-151. See also, for example, the various types of particles and nanoparticles, their preparation, and methods for their use, e.g., in delivering polynucleotides and polypeptides to cells, disclosed in US Patent Application Publications 2010/0311168, 2012/0023619, 2012/0244569, 2013/0145488, 2013/0185823, 2014/0096284, 2015/0040268, 2015/0047074, and 2015/0208663, all of which are incorporated herein by reference in their entirety.

In embodiments wherein the polynucleotide composition includes an RNA-guided nuclease, or a polynucleotide that encodes the RNA-guided nuclease, or wherein the method further includes the step of providing to the non-epidermal plant cell an RNA-guided nuclease or a polynucleotide that encodes the RNA-guided nuclease, one or more one chemical, enzymatic, or physical agent can similarly be employed. In embodiments, the RNA-guided nuclease (or polynucleotide encoding the RNA-guided nuclease) is provided separately, e.g., in a separate composition including the RNA-guided nuclease or polynucleotide encoding the RNA-guided nuclease. Such compositions can include other chemical or physical agents (e.g., solvents, surfactants, proteins or enzymes, transfection agents, particulates or nanoparticulates), such as those described above as useful in the polynucleotide composition used to provide the gRNA. For example, porous silica nanoparticles are useful for delivering a DNA recombinase into maize cells; see, e.g., Martin-Ortigosa et al. (2015) *Plant Physiol.,* 164:537-547. In an embodiment, the polynucleotide composition includes a gRNA and Cas9 nuclease, and further includes a surfactant and a cell-penetrating peptide. In an embodiment, the polynucleotide composition includes a plasmid that encodes both an RNA-guided nuclease and at least on gRNA, and further includes a surfactant and carbon nanotubes. In an embodiment, the polynucleotide composition includes multiple gRNAs and an mRNA encoding the RNA-guided nuclease, and further includes gold particles, and the polynucleotide composition is delivered to the plant cell by Biolistics.

In related embodiments, one or more one chemical, enzymatic, or physical agent can be used in one or more steps separate from (preceding or following) that in which the polynucleotide composition is provided to the non-epidermal plant cell. In an embodiment, the plant or plant part in which the non-epidermal plant cell is located is treated with an agent to assist in access to the interior of the plant or plant part, for example, with an abrasive, a caustic agent, a surfactant, or an enzyme, followed by application of the polynucleotide composition (and optionally the nuclease). In an embodiment, a halved seed or dissected embryo is treated with a surfactant such as Silwet L-77, followed by application of the polynucleotide composition (and optionally the nuclease). In an embodiment, the shoot apical meristem of a plant is treated with cellulase, followed by application of the polynucleotide composition.

In embodiments, the polynucleotide composition is provided/applied at a location in the plant or plant part other than the non-epidermal plant cell. In embodiments, the polynucleotide composition is applied to adjacent or distal non-meristematic cells and is transported (e.g., through the vascular system or by cell-to-cell movement) to meristematic non-epidermal plant cell. In embodiments, the polynucleotide composition is applied by soaking a seed or seed fragment or embryo in the polynucleotide composition, whereby the gRNA is delivered to non-epidermal cells in the seed or seed fragment or embryo. In embodiments, a flower bud or shoot tip is contacted with the polynucleotide composition, whereby the gRNA is delivered to non-epidermal cells in the flower bud or shoot tip, or to other non-epidermal cells in the plant. In embodiments, the polynucleotide composition is applied to the surface of a plant or of a part of a plant (e.g., a leaf surface), whereby the gRNA is delivered to non-epidermal cells in the plant. In embodiments a whole plant or plant tissue is subjected to particle- or nanoparticle-mediated delivery (e.g., Biolistics or carbon nanotube or nanoparticle delivery) of the polynucleotide composition, whereby the gRNA is delivered to non-epidermal plant cells.

Delivery of a gRNA by the method of the invention results in alteration of the target nucleotide sequence in the non-epidermal plant cell. In embodiments, the altered target nucleotide sequence includes at least one sequence modification selected from the group consisting of insertion of a nucleotide, deletion of a nucleotide, and replacement of a nucleotide. In embodiments, insertion of a nucleotide includes insertion of additional heterologous sequence. In embodiments, alteration of the target nucleotide sequence results in a change (e.g., increase or decrease or change in temporal or spatial specificity) in expression of the target nucleotide sequence, methylation or demethylation of the target nucleotide sequence (e.g., resulting in an epigenetic change), or a phenotype, or a combination of these. In embodiments, alteration of the target nucleotide sequence results in a phenotype or trait of interest observable in a seedling or plant grown or regenerated from the non-epidermal plant cell; in some embodiments the phenotype or trait is heritable to succeeding generations of plants. Thus, related embodiments include such succeeding generations of plants or their seeds having inherited the altered target nucleotide sequence.

A related aspect of the invention is directed to the non-epidermal plant cell including an altered target nucleotide sequence, provided by the method. Embodiments of the method further include one or more steps of growing or regenerating a plant from the non-epidermal plant cell including an altered target nucleotide sequence, wherein the grown or regenerated plant contains at least some cells or tissues having the altered target nucleotide sequence. In embodiments, callus is produced from the non-epidermal plant cell, and plantlets and plants produced from such callus. In other embodiments, whole seedlings or plants are grown directly from the non-epidermal plant cell without a callus stage. Thus, additional related aspects are directed to whole seedlings and plants grown or regenerated from the non-epidermal plant cell including an altered target nucleotide sequence, as well as the seeds of such plants. In embodiments, the grown or regenerated plant exhibits a phenotype associated with the altered target nucleotide sequence. In embodiments, the grown or regenerated plant includes in its genome two or more genetic modifications that in combination provide at least one phenotype of interest, wherein at least one genetic modification includes the altered target nucleotide sequence in the non-epidermal plant cell. In embodiments, a heterogeneous population of non-epidermal plant cells, at least some of which include one or more altered target nucleotide sequences, is provided by the method; related aspects include a plant having a phenotype of interest associated with the altered target nucleotide sequence, provided by either regeneration of a plant having the phenotype of interest from a cell selected from the heterogeneous population of non-epidermal plant cells, or by selection of a plant having the phenotype of interest from a heterogeneous population of plants grown or regenerated from the population of non-epidermal plant cells. Examples of phenotypes of interest include herbicide resistance, improved tolerance of abiotic stress (e.g., tolerance of temperature extremes, drought, or salt) or biotic stress (e.g., resistance to bacterial or fungal pathogens), improved utilization of nutrients or water, modified lipid, carbohydrate, or protein composition, improved flavour or appearance, improved storage characteristics (e.g., resistance to bruising, browning, or softening), increased yield, altered morphology (e.g., floral architecture or colour, plant height, branching, root structure). In an embodiment, a heterogeneous population of non-epidermal plant cells (or seedlings or plants grown or regenerated from the cells) is exposed to conditions permitting expression of the phenotype of interest; e.g., selection for herbicide resistance can include exposing the population of cells (or seedlings or plants) to an amount of herbicide or other substance that inhibits growth or is toxic, allowing identification and selection of those resistant cells (or seedlings or plants) that survive treatment. Also contemplated are heterogeneous populations, arrays, or libraries of such plants, succeeding generations or seeds of such plants, parts of the plants (including plant parts used in grafting as scions or rootstocks), or products (e.g., fruits or other edible plant parts, cleaned grains or seeds, edible oils, flours or starches, proteins, and other processed products) made from the plants or their seeds. Embodiments include plants that contain cells or tissues that do not have the altered nucleotide sequence, e.g., grafted plants in which the scion or rootstock contains the altered nucleotide sequence, or chimeric plants in which some but not all cells or tissues contain the altered nucleotide sequence. Plants in which grafting is commonly useful include many fruit trees and plants such as many citrus trees, apples, stone fruit (e.g., peaches, apricots, cherries, and plums), avocados, tomatoes, eggplant, cucumber, melons, watermelons, and grapes as well as various ornamental plants such as roses. Grafted plants can be grafts between the same or different (generally related) species. Additional related aspects include a hybrid plant provided by crossing a first plant grown or regenerated from a non-epidermal plant cell with an altered target nucleotide sequence, with a second plant, wherein the hybrid plant contains the altered target nucleotide sequence; also contemplated is seed produced by the hybrid plant.

Delivery of Effector Molecules to a Plant Cell

In related aspects, the delivery techniques, delivery agents, and compositions disclosed above under the heading "Methods of altering a target nucleotide sequence in a non-epidermal plant cell" are useful in general for delivering other molecules to effect an alteration in a nucleotide sequence in a plant cell capable of division and differentiation. Such "effector molecules" include other nucleases or polynucleotides encoding a nuclease capable of effecting site-specific alteration of a target nucleotide sequence, and guide polynucleotides that guide nucleases in a sequence-specific manner to a target nucleotide sequence.

Thus, a related aspect of the invention is a method of providing a plant having a genetic alteration, including: (a) delivery of at least one effector molecule to a plant cell capable of division and differentiation, resulting in a genetic alteration of the plant cell, wherein the plant cell is a cell in a plant or part of a plant selected from the group consisting of a plant tissue, a whole plant, an intact nodal bud, a shoot apex or shoot apical meristem, a root apex or root apical meristem, lateral meristem, intercalary meristem, a seedling (e.g., a germinating seed or small seedling or a larger seedling with one or more true leaves), a whole seed (e.g., an intact seed, or a seed with part or all of its seed coat removed or treated to make permeable), a halved seed or other seed fragment, an embryo (e.g., a mature dissected zygotic embryo, a developing embryo, a dry or rehydrated or freshly excised embryo), and callus; wherein the delivery of the at least one effector molecule includes at least one treatment selected from the group consisting of: direct application; soaking or imbibition; vacuum infiltration; application of negative or positive pressure; introduction into the vascular system; microinjection; application of ultrasound or vibration; application of hydrodynamic pressure, friction, cavitation or shear stress; vortexing; centrifugation; mechanical cell wall or cell membrane deformation or breakage; enzymatic cell wall or cell membrane breakage or permeabilization; abrasion; electroporation; and treatment with at least one chemical, enzymatic, or physical agent; and (b) regeneration of a plant from the plant cell having the genetic alteration, wherein the plant includes differentiated cells or tissues having the genetic alteration. In embodiments, delivery of the at least one effector molecule alters a target nucleotide sequence in the plant cell, resulting in a genetic alteration such as insertion of a nucleotide, deletion of a nucleotide, or replacement of a nucleotide. In embodiments, insertion of a nucleotide includes insertion of additional heterologous sequence. In embodiments, the genetic alteration results in a change (e.g., increase or decrease or change in temporal or spatial specificity) in expression of the target nucleotide sequence, methylation or demethylation of the target nucleotide sequence (e.g., resulting in an epigenetic change), or a phenotype, or a combination of these.

The target nucleotide sequence is one or more nucleotide sequences, including protein-coding sequence or non-coding sequence or a combination thereof. Embodiments include a plant nuclear sequence, a plant plastid sequence, a plant mitochondrial sequence, a sequence of a symbiont, pest, or pathogen of a plant, and combinations thereof. In embodiments, multiple target nucleotide sequences are altered, for example, by delivery of multiple effector molecules to the plant cell; the multiple target nucleotide sequences can be part of the same gene (e.g., different locations in a single coding region or in different exons of a protein-coding gene) or different genes.

Embodiments of effector molecules include: (a) a polynucleotide selected from the group consisting of an RNA guide for an RNA-guided nuclease, a DNA encoding an RNA guide for an RNA-guided nuclease; (b) a nuclease selected from the group consisting of an RNA-guided nuclease, an RNA-guided DNA endonuclease, a type II Cas nuclease, a Cas9, a type V Cas nuclease, a Cpf1, a CasY, a CasX, a C2c1, a C2c3, an engineered nuclease, a codon-optimized nuclease, a zinc-finger nuclease (ZFN), a transcription activator-like effector nuclease (TAL-effector nuclease), Argonaute, a meganuclease or engineered meganuclease; or (c) a polynucleotide encoding one or more nucleases capable of effecting site-specific alteration of a target nucleotide sequence. Any of these nucleases can be codon-optimized, e.g., plant-codon-optimized to function optimally in a plant cell. In embodiments, one or multiple effector molecules are delivered individually (e.g., in separate compositions) or in combinations (e.g., in a ribonucleoprotein), and in a single step or multiple steps.

Zinc finger nucleases (ZFNs) are engineered proteins including a zinc finger DNA-binding domain fused to a nucleic acid cleavage domain, e.g., a nuclease. The zinc finger binding domains provide specificity and can be engineered to specifically recognize any desired target DNA sequence. For a review of the construction and use of ZFNs in plants and other organisms, see, e.g., Urnov et al. (2010) *Nature Rev. Genet.,* 11:636-646. The zinc finger DNA binding domains are derived from the DNA-binding domain of a large class of eukaryotic transcription factors called zinc finger proteins (ZFPs). The DNA-binding domain of ZFPs typically contains a tandem array of at least three zinc "fingers" each recognizing a specific triplet of DNA. A number of strategies can be used to design the binding specificity of the zinc finger binding domain. One approach, termed "modular assembly", relies on the functional autonomy of individual zinc fingers with DNA. In this approach, a given sequence is targeted by identifying zinc fingers for each component triplet in the sequence and linking them into a multifinger peptide. Several alternative strategies for designing zinc finger DNA binding domains have also been developed. These methods are designed to accommodate the ability of zinc fingers to contact neighboring fingers as well as nucleotides bases outside their target triplet. Typically, the engineered zinc finger DNA binding domain has a novel binding specificity, compared to a naturally-occurring zinc finger protein. Engineering methods include, for example, rational design and various types of selection. Rational design includes, for example, the use of databases of triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, e.g., U.S. Pat. Nos. 6,453,242 and 6,534,261, both incorporated herein by reference in their entirety. Exemplary selection methods (e.g., phage display and yeast two-hybrid systems) are well known and described in the literature. In addition, enhancement of binding specificity for zinc finger binding domains has been described in U.S. Pat. No. 6,794,136, incorporated herein by reference in its entirety. In addition, individual zinc finger domains may be linked together using any suitable linker sequences. Examples of linker sequences are publicly known, e.g., see U.S. Pat. Nos. 6,479,626; 6,903,185; and 7,153,949, incorporated herein by reference in their entirety. The nucleic acid cleavage domain is non-specific and is typically a restriction endonuclease, such as Fokl. This endonuclease must dimerize to cleave DNA. Thus, cleavage by Fokl as part of a ZFN requires two adjacent and independent binding events, which must occur in both the correct orientation and with appropriate spacing to permit dimer formation. The requirement for two DNA binding events enables more specific targeting of long and potentially unique recognition sites. Fokl variants with enhanced activities have been described; see, e.g., Guo et al. (2010) *J. Mol. Biol.,* 400:96-107.

Transcription activator like effectors (TALEs) are proteins secreted by certain *Xanthomonas* species to modulate gene expression in host plants and to facilitate the colonization by and survival of the bacterium. TALEs act as transcription factors and modulate expression of resistance genes in the plants. Recent studies of TALEs have revealed the code linking the repetitive region of TALEs with their target DNA-binding sites. TALEs comprise a highly conserved and repetitive region consisting of tandem repeats of mostly 33 or 34 amino acid segments. The repeat monomers differ from each other mainly at amino acid positions 12 and 13. A strong correlation between unique pairs of amino acids at positions 12 and 13 and the corresponding nucleotide in the TALE-binding site has been found. The simple relationship between amino acid sequence and DNA recognition of the TALE binding domain allows for the design of DNA binding domains of any desired specificity. TALEs can be linked to a non-specific DNA cleavage domain to prepare genome editing proteins, referred to as TAL-effector nucleases or TALENs. As in the case of ZFNs, a restriction endonuclease, such as Fokl, can be conveniently used. For a description of the use of TALENs in plants, see Mahfouz et al. (2011) *Proc. Natl. Acad. Sci. USA,* 108:2623-2628 and Mahfouz (2011) *GM Crops,* 2:99-103.

Argonautes are proteins that can function as sequence-specific endonucleases by binding a polynucleotide (e.g., a single-stranded DNA or single-stranded RNA) that includes sequence complementary to a target nucleotide sequence) that guides the Argonaut to the target nucleotide sequence and effects site-specific alteration of the target nucleotide sequence; see, e.g., US Patent Application Publication 2015/0089681, incorporated herein by reference in its entirety.

In related embodiments, zinc finger nucleases, TALENs, and Argonautes are used in conjunction with other functional domains. For example, the nuclease activity of these nucleic acid targeting systems can be altered so that the enzyme binds to but does not cleave the DNA. Examples of functional domains include transposase domains, integrase domains, recombinase domains, resolvase domains, invertase domains, protease domains, DNA methyltransferase domains, DNA hydroxylmethylase domains, DNA demethylase domains, histone acetylase domains, histone deacetylase domains, nuclease domains, repressor domains, activator domains, nuclear-localization signal domains, transcription-regulatory protein (or transcription complex recruiting) domains, cellular uptake activity associated domains, nucleic acid binding domains, antibody presentation domains, histone modifying enzymes, recruiter of histone modifying enzymes; inhibitor of histone modifying enzymes, histone methyltransferases, histone demethylases, histone kinases, histone phosphatases, histone ribosylases, histone deribosylases, histone ubiquitinases, histone deubiquitinases, histone biotinases and histone tail proteases. Non-limiting examples of functional domains include a transcriptional activation domain, a transcription repression domain, and an SHH1, SUVH2, or SUVH9 polypeptide capable of reducing expression of a target nucleotide sequence via epigenetic modification; see, e.g., US Patent Application Publication 2016/0017348, incorporated herein by reference in its entirety. Genomic DNA may also be modified via base editing using a fusion between a catalytically inactive Cas9 (dCas9) is fused to a cytidine deaminase which convert cytosine (C) to uridine (U), thereby effecting a C to T substitution; see Komor et al. (2016) *Nature,* 533:420-424.

In embodiments, the plant cell capable of division and differentiation is diploid or polyploid. In embodiments, the plant cell is haploid or can be induced to become haploid; examples include but are not limited to plant cells in haploid plants and plant cells in reproductive tissues, e.g., flowers, developing flowers or flower buds, ovaries, ovules, megaspores, anthers, pollen, and microspores. In embodiments where the plant cell is haploid, the method can further include the step of chromosome doubling (e.g., by using a chromosome doubling agent such as colchicine) in the plant cell including the genetic alteration to produce a doubled haploid cell that is homozygous for the genetic alteration; yet other embodiments include regeneration of a doubled haploid plant from the doubled haploid cell, wherein the regenerated doubled haploid plant is homozygous for the genetic alteration. Thus, aspects of the invention are related to the haploid cell having the genetic alteration as well as a doubled haploid cell or a doubled haploid plant that is homozygous for the genetic alteration. Another aspect of the invention is related to a hybrid plant having at least one parent plant that is a doubled haploid plant provided by the method.

A related aspect of the invention is directed to the plant having a genetic alteration, provided by the method. In embodiments, the plant is a monocot or a dicot, or is haploid, diploid, polyploid, or doubled haploid. Embodiments include plants that contain cells or tissues that do not have the genetic alteration, e.g., grafted plants in which the scion or rootstock contains the genetic alteration, or chimeric plants in which some but not all cells or tissues contain the genetic alteration. In embodiments, the genetic alteration is heritable to succeeding generations; further aspects thus include seed and progeny plants of the plant having a genetic alteration, wherein the seed or progeny plants contain the genetic alteration, as well as parts of such seed or progeny plants (including plant parts used in grafting as scions or rootstocks), or products (e.g., fruits or other edible plant parts, cleaned grains or seeds, edible oils, flours or starches, proteins, and other processed products) made from the seed or progeny plants. In embodiments, callus is produced from the plant cell having the genetic alteration, and plantlets and plants produced from such callus. In other embodiments, whole seedlings or plants are grown directly from the plant cell having the genetic alteration without a callus stage. Thus, additional related aspects are directed to whole seedlings and plants grown or regenerated from the plant cell having the genetic alteration, as well as the seeds of such plants. In embodiments, the grown or regenerated plant exhibits a phenotype associated with the genetic alteration. Examples of phenotypes of interest include herbicide resistance, improved tolerance of abiotic stress (e.g., tolerance of temperature extremes, drought, or salt) or biotic stress (e.g., resistance to bacterial or fungal pathogens), improved utilization of nutrients or water, modified lipid, carbohydrate, or protein composition, improved flavour or appearance, increased yield, altered morphology (e.g., floral architecture, plant height, branching, root structure). In embodiments, the grown or regenerated plant includes in its genome two or more genetic modifications that in combination provide at least one phenotype of interest, wherein at least one genetic modification includes the genetic alteration provided by the plant cell treated by the method.

Methods for Investigating Reverse Genetics

Another aspect of the invention is related to methods for investigating reverse genetics, for example, a method of identifying a nucleotide sequence (or alteration of a nucleotide sequence, such as a native nucleotide sequence) that is associated with a phenotype of interest. In an embodiment, the method includes the steps of altering the genome of a population of plant cells (or plant protoplasts), optionally growing or regenerating a population of calli, seedlings, plantlets, or plants from the population of plant cells, and selecting the plant cells (or grown or regenerated calli, seedlings, plantlets, or plants) exhibiting the phenotype of interest and identifying the nucleotide sequence associated with the phenotype. Embodiments of the method include culturing or growing the plant cells or protoplasts (or calli, seedlings, plantlets, or plants) under conditions that permit expression of the phenotype of interest.

In an embodiment, the method includes the steps of: (a) contacting a population of plant cells (or protoplasts) with a library of gRNAs and optionally with an RNA-guided DNA nuclease, whereby the genome of the plant cells is altered, culturing the population of plant cells under conditions that permit expression of the phenotype of interest, selecting the plant cells that exhibit the phenotype of interest, and identifying the nucleotide sequence or alteration of a nucleotide sequence, wherein the nucleotide sequence thus identified is associated with the phenotype; or (b) contacting a population of plant cells (or protoplasts) with a library of gRNAs and optionally with an RNA-guided DNA nuclease, whereby the genome of the cells is altered, regenerating a population of plants from the population of plant cells, growing the population of plants under conditions that permit expression of the phenotype of interest, selecting the plants that exhibit the phenotype of interest, and identifying the nucleotide sequence or alteration of a nucleotide sequence, wherein the nucleotide sequence thus identified is associated with the phenotype. In embodiments, the plant cells in which the genome is altered are haploid cells (e.g., microspore or other gametophytic cells, or cells of a haploid plant) and the plants regenerated from these cells are haploid plants; in embodiments the method further includes the step of generating doubled-haploid cells or doubled-haploid plants from the haploid cells or plants.

In embodiments, the gRNA is provided as a polynucleotide composition including: (i) a CRISPR RNA (crRNA) that includes the gRNA, or a polynucleotide that encodes a crRNA, or a polynucleotide that is processed into a crRNA; or (ii) a single guide RNA (sgRNA) that includes the gRNA, or a polynucleotide that encodes an sgRNA, or a polynucleotide that is processed into an sgRNA. In embodiments, the plant cells contain or express the appropriate RNA-guided DNA nuclease; in other embodiments the RNA-guided DNA nuclease, or a polynucleotide encoding the RNA-guided DNA nuclease, is provided to the plant cells. In embodiments, the nuclease is selected from the group consisting of an RNA-guided nuclease, an RNA-guided DNA endonuclease, a type II Cas nuclease, a Cas9, a type V Cas nuclease, a Cpf1, a CasY, a CasX, a C2c1, a C2c3, an engineered nuclease, a codon-optimized nuclease, a zinc-finger nuclease (ZFN), a transcription activator-like effector nuclease (TAL-effector nuclease), Argonaute, a meganuclease or engineered meganuclease. Methods and compositions useful for delivering the library of gRNAs or the RNA-guided DNA nuclease are similar to those described under the heading "Methods of altering a target nucleotide sequence in a plant cell".

Compositions and Reaction Mixtures

Another aspect of the invention is related to compositions and reactions mixtures useful for carrying out methods such as those described herein. In one aspect, the invention is related to a composition or a reaction mixture including: (a) at least one non-epidermal plant cell, which in embodiments is a cell in whole plant, whole seed, embryo, plant part, or plant tissue; (b) at least one effector molecule for inducing a genetic alteration in the non-epidermal plant cell, wherein the at least one effector molecule is selected from the group consisting of: (i) a polynucleotide selected from the group consisting of an RNA guide for an RNA-guided nuclease, a DNA encoding an RNA guide for an RNA-guided nuclease; (ii) a nuclease selected from the group consisting of an RNA-guided nuclease, an RNA-guided DNA endonuclease, a type II Cas nuclease, a Cas9, a type V Cas nuclease, a Cpf1, a CasY, a CasX, a C2c1, a C2c3, an engineered nuclease, a codon-optimized nuclease, a zinc-finger nuclease (ZFN), a transcription activator-like effector nuclease (TAL-effector nuclease), Argonaute, a meganuclease or engineered meganuclease; or (iii) a polynucleotide encoding one or more nucleases capable of effecting site-specific alteration of a target nucleotide sequence; and (c) optionally, at least one delivery agent selected from the group consisting of solvents, fluorocarbons, glycols or polyols, surfactants; primary, secondary, or tertiary amines and quaternary ammonium salts; organosilicone surfactants; lipids, lipoproteins, lipopolysaccharides; acids, bases, caustic agents; peptides, proteins, or enzymes; cell-penetrating peptides; RNase inhibitors; cationic branched or linear polymers; dendrimers; counter-ions, amines or polyamines, osmolytes, buffers, and salts; polynucleotides; transfection agents; antibiotics; non-specific DNA double-strand-break-inducing agents; antioxidants; chelating agents; particles or nanoparticles, magnetic particles or nanoparticles, abrasive or scarifying agents, needles or microneedles, matrices, and grids.

In another aspect, the invention is related to a composition or a reaction mixture including: (a) at least one non-epidermal plant cell, which in embodiments is a cell in whole plant, whole seed, embryo, plant part, or plant tissue; (b) at least one guide RNA (gRNA) having a nucleotide sequence designed to alter a target nucleotide sequence in the non-epidermal plant cell, wherein the gRNA is provided as a polynucleotide composition including: (i) a CRISPR RNA (crRNA) that includes the gRNA, or a polynucleotide that encodes a crRNA, or a polynucleotide that is processed into a crRNA; or (ii) a single guide RNA (sgRNA) that includes the gRNA, or a polynucleotide that encodes an sgRNA, or a polynucleotide that is processed into an sgRNA; (c) optionally, at least one nuclease, or at least one polynucleotide that encodes the nuclease, wherein the nuclease is selected from the group consisting of an RNA-guided nuclease, an RNA-guided DNA endonuclease, a type II Cas nuclease, a Cas9, a type V Cas nuclease, a Cpf1, a CasY, a CasX, a C2c1, a C2c3, an engineered nuclease, a codon-optimized nuclease, a zinc-finger nuclease (ZFN), a transcription activator-like effector nuclease (TAL-effector nuclease), Argonaute, a meganuclease or engineered meganuclease; and (d) optionally, at least one delivery agent selected from the group consisting of solvents, fluorocarbons, glycols or polyols, surfactants; primary, secondary, or tertiary amines and quaternary ammonium salts; organosilicone surfactants; lipids, lipoproteins, lipopolysaccharides; acids, bases, caustic agents; peptides, proteins, or enzymes; cell-penetrating peptides; RNase inhibitors; cationic branched or linear polymers; dendrimers; counter-ions, amines or polyamines, osmolytes, buffers, and salts; polynucleotides; transfection agents; antibiotics; non-specific DNA double-strand-break-inducing agents; antioxidants; chelating agents; particles or nanoparticles, magnetic particles or nanoparticles, abrasive or scarifying agents, needles or microneedles, matrices, and grids. In embodiments, the gRNA is a single guide RNA (sgRNA) that includes the gRNA, wherein the composition further includes an RNA-guided nuclease, and wherein the sgRNA and RNA guided-nuclease are provided as a ribonucleoprotein (RNP) complex. In embodiments, the at least one plant cell or plant protoplast is a population of plant cells or plant protoplasts, the at least one gRNA is two or more sgRNAs, wherein the composition further includes an RNA-guided nuclease, and wherein the two or more sgRNAs are each provided are provided as a ribonucleoprotein (RNP) complex with the RNA guided-nuclease.

In embodiments of these compositions and reaction mixtures, the at least one non-epidermal plant cell is a plant cell located in plant tissue, a plant part, or an intact plant or seed, or is a plant cell in callus. In embodiments, the at least one non-epidermal plant cell is obtained from a monocot or a dicot. In various embodiments, the at least one non-epidermal plant cell is haploid, diploid, or polyploid.

The foregoing description and the examples presented in this disclosure describe the subject matter of this invention, which includes the following: (I) a method of delivering a guide RNA (gRNA) to a non-epidermal plant cell, wherein the non-epidermal plant cell is in a plant or part of a plant, wherein the gRNA has a nucleotide sequence designed to alter a target nucleotide sequence in the non-epidermal plant cell, and wherein the gRNA is provided as a polynucleotide composition including: (i) a CRISPR RNA (crRNA) that includes the gRNA, or a polynucleotide that encodes a crRNA, or a polynucleotide that is processed into a crRNA; or (ii) a single guide RNA (sgRNA) that includes the gRNA, or a polynucleotide that encodes an sgRNA, or a polynucleotide that is processed into an sgRNA; wherein the delivery of the polynucleotide composition includes at least one treatment selected from the group consisting of: direct application; soaking or imbibition; vacuum infiltration; application of negative or positive pressure; introduction into the vascular system; microinjection; application of ultrasound or vibration; application of hydrodynamic pressure, friction, cavitation or shear stress; vortexing; centrifugation; mechanical cell wall or cell membrane deformation or breakage; enzymatic cell wall or cell membrane breakage or permeabilization; abrasion; electroporation; and treatment with at least one chemical, enzymatic, or physical agent; whereby the gRNA is delivered to the non-epidermal plant cell; wherein the method is optionally further characterized by one or more of the following: (1) wherein the plant or part of a plant is selected from the group consisting of a plant tissue, a whole plant, an intact nodal bud, a shoot apex or shoot apical meristem, a root apex or root apical meristem, lateral meristem, intercalary meristem, a seedling, a whole seed, a halved seed or other seed fragment, an embryo, and callus; (2) wherein the plant is a dicot or a monocot; (3) wherein delivery of the gRNA results in alteration of the target nucleotide sequence in the non-epidermal plant cell; (4) wherein: (a) the polynucleotide composition optionally includes an RNA-guided nuclease, or a polynucleotide that encodes the RNA-guided nuclease; or (b) the method further includes the step of providing to the non-epidermal plant cell an RNA-guided nuclease or a polynucleotide that encodes the RNA-guided nuclease; or (c) the non-epidermal plant cell includes an RNA-guided nuclease or a polynucleotide that encodes the RNA-guided nuclease; (5) wherein (a) the polynucleotide composition further includes a chemical agent or a physical agent or a combination of both chemical and physical agents, or (b) the method further includes the step of treating the plant cell with a chemical agent or a physical agent or a combination of both chemical and physical agents; wherein the chemical agent is at least one selected from the group consisting of solvents, fluorocarbons, glycols or polyols, surfactants; primary, secondary, or tertiary amines and quaternary ammonium salts; saponins; organosilicone surfactants; lipids, lipoproteins, lipopolysaccharides; acids, bases, caustic agents; peptides, proteins, or enzymes; cell-penetrating peptides; RNase inhibitors; cationic branched or linear polymers; dendrimers; counter-ions, amines or polyamines, osmolytes, buffers, and salts; polynucleotides; transfection agents; antibiotics; non-specific DNA double-strand-break-inducing agents; antioxidants; and chelating agents; and wherein the physical agent is at least one selected from the group consisting of particles or nanoparticles, magnetic particles or nanoparticles, abrasive or scarifying agents, needles or microneedles, matrices, and grids; (6) wherein the crRNA, the polynucleotide that encodes a crRNA, the polynucleotide that is processed into a crRNA, the sgRNA, the polynucleotide that encodes an sgRNA, or the polynucleotide that is processed into an sgRNA further includes one or more additional nucleotide sequences selected from the group consisting of an aptamer or riboswitch sequence, a nucleotide sequence that provides secondary structure, a nucleotide sequence that provides a sequence-specific site for an enzyme, T-DNA sequence, a DNA nuclear-targeting sequence, a regulatory sequence, and a transcript-stabilizing sequence; (7) wherein the crRNA, the polynucleotide that encodes a crRNA, the polynucleotide that is processed into a crRNA, the sgRNA, the polynucleotide that encodes an sgRNA, or the polynucleotide that is processed into an sgRNA includes: (a) double-stranded RNA, (b) single-stranded RNA; (c) chemically modified RNA; (d) a combination of (a)-(c); (8) wherein the polynucleotide composition includes a liquid, a solution, a suspension, an emulsion, a reverse emulsion, a colloid, a dispersion, a gel, liposomes, micelles, an injectable material, an aerosol, a solid, a powder, a particulate, a nanoparticle, or a combination thereof; (9) wherein the polynucleotide composition is provided at a location in the plant or plant part other than the non-epidermal plant cell; (10) wherein: (a) the polynucleotide composition optionally includes an RNA-guided nuclease, or a polynucleotide that encodes the RNA-guided nuclease; or (b) the method further includes the step of providing to the non-epidermal plant cell an RNA-guided nuclease or a polynucleotide that encodes the RNA-guided nuclease; or (c) the non-epidermal plant cell includes an RNA-guided nuclease or a polynucleotide that encodes the RNA-guided nuclease; and wherein the RNA-guided nuclease is selected from the group consisting of an RNA-guided DNA endonuclease, a type II Cas nuclease, a Cas9, a type V Cas nuclease, a Cpf1, a CasY, a CasX, a C2c1, a C2c3, an engineered nuclease, and a codon-optimized nuclease; (11) wherein: (a) the polynucleotide composition optionally includes an RNA-guided nuclease, or a polynucleotide that encodes the RNA-guided nuclease; or (b) the method further includes the step of providing to the non-epidermal plant cell an RNA-guided nuclease or a polynucleotide that encodes the RNA-guided nuclease; or (c) the non-epidermal plant cell includes an RNA-guided nuclease or a polynucleotide that encodes the RNA-guided nuclease; and wherein the RNA-guided nuclease or polynucleotide that encodes the RNA-guided nuclease is provided: (a) as a ribonucleoprotein complex including the crRNA and the RNA-guided nuclease; (b) as a complex including the RNA-guided nuclease or polynucleotide that encodes the RNA-guided nuclease and at least one peptide selected from the group consisting of a cell-penetrating peptide, viral movement protein, or transfecting peptide; (c) as a fusion protein including the RNA-guided nuclease and at least one peptide selected from the group consisting of a cell-penetrating peptide, viral movement protein, or transfecting peptide; (d) on a carrier molecule or a particulate; (e) in a liposome, micelle, protoplast or protoplast fragment; or (f) using a combination of any of (a)-(e); (12) wherein: (a) the polynucleotide composition optionally includes an RNA-guided nuclease, or a polynucleotide that encodes the RNA-guided nuclease; or (b) the method further includes the step of providing to the non-epidermal plant cell an RNA-guided nuclease or a polynucleotide that encodes the RNA-guided nuclease; or (c) the non-epidermal plant cell includes an RNA-guided nuclease or a polynucleotide that encodes the RNA-guided nuclease; and wherein the RNA-guided nuclease is provided: (a) by contacting the non-epidermal plant cell with the RNA-guided nuclease or polynucleotide that encodes the RNA-guided nuclease; (b) by transporting the RNA-guided nuclease or polynucleotide that encodes the RNA-guided nuclease into the non-epidermal plant cell using a chemical, enzymatic, or physical agent; (c) by bacterially mediated transfection with a polynucleotide encoding the RNA-guided nuclease; or (d) by transcription of a polynucleotide that encodes the RNA-guided nuclease; and (13) wherein the non-epidermal plant cell is: (a) diploid or (b) haploid.

The subject matter of this invention further includes: (II) A non-epidermal plant cell including an altered target nucleotide sequence, provided by at least one of the methods described above under (I), wherein the method is optionally further characterized by further including growth or regeneration of a plant from the non-epidermal plant cell including an altered target nucleotide sequence, wherein the plant includes cells having the altered target nucleotide sequence. The subject matter of this invention therefore further includes: (III) A regenerated plant provided by at least one of the methods described above under (I), or seed or plant parts of the regenerated plant, wherein the method further includes growth or regeneration of a plant from the non-epidermal plant cell including an altered target nucleotide sequence, wherein the plant includes cells having the altered target nucleotide sequence; and wherein the regenerated plant is optionally further characterized by one or more of the following: (1) wherein the regenerated plant exhibits a phenotype associated with the altered target nucleotide sequence; and (2) wherein the regenerated plant includes in its genome two or more genetic modifications that in combination provide at least one phenotype of interest, wherein at least one genetic modification includes the altered target nucleotide sequence in the non-epidermal plant cell.

The subject matter of this invention further includes: (IV) At least one of the methods described above under (I), wherein the method further includes the step of chromosome doubling in the non-epidermal plant cell including the altered target nucleotide sequence to produce a doubled haploid cell that is homozygous for the altered target nucleotide sequence; and wherein the method optionally further includes the step of regeneration of a doubled haploid plant from the doubled haploid cell, wherein the regenerated doubled haploid plant includes cells that are homozygous for the altered target nucleotide sequence. The subject matter of this invention therefore further includes: (V) A doubled haploid cell that is homozygous for the altered target nucleotide sequence, provided by at least one of the methods described above under (I), wherein the method further includes the step of chromosome doubling in the non-epidermal plant cell including the altered target nucleotide sequence to produce a doubled haploid cell that is homozygous for the altered target nucleotide sequence. The subject matter of this invention therefore further includes: (VI) A regenerated doubled haploid plant, or seed or plant parts of the regenerated doubled haploid plant, wherein the regenerated doubled haploid plant is provided by at least one of the methods described above under (I), wherein the method further includes the steps of (a) chromosome doubling in the non-epidermal plant cell including the altered target nucleotide sequence to produce a doubled haploid cell that is homozygous for the altered target nucleotide sequence, and (b) regeneration of a doubled haploid plant from the doubled haploid cell, wherein the regenerated doubled haploid plant includes cells that are homozygous for the altered target nucleotide sequence. The subject matter of this invention also further includes: (VII) A hybrid plant having at least one parent plant that is a regenerated doubled haploid plant provided according to (VI) above.

The subject matter of this invention further includes: (VIII) A method of providing a plant having a genetic alteration, including: (a) delivery of an effector molecule to a plant cell capable of division and differentiation, resulting in a genetic alteration of the plant cell; wherein the plant cell is a cell in a plant or part of a plant selected from the group consisting of a plant tissue, a whole plant, an intact nodal bud, a shoot apex or shoot apical meristem, a root apex or root apical meristem, lateral meristem, intercalary meristem, a seedling, a whole seed, a halved seed or other seed fragment, an embryo, and callus; wherein the plant is a monocot or a dicot; wherein the effector molecule is at least one selected from the group consisting of: (i) a polynucleotide selected from the group consisting of an RNA guide for an RNA-guided nuclease, a DNA encoding an RNA guide for an RNA-guided nuclease; (ii) a nuclease selected from the group consisting of an RNA-guided nuclease, an RNA-guided DNA endonuclease, a type II Cas nuclease, a Cas9, a type V Cas nuclease, a Cpf1, a CasY, a CasX, a C2c1, a C2c3, an engineered nuclease, a codon-optimized nuclease, a zinc-finger nuclease (ZFN), a transcription activator-like effector nuclease (TAL-effector nuclease), Argonaute, a meganuclease or engineered meganuclease; or (iii) a polynucleotide encoding one or more nucleases capable of effecting site-specific alteration of a target nucleotide sequence; wherein delivery includes at least one treatment selected from the group consisting of at least one treatment selected from the group consisting of: direct application; soaking or imbibition; vacuum infiltration; application of negative or positive pressure; introduction into the vascular system; microinjection; application of ultrasound or vibration; application of hydrodynamic pressure, friction, cavitation or shear stress; vortexing; centrifugation; mechanical cell wall or cell membrane deformation or breakage; enzymatic cell wall or cell membrane breakage or permeabilization; abrasion; electroporation; and treatment with at least one chemical, enzymatic, or physical agent; and (b) regeneration of a plant from the plant cell, wherein the plant includes differentiated cells or tissues having the genetic alteration; wherein the method is optionally further characterized by one or more of the following: (1) wherein the genetic alteration is at least one sequence alteration selected from the group consisting of insertion of a nucleotide, deletion of a nucleotide, or replacement of a nucleotide; (2) wherein the genetic alteration is heritable to succeeding generations; and (3) wherein the plant cell is a cell in a seedling, a whole seed, a seed fragment, a mature dissected zygotic embryo, or a developing embryo, and wherein the regeneration of a plant from the plant cell includes growing the plant from the seedling, whole seed, seed fragment, mature dissected zygotic embryo, or developing embryo.

The subject matter of this invention also further includes: (IX) A plant having a genetic alteration produced by any of the methods described above under (VIII), as well as seed of such a plant, wherein the seed contains the genetic alteration.

The subject matter of this invention further includes: (X) A method of identifying a nucleotide sequence associated with a phenotype of interest, including: (a) contacting a population of plant cells/protoplasts with a library of gRNAs or a library of polynucleotides encoding gRNAs and optionally with an RNA-guided DNA nuclease, whereby the genome of the cells/protoplasts is altered, culturing the population of plant cells or plant protoplasts under conditions that permit expression of the phenotype of interest, selecting the plant cells or plant protoplasts that exhibit the phenotype of interest, and identifying the nucleotide sequence or alteration of a nucleotide sequence, wherein the nucleotide sequence thus identified is associated with the phenotype; or (b) contacting a population of plant cells/protoplasts with a library of gRNAs or a library of polynucleotides encoding gRNAs and optionally with an RNA-guided DNA nuclease, whereby the genome of the cells/protoplasts is altered, regenerating a population of plants from the population of plant cells or plant protoplasts, growing the population of plants under conditions that permit expression of the phenotype of interest, selecting the plants that exhibit the phenotype of interest, and identifying the nucleotide sequence or alteration of a nucleotide sequence, wherein the nucleotide sequence thus identified is associated with the phenotype.

The above-described subject matter is further illustrated by the non-limiting embodiments described throughout the specification and in the Examples that follow.

EXAMPLES

Example 1

This example illustrates a method of delivering at least one effector molecule to a plant cell wherein the plant cell is located in a plant or plant part. More specifically, this non-limiting example describes delivery of an RNA guide for an RNA-guided nuclease (i.e., an sgRNA) and the corresponding RNA-guided nuclease (i.e., Cas9) to a non-epidermal plant cell (i.e., a cell in a soybean embryo), resulting in editing of an endogenous plant gene (i.e., phytoene desaturase, PDS) in germline cells of excised soybean embryos. This example demonstrates delivery of polynucleotides encoding effector molecules (sgRNAs, nucleases) through multiple barriers (e.g., multiple cell layers, seed coat, cell walls, plasma membrane) directly into soybean germline cells, resulting in a heritable alteration of the target nucleotide sequence, PDS. The methods described do not employ the common techniques of bacterially mediated transformation (e.g., by *Agrobacterium* sp.) or biolistics.

Plasmids were designed for delivery of Cas9 (Csnl) endonuclease from the *Streptococcus pyogenes* Type II CRISPR/Cas system and a single guide RNA (sgRNA) targeting the endogenous phytoene desaturase (PDS) in soybean, *Glycine max*. The sequences of these plasmids and specific elements contained therein are described in Tables 1 and 2 below.

TABLE 1 sgRNA vector (SEQ ID NO: 1), 3079 base pairs DNA

| Nucleotide position in SEQ ID NO: 1 | Description | Comment |
|---|---|---|
| 1-3079 | Intact plasmid | SEQ ID NO: 1 |
| 379-395 | M13 forward primer for sequencing | |
| 412-717 | *Glycine max* U6 promoter | |
| 717-736 | *Glycine max* phytoene desaturase targeting sequence (gRNA) | SEQ ID NO: 2 |
| 737-812 | guide RNA scaffold sequence for *S. pyogenes* CRISPR/Cas9 system | SEQ ID NO: 3 |
| 856-874 | M13 reverse primer for sequencing | complement |
| 882-898 | lac repressor encoded by lacI | |
| 906-936 | lac promoter for the *E. coli* lac operon | complement |
| 951-972 | *E. coli* catabolite activator protein (CAP) binding site | |
| 1260-1848 | high-copy-number ColE1/pMB1/pBR322/pUC origin of replication (left direction) | complement |
| 2019-2879 | CDS for bla, beta-lactamase, AmpR | complement; ampicillin selection |
| 2880-2984 | bla promoter | complement |

The sgRNA vector having the sequence of SEQ ID NO:1 contains nucleotides at positions 717-812 encoding a single guide RNA having the sequence of SEQ ID NO:4, which includes both a targeting sequence (gRNA) (SEQ ID NO:2) and a guide RNA scaffold (SEQ ID NO:3); transcription of the sgRNA is driven by a *Glycine max* U6 promoter at nucleotide positions 412-717. The sgRNA vector also includes lac operon and ampicillin resistance sequences for convenient selection of the plasmid in bacterial cultures.

TABLE 2 endonuclease vector (SEQ ID NO: 5), 8569 base pairs DNA

| Nucleotide position in SEQ ID NO: 4 | Description | Comment |
|---|---|---|
| 1-8569 | Intact plasmid | SEQ ID NO: 5 |
| 379-395 | M13 forward primer for sequencing | |
| 419-1908 | *Glycine max* UbiL promoter | |
| 1917-6020 | Cas9 (Csn1) endonuclease from the *Streptococcus pyogenes* type II CRISPR/Cas system | SEQ ID NO: 6 (encodes protein with sequence of SEQ ID NO: 7) |
| 6033-6053 | nuclear localization signal of SV40 large T antigen | SEQ ID NO: 8 (encodes peptide with sequence of SEQ ID NO: 9 |
| 6065-6317 | nopaline synthase (NOS) terminator and poly(A) signal | |
| 6348-6364 | M13 reverse primer for sequencing | complement |
| 6372-6388 | lac repressor encoded by lacI | |
| 6396-6426 | lac promoter for the *E. coli* lac operon | complement |
| 6441-6462 | *E. coli* catabolite activator protein (CAP) binding site | |
| 6750-7338 | high-copy-number ColE1/pMB1/pBR322/pUC origin of replication (left direction) | complement |
| 7509-8369 | CDS for bla, beta-lactamase, AmpR | complement; ampicillin selection |
| 8370-8474 | bla promoter | complement |

The endonuclease vector having the sequence of SEQ ID NO:5 contains nucleotides at positions 1917-6020 having the sequence of SEQ ID NO:6 and encoding the Cas9 nuclease from *Streptococcus pyogenes* that has the amino acid sequence of SEQ ID NO:7, and nucleotides at positions 6033-6053 having the sequence of SEQ ID NO:8 and encoding the nuclear localization signal (NLS) of simian virus 40 (SV40) large T antigen that has the amino acid sequence of SEQ ID NO:9. Transcription of the Cas9 nuclease and adjacent SV40 nuclear localization signal is driven by a *Glycine max* UbiL promoter at nucleotide positions 419-1908; the resulting transcript including nucleotides at positions 1917-6053 having the sequence of SEQ ID NO:10 encodes a fusion protein having the sequence of SEQ ID NO:11 wherein the Cas9 nuclease is linked through a 4-residue peptide linker to the SV40 nuclear localization signal. The endonuclease vector also includes lac operon and ampicillin resistance sequences for convenient selection of the plasmid in bacterial cultures.

Similar vectors for expression of nucleases and sgRNAs are also described, e.g., in Fauser et al. (2014) *Plant J.,* 79:348-359; and described at www[dot]addgene[dot]org/crispr. It will be apparent to one skilled in the art that analogous plasmids are easily designed to encode other guide polynucleotide or nuclease sequences, optionally including different elements (e.g., different promoters, terminators, selectable or detectable markers, a cell-penetrating peptide, a nuclear localization signal, a chloroplast transit peptide, or a mitochondrial targeting peptide, etc.), and used in a similar manner. Embodiments of nuclease fusion proteins include fusions (with or without an optional peptide linking sequence) between the Cas9 nuclease from *Streptococcus pyogenes* that has the amino acid sequence of SEQ ID NO:7 and at least one of the following peptide sequences: (a) GRKKRRQRRRPPQ ("HIV-1 Tat (48-60)", SEQ ID NO:12), (b) GRKKRRQRRRPQ ("TAT", SEQ ID NO:13), (c) YGRKKRRQRRR ("TAT (47-57)", SEQ ID NO:14), (d) KLALKLALKALKAALKLA ("MAP (KLAL)", SEQ ID NO:15), (e) RQIRIWFQNRRMRWRR ("Penetratin-Arg", SEQ ID NO:16), (0 CSIPPEVKFNKPFVYLI ("antitrypsin (358-374)", SEQ ID NO:17), (g) RRRQRRKKRGGDIMGEWGNEIFGAIAGFLG ("TAT-HA2 Fusion Peptide", SEQ ID NO:18), (h) FVQWFSKFL-GRIL-NH2 ("Temporin L, amide", SEQ ID NO:19), (i) LLIILRRRIRKQAHAHSK ("pVEC (Cadherin-5)", SEQ ID NO:20), (j) LGTYTQDFNKFHTFPQTAIGVGAP ("Calcitonin", SEQ ID NO:21), (k) GAAEAAARVYDLGLRRLRQRRRLRRERVRA ("Neurturin", SEQ ID NO:22), (1) MGLGLHLLV-LAAALQGAWSQPKKKRKV ("Human P1", SEQ ID NO:23), (m) RQIKIWFQNRRMKWKKGG ("Penetratin", SEQ ID NO:24), poly-arginine peptides including (n) RRRRRRRR ("octo-arginine", SEQ ID NO:25) and (o) RRRRRRRRR ("nono-arginine", SEQ ID NO:26), and (p) KKLFKKILKYLKKLFKKILKYLKKKKKKKK ("(BP100x2)-K8", SEQ ID NO:27); these nuclease fusion proteins are specifically claimed herein. In other embodiments, such vectors are used to produce a guide RNA (such as one or more crRNAs or sgRNAs) or the nuclease protein; guide RNAs and nucleases can be combined to produce a specific ribonucleoprotein complex for delivery to the plant cell; in an example, a ribonucleoprotein including the sgRNA having the sequence of SEQ ID NO:4 and the Cas9-NLS fusion protein having the sequence of SEQ ID NO:11 is produced for delivery to the plant cell. Related aspects of the invention thus encompass ribonucleoprotein compositions containing the ribonucleoprotein including the sgRNA having the sequence of SEQ ID NO:4 and a Cas9 fusion protein such as the Cas9-NLS fusion protein having the sequence of SEQ ID NO:11, and polynucleotide compositions containing one or more polynucleotides including the sequences of SEQ ID NOs: 4 or 10. The above sgRNA and nuclease vectors are delivered to plant cells using compositions and methods described in the specification.

In a first series of experiments, the sgRNA and nuclease vectors were delivered to non-epidermal plant cells in soybean embryos using combinations of delivery agents and electroporation. Mature, dry soybean seeds (cv. Williams 82) were surface-sterilized as follows. Dry soybean seeds were held for 4 hours in an enclosed chamber holding a beaker containing 100 milliliters 5% sodium hypochlorite solution to which 4 milliliters hydrochloric acid were freshly added. Seeds remained desiccated after this sterilization treatment. The sterilized seeds were split into 2 halves by manual application of a razor blade and the embryos manually separated from the cotyledons. Each test or control treatment was carried out on 20 excised embryos.

Experiment 1: A delivery solution containing the sgRNA and nuclease vectors (100 nanograms per microliter of each plasmid) in 0.01% CTAB (cetyltrimethylammonium bromide, a quaternary ammonium surfactant) in sterile-filtered milliQ water was prepared. Each solution was chilled to 4 degrees Celsius and 500 microliters were added directly to the embryos, which were then immediately placed on ice in a vacuum chamber and subjected to a negative pressure ($2\times10^{-3}$ millibar) treatment for 15 minutes. Following the chilling/negative pressure treatments, the embryos were treated with electric current using a BTX-Harvard ECM-830 electroporation device set with the following parameters: 50V, 25 millisecond pulse length, 75 millisecond pulse interval for 99 pulses.

Experiment 2: conditions identical to Experiment 1, except that the initial contacting with delivery solution and negative pressure treatments were carried out at room temperature.

Additional experiments are performed as follows:

Experiment 3: conditions identical to Experiment 1, except that the delivery solution is prepared without CTAB but includes 0.1% Silwet L-77 (CAS Number 27306-78-1, available from Momentive Performance Materials, Albany, N.Y). Half (10 of 20) of the embryos receiving each treatment undergo electroporation, and the other half of the embryos do not.

Experiment 4: conditions identical to Experiment 3, except that several delivery solutions are prepared, where each further includes 20 micrograms/milliliter of one single-walled carbon nanotube preparation selected from those with catalogue numbers 704113, 750530, 724777, and 805033, all obtainable from Sigma-Aldrich, St. Louis, MO. Half (10 of 20) of the embryos receiving each treatment undergo electroporation, and the other half of the embryos do not.

Experiment 5: conditions identical to Experiment 3, except that the delivery solution further includes 20 micrograms/milliliter of triethoxylpropylaminosilane-functionalized silica nanoparticles (catalogue number 791334, Sigma-Aldrich, St. Louis, MO Half (10 of 20) of the embryos receiving each treatment undergo electroporation, and the other half of the embryos do not.

Experiment 6: conditions identical to Experiment 3, except that the delivery solution further includes 9 micrograms/milliliter branched polyethylenimine, molecular weight 25,000 (CAS Number 9002-98-6, catalogue number 408727, Sigma-Aldrich, St. Louis, MO) or 9 micrograms/milliliter branched polyethylenimine, molecular weight ~800 (CAS Number 25987-06-8, catalogue number 408719, Sigma-Aldrich, St. Louis, MO). Half (10 of 20) of the embryos receiving each treatment undergo electroporation, and the other half of the embryos do not.

Experiment 7: conditions identical to Experiment 3, except that the delivery solution further includes 20% v/v dimethylsulfoxide (DMSO, catalogue number D4540, Sigma-Aldrich, St. Louis, MO). Half (10 of 20) of the embryos receiving each treatment undergo electroporation, and the other half of the embryos do not.

Experiment 8: conditions identical to Experiment 3, except that the delivery solution further contains 50 micromolar nono-arginine (RRRRRRRRR, SEQ ID NO:26). Half (10 of 20) of the embryos receiving each treatment undergo electroporation, and the other half of the embryos do not.

Experiment 9: conditions identical to Experiment 3, except that following the vacuum treatment, the embryos and treatment solutions are transferred to microcentrifuge tubes and centrifuged 2, 5, 10, or 20 minutes at 4000x g. Half (10 of 20) of the embryos receiving each treatment undergo electroporation, and the other half of the embryos do not.

Experiment 10: conditions identical to Experiment 3, except that following the vacuum treatment, the embryos and treatment solutions are transferred to microcentrifuge tubes and centrifuged 2, 5, 10, or 20 minutes at 4000x g.

Experiment 11: conditions identical to Experiment 4, except that following the vacuum treatment, the embryos and treatment solutions are transferred to microcentrifuge tubes and centrifuged 2, 5, 10, or 20 minutes at 4000x g.

Experiment 12: conditions identical to Experiment 5, except that following the vacuum treatment, the embryos and treatment solutions are transferred to microcentrifuge tubes and centrifuged 2, 5, 10, or 20 minutes at 4000x g.

After the delivery treatment, each treatment group of embryos is washed 5 times with sterile water, transferred to a petri dish containing ½ MS solid medium (2.165 g Murashige and Skoog medium salts, catalogue number MSP0501, Caisson Laboratories, Smithfield, UT), 10 grams sucrose, and 8 grams Bacto agar, made up to 1.00 liter in distilled water), and placed in a tissue culture incubator set to 25 degrees Celsius. After the embryos have elongated, developed roots and true leaves have emerged, the seedlings are transferred to soil and grown out. Modification of all endogenous PDS alleles results in a plant unable to produce chlorophyll and having a visible bleached phenotype. Modification of a fraction of all endogenous PDS alleles results in plants still able to produce chlorophyll; plants that are heterozygous for an altered PDS gene will are grown out to seed and the efficiency of heritable genome modification is determined by molecular analysis of the progeny seeds.

Example 2

This example illustrates a method of delivering polynucleotides encoding effector molecules (sgRNAs, nucleases) to a plant cell wherein the plant cell is located in a plant or plant part. More specifically, this non-limiting example describes delivery of an RNA guide for an RNA-guided nuclease (i.e., an sgRNA) and the corresponding RNA-guided nuclease (i.e., Cas9) to a non-epidermal plant cell (i.e., a cell in a soybean embryo), resulting in editing of an endogenous plant gene (i.e., phytoene desaturase, PDS) in germline cells of excised soybean embryos. The polynucleotides are delivered using combinations of chemical agents such as cationic polymers, and physical treatments such as use of negative pressure.

The sgRNA vector (SEQ ID NO:1) and nuclease vector (SEQ ID NO:5) described in Example 1 are used in a series of experiments. Mature, dry soybean seeds (cv. Williams 82)

are surface-sterilized as follows. Dry soybean seeds are held for 4 hours in an enclosed chamber holding a beaker containing 100 milliliters 5% sodium hypochlorite solution to which 4 milliliters hydrochloric acid are freshly added. Seeds remained desiccated after this sterilization treatment. The sterilized seeds are split into 2 halves by manual application of a razor blade and the embryos manually separated from the cotyledons. Each test and control treatment experiment is carried out on 20 excised embryos, with treatments carried out in 96-well plates (two embryos per well).

Solutions are prepared with branched polyethylenimine ("PEI", CAS Number 9002-98-6) in sterile-filtered milliQ water. Three molecular weights of PEI are used: molecular weight ~25,000 (catalogue number 408727), ~5,000 (catalogue number 764582), and ~2,500 (catalogue number 764604) (all from Sigma Aldrich, St. Louis, MO). Four concentrations of PEI are used: 1, 5, 25, and 125 micrograms/milliliter final concentrations. The sgRNA and nuclease vectors (final concentrations of 5 micrograms/microliter of each plasmid) are added to the PEI solutions, and the mixtures incubated for 1 hour at room temperature to allow PEI/DNA complexes to form. Each solution is then chilled to 4 degrees Celsius and 500 microliters is added directly to the embryos, which are then immediately placed on ice and vacuum infiltrated ($2\times10^{-3}$ millibar) for 2 hours with shaking at 100 rpm.

Following vacuum infiltration, the embryos are rinsed with 5% sodium hypochlorite solution, washed 5 times with sterile water, transferred to a petri dish containing ½×MS medium (2.165 g Murashige and Skoog medium salts, catalogue number MSP0501, Caisson Laboratories, Smithfield, UT), 10 grams sucrose, and 8 grams Bacto agar, made up to 1.00 liter in distilled water), and placed in a tissue culture incubator set to 25 degrees Celsius. After the embryos have elongated, developed roots and true leaves have emerged, the seedlings are transferred to soil and grown out. Modification of all endogenous PDS alleles results in a plant unable to produce chlorophyll and having a visible bleached phenotype. Modification of a fraction of all endogenous PDS alleles results in plants still able to produce chlorophyll; plants that are heterozygous for an altered PDS gene will are grown out to seed and the efficiency of heritable genome modification is determined by molecular analysis of the progeny seeds.

Example 3

This example illustrates a method of delivering polynucleotides encoding effector molecules (sgRNAs, nucleases) to a plant cell wherein the plant cell is located in a plant or plant part. More specifically, this non-limiting example describes delivery of a single vector encoding both an RNA guide for an RNA-guided nuclease (i.e., an sgRNA) and the corresponding RNA-guided nuclease (i.e., Cas9) to a non-epidermal plant cell (i.e., a cell in a soybean embryo), resulting in editing of the endogenous phytoene desaturase (PDS) in germline cells of excised soybean embryos. The polynucleotides are delivered using combinations of chemical agents such as a cell-penetrating peptide or a cationic polymer, and physical treatments such as use of negative pressure.

A plasmid ("pCas9TPC-GmPDS") having the nucleotide sequence of SEQ ID NO:28 was designed for delivery of Cas9 (Csnl) endonuclease from the *Streptococcus pyogenes* Type II CRISPR/Cas system and a single guide RNA (sgRNA) targeting the endogenous phytoene desaturase (PDS) in soybean, *Glycine max*. The sequences of this plasmid and specific elements contained therein are described in Table 3 below.

TABLE 3 pCas9TPC-GmPDS vector (SEQ ID NO: 28), 14548 base pairs DNA

| Nucleotide position in SEQ ID NO: 28 | Description | Comment |
|---|---|---|
| 1-14548 | Intact plasmid | SEQ ID NO: 28 |
| 1187-1816 | pVS1 StaA | stability protein from the *Pseudomonas* plasmid pVS1 |
| 2250-3317 | pVS1 RepA | replication protein from the *Pseudomonas* plasmid pVS1 |
| 3383-3577 | pVS1 oriV | origin of replication for the *Pseudomonas* plasmid pVS1 |
| 3921-4061 | basis of mobility region from pBR322 | |
| 4247-4835 | high-copy-number ColE1/pMB1/pBR322/pUC origin of replication (left direction) | complement |
| 5079-5870 | aminoglycoside adenylyltransferase (aadA), confers resistance to spectinomycin and streptomycin | complement |
| 6398-6422 | left border repeat from nopaline C58 T-DNA | |
| 6599-6620 | *E. coli* catabolite activator protein (CAP) binding site | |
| 6635-6665 | lac promoter for the *E. coli* lac operon | |
| 6673-6689 | lac repressor encoded by lacI | |
| 6697-6713 | M13 reverse primer for sequencing | |
| 6728-7699 | PcUbi4-2 promoter | |
| 7714-11817 | Cas9 (Csn1) endonuclease from the *Streptococcus pyogenes* type II CRISPR/Cas system | SEQ ID NO: 6 (encodes protein with sequence of SEQ ID NO: 7) |
| 11830-11850 | nuclear localization signal of SV40 large T antigen | SEQ ID NO: 8 (encodes peptide with sequence of SEQ ID NO: 9 |
| 11868-12336 | Pea3A terminator | |
| 12349-12736 | AtU6-26 promoter | |
| 12737-12756 | *Glycine max* phytoene desaturase targeting sequence (gRNA) | SEQ ID NO: 2 |
| 12757-12832 | guide RNA scaffold sequence for *S. pyogenes* CRISPR/Cas9 system | SEQ ID NO: 3 |
| 12844-12868 | attB2; recombination site for Gateway ® BP reaction | complement |
| 13549-14100 | *Streptomyces hygroscopicus bar* or *pat*, encodes phosphinothricin acetyltransferase, confers resistance to bialophos or phosphinothricin | |
| 14199-14215 | M13 forward primer, for sequencing | complement |
| 14411-14435 | right border repeat from nopaline C58 T-DNA | |

The pCas9TPC-GmPDS vector having the sequence of SEQ ID NO:28 contains nucleotides at positions 12737-12832 encoding a single guide RNA having the sequence of SEQ ID NO:4, which includes both a targeting sequence (gRNA) (SEQ ID NO:2) and a guide RNA scaffold (SEQ ID NO:3); transcription of the single guide RNA is driven by a AtU6-26 promoter at nucleotide positions 12349-12736. This vector further contains nucleotides at positions 7714-11817 having the sequence of SEQ ID NO:6 and encoding the Cas9 nuclease from *Streptococcus pyogenes* that has the amino acid sequence of SEQ ID NO:7, and nucleotides at positions 11830-11850 having the sequence of SEQ ID NO:8 and encoding the nuclear localization signal (NLS) of simian virus 40 (SV40) large T antigen that has the amino acid sequence of SEQ ID NO:9. Transcription of the Cas9 nuclease and adjacent SV40 nuclear localization signal is driven by a PcUbi4-2 promoter at nucleotide positions 6728-7699; the resulting transcript including nucleotides at positions 7714-11850 having the sequence of SEQ ID NO:10 encodes a fusion protein having the sequence of SEQ ID NO:11 wherein the Cas9 nuclease is linked through a 4-residue peptide linker to the SV40 nuclear localization signal. The pCas9TPC-GmPDS vector also includes lac operon, aminoglycoside adenylyltransferase, and phosphinothricin acetyltransferase sequences for convenient selection of the plasmid in bacterial or plant cultures.

In a series of experiments, the pCas9TPC-GmPDS vector (SEQ ID NO:28) was delivered to non-epidermal plant cells in soybean embryos using combinations of delivery agents and application of negative pressure. Mature, dry soybean seeds (cv. Williams 82) were surface-sterilized as follows. Dry soybean seeds were held for 4 hours in an enclosed chamber holding a beaker containing 100 milliliters 5% sodium hypochlorite solution to which 4 milliliters hydrochloric acid were freshly added. Seeds remained desiccated after this sterilization treatment. The sterilized seeds were split into 2 halves by manual application of a razor blade and the embryos manually separated from the cotyledons. Each test or control treatment experiment was carried out on 10 dry excised embryos. The excised embryos were transferred to 1.5-microliter microcentrifuge tubes.

Treatments included use of delivery agents including a cell-penetrating peptide ("CPP") having the amino acid sequence KKLFKKILKYLKKLFKKILKYLKKKKKKKK ("(BP100x2)-K8", SEQ ID NO:27), and a cationic polymer, branched polyethylenimine ("PEI"), molecular weight 25,000 (CAS Number 9002-98-6, catalogue number 408727, Sigma-Aldrich, St. Louis, MO). Stock solutions of the pCas9TPC-GmPDS vector (SEQ ID NO:28) (500 nanograms/microliter), CPP (10 micrograms/microliter), and PEI (10 micrograms/microliter) were prepared. Treatment solutions were prepared according to Table 4 and incubated 1 hour at room temperature to allow the plasmid to form complexes with the CPP or PEI delivery agents. Control treatment solutions included sterile milliQ water (no plasmid, no delivery agents) as well as a solution of the plasmid in milliQ water with no delivery agents.

TABLE 4

| Treatment | Plasmid (SEQ ID NO: 28), micrograms/ milliliter | Cell-penetrating peptide (SEQ ID NO: 27), micrograms/milliliter | Branched PEI, micrograms/ milliliter |
|---|---|---|---|
| CPP-1 | 20 | 1 | 0 |
| CPP-2 | 20 | 10 | 0 |
| CPP-3 | 20 | 500 | 0 |
| CPP-4 | 1 | 500 | 0 |
| PEI-1 | 5 | 0 | 50 |
| PEI-2 | 5 | 0 | 75 |
| PEI-3 | 5 | 0 | 100 |
| PEI-4 | 5 | 0 | 250 |

Each tube received 1000 microliters of the prepared treatment solutions and placed on ice. The tubes were vacuum infiltrated ($2\times10^{-3}$ millibar) for 2 hours in a desiccator submerged in ice. Following vacuum infiltration, the embryos were rinsed with 5% sodium hypochlorite solution, washed 5 times with sterile water, transferred to a petri dish containing ½×MS medium (2.165 g Murashige and Skoog medium salts, catalogue number MSP0501, Caisson Laboratories, Smithfield, UT), 10 grams sucrose, and 8 grams Bacto agar, made up to 1.00 liter in distilled water), and placed in a tissue culture incubator set to 25 degrees Celsius. After the embryos have elongated, developed roots and true leaves have emerged, the seedlings are transferred to soil and grown out to seed. Modification of all endogenous PDS alleles results in a plant unable to produce chlorophyll and having a visible bleached phenotype. Modification of a fraction of all endogenous PDS alleles results in plants still able to produce chlorophyll; plants that are heterozygous for an altered PDS gene will are grown out to seed and the efficiency of heritable genome modification is determined by molecular analysis of the progeny seeds.

Example 4

This example illustrates a method of delivering at least one effector molecule to a plant cell wherein the plant cell is located in a plant or plant part. More specifically, this non-limiting example illustrates a method of delivering a polynucleotide composition including a guide RNA (gRNA) to a non-epidermal plant cell in a seed of a plant and editing of an endogenous plant gene (phytoene desaturase, PDS) in germline cells of *Nicotiana benthamiana* seeds. This example demonstrates delivery of polynucleotides encoding effector molecules (sgRNAs, nucleases) through multiple barriers (e.g., multiple cell layers, seed coat, cell walls, plasma membrane) directly into *Nicotiana benthamiana* germline cells, resulting in a heritable alteration of the target nucleotide sequence, PDS. The methods described do not employ the common techniques of bacterially mediated transformation (e.g., by *Agrobacterium* sp.) or biolistics.

A plasmid ("pCas9TPC-NbPDS") having the nucleotide sequence of SEQ ID NO:29 was designed for delivery of Cas9 (Csnl) endonuclease from the *Streptococcus pyogenes* Type II CRISPR/Cas system and a single guide RNA (sgRNA) targeting the endogenous phytoene desaturase (PDS) in *Nicotiana benthamiana*; see Nekrasov et al. (2013) *Nature Biotechnol.,* 31:691-693. The sequences of this plasmid and specific elements contained therein are described in Table 5 below.

TABLE 5 pCas9TPC-NbPDS vector (SEQ ID NO: 29), 14548 base pairs DNA

| Nucleotide position in SEQ ID NO: 29 | Description | Comment |
|---|---|---|
| 1-14548 | Intact plasmid | SEQ ID NO: 29 |
| 1187-1816 | pVS1 StaA | stability protein from the *Pseudomonas* plasmid pVS1 |
| 2250-3317 | pVS1 RepA | replication protein from the *Pseudomonas* plasmid pVS1 |
| 3383-3577 | pVS1 oriV | origin of replication for the *Pseudomonas* plasmid pVS1 |
| 3921-4061 | basis of mobility region from pBR322 | |
| 4247-4835 | high-copy-number ColE1/pMB1/pBR322/pUC origin of replication (left direction) | Complement |
| 5079-5870 | aminoglycoside adenylyltransferase resistance to (aadA), confers spectinomycin and streptomycin | Complement |

TABLE 5-continued pCas9TPC-NbPDS vector (SEQ ID NO: 29), 14548 base pairs DNA

| Nucleotide position in SEQ ID NO: 29 | Description | Comment |
|---|---|---|
| 6398-6422 | left border repeat from nopaline C58 T-DNA | |
| 6599-6620 | *E. coli* catabolite activator protein (CAP) binding site | |
| 6635-6665 | lac promoter for the *E. coli* lac operon | |
| 6673-6689 | lac repressor encoded by lacI | |
| 6697-6713 | M13 reverse primer for sequencing | |
| 6728-7699 | PcUbi4-2 promoter | |
| 7714-11817 | Cas9 (Csn1) endonuclease from the *Streptococcus pyogenes* type II CRISPR/Cas system | SEQ ID NO: 6 (encodes protein with sequence of SEQ ID NO: 7) |
| 11830-11850 | nuclear localization signal of SV40 large T antigen | SEQ ID NO: 8 (encodes peptide with sequence of SEQ ID NO: 9 |
| 11868-12336 | Pea3A terminator | |
| 12349-12736 | AtU6-26 promoter | |
| 12737-12756 | *Nicotiana benthamiana* phytoene desaturase targeting sequence | SEQ ID NO: 30 |
| 12757-12832 | guide RNA scaffold sequence for *S. pyogenes* CRISPR/Cas9 system | SEQ ID NO: 3 |
| 12844-12868 | attB2; recombination site for Gateway ® BP reaction | Complement |
| 13549-14100 | *Streptomyces hygroscopicus bar* or *pat*, encodes phosphinothricin acetyltransferase, confers resistance to bialophos or phosphinothricin | |
| 14199-14215 | M13 forward primer, for sequencing | Complement |
| 14411-14435 | right border repeat from nopaline C58 T-DNA | |

The pCas9TPC-NbPDS vector having the sequence of SEQ ID NO:29 contains nucleotides at positions 12737-12832 encoding a single guide RNA having the sequence of SEQ ID NO:31, which includes both a targeting sequence (gRNA) (SEQ ID NO:30) and a guide RNA scaffold (SEQ ID NO:3); transcription of the single guide RNA is driven by a AtU6-26 promoter at nucleotide positions 12349-12736. This vector further contains nucleotides at positions 7714-11817 having the sequence of SEQ ID NO:6 and encoding the Cas9 nuclease from *Streptococcus pyogenes* that has the amino acid sequence of SEQ ID NO:7, and nucleotides at positions 11830-11850 having the sequence of SEQ ID NO:8 and encoding the nuclear localization signal (NLS) of simian virus 40 (SV40) large T antigen that has the amino acid sequence of SEQ ID NO:9. Transcription of the Cas9 nuclease and adjacent SV40 nuclear localization signal is driven by a PcUbi4-2 promoter at nucleotide positions 6728-7699; the resulting transcript including nucleotides at positions 7714-11850 having the sequence of SEQ ID NO:10 encodes a fusion protein having the sequence of SEQ ID NO:11 wherein the Cas9 nuclease is linked through a 4-residue peptide linker to the SV40 nuclear localization signal. The pCas9TPC-NbPDS vector also includes lac operon, aminoglycoside adenylyltransferase, and phosphinothricin acetyltransferase sequences for convenient selection of the plasmid in bacterial or plant cultures.

In a series of experiments, the pCas9TPC-NbPDS (SEQ ID NO:29) was delivered to non-epidermal plant cells in *Nicotiana benthamiana* intact seeds using combinations of delivery agents and physical techniques. Mature, dry *N. benthamiana* seeds were surface-sterilized as follows. Dry *N. benthamiana* seeds were held for 3 hours in an enclosed chamber holding a beaker containing 100 milliliters 5% sodium hypochlorite solution to which 4 milliliters hydrochloric acid were freshly added. Seeds remained desiccated after this sterilization treatment. Each test or control treatment experiment was carried out on 10 sterilized seeds. The following treatments were performed:

Treatment 1 (vacuum control): Seeds were pre-incubated in 400 microliters Tris-EDTA (TE) buffer on ice for 3 hours under vacuum, followed by an overnight incubation at 4 degrees Celsius and then a recovery period of 7 hours at room temperature. The TE buffer was removed by aspiration and the seeds resuspended in 400 microliters of 50% glycerol in milliQ water. Seeds were plated on ½ MS solid media (see Example 1) and germination scored.

Treatment 2 (vacuum/electroporation control): identical to treatment 1, except that after removal of the TE buffer, the seeds were resuspended in 400 or 800 microliters of 50% glycerol in milliQ water, transferred respectively to a 2 or 4 millimeter gap cuvette, and subjected to electroporation using a BTX-Harvard ECM-830 electroporation device set with the following parameters: 100V, 25 millisecond pulse length, 75 millisecond pulse interval for 99 pulses, followed by 400V, 99 millisecond pulse length, 297 millisecond pulse interval for 5 pulses. The seeds were then plated on ½ MS solid media (see Example 1) and germination scored.

Treatment 3 (vacuum/DNA): identical to treatment 1, except that seeds were incubated in a solution of 1 microgram of the pCas9TPC-NbPDS (SEQ ID NO:29) DNA in 200 microliters TE buffer.

Treatment 4: (vacuum/electroporation/DNA): identical to treatment 2, except that seeds were incubated in a solution of 1 microgram of the pCas9TPC-NbPDS (SEQ ID NO:29) DNA in 200 microliters TE buffer, and the electroporation solution further includes 5 nanograms/microliter of the pCas9TPC-NbPDS (SEQ ID NO:29) DNA.

Modification of all endogenous PDS alleles results in a plant unable to produce chlorophyll and having a visible bleached phenotype. Modification of a fraction of all endogenous PDS alleles results in plants still able to produce chlorophyll; plants that are heterozygous for an altered PDS gene will are grown out to seed and the efficiency of heritable genome modification is determined by molecular analysis of the progeny seeds.

Example 5

This example illustrates a method of delivering at least one effector molecule to a plant cell wherein the plant cell is located in a plant or plant part. More specifically, this non-limiting example illustrates a method of delivering a polynucleotide composition including a guide RNA (gRNA) to a non-epidermal plant cell in a seed of a plant and editing of an endogenous plant gene (alcohol dehydrogenase, ADH1, NCBI locus tag ZEAMMB73_889219, with the sequence of SEQ ID NO:32) in germline cells of maize (*Zea mays*) seeds. This example demonstrates delivery of effector molecules including polynucleotides (multiple crRNA: tracrRNA combinations) and an RNA-guided nuclease in the form of a ribonucleoprotein complex, through multiple barriers (e.g., multiple cell layers, seed coat, cell walls, plasma membrane) directly into *Zea mays* germline cells, resulting in a selectable, heritable alteration of the target nucleotide sequence, ADH1, thus conferring resistance to allyl alcohol. The methods described do not employ the common techniques of bacterially mediated transformation (e.g., by *Agrobacterium* sp.) or biolistics.

Three individual crRNAs (Alt-RTM) including the guide RNA (gRNA) sequences GGCAAGCCACTGTCGATCG (SEQ ID NO:33), GGCCTCCCAGAAGTAGACGT (SEQ ID NO:34), and ACGCGCACCTCCATGGCCTG (SEQ ID NO:35) were synthesized by IDT (Coralville, IA). Individual crRNA:tracrRNA duplex solutions are prepared by combining equimolar amounts of a single crRNA with a tracrRNA synthesized by IDT (Coralville, IA) to a final concentration of 100 micromolar; each crRNA/tracrRNA mixture is heated to 95 degrees Celsius for 5 minutes and then allowed to cool to room temperature to form the crRNA:tracrRNA duplex solutions. Ribonucleoprotein (RNP) solutions are prepared by combining equimolar amounts of each crRNA:tracrRNA duplex and a purified Cas9 fusion protein having a nuclear localization signal (NLS) on either terminus (sNLS-spCas9-sNLS, purchased from Aldevron, Fargo, ND) to a final concentration of 100 micromolar and incubating the mixtures at room temperature for 5 minutes to allow the ribonucleoprotein complexes to form.

Mature, dry kernels (seeds) of B73 maize are surface-sterilized as follows. Dry maize kernels are held for 4 hours in an enclosed chamber holding a beaker containing 100 milliliters 5% sodium hypochlorite solution to which 4 milliliters hydrochloric acid are freshly added. The kernels remain desiccated after this sterilization treatment. Embryos are manually separated from the cotyledons and endosperm using a scalpel blade. Each test or control treatment experiment is carried out on 10 dry excised embryos. The excised embryos are transferred to 1.5-microliter microcentrifuge tubes.

To each microfuge tube is added 180 microliters of maize washing solution (0.6 molar D-mannitol, 4 millimolar 2-(N-morpholino)ethanesulfonic acid (MES) buffer, pH 5.7, 20 millimolar KCl) and 20 microliters of the RNP solution. The microcentrifuge tubes are tapped gently to mix and immediately placed on ice and vacuum infiltrated ($2\times10^{-3}$ millibar) for 2 hours with shaking at 100 rpm. Following vacuum infiltration, the embryos are rinsed with 5% sodium hypochlorite solution, washed 5 times with sterile water, transferred to a petri dish containing ½xMS medium (2.165 g Murashige and Skoog medium salts, catalogue number MSP0501, Caisson Laboratories, Smithfield, UT), 10 grams sucrose, and 8 grams Bacto agar, made up to 1.00 liter in distilled water), and placed in a tissue culture incubator set to 25 degrees Celsius. After the embryos have elongated, developed roots and true leaves have emerged, the seedlings are treated with 5 or 20 micromolar allyl alcohol for 24 hours. The seedlings are then washed 5 times with sterile water, transferred to soil and grown out. Modification of the endogenous ADH1 results in a plant having an observable phenotype, i.e., resistance to allyl alcohol-induced toxicity. Surviving maize seedlings are grown out to seed and the efficiency of heritable genome modification is determined by molecular analysis of the progeny seeds.

Example 6

This example illustrates a method of delivering at least one effector molecule to a plant cell wherein the plant cell is located in a plant or plant part. More specifically, this non-limiting example illustrates a method of delivering a polynucleotide composition including at least one crRNA or gRNA or sgRNA to a non-epidermal plant cell in a seed of a plant, resulting in editing of at least one endogenous plant gene. This example demonstrates direct delivery by microinjection of effector molecules (e.g., at least one crRNA or sgRNA or a polynucleotide encoding at least one crRNA or sgRNA or an RNA-guided nuclease or a polynucleotide that encodes the RNA-guided nuclease) directly into maize (*Zea mays*) zygotes; the embryos are isolated and allowed to shoot, and the resulting maize plants containing the desired genomic edit or alteration of the target nucleotide sequence are subsequently identified. The methods described do not employ the common techniques of bacterially mediated transformation (e.g., by *Agrobacterium* sp.) or biolistics.

A non-limiting example of a microinjection protocol utilized maize B73 fertilized cobs (ears) (collected 1 day after pollination). All steps of this protocol were performed under a laminal flow hood. Husks and silks were removed from the cobs. The cobs were transversely cut into approximately 3-centimeter segments with the top and bottom two centimeters of each cob discarded. The segments were surface-sterilized for 10 minutes in 70% ethanol followed by three washes in distilled, autoclaved water of one minute each.

Ethanol-sterilized fifty-milliliter tube caps were used as specimen mounting blocks, to which two pairs of ovaries cut from the prepared cob slices were glued with a thin layer of fast-facing adhesive (e.g., Loctite Control Gel Premium Super Glue); one pair of ovaries was mounted facing the other pair's basal ends. The mounted ovaries were attached to a modified specimen tray of a Vibratome (PELCO easiSlicer™, Ted Pella, Inc.) with the stylar ends facing the blade. Ovaries were sectioned at 220 micrometers from the ovarian surface. Sections that contained embryo sacs were collected for microinjection on MMIM (modified maize induction medium). To prepare MMIM, 2.2 g Murashige and Skoog (MS) medium, 50 g sucrose, 10 g mannitol, and 2.5 g Phytagel were dissolved in 500 milliliters water and pH adjusted to 5.8; after autoclaving, indole acetic acid or 1-naphthaleneacetic acid (0.1 milligrams/liter final concentration), 6-benzylaminopurine (0.5 milligrams/liter final concentration), and vitamins (1× final concentration) are added.

The target gene selected for editing was the maize (*Zea mays*) alcohol dehydrogenase ADH1 (see www[dot]maizegdb[dot]org/gene center/gene/GRMZM2G442658) with the partial genomic sequence:

(SEQ ID NO: 36)

```
GAACAGTGCCGCAGTGGCGCTGATCTTGTATGCTATCCTGCAATCGTGG
TGAACTTATTTCTTTTATATCCTTTACTCCCATGAAAAGGCTAGTAATC
TTTCTCGATGTAACATCGTCCAGCACTGCTATTACCGTGTGGTCCATCC
GACAGTCTGGCTGAACACATCATACGATCTATGGAGCAAAAATCTATCT
TCCCTGTTCTTTAATGAAGGACGTCATTTTCATTAGTATGATCTAGGAA
TGTTGCAACTTGCAAGGAGGCGTTTCTTTCTTTGAATTTAACTAACTCG
TTGAGTGGCCCTGTTTCTCGGACGTAAGGCCTTTGCTGCTCCACACATG
TCCATTCGAATTTTACCGTGTTTAGCAAGGGCGAAAAGTTTGCATCTTG
ATGATTTAGCTTGACTATGCGATTGCTTTCCTGGACCCGTGCAGCTGCG
GTGGCATGGGAGGCCGGCAAGCCACTGTCGATCGAGGAGGTGGAGGTAG
CGCCTCCGCAGGCCATGGAGGTGCGCGTCAAGATCCTCTTCACCTCGCT
```

-continued

CTGCCACACCGACGTCTACTTCTGGGAGGCCAAGGTATCTAATCAGCCA

TCCCATTTGTGATCTTTGTCAGTAGATATGATACAACAACTCGCGGTTG

ACTTGCGCCTTCTTGGCGGCTTATCTGTCTTAGGGGCAGACTCCCGTGT

TCCCTCGGATCTTTGGCCACGAGGCTGGAGGGTA, the first exon (SEQ ID NO:37), located at nucleotide positions 409-571 of SEQ ID NO:36 is indicated by bold, underlined text and guide RNA (crRNA) sequences were designed to edit this exon.

A ribonucleoprotein (RNP) was prepared with Cas9 nuclease (Aldevron, Fargo, ND) and a guide RNA complex of a crRNA (ZmADH1-B) having the sequence GGCCUCCCAGAAGUAGACGUGUUUUAGAGCUAUGCU (SEQ ID NO:38) and a tracrRNA (both purchased from Integrated DNA Technologies, Coralville, IA). A guide RNA (gRNA) complex was prepared as follows: 30 microliters of 100 micromolar crRNA were mixed with 30 microliters of 100 micromolar tracrRNA, heated at 95 degrees Celsius for 5 minutes, and then cooled to room temperature. To the cooled gRNA solution, 100 micrograms Cas9 nuclease (Aldevron, Fargo, ND) was added and the mixture incubated 5 minutes at room temperature to allow the ribonucleoprotein (RNP) complex to form. A microinjection mixture containing the RNP complex was prepared by taking a volume (e. g., 30 microliters) of the RNP solution and adding sufficient 10× Cas9 reaction buffer (20 millimolar HEPES, 1 molar NaCl, 50 millimolar MgCl2, 1 millimolar EDTA) to yield a 1× buffer concentration in the final mixture. The microinjection mixture was centrifuged through a Millipore filter (UFC30VV25) at 13,000 rpm for 10 minutes at room temperature.

For microinjection of the maize zygotes, 2.5 microliters of the filtered injection mix were loaded into a borosilicate needle (catalogue number G100E-4, Warner Instruments, Hamden, CT), previously pulled with a P1000 micropipette puller (Sutter Instrument, Novato, CA) with the following settings: Heat: Ramp-20; Pull: 140; Velocity: 70; Delay: 200; Pressure: 510; Ramp: 499. The needle was opened with a micropipette beveller (BV-10, Sutter Instrument, Novato, CA) with an angle of 35 degrees. The egg apparatus was visualized with basal illumination with a fluorescence stereoscope (model SMZ18, Nikon, Tokyo, Japan). The injection mix was injected into the egg apparatus using a FemtoJet 4i with a PatchMan micromanipulator (both from Eppendorf, Hauppauge, NY). Embryo sacs were recovered in MMIM medium. The embryos were kept in the dark at 26 degrees Celsius until shoots formed, and then kept in light at 26 degrees Celsius. Shoots thus produced are optionally grown under culture conditions including exposure to low concentrations (e.g., 5 or 20 micromolar) of allyl alcohol (which is converted by a functional ADH1 to acrolein, which is toxic to the cell), thus permitting selection by expression of the predicted phenotype, i.e., decreased allyl alcohol susceptibility in shoots or plants wherein one or both copies of the endogenous ADH1 gene has been disrupted. Surviving maize seedlings are grown out to seed and the efficiency of heritable genome modification is determined by molecular analysis of the progeny seeds.

One of skill in the art would recognize that there are alternative reagents and compositions including such reagents that are useful for introducing alterations or edits into the genome (e.g., use of CRISPR nucleases other than Cas9, such as CasX, CasY, and Cpf1, zinc-finger nucleases (ZFNs), transcription activator-like effector nucleases (TAL-effector nucleases or TALENs), Argonaute proteins, or a meganuclease or engineered meganuclease) and thus similar embodiments of the microinjection technique described herein include use of any of these reagents. Similarly, the microinjection technique described herein is generally applicable to any plant cell of sufficient size to permit microinjection (e.g., germline cells or cells that develop into germline cells, egg cells, zygote cells, embryo cells, meristematic cells), and of any plant species (e.g., alfalfa (*Medicago sativa*), almonds (*Prunus dulcis*), apples (*Malus x domestica*), apricots (*Prunus armeniaca, P. brigantine, P. mandshurica, P. mume, P. sibirica*), asparagus (*Asparagus officinalis*), bananas (*Musa* spp.), barley (*Hordeum vulgare*), beans (*Phaseolus* spp.), blueberries and cranberries (*Vaccinium* spp.), cacao (*Theobroma cacao*), canola and rapeseed or oilseed rape, (*Brassica napus*), carnation (*Dianthus caryophyllus*), carrots (*Daucus carota sativus*), cassava (*Manihot esculentum*), cherry (*Prunus avium*), chickpea (*Cider arietinum*), chicory (*Cichorium intybus*), chili peppers and other capsicum peppers (*Capsicum annuum, C. frutescens, C. chinense, C. pubescens, C. baccatum*), chrysanthemums (*Chrysanthemum* spp.), coconut (*Cocos nucifera*), coffee (*Coffea* spp. including *Coffea arabica* and *Coffea canephora*), cotton (*Gossypium hirsutum* L.), cowpea (*Vigna unguiculata*), cucumber (*Cucumis sativus*), currants and gooseberries (*Ribes* spp.), eggplant or aubergine (*Solanum melongena*), eucalyptus (*Eucalyptus* spp.), flax (*Linum usitatissumum* L.), geraniums (*Pelargonium* spp.), grapefruit (*Citrus x paradisi*), grapes (*Vitus* spp.) including wine grapes (*Vitus vinifera*), guava (*Psidium guajava*), irises (*Iris* spp.), lemon (*Citrus limon*), lettuce (*Lactuca sativa*), limes (*Citrus* spp.), maize (*Zea mays* L.), mango (*Mangifera indica*), mangosteen (*Garcinia mangostana*), melon (*Cucumis melo*), millets (*Setaria* spp, *Echinochloa* spp, *Eleusine* spp, *Panicum* spp., *Pennisetum* spp.), oats (*Avena sativa*), oil palm (*Ellis quineensis*), olive (*Olea europaea*), onion (*Allium cepa*), orange (*Citrus sinensis*), papaya (*Carica papaya*), peaches and nectarines (*Prunus persica*), pear (*Pyrus* spp.), pea (*Pisa sativum*), peanut (*Arachis hypogaea*), peonies (*Paeonia* spp.), petunias (*Petunia* spp.), pineapple (*Ananas comosus*), plantains (*Musa* spp.), plum (*Prunus domestica*), poinsettia (*Euphorbia pulcherrima*), Polish canola (*Brassica rapa*), poplar (*Populus* spp.), potato (*Solanum tuberosum*), pumpkin (*Cucurbita pepo*), rice (*Oryza sativa* L.), roses (*Rosa* spp.), rubber (*Hevea brasiliensis*), rye (*Secale cereale*), safflower (*Carthamus tinctorius* L), sesame seed (*Sesame indium*), sorghum (*Sorghum bicolor*), soybean (*Glycine max* L.), squash (*Cucurbita pepo*), strawberries (*Fragaria* spp., *Fragaria x ananassa*), sugar beet (*Beta vulgaris*), sugarcanes (*Saccharum* spp.), sunflower (*Helianthus annus*), sweet potato (*Ipomoea batatas*), tangerine (*Citrus tangerina*), tea (*Camellia sinensis*), tobacco (*Nicotiana tabacum* L.), tomato (*Lycopersicon esculentum*), tulips (*Tulipa* spp.), turnip (*Brassica rapa rapa*), walnuts (*Juglans* spp. L.), watermelon (*Citrulus lanatus*), wheat (*Tritium aestivum*), and yams (*Discorea* spp.)). Non-limiting embodiments include microinjection delivery of DNA or RNP editing reagents to egg cells, zygote cells, embryo cells, and meristematic cells of maize, rice, wheat, barley, rye, millet, sorghum, soybean, cotton, brassicas (including oilseed brassicas and sugar beet), solanaceous plants (including tomato, pepper, potato, and eggplant), strawberry, banana, plantain, citrus fruits, coffee, cacao, and sugarcanes.

Example 7

This example illustrates a method of delivering at least one effector molecule to a plant cell wherein the plant cell is located in a plant or plant part. More specifically, this non-limiting example illustrates a method of delivering a polynucleotide composition including at least one crRNA or gRNA or sgRNA to non-epidermal plant cells, resulting in editing of at least one endogenous plant gene. This example demonstrates direct delivery of effector molecules (e.g., at least one crRNA or sgRNA or a polynucleotide encoding at least one crRNA or sgRNA or an RNA-guided nuclease or a polynucleotide that encodes the RNA-guided nuclease) by gold microparticle bombardment directly into germline cells of excised soybean (*Glycine max*) embryos.

The target genes selected for editing were two endogenous soybean (*Glycine max*) phytoene desaturase (PDS) genes, Glyma.11g239000 and Glyma.18g003900 (see, e.g., www[dot]soybase[dof]org/sbt/search/search_results.php?category=FeatureName&version=Glyma2[dot]0&search term=Glyma[dot]18g003900). The first PDS gene, Glyma.11g239000 has the genomic sequence of SEQ ID NO:39. The second PDS gene, Glyma.18g003900, has the genomic sequence of SEQ ID NO:40.

Four guide RNA (gRNA) sequences were designed to cleave both soybean PDS genes, Glyma.11g253000 (SEQ ID NO:39) and Glyma18g003900 (SEQ ID NO:40): GmPDS gRNA.1 GAAGCAAGAGACGUUCUAGG (SEQ ID NO:41), GmPDS gRNA.2 GGUUGCUGCAUGGAAAGACA (SEQ ID NO:42), GmPDS gRNA.3 CCAUAUGUUGAGGCUCAAGA (SEQ ID NO:43), and GmPDS gRNA.4 GAUCAUAUUCAGUCCUUGGG (SEQ ID NO:44). These were provided as single guide RNAs (sgRNAs), chimeric RNAs, each of which included one of the gRNA sequences and a guide RNA scaffold sequence (SEQ ID NO:3). All four gRNA sequences had been previously validated by an in vitro Cas9 assay and were shown to be capable of cleaving both soybean phytoene desaturase genes. The first PDS gene, Glyma.11g239000 (SEQ ID NO:39) is cleaved between nucleotide positions 2379-2340, 2653-2654, 3931-3932, and 4795-4796. The second PDS gene, Glyma.18g003900, (SEQ ID NO:40) is cleaved between nucleotide positions 2217-2218, 2490-2491, 5370-5371, and 6130-6131.

In a first series of experiments, the sgRNA and nuclease vectors were delivered by gold microparticle bombardment to non-epidermal cells in soybean embryonic axes. Mature, dry soybean seeds (cv. Williams 82) were surface-sterilized by holding overnight in an enclosed chamber holding a beaker containing 100 milliliters 5% sodium hypochlorite solution to which 4 milliliters hydrochloric acid were freshly added. The sterilized seeds were imbibed in sterile water for 2-20 hours. Seeds were divided by inserting a razor blade into the hilum leaving the embryonic axes intact. The pericarp was removed and the tip of the radicle excised. The leaf primordia and a thin layer of the shoot apical meristems were excised with a scalpel with the aid of a dissecting microscope. Prepared explants were placed on pre-bombardment medium ("Recipe X" with the addition of 2 milligrams/liter 6-benzylaminopurine) for 2-3 days in the dark at 26 (plus or minus 2) degrees Celsius. In an alternative protocol, explants were placed on osmoticum medium ("Recipe X" modified by the addition of 36.8 grams/liter sorbitol and 36.8 grams/liter mannitol) for four hours prior to bombardment. To make a 1-liter quantity of "Recipe X" medium, mix 4.43g MS salts with B5 vitamins, 10 milliliter 0.2 molar MES hydrate stock solution, 100 milligrams myo-inositol, 30 grams sucrose, 8 grams Oxoid agar (Remel, Inc. Lenexa, KS) and bring volume to 1 liter with water. Adjust pH to 5.8 before adding agar and autoclaving. Add 6-benzylaminopurine (BA) after cooling to about 50 degrees Celsius.

Gold microparticles were prepared as follows. In the following non-limiting experiments, 1.0 micrometer gold microparticles were used (Bio-Rad, Hercules, CA). In other protocols, gold microparticles of other sizes (e.g., 0.6 or 1.6 micrometer) are also useful gold. Approximately 15-20 milligrams of gold microparticles were transferred to sterile 1.5 milliliter microcentrifuge tubes. Cold absolute ethanol (500 microliters) was added to each tube, and the tubes were placed in the ultrasonicating water bath for 15 seconds. Gold microparticles were allowed to settle ~10-30 minutes followed by pelleting by centrifugation for 1 minute at 3000 rpm. The supernatant was removed and the pellet was carefully rinsed with 1 milliliter ice-cold sterile water. The tubes were tapped gently to disturb the pellets, which were then allowed to settle again. The rinse step was repeated two more times. After the third rinse, the microparticles were pelleted 15 seconds at 5000 rpm, and the final supernatant removed. The pellet was resuspended in 500 microliters sterile water to form a "1X" concentration, placed in the ultrasonicating water bath for 15 seconds, and immediately after was vortexed. Aliquots of 50 microliters were transferred to 1.5-millilter microcentrifuge tubes, with the original preparation continually vortexed during the transfers. The 1X aliquots were stored at −20 degrees Celsius.

Prior to precipitation of DNA on gold microparticles, soy explants are embedded in pre-bombardment medium with the shoot apical meristem arranged parallel with the medium's surface and directly facing the trajectory of the DNA coated microparticles. Approximately, 20-40 explants were placed in the center of the plate, corresponding to the ~3.5-centimeter diameter circle of the tissue platform (Bio-Rad, Hercules, CA). A tube of 1X prepared gold was used for bombardment of three media plates of soy explants. Prepared 1X tubes were thawed on ice, placed in the ultrasonicating water bath for 15 seconds, and then centrifuged at 2000 rpm for 2 minutes. The supernatant was removed and the gold microparticles were resuspended in either 25 microliters DNA (1 microgram/microliter) solution or 25 microliters sterile water as a control. The following was added in order, vortexing between each addition: 220 microliters sterile water, 250 microliters 2.5 molar calcium chloride, and 50 microliters 0.1 molar spermidine. The tubes were placed on ice for 5 minutes, vortexed for ~2 minutes at room temperature, and then centrifuged at 500 rpm for 5 minutes. The supernatant was removed and the pellet was resuspended in 600 microliters absolute ethanol. The tubes were centrifuged for 1 minute at 14K rpm. The supernatant was removed and the pellet was resuspended in 36 microliters absolute ethanol. (To conserve the amount of gold used, the pellet can be resuspended in about 90 microliters absolute ethanol, and about 10 microliters or about 444 nanograms gold used for each shot for 9 shots.) DNA-coated gold (11 microliters) was placed in the center of autoclaved macrocarriers (Bio-Rad, Hercules, CA) and allowed to dry for approximately 5-10 minutes. The PDS-1000/He biolistic® particle delivery system (Bio-Rad, Hercules, CA) was assembled. The rupture discs (1,100 psi rupture discs, Bio-Rad, Hercules, CA; 900 or 650 psi rupture discs can also be used) were dipped in 70% ethanol to sterilize, placed in the retaining cap, and tightened with the manufacturer's supplied wrench. The autoclaved stopping screen was placed in the macrocarrier assembly followed by the DNA-coated gold macrocarrier. The system was assembled as directed in the manual. The distance used from stopping screen to soy explants was 6 centimeters. The gun was fired when the vacuum in the chamber reached 27-28 inches of Hg.

After bombardment, explants were transferred to Recipe X medium containing 0.5 milligrams/liter 6-benzylaminopurine. Plates with bombarded explants were placed in the dark for 2-4 days at 26 (plus or minus 2) degrees Celsius, then moved to a 16-hour light (75 micromoles)/8-hour dark light regime at 26 (plus or minus 2) degrees Celsius for several days to weeks depending on assay performed. For non-destructive assays, soybean shoots were sampled and explants moved to fresh Recipe X medium containing 0.5 milligrams/liter 6-benzylaminopurine. When shoots reached about 2-3 centimeters in length, explants where transferred to shoot elongation media ("Recipe Y"). To make 1 liter of "Recipe Y" medium, mix 4.43 grams MS salts with B5 vitamins, 0.59 grams MES hydrate, and 30 grams sucrose in 1 liter water, adjust pH to 5.7, and add 3 grams Phytagel. Autoclave 35 minutes on liquid cycle and cool to 50 degrees Celsius. In a laminar flow hood, add to 1 liter of cooled medium 0.5 milligrams gibberellic acid (as a premade stock, G362, PhytoTechnologies Laboratories, Shawnee Mission, KS), 500 microliters 50 milligrams/milliliter asparagine stock solution, 5 milligrams glutamine, 400 microliters indole acetic acid (as a 1 milligram/milliliter stock), and 1 milligram trans-zeatin riboside. Pour 100 milliliters per phytatray and allow to cool; store at room temperature. After approximately two weeks of shoot elongation, shoots were of sufficient size to transfer to Jiffy peat pellets, and were later transplanted to soilless mix in pots for maturation. Modification of the endogenous PDS gene(s) results in a plant having an observable bleached phenotype.

In another series of experiments, ribonucleoprotein (RNP) including a Cas9 nuclease and a guide RNA (gRNA) complex (crRNA-tracrRNA complex) was used for delivery of soybean phytoene desaturase guide RNAs to shoot apical meristem cells via gold microparticle bombardment. The RNP was prepared using procedures similar to those described in Example 6, but using 6 microliters of 100 micromolar crRNA (containing the soybean PDS guide RNA sequences described above) annealed with 6 microliters of 100 micromolar tracrRNA, and complexed with 20 micrograms Cas9 nuclease. The RNP preparation was added to a tube of 1X gold microparticles in 50 microliters water, mixed gently, and used at a rate of 14 microliters RNP-coated gold per macrocarrier. Sixty microliters 2.5 molar calcium chloride and 20 microliters 0.1 molar spermidine were optionally added, with vortexing, to this preparation. (To conserve the amount of gold used, one tube of ~1.5 mg of gold coated with 5 micrograms Cas9 complexed with 2.5 micrograms crRNA-tracrRNA complex is sufficient for 9 shots.) The samples were dried in Petri dishes with Drierite desiccant (W. A. Hammond DRIERITE Co., LTD, Xenia, OH) for 1-2 hours. The rest of the bombardment procedure was similar to that described above for the DNA-coated gold microparticles.

The shoot apical meristems of 48 soybean embryonic axes were sampled 5 days after bombardment by RNPs containing GmPDS g.RNA4 (SEQ ID NO:44). PCR amplification flanking the guide region was performed and six products were pooled together prior to Monarch PCR purification. The GmPDS gRNA.4 sequence contains a Styl restriction site which allows for enrichment of edited sequences; Styl restriction digest of the wild-type (unedited) sequence enriches the sample for edited sequences. After PCR purification, the products were digested for 4 hours with Styl at 37 degrees Celsius. The reactions were loaded on 2% E-gels (Invitrogen, Carlsbad, CA) and the uncut ~280 base-pair product was excised and purified using the Monarch Gel Extraction kit (New England Biolabs). The eluted product was submitted for Sanger sequencing and analyzed for editing. From the six pools representing 48 bombarded soybean axes, one pool showed evidence of editing at the correct location on the genome predicted to be edited by the GmPDS g.RNA4 (SEQ ID NO:44) guide sequence.

Addition bombardment experiments using GmPDS gRNA.1 (SEQ ID NO:41) delivered as DNA-coated or RNP-coated gold microparticles, or GmPDS gRNA.1 (SEQ ID NO:41) and GmPDS gRNA.2 (SEQ ID NO:42) delivered as RNP-coated gold microparticles, were evaluated for editing of the endogenous soybean PDS genes by various molecular assays, including, e.g., T7E1 assay, fragment analyzer assay, Sanger sequencing, and enrichment of edited amplicons by restriction digest and NGS amplicon sequencing.

One of skill in the art would recognize that there are alternative reagents and compositions (e.g., DNA encoding a nuclease or RNPs including a nuclease) including such reagents that are useful for introducing alterations or edits into the genome (e.g., use of CRISPR nucleases other than Cas9, such as CasX, CasY, and Cpf1, zinc-finger nucleases (ZFNs), transcription activator-like effector nucleases (TAL-effector nucleases or TALENs), Argonaute proteins, or a meganuclease or engineered meganuclease) and thus similar embodiments of the bombardment technique described herein include use of any of these reagents or compositions. Similarly, the bombardment technique described herein is generally applicable to any plant part, plant tissue, or whole plant, seed, seedling, or embryo (e.g., excised embryos, callus, leaf or other plant part, meristematic tissue), and of any plant species (e.g., alfalfa (*Medicago sativa*), almonds (*Prunus dulcis*), apples (*Malus x domestica*), apricots (*Prunus armeniaca, P. brigantine, P. mandshurica, P. mume, P. sibirica*), asparagus (*Asparagus officinalis*), bananas (*Musa* spp.), barley (*Hordeum vulgare*), beans (*Phaseolus* spp.), blueberries and cranberries (*Vaccinium* spp.), cacao (*Theobroma cacao*), canola and rapeseed or oilseed rape, (*Brassica napus*), carnation (*Dianthus caryophyllus*), carrots (*Daucus carota sativus*), cassava (*Manihot esculentum*), cherry (*Prunus avium*), chickpea (*Cider arietinum*), chicory (*Cichorium intybus*), chili peppers and other capsicum peppers (*Capsicum annuum, C. frutescens, C. chinense, C. pubescens, C. baccatum*), chrysanthemums (*Chrysanthemum* spp.), coconut (*Cocos nucifera*), coffee (*Coffea* spp. including *Coffea arabica* and *Coffea canephora*), cotton (*Gossypium hirsutum* L.), cowpea (*Vigna unguiculata*), cucumber (*Cucumis sativus*), currants and gooseberries (*Ribes* spp.), eggplant or aubergine (*Solanum melongena*), eucalyptus (*Eucalyptus* spp.), flax (*Linum usitatissumum* L.), geraniums (*Pelargonium* spp.), grapefruit (*Citrus x paradisi*), grapes (*Vitus* spp.) including wine grapes (*Vitus vinifera*), guava (*Psidium guajava*), irises (*Iris* spp.), lemon (*Citrus limon*), lettuce (*Lactuca sativa*), limes (*Citrus* spp.), maize (*Zea mays* L.), mango (*Mangifera indica*), mangosteen (*Garcinia mangostana*), melon (*Cucumis melo*), millets (*Setaria* spp, *Echinochloa* spp, *Eleusine* spp, *Panicum* spp., *Pennisetum* spp.), oats (*Avena sativa*), oil palm (*Ellis quineensis*), olive (*Olea europaea*), onion (*Allium cepa*), orange (*Citrus sinensis*), papaya (*Carica papaya*), peaches and nectarines (*Prunus persica*), pear (*Pyrus* spp.), pea (*Pisa sativum*), peanut (*Arachis hypogaea*), peonies (*Paeonia* spp.), petunias (*Petunia* spp.), pineapple (*Ananas comosus*), plantains (*Musa* spp.), plum (*Prunus domestica*), poinsettia (*Euphorbia pulcherrima*), Polish canola (*Brassica rapa*), poplar (*Populus* spp.), potato (*Solanum tuberosum*), pumpkin (*Cucurbita pepo*), rice (*Oryza sativa* L.), roses (*Rosa* spp.), rubber (*Hevea brasiliensis*), rye (*Secale cereale*), safflower (*Carthamus tinctorius* L), sesame seed (*Sesame indium*), sorghum (*Sorghum bicolor*), soybean (*Glycine max* L.), squash (*Cucurbita pepo*), strawberries (*Fragaria* spp., *Fragaria x ananassa*), sugar beet (*Beta vulgaris*), sugarcanes (*Saccharum* spp.), sunflower (*Helianthus annus*), sweet potato (*Ipomoea batatas*), tangerine (*Citrus tangerina*), tea (*Camellia sinensis*), tobacco (*Nicotiana tabacum* L.), tomato (*Lycopersicon esculentum*), tulips (*Tulipa* spp.), turnip (*Brassica rapa rapa*), walnuts (*Juglans* spp. L.), watermelon (*Citrulus lanatus*), wheat (*Tritium aestivum*), and yams (*Discorea* spp.)). Non-limiting embodiments include microparticle or nanoparticle bombardment delivery of DNA or RNP editing reagents to embryos, seeds, seedlings, meristematic tissue, or callus of maize, rice, wheat, barley, rye, millet, sorghum, soybean, cotton, brassicas (including oilseed brassicas and sugar beet), solanaceous plants (including tomato, pepper, potato, and eggplant), strawberry, banana, plantain, citrus fruits, coffee, cacao, and sugarcanes.

Example 8

This example illustrates a method of delivering at least one effector molecule to a plant cell wherein the plant cell is located in a plant or plant part. This example illustrates a method of delivering a polynucleotide composition including at least one crRNA or gRNA or sgRNA to a non-epidermal plant cell in a seed of a plant, resulting in editing of at least one endogenous plant gene: in this case, wheat phytoene desaturase (PDS) genes in germline cells of wheat (*Triticum aestivum*) seeds. More specifically, this example illustrates a method of effecting a genetic alteration in the genome of a whole seed or part of a seed, comprising imbibition of the whole seed or part of a seed in an aqueous solution that comprises: (a) an RNA-guided nuclease or a polynucleotide that encodes the RNA-guided nuclease, and (b) at least one guide RNA or polynucleotide encoding a guide RNA; wherein the at least one guide RNA is capable of directing the RNA-guided nuclease to a defined location in the genome, thereby effecting a genetic alteration at the defined location in the genome; and wherein the genetic alteration is at least one alteration selected from the group consisting of insertion of at least one nucleotide, deletion of at least one nucleotide, or replacement of at least one nucleotide at the defined location in the genome. This non-limiting example demonstrates direct delivery by imbibition of effector molecules including polynucleotides encoding single-guide RNAs (sgRNAs) and a polynucleotide that encodes an RNA-guided nuclease, through multiple barriers (e.g., multiple cell layers, seed coat, cell walls, plasma membrane) directly into germline cells of *Triticum aestivum* seeds, resulting in an alteration of the target nucleotide sequence, PDS. The methods described do not employ the common techniques of bacterially mediated transformation (e.g., by *Agrobacterium* sp.) or biolistics.

Common or bread wheat, *Triticum aestivum*, is an allohexaploid. The three wheat genomes, i.e., the wheat 4A, 4B, and 4D genomes each contain a phytoene desaturase (PDS) gene, respectively: TaPDS-4A (SEQ ID NO:45), TaPDS-4B (SEQ ID NO:46), and TaPDS-4D (SEQ ID NO:47). Three vectors were designed for editing the endogenous wheat PDS genes. One vector (SEQ ID NO:48, Table 6) was designed for expression of Cas9 nuclease. Two vectors (SEQ ID NO:49, Table 7 and SEQ ID NO:50, Table 8) were designed for expression of sgRNAs; one of skill would understand that other sgRNA sequences for alternative target genes could be substituted in the plasmid.

TABLE 6 pVL40.52 Cas9 vector (SEQ ID NO: 48), 9453 base pairs DNA

| Nucleotide position in SEQ ID NO: | Description | Comment |
|---|---|---|
| 1-9453 | Intact plasmid | SEQ ID NO: 48 |
| 378-395 | M13 forward primer for sequencing | |
| 439-1557 | *Oryza sativa* Actin 1 promoter | |
| 1558-1620 | *Oryza sativa* Actin 1, 5'-untranslated leader sequence | Also includes exon 1 |
| 1621-1703 | *Oryza sativa* Actin 1 intron 1 | |
| 1719-6161 | Monocot codon optimized Cas9 with an intron | |
| 3258-3446 | Potato IV2 intron | Disrupts the Cas9 coding sequence |
| 6168-6414 | *Oryza sativa* Actin 1, 3'-untranslated sequence | |
| 6415-7168 | *Oryza sativa* Actin 1 terminator | |
| 7228-7248 | M13 reverse primer for sequencing | Complement |
| 7280-7310 | Lac promoter for the *E. Coli* lac operon | |
| 7616-8298 | High copy number ColE1/pMB1/pBR322/pUC origin of replication | Complement |
| 8396-9055 | CDS for bla, beta-lactamase, AmpR | Complement, ampicillin selection |

TABLE 7 pVL40.30 “PDS guide 2” sgRNA vector (SEQ ID NO: 49), 3493 base pairs DNA

| Nucleotide position in SEQ ID NO: | Description | Comment |
|---|---|---|
| 1-3493 | Intact plasmid | SEQ ID NO: 49 |
| 272-1462 | Tet | Tetracycline resistance marker |
| 1637-1655 | T7 promoter for sequencing | |
| 1765-2063 | *Oryza sativa* U6 promoter | |
| 2064-2083 | *Oryza sativa* phytoene desaturase targeting sequence (gRNA, not showing the PAM sequence) | either “PDS guide 2” for TaPDS-4A, SEQ ID NO: 52) or “PDS guide 2” for TaPDS-4B or TaPDS-4D, SEQ ID NO: 53) |
| 2084-2159 | Guide RNA scaffold sequence for *S. pyogenes* CRISPR/Cas9 system | SEQ ID NO: 3 |
| 2326-2945 | pBB322 origin of replication | |

TABLE 8 pVL40.23 “PDS guide 1” sgRNA vector (SEQ ID NO: 50), 3493 base pairs DNA

| Nucleotide position in SEQ ID NO: | Description | Comment |
|---|---|---|
| 1-3493 | Intact plasmid | SEQ ID NO: 50 |
| 272-1462 | Tet | Tetracycline resistance marker |
| 1637-1655 | T7 promoter for sequencing | |
| 1765-2063 | *Oryza sativa* U6 promoter | |

TABLE 8-continued

| pVL40.23 "PDS guide 1" sgRNA vector (SEQ ID NO: 50), 3493 base pairs DNA | | |
|---|---|---|
| Nucleotide position in SEQ ID NO: | Description | Comment |
| 2064-2083 | *Oryza sativa* phytoene desaturase targeting sequence (gRNA, not showing the PAM sequence) | "PDS guide 1", SEQ ID NO: 51 |
| 2084-2159 | Guide RNA scaffold sequence for *S. pyogenes* CRISPR/Cas9 system | SEQ ID NO: 3 |
| 2326-2945 | pBB322 origin of replication | |

Glenn hard red spring wheat seed (product ID 292G, Johnny's Selected Seed, Fairfield, ME) were surface sterilized by wetting in 95% ethanol for 1 minute at room temperature followed by 20 minutes in sterilization solution (20% bleach, 0.1% Tween-20) on a rocker at room temperature. Seed were rinsed 5 times with sterile water and air dried in a sterile laminar flow hood, then stored in the dark in a low humidity environment until use.

Twenty seed were rehydrated in 2 milliliters of sterile imbibition solution (15 millimolar sodium chloride, 1.5 millimolar sodium citrate, 20% dimethylsulfoxide) containing 100 micrograms each of: (1) pVL40.52 Cas9 vector (SEQ ID NO:48) (Table 6), (2) pVL40.23 "PDS guide 1" sgRNA vector (SEQ ID NO:50) (Table 8) including the TaPDS "PDS guide 1" sgRNA sequence (as the DNA equivalent, not showing the PAM sequence) TTTGCCATGCCAAACAAACC ("PDS guide 1" common to TaPDS-4A, TaPDS-4B, and TaPDS-4D, SEQ ID NO:51), and (3) pVL40.30 "PDS guide 2" sgRNA vector (SEQ ID NO:49) (Table 7) including one of the TaPDS "PDS guide 2" sgRNA sequences (as the DNA equivalent, not showing the PAM sequence), i.e., TCCTGATCGGGTCAACGACG ("PDS guide 2" for TaPDS-4A, SEQ ID NO:52) or TCCTGATCGAGTCAACGACG ("PDS guide 2" for TaPDS-4B or TaPDS-4D, SEQ ID NO:53), for 42-58 hours in darkness at room temperature (22 degrees Celsius). A control treatment was treated similarly with an imbibition solution lacking any plasmid DNA. After imbibition, seeds were washed with sterile water then placed in sterile petri dishes in a growth cabinet (16/8 hour light/dark cycle; 24/20 degrees Celsius) to germinate for approximately 7 days.

The first two leaves from each germinated seedling were excised and pooled appropriately into treated or control groups. Genomic DNA (gDNA) was extracted using the CTAB procedure (Doyle, J. J. and J. L. Doyle (1987) *Phytochem. Bull.,* 19:11-15). The gDNA template was subjected to PCR amplification using primers 0-696 (CTTTTCAGTTGGAGCTTATCCCA, SEQ ID NO:54) and 0-697 (CCTGCTGAAAAGAAGGTGGTCATAC, SEQ ID NO:55) at 0.5 micromolar, with 100 nanograms gDNA template, 25 microliters of Phusion 2X Master Mix (New England Biolabs, Ipswich, MA) in a 50 microliter reaction mix. The thermocycling program consisted of 98 degrees Celsius for 1 minute followed by 30 cycles of 98 degrees Celsius for 10 seconds, 55 degrees Celsius for 10 seconds and 72 degrees Celsius for 105 seconds. The final extension was 72 degrees Celsius for 10 minutes. Products were resolved by loading 20 microliters of each reaction on a 1% E-gel (Invitrogen, Carlsbad, CA). The wild-type or non-edited (1778 base pair) band was excised and the DNA purified using the Monarch gel extraction kit (New England Biolabs). The DNA was subjected to Sanger sequence analysis using the same primers used for the PCR amplification (SEQ ID NO:54 and SEQ ID NO:55).

The sequencing results showed evidence of Cas9 activity at the TaPDS "PDS guide 1" sgRNA cut site. To further refine results, PDS primers (Table 9) specific to the wheat 4A, 4B and 4D genome were used to amplify each copy in isolation for sequence analysis. The gDNA from 15 plants was prepared using the CTAB method. PCR conditions were identical to those used in the previous amplification. Products were resolved by loading 20 microliters of each reaction on a 1% E-gel (Invitrogen).

TABLE 9

| Genome-specific primers for wheat phytoene desaturase | | | | |
|---|---|---|---|---|
| Genome | Primer 1 | SEQ ID NO: | Primer 2 | SEQ ID NO: |
| 4A | MZ139_TaPDS_4A-F | SEQ ID NO: 56 | MZ142_TaPDS-4a,4b,4d-R | SEQ ID NO: 57 |
| 4B | MZ155-TaPDS-4B-F | SEQ ID NO: 58 | MZ142_TaPDS-4a,4b,4d-R | SEQ ID NO: 57 |
| 4D | MZ148_TaPDS_4D-F | SEQ ID NO: 59 | MZ142_TaPDS-4a,4b,4d-R | SEQ ID NO: 57 |

The ~1.8 kb DNA bands were excised and purified using the Monarch gel extraction kit (New England Biolabs) and the DNA was subjected to Sanger sequence analysis. The PDS 4A band was sequenced using primer MZ139_TaPDS_4A-F (SEQ ID NO:56), the PDS 4B band was sequenced using primer MZ164 (NNNNNNCAGTTGGAGCTTATCCCAATGTAC, SEQ ID NO:60) and the PDS 4D band was sequenced using MZ148_TaPDS_4D-F (SEQ ID NO:59). The results are shown in Table 10. Under these experimental conditions, the majority of Cas9 editing activity (genomic alterations) was detected at the 4B-PDS gene; no Cas9 editing activity (genomic alterations) was detected at the 4A-PDS gene and in one line (#9) at the 4D-PDS gene.

TABLE 10

| Plant | 4A-PDS | 4B-PDS | 4D-PDS |
|---|---|---|---|
| Control | wt | wt | wt |
| 1 | wt | Edited at guide#1 | wt |
| 2 | wt | Edited at guide#1 | wt |
| 3 | wt | wt | wt |
| 4 | wt | wt | wt |
| 5 | wt | wt | wt |
| 6 | wt | wt | wt |
| 7 | wt | wt | wt |
| 8 | wt | wt | wt |
| 9 | wt | Edited at guide#1 | Edited at guide#1 |
| 10 | wt | Edited at guide#1 | wt |
| 11 | wt | PCR failed | wt |
| 12 | wt | Edited at guide#1 | wt |
| 13 | wt | Not analyzed* | wt |
| 14 | wt | Not analyzed* | wt |
| 15 | wt | Not analyzed* | wt |

wt = wild-type sequence (unedited)
*not enough gDNA left for analysis

Wheat seeds that have been subjected to this imbibition/editing treatment can also be grown out for observation of a visible bleached phenotype due to modification of the endogenous PDS gene(s) results in a plant having an observable bleached phenotype. Plants that survive to reproductive maturity are allowed to set seed, and progeny seed are subjected to molecular analysis for the presence of heritable alterations to one or more of the endogenous PDS genes(s).

One of skill in the art would recognize that there are alternative reagents and compositions (e.g., DNA encoding a nuclease or RNPs including a nuclease) including such reagents that are useful for introducing alterations or edits into the genome (e.g., use of CRISPR nucleases other than Cas9, such as CasX, CasY, and Cpf1, zinc-finger nucleases (ZFNs), transcription activator-like effector nucleases (TAL-effector nucleases or TALENs), Argonaute proteins, or a meganuclease or engineered meganuclease) and thus similar embodiments of the imbibition technique described herein include use of any of these reagents or compositions. Similarly, the imbibition technique described herein is generally applicable to any plant part, plant tissue, or whole plant, seed, seedling, or embryo (e.g., whole seed or part of a seed, excised embryos, callus, leaf or other plant part, meristematic tissue), and of any plant species (e.g., alfalfa (*Medicago sativa*), almonds (*Prunus dulcis*), apples (*Malus x domestica*), apricots (*Prunus armeniaca, P. brigantine, P. mandshurica, P. mume, P. sibirica*), asparagus (*Asparagus officinalis*), bananas (*Musa* spp.), barley (*Hordeum vulgare*), beans (*Phaseolus* spp.), blueberries and cranberries (*Vaccinium* spp.), cacao (*Theobroma cacao*), canola and rapeseed or oilseed rape, (*Brassica napus*), carnation (*Dianthus caryophyllus*), carrots (*Daucus carota sativus*), cassava (*Manihot esculentum*), cherry (*Prunus avium*), chickpea (*Cider arietinum*), chicory (*Cichorium intybus*), chili peppers and other capsicum peppers (*Capsicum annuum, C. frutescens, C. chinense, C. pubescens, C. baccatum*), chrysanthemums (*Chrysanthemum* spp.), coconut (*Cocos nucifera*), coffee (*Coffea* spp. including *Coffea arabica* and *Coffea canephora*), cotton (*Gossypium hirsutum* L.), cowpea (*Vigna unguiculata*), cucumber (*Cucumis sativus*), currants and gooseberries (*Ribes* spp.), eggplant or aubergine (*Solanum melongena*), eucalyptus (*Eucalyptus* spp.), flax (*Linum usitatissumum* L.), geraniums (*Pelargonium* spp.), grapefruit (*Citrus x paradisi*), grapes (*Vitus* spp.) including wine grapes (*Vitus vinifera*), guava (*Psidium guajava*), irises (*Iris* spp.), lemon (*Citrus limon*), lettuce (*Lactuca sativa*), limes (*Citrus* spp.), maize (*Zea mays* L.), mango (*Mangifera indica*), mangosteen (*Garcinia mangostana*), melon (*Cucumis melo*), millets (*Setaria* spp, *Echinochloa* spp, *Eleusine* spp, *Panicum* spp., *Pennisetum* spp.), oats (*Avena sativa*), oil palm (*Ellis quineensis*), olive (*Olea europaea*), onion (*Allium cepa*), orange (*Citrus sinensis*), papaya (*Carica papaya*), peaches and nectarines (*Prunus persica*), pear (*Pyrus* spp.), pea (*Pisa sativum*), peanut (*Arachis hypogaea*), peonies (*Paeonia* spp.), petunias (*Petunia* spp.), pineapple (*Ananas comosus*), plantains (*Musa* spp.), plum (*Prunus domestica*), poinsettia (*Euphorbia pulcherrima*), Polish canola (*Brassica rapa*), poplar (*Populus* spp.), potato (*Solanum tuberosum*), pumpkin (*Cucurbita pepo*), rice (*Oryza sativa* L.), roses (*Rosa* spp.), rubber (*Hevea brasiliensis*), rye (*Secale cereale*), safflower (*Carthamus tinctorius* L), sesame seed (*Sesame indium*), sorghum (*Sorghum bicolor*), soybean (*Glycine max* L.), squash (*Cucurbita pepo*), strawberries (*Fragaria* spp., *Fragaria x ananassa*), sugar beet (*Beta vulgaris*), sugarcanes (*Saccharum* spp.), sunflower (*Helianthus annus*), sweet potato (*Ipomoea batatas*), tangerine (*Citrus tangerina*), tea (*Camellia sinensis*), tobacco (*Nicotiana tabacum* L.), tomato (*Lycopersicon esculentum*), tulips (*Tulipa* spp.), turnip (*Brassica rapa rapa*), walnuts (*Juglans* spp. L.), watermelon (*Citrulus lanatus*), wheat (*Tritium aestivum*), and yams (*Discorea* spp.)). Non-limiting embodiments include imbibition delivery of DNA or RNP editing reagents to whole seed or part of a seed, embryos, callus, pollen, anthers, stamens, leaf or other plant part, and meristematic tissue of maize, rice, wheat, barley, rye, millet, sorghum, soybean, cotton, brassicas (including oilseed brassicas and sugar beet), solanaceous plants (including tomato, pepper, potato, and eggplant), strawberry, banana, plantain, citrus fruits, coffee, cacao, and sugarcanes.

All cited patents and patent publications referred to in this application are incorporated herein by reference in their entirety. All of the materials and methods disclosed and claimed herein can be made and used without undue experimentation as instructed by the above disclosure and illustrated by the examples. Although the materials and methods of this invention have been described in terms of embodiments and illustrative examples, it will be apparent to those of skill in the art that substitutions and variations can be applied to the materials and methods described herein without departing from the concept, spirit, and scope of the invention. For instance, while the particular examples provided illustrate the methods and embodiments described herein using a specific plant, the principles in these examples are applicable to any plant of interest; similarly, while the particular examples provided illustrate the methods and embodiments described herein using a particular sequence-specific nuclease such as Cas9, one of skill in the art would recognize that alternative sequence-specific nucleases (e.g., CRISPR nucleases other than Cas9, such as CasX, CasY, and Cpf1, zinc-finger nucleases, transcription activator-like effector nucleases, Argonaute proteins, and meganucleases) are useful in various embodiments. All such similar substitutes and modifications apparent to those skilled in the art are deemed to be within the spirit, scope, and concept of the invention as encompassed by the embodiments of the inventions recited herein and the specification and appended claims.

What is claimed is:

1. A method of effecting a genetic alteration in the genome of a non-epidermal monocot plant cell in a whole monocot seed, comprising imbibition of the whole monocot seed in an aqueous polynucleotide composition that comprises: (a) a polynucleotide that encodes an RNA-guided nuclease, (b) at least one guide RNA or polynucleotide encoding a guide RNA, and (c) dimethylsulfoxide, wherein the aqueous polynucleotide composition is without polyethylene glycol;

wherein the at least one guide RNA is capable of directing the RNA-guided nuclease to a defined location in the genome, thereby effecting a genetic alteration at the defined location in the genome of the non-epidermal plant cell;

wherein the genetic alteration is at least one alteration selected from the group consisting of insertion of at least one nucleotide, deletion of at least one nucleotide, and replacement of at least one nucleotide at the defined location in the genome of the non-epidermal plant cell.

2. The method of claim 1, wherein the RNA-guided nuclease is selected from the group consisting of an RNA-guided DNA endonuclease, a type II Cas nuclease, a Cas9, a type V Cas nuclease, a Cpf1, a CasY, a CasX, a C2c1, a C2c3, an engineered nuclease, and a codon-optimized nuclease.

3. The method of claim 1, wherein the genetic alteration is heritable to succeeding generations.

4. The method of claim 1, wherein the whole seed is a maize or wheat whole seed.

5. The method of claim 1, wherein polynucleotide composition is delivered using negative or positive pressure.

6. The method of claim 5, wherein polynucleotide composition is delivered using vacuum infiltration or application of hydrodynamic or fluid pressure.

7. The method of claim 1, further comprising the step of growing or regenerating a plant from the non-epidermal plant cell comprising the genetic alteration.

8. The method of claim 1, wherein callus is produced from the non-epidermal plant cell comprising the genetic alteration and a plant is produced from the callus.

9. The method of claim 7, wherein whole seedlings or plants are grown from the non-epidermal plant cell without a callus stage.

10. The method of claim 1, wherein the dimethylsulfoxide is at a concentration of about 20%.

* * * * *